(12) United States Patent
Rosales et al.

(10) Patent No.: US 8,501,735 B2
(45) Date of Patent: Aug. 6, 2013

(54) N-CONTAINING HETEROARYL DERIVATIVES AS JAK3 KINASE INHIBITORS

(75) Inventors: Carmen Almansa Rosales, Barcelona (ES); Jorge Salas Solana, Granollers (ES); Robert Soliva Soliva, Sant Feliu de Llobregat (ES); Sergio Rodriguez Escrich, Tarragona (ES); Maria Cristina Sicre González, Pontevedra (ES)

(73) Assignee: Palau Pharma, S.A., Barcelona (ES)

( * ) Notice: Subject to any disclaimer, the term of this patent is extended or adjusted under 35 U.S.C. 154(b) by 0 days.

(21) Appl. No.: 13/504,157

(22) PCT Filed: Oct. 29, 2010

(86) PCT No.: PCT/EP2010/066476
§ 371 (c)(1),
(2), (4) Date: Jun. 7, 2012

(87) PCT Pub. No.: WO2011/051452
PCT Pub. Date: May 5, 2011

(65) Prior Publication Data
US 2012/0245140 A1   Sep. 27, 2012
US 2013/0131038 A9   May 23, 2013

Related U.S. Application Data

(60) Provisional application No. 61/291,051, filed on Dec. 30, 2009, provisional application No. 61/329,927, filed on Apr. 30, 2010.

(30) Foreign Application Priority Data

Oct. 29, 2009  (EP) ..................................... 09382233

(51) Int. Cl.
   *A61K 31/52*  (2006.01)
   *A61K 31/522*  (2006.01)
   *C07D 473/00*  (2006.01)

(52) U.S. Cl.
   USPC ..................................... 514/230.5; 544/265

(58) Field of Classification Search
   USPC .......................................................... 544/265
   See application file for complete search history.

(56) References Cited

U.S. PATENT DOCUMENTS

| | | | |
|---|---|---|---|
| 2007/0021443 A1 | 1/2007 | Ohlmeyer et al. | |
| 2008/0085898 A1 | 4/2008 | Lu et al. | |
| 2008/0119496 A1* | 5/2008 | Ohlmeyer et al. | 514/263.21 |
| 2008/0214580 A1 | 9/2008 | Neagu et al. | |
| 2008/0287468 A1 | 11/2008 | Ohlmeyer et al. | |
| 2009/0069289 A1* | 3/2009 | Neagu et al. | 514/210.21 |
| 2009/0203690 A1 | 8/2009 | Akritopoulou-Zanze et al. | |
| 2009/0258888 A1 | 10/2009 | Nagarathnam et al. | |

FOREIGN PATENT DOCUMENTS

| | | | |
|---|---|---|---|
| EP | 1505064 A1 | | 2/2005 |
| EP | 1790650 A1 | | 5/2007 |
| JP | 2011136925 A | * | 7/2011 |
| WO | WO 2004/039796 A1 | | 5/2004 |
| WO | WO 2006/053109 A1 | | 5/2006 |
| WO | WO 2006/108103 A1 | | 10/2006 |
| WO | WO 2006/110763 A1 | | 10/2006 |
| WO | WO 2006/124874 A2 | | 11/2006 |
| WO | WO 2007/072163 A2 | | 6/2007 |
| WO | WO 2007/140222 A2 | | 12/2007 |
| WO | WO-2008-043019 A1 | | 4/2008 |
| WO | WO 2008/043031 A1 | | 4/2008 |
| WO | WO 2008/051493 A2 | | 5/2008 |
| WO | WO 2008/060301 A1 | | 5/2008 |
| WO | WO 2008/143674 A1 | | 11/2008 |
| WO | WO 2009/048474 A1 | | 4/2009 |
| WO | WO 2009/068512 A1 | | 6/2009 |
| WO | WO 2009/077608 A1 | | 6/2009 |
| WO | WO 2009/080721 A2 | | 7/2009 |
| WO | WO 2010/020432 A2 | | 2/2010 |
| WO | WO 2010/022358 A1 | | 2/2010 |
| WO | WO 2011/076878 A1 | | 6/2011 |

OTHER PUBLICATIONS

Beller et al. Angew. Chem. Int. Ed. 2009, 48, 4114-4133.*
International Search Report, PCT/EP2010/066476, mailed Dec. 28, 2010.

* cited by examiner

*Primary Examiner* — Noble Jarrell
*Assistant Examiner* — Laura Daniel
(74) *Attorney, Agent, or Firm* — Finnegan, Henderson, Farabow, Garrett & Dunner

(57) ABSTRACT

N-containing heteroaryl derivatives of formula I or II, wherein the meanings for the various substituents are as disclosed in the description. These compounds are useful as JAK, particularly JAK3, kinase inhibitors.

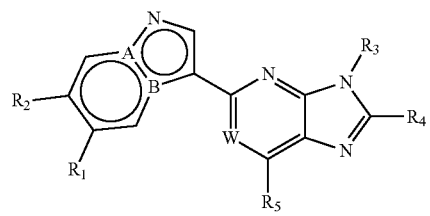

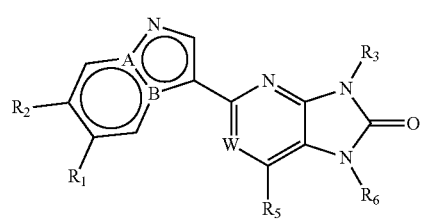

36 Claims, No Drawings

N-CONTAINING HETEROARYL DERIVATIVES AS JAK3 KINASE INHIBITORS

This is a national stage thing under 35 U.S.C. §371 of International Application No. PCT/EP2010/066476, filed on Oct. 29, 2010, which claims priority to European Patent Application No. 09382233.6, filed Oct. 29, 2009, and Provisional Application No. 61/291,051, filed Dec. 30, 2009, and Provisional Application No. 61/329,927, filed Apr. 30, 2010. The contents of all applications are incorporated herein by reference.

FIELD OF THE INVENTION

The present invention relates to a new series of N-containing heteroaryl derivatives, as well as to processes for their preparation, to pharmaceutical compositions comprising them and to their use in therapy.

BACKGROUND OF THE INVENTION

The Janus kinases (JAKs) are cytoplasmic protein tyrosine kinases that play pivotal roles in pathways that modulate cellular functions in the lympho-hematopoietic system that are critical for cell proliferation and cell survival. JAKs are involved in the initiation of cytokine-triggered signaling events by activating through tyrosine phosphorylation the signal transducers and activators of transcription (STAT) proteins. JAK/STAT signaling has been implicated in the mediation of many abnormal immune responses such as transplant rejection and autoimmune diseases, as well as in solid and hematologic malignancies such as leukemias and lymphomas and in myeloproliferative disorders, and has thus emerged as an interesting target for drug intervention.

Four members of the JAK family have been identified so far: JAK1, JAK2, JAK3 and Tyk2. Unlike JAK1, JAK2 and Tyk2, whose expression is ubiquitous, JAK3 is mainly found in hematopoietic cells. JAK3 is associated in a non-covalent manner with the γc subunit of the receptors of IL-2, IL-4, IL-7, IL-9, IL-13 and IL-15. These cytokines play an important role in the proliferation and differentiation of T lymphocytes. JAK3-deficient mouse T cells do not respond to IL-2. This cytokine is fundamental in the regulation of T lymphocytes. In this regard, it is known that antibodies directed against the IL-2 receptor are able to prevent transplant rejection. In patients with X severe combined immunodeficiency (X-SCID), very low levels of JAK3 expression as well as genetic defects in the γc subunit of the receptor have been identified, which indicates that immunosuppression is a consequence of an alteration in the JAK3 signaling pathway.

Animal studies have suggested that JAK3 not only plays a critical role in T and B lymphocyte maturation, but also that JAK3 is required to maintain lymphocyte function. Modulation of the immunological activity through this new mechanism can prove useful in the treatment of T cell proliferative disorders such as transplant rejection and autoimmune diseases.

JAK3 has also been shown to play an important role in mast cells, because antigen-induced degranulation and mediator release have been found to be substantially reduced in mast cells from JAK3 deficient mice. JAK3 deficiency does not affect mast cell proliferation nor IgE receptor expression levels. On the other hand, JAK3−/− and JAK3+/+ mast cells contain the same intracellular mediators. Therefore, JAK3 appears to be essential in the IgE-induced release of mediators in mast cells and its inhibition would be, thus, an effective treatment for allergic reactions.

In conclusion, JAK3 kinase inhibitors have been recognised as a new class of effective immunosuppressive agents useful for transplant rejection prevention and in the treatment of immune, autoimmune, inflammatory and proliferative diseases such as psoriasis, psoriatic arthritis, rheumatoid arthritis, multiple sclerosis, inflammatory bowel diseases, systemic lupus erythematosus, type I diabetes and complications from diabetes, allergic reactions and leukemia (see e.g. O'Shea J. J. et al., Nat. Rev. Drug. Discov. 2004, 3(7):555-64; Cetkovic-Cvrlje M. et al, Curr. Pharm, Des. 2004, 10(15):1767-84; Cetkovic-Cvrlje M. et al, Arch. Immunol. Ther. Exp. (Warsz), 2004, 52(2):69-82).

Accordingly, it would be desirable to provide novel compounds that are capable of inhibiting JAK/STAT signaling pathways, and in particular which are capable of inhibiting JAK3 activity, and which are good drug candidates. Compounds should exhibit good activity in in vitro and in vivo pharmacological assays, good oral absorption when administered by the oral route, as well as be metabolically stable and exhibit a favourable pharmacokinetic profile. Moreover, compounds should not be toxic and exhibit few side effects.

DESCRIPTION OF THE INVENTION

One aspect of the invention relates to a compound of formula I or II

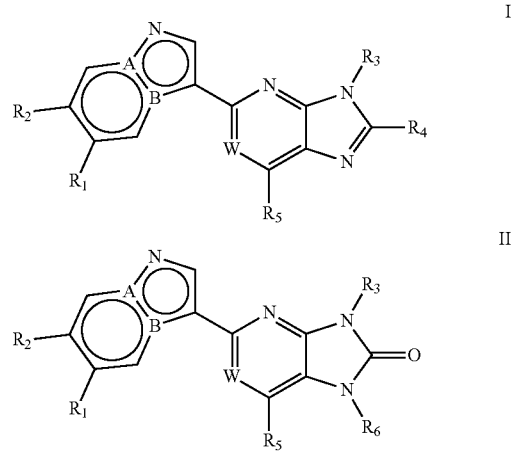

wherein
A is carbon and B is nitrogen, or A is nitrogen and B is carbon;
W is CH or N;
$R_1$ and $R_2$ independently are hydrogen, $C_{1-4}$alkyl, hydroxy$C_{1-4}$alkyl, cyano$C_{1-4}$alkyl, $C_{1-4}$alkoxy$C_{1-4}$alkyl, halogen, —CN, —$OR_8$, or —$SR_8$;
$R_3$ is $C_{1-4}$alkyl, $R_9$—$C_{1-4}$alkyl, $Cy_1$ or $Cy_2$-$C_{1-4}$alkyl, wherein $Cy_1$ and $Cy_2$ are optionally substituted with one or more $R_{10}$;
$R_4$ is hydrogen, $C_{1-4}$alkyl, halo$C_{1-4}$alkyl, $C_{1-4}$alkoxy $C_{1-4}$alkyl, hydroxy$C_{1-4}$alkyl, cyano$C_{1-4}$alkyl, $R_{12}R_7N$—$C_{0-4}$alkyl, $R_{13}CONR_7$—$C_{0-4}$alkyl, $R_{13}R_7NCO$—$C_{0-4}$alkyl, $R_{12}R_7NCONR_7$—$C_{0-4}$alkyl, $R_{13}CO_2NR_7$—$C_{0-4}$alkyl, $R_{13}SO_2NR_7$—$C_{0-4}$alkyl, —$OR_{12}$ or $Cy_2$-$C_{0-4}$alkyl; wherein $Cy_2$ is optionally substituted with one or more $R_{11}$;
$R_5$ is hydrogen, $C_{1-4}$alkyl, halo$C_{1-4}$alkyl, $C_{1-4}$alkoxy $C_{1-4}$alkyl, hydroxy$C_{1-4}$alkyl, cyano$C_{1-4}$alkyl, halogen, —CN, —$OR_{12}$, —$NR_7R_{12}$, or $Cy_2$-$C_{0-4}$alkyl, wherein $Cy_2$ is optionally substituted with one or more $R_{11}$;

R₆ is hydrogen, C₁₋₄alkyl, C₁₋₄alkoxyC₁₋₄alkyl, hydroxyC₁₋₄alkyl, R₁₂R₇N—C₁₋₄alkyl, R₁₆CO—C₀₋₄alkyl, R₁₆CO₂—C₀₋₄alkyl, R₁₆CO—O—C₁₋₄alkyl, cyanoC₁₋₄alkyl, Cy₁ or Cy₂-C₁₋₄alkyl, wherein Cy₁ and Cy₂ are optionally substituted with one or more R₁₁;

R₇ is hydrogen or C₁₋₄alkyl;

R₈ is hydrogen, C₁₋₄alkyl, haloC₁₋₄alkyl, hydroxyC₁₋₄alkyl, or C₁₋₄alkoxyC₁₋₄alkyl;

R₉ is halogen, —CN, —CONR₇R₁₂, —COR₁₃, —CO₂R₁₂, —OR₁₂, —OCONR₇R₁₂, —SO₂R₁₃, —SO₂NR₇R₁₂, —NR₇R₁₂, —NR₇COR₁₂, —NR₇CONR₇R₁₂, —NR₇CO₂R₁₃ or —NR₇SO₂R₁₃;

R₁₀ is C₁₋₄alkyl or R₉—C₀₋₄alkyl;

R₁₁ is C₁₋₄alkyl, haloC₁₋₄alkyl, C₁₋₄alkoxyC₁₋₄alkyl, hydroxyC₁₋₄alkyl, cyanoC₁₋₄alkyl, halogen, —CN, —CONR₇R₁₄, —COR₁₄, —CO₂R₁₅, —OR₁₄, —OCONR₇R₁₄, —SO₂R₁₅, —SO₂NR₇R₁₄, —NR₇R₁₄, —NR₇COR₁₄, —NR₇CONR₇R₁₄, —NR₇CO₂R₁₅ or —NR₇SO₂R₁₅;

R₁₂ is hydrogen or R₁₃;

R₁₃ is C₁₋₅alkyl, haloC₁₋₄alkyl, C₁₋₄alkoxyC₁₋₄alkyl, hydroxyC₁₋₄alkyl, cyanoC₁₋₄alkyl, Cy₂-C₀₋₄alkyl or R₁₄R₇N—C₁₋₄alkyl; wherein Cy₂ is optionally substituted with one or more R₁₁;

R₁₄ is hydrogen or R₁₅;

R₁₅ is C₁₋₄alkyl, haloC₁₋₄alkyl, C₁₋₄alkoxyC₁₋₄alkyl, hydroxyC₁₋₄alkyl or cyanoC₁₋₄alkyl;

R₁₆ is C₁₋₄alkyl, haloC₁₋₄alkyl, C₁₋₄alkoxyC₁₋₄alkyl or cyanoC₁₋₄alkyl;

Cy₁ is a 3- to 7-membered monocyclic or 6- to 11-membered bicyclic ring, which is saturated, partially unsaturated or aromatic, and which is carbocyclic or heterocyclic containing from 1 to 4 heteroatoms independently selected from N, S and O, wherein said ring is bonded to the rest of the molecule through any available C atom, and wherein one or more C or S ring atoms are optionally oxidized forming CO, SO or SO₂; and Cy₂ is a 3- to 7-membered monocyclic or 6- to 11-membered bicyclic ring, which is saturated, partially unsaturated or aromatic, and which is carbocyclic or heterocyclic containing from 1 to 4 heteroatoms independently selected from N, S and O, wherein said ring is bonded to the rest of the molecule through any available C or N atom, and wherein one or more C or S ring atoms are optionally oxidized forming CO, SO or SO₂

The compounds of formula I or II are JAK, particularly JAK3, kinase inhibitors and therefore can be useful for the treatment or prevention of any disease mediated by JAKs, and particularly JAK3.

Thus, another aspect of the invention relates to a compound of formula I or II

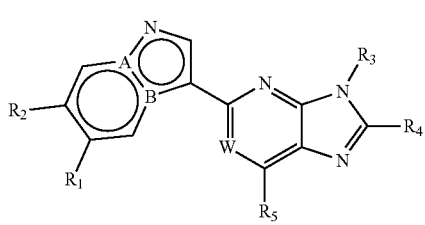

I

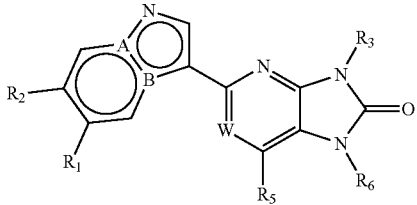

II wherein

A is carbon and B is nitrogen, or A is nitrogen and B is carbon;

W is CH or N;

R₁ and R₂ independently are hydrogen, C₁₋₄alkyl, haloC₁₋₄alkyl, hydroxyC₁₋₄alkyl, cyanoC₁₋₄alkyl, C₁₋₄alkoxyC₁₋₄alkyl, halogen, —CN, —OR₈, or —SR₈;

R₃ is C₁₋₄alkyl, R₉—C₁₋₄alkyl, Cy₁ or Cy₂-C₁₋₄alkyl, wherein Cy₁ and Cy₂ are optionally substituted with one or more R₁₀;

R₄ is hydrogen, C₁₋₄alkyl, haloC₁₋₄alkyl, C₁₋₄alkoxyC₁₋₄alkyl, hydroxyC₁₋₄alkyl, cyanoC₁₋₄alkyl, R₁₂R₇N—C₀₋₄alkyl, R₁₃CONR₇—C₀₋₄alkyl, R₁₃R₇NCO—C₀₋₄alkyl, R₁₂R₇NCONR₇—C₀₋₄alkyl, R₁₃CO₂NR₇—C₀₋₄alkyl, R₁₃SO₂NR₇—C₀₋₄alkyl, —OR₁₂ or Cy₂-C₁₋₄alkyl; wherein Cy₂ is optionally substituted with one or more R₁₁;

R₅ is hydrogen, C₁₋₄alkyl, haloC₁₋₄alkyl, C₁₋₄alkoxyC₁₋₄alkyl, hydroxyC₁₋₄alkyl, cyanoC₁₋₄alkyl, halogen, —CN, —OR₁₂, —NR₇R₁₂, or Cy₂-C₀₋₄alkyl, wherein Cy₂ is optionally substituted with one or more R₁₁;

R₆ is hydrogen, C₁₋₄alkyl, C₁₋₄alkoxyC₁₋₄alkyl, hydroxyC₁₋₄alkyl, R₁₂R₇N—C₁₋₄alkyl, R₁₆CO—C₀₋₄alkyl, R₁₆CO₂—C₀₋₄alkyl, R₁₆CO—O—C₁₋₄alkyl, cyanoC₁₋₄alkyl, Cy₁ or Cy₂-C₁₋₄alkyl, wherein Cy₁ and Cy₂ are optionally substituted with one or more R₁₁;

R₇ is hydrogen or C₁₋₄alkyl;

R₈ is hydrogen, C₁₋₄alkyl, haloC₁₋₄alkyl, hydroxyC₁₋₄alkyl, or C₁₋₄alkoxyC₁₋₄alkyl;

R₉ is halogen, —CN, —CONR₇R₁₂, —COR₁₃, —CO₂R₁₂, —OR₁₂, —OCONR₇R₁₂, —SO₂R₁₃, —SO₂NR₇R₁₂, —NR₇R₁₂, —NR₇COR₁₂, —NR₇CONR₇R₁₂, —NR₇CO₂R₁₃ or —NR₇SO₂R₁₃;

R₁₀ is C₁₋₄alkyl or R₉—C₀₋₄alkyl;

R₁₁ is C₁₋₄alkyl, haloC₁₋₄alkyl, C₁₋₄alkoxyC₁₋₄alkyl, hydroxyC₁₋₄alkyl, cyanoC₁₋₄alkyl, halogen, —CN, —CONR₇R₁₄, —COR₁₄, —CO₂R₁₆, —OR₁₄, —OCONR₇R₁₄, —SO₂R₁₅, —SO₂NR₇R₁₄, —NR₇R₁₄, —NR₇COR₁₄, —NR₇CONR₇R₁₄, —NR₇CO₂R₁₅ or —NR₇SO₂R₁₅;

R₁₂ is hydrogen or R₁₃,

R₁₃ is C₁₋₅alkyl, haloC₁₋₄alkyl, C₁₋₄alkoxyC₁₋₄alkyl, hydroxyC₁₋₄alkyl, cyanoC₁₋₄alkyl, Cy₂-C₀₋₄alkyl or R₁₄R₇N—C₁₋₄alkyl; wherein Cy₂ is optionally substituted with one or more R₁₁;

R₁₄ is hydrogen or R₁₅;

R₁₅ is C₁₋₄alkyl, haloC₁₋₄alkyl, C₁₋₄alkoxyC₁₋₄alkyl, hydroxyC₁₋₄alkyl or cyanoC₁₋₄alkyl;

R₁₆ is C₁₋₄alkyl, haloC₁₋₄alkyl, C₁₋₄alkoxyC₁₋₄alkyl or cyanoC₁₋₄alkyl;

Cy₁ is a 3- to 7-membered monocyclic or 6- to 11-membered bicyclic ring, which is saturated, partially unsaturated or aromatic, and which is carbocyclic or heterocyclic containing from 1 to 4 heteroatoms independently selected from N, S and O, wherein said ring is bonded to the rest of the molecule through any available C atom, and wherein one or more C or S ring atoms are optionally oxidized forming CO, SO or $SO_2$; and $Cy_2$ is a 3- to 7-membered monocyclic or 6- to 11-membered bicyclic ring, which is saturated, partially unsaturated or aromatic, and which is carbocyclic or heterocyclic containing from 1 to 4 heteroatoms independently selected from N, S and O, wherein said ring is bonded to the rest of the molecule through any available C or N atom, and wherein one or more C or S ring atoms are optionally oxidized forming CO, SO or $SO_2$;

for use in therapy.

Another aspect of the invention relates to a pharmaceutical composition which comprises a compound of formula I or II or a pharmaceutically acceptable salt thereof and one or more pharmaceutically acceptable excipients.

Another aspect of the present invention relates to the use of a compound of formula I or II or a pharmaceutically acceptable salt thereof for the manufacture of a medicament for the treatment or prevention of a disease mediated by JAKs, particularly JAK3. More preferably, the disease mediated by JAKs, particularly JAK3, is at least one disease selected from transplant rejection, immune, autoimmune or inflammatory diseases, neurodegenerative diseases, or proliferative disorders, in a further preferred embodiment, the disease mediated by JAKs, particularly JAK3, is selected from transplant rejection or immune, autoimmune or inflammatory diseases. In a further preferred embodiment, the disease mediated by JAKs, particularly JAK3, is a proliferative disorder.

Another aspect of the present invention relates to the use of a compound of formula I or II or a pharmaceutically acceptable salt thereof for the manufacture of a medicament for the treatment or prevention of at least one disease selected from transplant rejection, immune, autoimmune or inflammatory diseases, neurodegenerative diseases, or proliferative disorders. In a preferred embodiment, the disease is selected from transplant rejection or immune, autoimmune or inflammatory diseases. In a further preferred embodiment, the disease is a proliferative disorder.

Another aspect of the present invention relates to the use of a compound of formula I or II or a pharmaceutically acceptable salt thereof for the manufacture of a medicament for the treatment or prevention of a disease selected from transplant rejection, rheumatoid arthritis, psoriatic arthritis, psoriasis, type I diabetes, complications from diabetes, multiple sclerosis, systemic lupus erythematosus, atopic dermatitis, mast cell-mediated allergic reactions, inflammatory or autoimmune ocular diseases, leukemias, lymphomas, and thromboembolic and allergic complications associated with leukemias and lymphomas.

Another aspect of the present invention relates to a compound of formula I or II or a pharmaceutically acceptable salt thereof for use in the treatment or prevention of a disease mediated by JAKs, particularly JAK3. More preferably, the disease mediated by JAKs, particularly JAK3, is at least one disease selected from transplant rejection, immune, autoimmune or inflammatory diseases, neurodegenerative diseases, or proliferative disorders. In a further preferred embodiment, the disease mediated by JAKs, particularly JAK3, is selected from transplant rejection or immune, autoimmune or inflammatory diseases. In a further preferred embodiment, the disease mediated by JAKs, particularly JAK3, is a proliferative disorder.

Another aspect of the present invention relates to a compound of formula I or II or a pharmaceutically acceptable salt thereof for use in the treatment or prevention of at least one disease selected from transplant rejection, immune, autoimmune or inflammatory diseases, neurodegenerative diseases, or proliferative disorders. In a preferred embodiment, the disease is selected from transplant rejection or immune, autoimmune or inflammatory diseases, in a further preferred embodiment, the disease is a proliferative disorder.

Another aspect of the present invention relates to a compound of formula I or Er or a pharmaceutically acceptable salt thereof for use in the treatment or prevention of a disease selected from transplant rejection, rheumatoid arthritis, psoriatic arthritis, psoriasis, type I diabetes, complications from diabetes, multiple sclerosis, systemic lupus erythematosus, atopic dermatitis, mast cell-mediated allergic reactions, inflammatory or autoimmune ocular diseases, leukemias, lymphomas, and thromboembolic and allergic complications associated with leukemias and lymphomas.

Another aspect of the present invention relates to the use of a compound of formula I or II or a pharmaceutically acceptable salt thereof for the treatment or prevention of a disease mediated by JAKs, particularly JAK3. More preferably, the disease mediated by JAKs, particularly JAK3, is at least one disease selected from transplant rejection, immune, autoimmune or inflammatory diseases, neurodegenerative diseases, or proliferative disorders. In a further preferred embodiment, the disease mediated by JAKs, particularly JAK3, is selected from transplant rejection or immune, autoimmune or inflammatory diseases. In a further preferred embodiment, the disease mediated by JAKs, particularly JAK3, is a proliferative disorder.

Another aspect of the present invention relates to the use of a compound of formula I or II or a pharmaceutically acceptable salt thereof for the treatment or prevention of at least one disease selected from transplant rejection, immune, autoimmune or inflammatory diseases, neurodegenerative diseases, or proliferative disorders. In a preferred embodiment, the disease is selected from transplant rejection or immune, autoimmune or inflammatory diseases. In a further preferred embodiment, the disease is a proliferative disorder.

Another aspect of the present invention relates to the use of a compound of formula I or II or a pharmaceutically acceptable salt thereof for the treatment or prevention of a disease selected from transplant rejection, rheumatoid arthritis, psoriatic arthritis, psoriasis, type I diabetes, complications from diabetes, multiple sclerosis, systemic lupus erythematosus, atopic dermatitis, mast cell-mediated allergic reactions, inflammatory or autoimmune ocular diseases, leukemias, lymphomas, and thromboembolic and allergic complications associated with leukemias and lymphomas.

Another aspect of the present invention relates to a method of treating or preventing a disease mediated by JAKs, particularly JAK3, in a subject in need thereof, especially a human being, which comprises administering to said subject an amount of a compound of formula I or II or a pharmaceutically acceptable salt thereof effective to treat said disease. More preferably, the disease mediated by JAKs, particularly JAK3, is at least one disease selected from transplant rejection, immune, autoimmune or inflammatory diseases, neurodegenerative diseases, or proliferative disorders. In a further preferred embodiment, the disease mediated by JAKs, particularly JAK3, is selected from transplant rejection or immune, autoimmune or inflammatory diseases. In a further preferred embodiment, the disease mediated by JAKs, particularly JAK3, is a proliferative disorder.

Another aspect of the present invention relates to a method of treating or preventing at least one disease selected from transplant rejection, immune, autoimmune or inflammatory diseases, neurodegenerative diseases, or proliferative disorders in a subject in need thereof, especially a human being, which comprises administering to said subject an amount of a compound of formula I or II or a pharmaceutically acceptable salt thereof effective to treat said disease. In a preferred embodiment, the disease is selected from transplant rejection or immune, autoimmune or inflammatory diseases. In a further preferred embodiment, the disease is a proliferative disorder.

Another aspect of the present invention relates to a method of treating or preventing a disease selected from transplant rejection, rheumatoid arthritis, psoriatic arthritis, psoriasis, type I diabetes, complications from diabetes, multiple sclerosis, systemic lupus erythematosus, atopic dermatitis, mast cell-mediated allergic reactions, inflammatory or autoimmune ocular diseases, leukemias, lymphomas, and thromboembolic and allergic complications associated with leukemias and lymphomas in a subject in need thereof, especially a human being, which comprises administering to said subject an amount of a compound of formula I or II or a pharmaceutically acceptable salt thereof effective to treat said disease.

Another aspect of the present invention relates to a process for the preparation of a compound of formula I or II as defined above, which comprises:

(a) for a compound of formula I, reacting a compound of formula VI with a compound of formula III

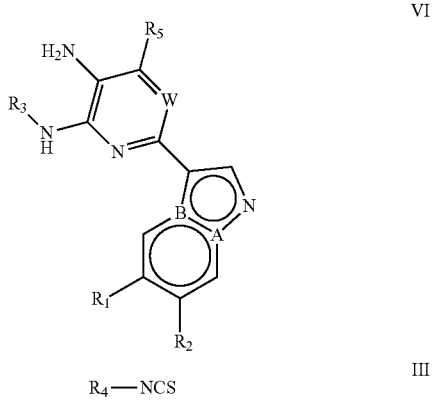

VI $R_4$—NCS

III wherein A, B, W, $R_1$, $R_2$, $R_3$, $R_4$ and $R_5$ have the meaning previously described in relation with a compound of formula I or II; or (b) for a compound of formula I, reacting a compound of formula VI with a compound of formula IV

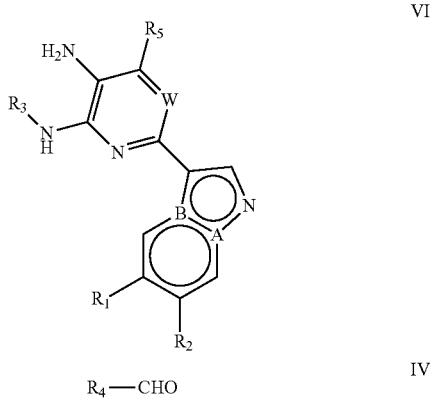

VI $R_4$—CHO

IV wherein A, B, W, $R_1$, $R_2$, $R_3$, $R_4$ and $R_5$ have the meaning previously described in relation with a compound of formula I or II; or (c) when in a compound of formula II $R_6$ is hydrogen (a compound of formula IIa) reacting a compound of formula VI, as defined above, with a synthetic equivalent for the CO synthon.

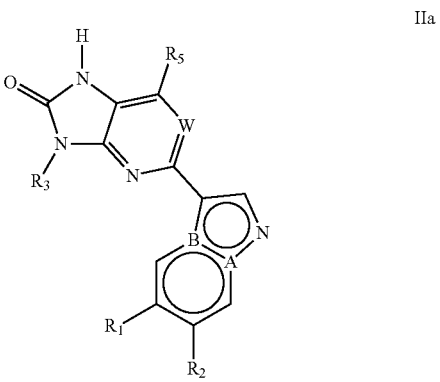

IIa wherein A, B, W, $R_1$, $R_2$, $R_3$ and $R_5$ have the meaning previously described in relation with a compound of formula I or II; or (d) when in a compound of formula II $R_6$ is other than hydrogen, reacting a compound of formula IIa with a compound of formula V ($R_6$—X) in the presence of a base, wherein X is a leaving group; or (e) converting, in one or a plurality of steps, a compound of formula I or II into another compound of formula I or II.

In the above definitions, the term $C_{1-5}$ alkyl, as a group or part of a group, means a straight or branched alkyl chain which contains from 1 to 5 carbon atoms and includes among others the groups methyl, ethyl, propyl, isopropyl, butyl, isobutyl, sec-butyl, tert-butyl, pentyl and iso-pentyl. Likewise, the term $C_{1-4}$ alkyl, as a group or part of a group, means a straight or branched alkyl chain which contains from 1 to 4 carbon atoms and includes the groups methyl, ethyl, propyl, isopropyl, butyl, isobutyl, sec-butyl and tert-butyl.

A $C_{1-4}$alkoxy group, as a group or part of a group, means a group of formula —O$C_{1-4}$alkyl, wherein the $C_{1-4}$alkyl moiety has the same meaning as previously described. Examples include methoxy, ethoxy, propoxy, isopropoxy, butoxy, isobutoxy, sec-butoxy and tert-butoxy.

A $C_{1-4}$alkoxy$C_{1-4}$alkyl group means a group resulting from the replacement of one or more hydrogen atoms from a $C_{1-4}$alkyl group with one or more $C_{1-4}$alkoxy groups as defined above, which can be the same or different. Examples include, among others, the groups methoxymethyl, ethoxymethyl, propoxymethyl, isopropoxymethyl butoxymethyl, isobutoxymethyl, sec-butoxymethyl, tert-butoxymethyl, dimethoxymethyl, 1-methoxyethyl, 2-methoxyethyl, 2-ethoxyethyl, 1,2-diethoxyethyl, 1-butoxyethyl, 2-sec-butoxyethyl, 3-methoxypropyl, 2-butoxypropyl, 1-methoxy-2-ethoxypropyl, 3-tert-butoxypropyl and 4-methoxybutyl.

Halogen or its abbreviation halo means fluoro, chloro, bromo or iodo.

A halo$C_{1-4}$alkyl group means a group resulting from the replacement of one or more hydrogen atoms from a $C_{1-4}$alkyl group with one or more halogen atoms (i.e., fluoro, chloro, bromo or iodo), which can be the same or different. Examples include, among others, the groups trifluoromethyl, fluoromethyl, 1-chloroethyl, 2-chloroethyl, 1-fluoroethyl, 2-fluoroethyl, 2-bromoethyl, 2-iodoethyl, 2,2,2-trifluoroethyl, pentafluoroethyl, 3-fluoropropyl, 3-chloropropyl, 2,2,3,3-tetrafluoropropyl, 2,2,3,3,3-pentafluoropropyl, heptafluoropropyl, 4-fluorobutyl, nonafluorobutyl, 1-chloro-2-fluoroethyl and 2-bromo-1-chloro-1-fluoropropyl.

A hydroxyC$_{1-4}$alkyl group means a group resulting from the replacement of one or more hydrogen atoms from a C$_{1-4}$alkyl group with one or more hydroxy groups. Examples include, among others, the groups hydroxymethyl, 1-hydroxyethyl, 2-hydroxyethyl, 1,2-dihydroxyethyl, 3-hydroxypropyl, 2-hydroxypropyl, 1-hydroxypropyl, 2,3-dihydroxypropyl, 4-hydroxybutyl, 3-hydroxybutyl, 2-hydroxybutyl and 1-hydroxybutyl.

A cyanoC$_{1-4}$alkyl group means a group resulting from the replacement of one or more hydrogen atoms from a C$_{1-4}$alkyl group with one or more cyano groups. Examples include, among others, the groups cyanomethyl, dicyanomethyl, 1-cyanoethyl, 2-cyanoethyl, 3-cyanopropyl, 2,3-dicyanopropyl and 4-cyanobutyl.

A haloC$_{1-4}$alkoxy group means a group resulting from the replacement of one or more hydrogen atoms from a C$_{1-4}$ alkoxy group with one or more halogen atoms (i.e. fluoro, chloro, bromo or iodo), which can be the same or different. Examples include, among others, the groups trifluoromethoxy, fluoromethoxy, 1-chloroethoxy, 2-chloroethoxy, 1-fluoroethoxy, 2-fluoroethoxy, 2-bromoethoxy, 2-iodoethoxy, 2,2,2-trifluoroethoxy, pentafluoroethoxy, 3-fluoropropoxy, 3-chloropropoxy, 2,2,3,3-tetrafluoropropoxy, 2,2,3,3,3-pentafluoropropoxy, heptafluoropropoxy, 4-fluorobutoxy, nonafluorobutoxy, 1-chloro-2-fluoroethoxy and 2-bromo-1-chloro-1-fluoropropoxy.

The term C$_0$ alkyl indicates that the alkyl group is absent. Thus, the term R$_9$—C$_{1-4}$ alkyl includes R$_9$ and R$_9$—C$_{1-4}$ alkyl. The term R$_9$—C$_{1-4}$ alkyl relates to a group resulting from the substitution of one hydrogen atom of a C$_{1-4}$ alkyl group with one R$_9$ group.

The terms R$_{12}$R$_7$N—C$_{0-4}$alkyl, R$_{13}$CONR$_7$—C$_{0-4}$alkyl, R$_{13}$R$_7$NCO—C$_{0-4}$alkyl, R$_{12}$R$_7$NCONR$_7$—C$_{0-4}$alkyl, R$_{13}$CO$_2$NR$_7$—C$_{0-4}$alkyl, R$_{13}$SO$_2$NR$_7$—C$_{0-4}$alkyl, R$_{16}$CO—C$_{0-4}$alkyl and R$_{16}$CO$_2$—C$_{0-4}$alkyl include —NR$_7$R$_{12}$ and R$_{12}$R$_7$N—C$_{1-4}$alkyl, —NR$_7$COR$_{13}$ and R$_{13}$CONR$_7$—C$_{1-4}$alkyl, —CONR$_7$R$_{13}$ and R$_{13}$R$_7$NCO—C$_{1-4}$alkyl, —NR$_7$CONR$_7$R$_{12}$ and R$_{12}$R$_7$NCONR$_7$—C$_{1-4}$alkyl, —NR$_2$CO$_2$R$_{13}$ and R$_{13}$CO$_2$NR$_7$—C$_{1-4}$alkyl, —NR$_7$SO$_2$R$_{13}$ and R$_{13}$SO$_2$NR$_2$—C$_{1-4}$alkyl, —COR$_{16}$ and R$_{16}$CO—C$_{1-4}$alkyl, and —CO$_2$R$_{16}$ and R$_{16}$CO$_2$—C$_{1-4}$alkyl, respectively.

A group R$_{12}$R$_7$N—C$_{1-4}$alkyl, R$_{14}$R$_7$N—C$_{1-4}$alkyl, R$_{13}$CONR$_7$—C$_{1-4}$alkyl, R$_{13}$R$_7$NCO—C$_{1-4}$alkyl, R$_{12}$R$_7$NCONR$_7$—C$_{1-4}$alkyl, R$_{13}$CO$_2$NR$_7$—C$_{1-4}$alkyl, R$_{13}$SO$_2$NR$_7$—C$_{1-4}$alkyl, R$_{16}$CO—C$_{1-4}$alkyl, R$_{16}$CO$_2$—C$_{1-4}$alkyl or R$_{16}$CO—O—C$_{1-4}$alkyl means a group resulting from the replacement of one hydrogen atom from a C$_{1-4}$alkyl group with one —NR$_7$R$_{12}$, —NR$_7$R$_{14}$, —NR$_7$COR$_{13}$, —CONR$_7$R$_{13}$, —NR$_7$CONR$_7$R$_{12}$, —NR$_7$CO$_2$R$_{13}$ NR$_7$SO$_2$R$_{13}$, —COR$_{16}$, —CO$_2$R$_{16}$ or —OCOR$_{16}$ group, respectively.

A Cy$_1$ group refers to a 3- to 7-membered monocyclic or 6- to 11-membered bicyclic carbocyclic or heterocyclic ring, which is saturated, partially unsaturated or aromatic. When heterocyclic, it contains from 1 to 4 heteroatoms independently selected from N, S and a Bicyclic rings are formed either by two rings fused through two adjacent C or N atoms, or through two non-adjacent C or N atoms forming a bridged ring, or else they are formed by two rings bonded through a single common C atom forming a spiro ring, Cy$_1$ is bonded to the rest of the molecule through any available C atom. When Cy$_1$ is saturated or partially unsaturated, one or more C or S atoms of said ring are optionally oxidized forming CO, SO or SO$_2$ groups. Cy$_1$ is optionally substituted as disclosed above in the definition of a compound of formula I or II, said substituents can be the same or different and can be placed on any available position of the ring system.

A Cy$_2$ group refers to a 3- to 7-membered monocyclic or 6- to 11-membered bicyclic carbocyclic or heterocyclic ring, which is saturated, partially unsaturated or aromatic. When heterocyclic, it contains from 1 to 4 heteroatoms independently selected from N, S and O. Bicyclic rings are formed either by two rings fused through two adjacent C or N atoms, or through two non-adjacent C or N atoms forming a bridged ring, or else they are formed by two rings bonded through a single common C atom forming a spiro ring. Cy$_2$ is bonded to the rest of the molecule through any available C or N atom. When Cy$_2$ is saturated or partially unsaturated, one or more C or S atoms of said ring are optionally oxidized forming CO, SO or SO$_2$ groups. Cy$_2$ is optionally substituted as disclosed above in the definition of a compound of formula I or II, said substituents can be the same or different and can be placed on any available position of the ring system.

Examples of either Cy$_1$ or Cy$_2$ include, among others, cyclopropyl, cyclobutyl, cyclopentyl, cyclohexyl, cycloheptyl, azetidinyl, aziridinyl, oxiranyl, oxetanyl, imidazolidinyl, isothiazolidinyl, isoxazolidinyl, oxazolidinyl, pyrazolidinyl, pyrrolidinyl, thiazolidinyl, dioxanyl, morpholinyl, thiomorpholinyl, 1,1-dioxothiomorpholinyl, piperazinyl, homopiperazinyl, piperidinyl, pyranyl, tetrahydropyranyl, homopiperidinyl, oxazinyl, oxazolinyl, pyrrolinyl, thiazolinyl, pyrazolinyl, imidazolinyl, isoxazolinyl, isothiazolinyl, 2-oxo-pyrrolidinyl, 2-oxo-piperidinyl, 4-oxo-piperidinyl, 2-oxo-piperazinyl, 2-oxo-1,2-dihydropyridinyl, 2-oxo-1,2-dihydropyrazinyl, 2-oxo-1,2-dihydropyrimidinyl, 3-oxo-2,3-dihydropyridazyl, phenyl, naphthyl, thienyl, furyl, pyrrolyl, thiazolyl, isothiazolyl, oxazolyl, isoxazolyl, imidazolyl, pyrazolyl, 1,2,3-triazolyl, 1,2,4-triazolyl, tetrazolyl, 1,3,4-oxadiazolyl, 1,3,4-thiadiazolyl, 1,2,4-oxadiazolyl, 1,2,4-thiadiazolyl, pyridyl, pyrazinyl, pyrimidinyl, pyridazinyl, benzimidazolyl, benzooxazolyl, benzofuranyl, isobenzofuranyl, indolyl, isoindolyl, benzothiophenyl, benzothiazolyl, quinolinyl, isoquinolinyl, phtalazinyl, quinazolinyl, quinoxalinyl, cinolinyl, naphthyridinyl, indazolyl, imidazopyridinyl, pyrrolopyridinyl, thienopyridinyl, imidazopyrimidinyl, imidazopyrazinyl, imidazopyridazinyl, pyrazolopyrazinyl, pyrazolopyridinyl, pyrazolopyrimidinyl, benzo[1,3]dioxolyl, phtalimidyl, 1-oxo-1,3-dihydroisobenzofuranyl, 1,3-dioxo-1,3-dihydroisobenzofuranyl, 1-oxo-2,3-dihydro-1H-isoindolyl, chromanyl, perhydroquinolinyl, 1-oxoperhydroisoquinolinyl, 1-oxo-1,2-dihydroisoquinolinyl, 4-oxo-3,4-dihydroquinazolinyl, 2-aza-bicyclo[2.2.1]heptanyl, 5-aza-bicyclo[2.1.1]hexanyl, 2H-spiro[benzofuran-3,4'-piperidinyl], 3H-spiro[isobenzofuran-1,4'-piperidinyl], 1-oxo-2,8-diazaspiro[4.5]decanyl and 1-oxo-2,7-diazaspiro[4.5]decanyl.

When in the definitions used throughout the present specification for cyclic groups the examples given refer to a radical of a ring in general terms, for example piperidinyl, tetrahydropyranyl or indolyl, all the available bonding positions are included, unless a limitation is indicated in the corresponding definition for said cyclic group, for example that the ring is bonded through a C atom in Cy$_1$, in which case such limitation applies. Thus for example, in the definitions of Cy$_2$, which do not include any limitation regarding the bonding position, the term piperidinyl includes 1-piperidinyl, 2-piperidinyl, 3-piperidinyl and 4-piperidinyl; tetrahydropyranyl includes 2-tetrahydropyranyl, 3-tetrahydropyranyl and 4-tetrahydropyranyl; and indolyl includes 1-indolyl, 2-indolyl, 3-indolyl, 4-indolyl, 5-indolyl, 6-indolyl and 7-indolyl.

In the above definitions of Cy$_1$ and Cy$_2$, when the examples listed refer to a bicycle in general terms, all possible dispositions of the atoms are included. Thus, for example, the term pyrazolopyridinyl includes groups such as 1H-pyrazolo[3,4-b]pyridinyl, 1H-pyrazolo[1,5-a]pyridinyl, 1H-pyrazolo[3,4-c]pyridinyl, 1H-pyrazolo[4,3-c]pyridinyl and 1H-pyrazolo[4,3-b]pyridinyl, the term imidazopyrazinyl includes groups such as 1H-imidazo[4,5-b]pyrazinyl, imidazo[1,2-a]pyrazinyl and imidazo[1,5-a]pyrazinyl and the term pyrazolopyrimidinyl includes groups such as 1H-pyrazolo[3,4-d]pyrimidinyl, 1H-pyrazolo[4,3-d]pyrimidinyl, pyrazolo[1,5-a]pyrimidinyl and pyrazolo[1,5-c]pyrimidinyl.

The term $Cy_2\text{-}C_{0-4}\text{alkyl}$ includes $Cy_2$ and $Cy_2\text{-}C_{1-4}\text{alkyl}$.

A $Cy_2\text{-}C_{1-4}\text{alkyl}$ group means a group resulting from the replacement of one hydrogen atom from a $C_{1-4}\text{alkyl}$ group with one $Cy_2$ group. Examples include, among others, the groups (piperidinyl-4-ylmethyl, 2-(piperidinyl-4-yl)ethyl, 3-(piperidinyl-4-yl)propyl, 4-(piperidinyl-4-yl)butyl, (tetrahydropyran-4-ylmethyl, 2-(tetrahydropyran-4-yl)ethyl, 3-(tetrahydropyran-4-yl)propyl, 4-(tetrahydropyran-4-yl)butyl, benzyl, phenethyl, 3-phenylpropyl, 4-phenylbutyl, (indolinyl-1-ylmethyl, 2-(indolinyl-1-yl)ethyl, 3-(indolinyl-1-yl)propyl and 4-(indolinyl-1-yl)butyl.

In the definition of a compound of formula I or II, either A is carbon and B is nitrogen, or A is nitrogen and B is carbon, Thus, the compounds of formula I or II include the following types of compounds:

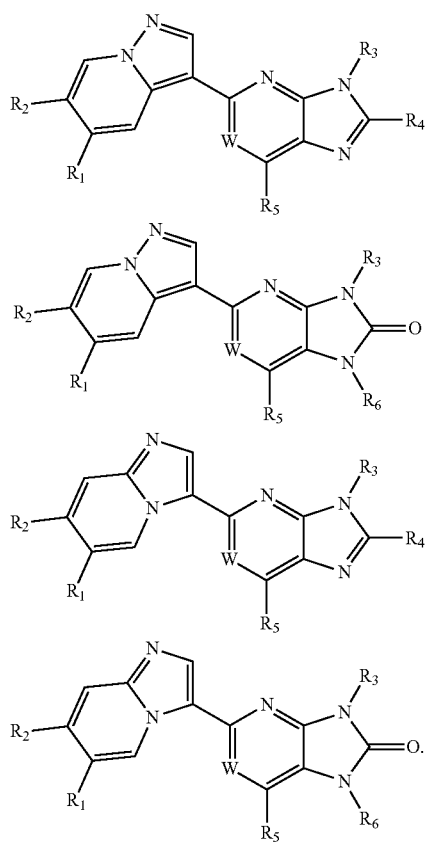

The expression "optionally substituted with one or more" means that a group can be substituted with one or more, preferably with 1, 2, 3 or 4 substituents, more preferably with 1, 2 or 3 substituents, and still more preferably with 1 or 2 substituents, provided that said group has enough positions susceptible of being substituted. The substituents can be the same or different and are placed on any available position.

In certain embodiments of $Cy_1$ mentioned below, a nitrogen atom that can be substituted means a nitrogen atom that has a hydrogen substituent.

Throughout the present specification, by the term "treatment" is meant eliminating, reducing or ameliorating the cause or the effects of a disease. For purposes of this invention treatment includes, but is not limited to, alleviation, amelioration or elimination of one or more symptoms of the disease; diminishment of the extent of the disease; stabilized (i.e. not worsening) state of disease; delay or slowing of disease progression; amelioration or palliation of the disease state; and remission of the disease (whether partial or total).

As used herein, "prevention" refers to preventing the occurrence of a disease in a subject that is predisposed to or has risk factors but does not yet display symptoms of the disease. Prevention includes also preventing the recurrence of a disease in a subject that has previously suffered said disease.

Any formula given herein is intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labelled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of the invention can generally be prepared by carrying out the procedures disclosed in the schemes or in the examples and preparations described below by substituting a readily available isotopically labeled reagent for a non-isotopically labeled reagent. In addition to the unlabeled form, all isotopically labeled forms of the compounds of formula I and II are included within the scope of the invention.

Any formula given herein is also intended to represent the corresponding tautomers forms. "Tautomer" refers to alternate forms of a molecule that differ in the position of a proton. Examples include, among others, enol-keto and imine-enamine tautomers, and the tautomeric forms of heteroaryl groups containing a —N=CH—NH— ring atom arrangement, such as pyrazoles, imidazoles, benzimidazoles, triazoles and tetrazoles.

The invention thus relates to the compounds of formula I or H as defined above.

In another embodiment, the invention relates to a compound of formula I or II

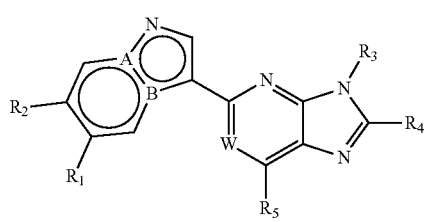

-continued

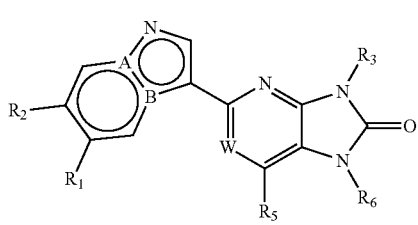

wherein

A is carbon and B is nitrogen, or A is nitrogen and B is carbon;

W is CH or N;

$R_1$ and $R_2$ independently are hydrogen, $C_{1-4}$alkyl, halo$C_{1-4}$alkyl, hydroxy$C_{1-4}$alkyl, cyano$C_{1-4}$alkyl, $C_{1-4}$alkoxy$C_{1-4}$alkyl, halogen, —CN, —$OR_8$ or —$SR_8$;

$R_3$ is $C_{1-4}$alkyl, $R_9$—$C_{1-4}$alkyl, $Cy_1$ or $Cy_2$-$C_{1-4}$alkyl, wherein $Cy_1$ and $Cy_2$ are optionally substituted with one or more $R_{10}$;

$R_4$ is hydrogen, $C_{1-4}$alkyl, halo$C_{1-4}$alkyl, $C_{1-4}$alkoxy $C_{1-4}$alkyl, hydroxy$C_{1-4}$alkyl, cyano$C_{1-4}$alkyl, $R_{12}R_7N$—$C_{0-4}$alkyl, $R_{13}CONR_7$—$C_{0-4}$alkyl, $R_{13}R_7NCO$—$C_{0-4}$alkyl, $R_{12}R_7NCONR_7$—$C_{0-4}$alkyl, $R_{13}CO_2NR_7$—$C_{0-4}$alkyl, $R_{13}SO_2NR_7$—$C_{0-4}$alkyl, —$OR_{12}$ or $Cy_2$-$C_{0-4}$alkyl; wherein $Cy_2$ is optionally substituted with one or more $R_{11}$;

$R_5$ is hydrogen, $C_{1-4}$alkyl, halo$C_{1-4}$alkyl, $C_{1-4}$alkoxy $C_{1-4}$alkyl, hydroxy$C_{1-4}$alkyl, cyano$C_{1-4}$alkyl, halogen, —CN, —$OR_{12}$, —$NR_7R_{12}$, or $Cy_2$-$C_{0-4}$alkyl, wherein $Cy_2$ is optionally substituted with one or more $R_{11}$;

$R_6$ is hydrogen, $C_{1-4}$alkyl, $C_{1-4}$alkoxy$C_{1-4}$alkyl, hydroxy$C_{1-4}$alkyl, $R_{12}R_7N$—$C_{1-4}$alkyl, $Cy_1$ or $Cy_2$-$C_{1-4}$alkyl, wherein $Cy_1$ and $Cy_2$ are optionally substituted with one or more $R_{11}$;

$R_7$ is hydrogen or $C_{1-4}$alkyl;

$R_8$ is hydrogen, $C_{1-4}$alkyl, hydroxy$C_{1-4}$alkyl, hydroxy $C_{1-4}$alkyl, or $C_{1-4}$alkoxy$C_{1-4}$alkyl;

$R_9$ is halogen, —CN, —$CONR_7R_{12}$, —$COR_{13}$, —$CO_2R_{12}$, —$OCONR_7R_{12}$, —$SO_2R_{13}$, —$SO_2NR_7R_{12}$, —$NR_7R_{12}$, —$NR_7COR_{12}$ —$NR_7CONR_7R_{12}$, —$NR_7CO_2R_{13}$ or —$NR_7SO_2R_{13}$;

$R_{10}$ is $C_{1-4}$alkyl or $R_9$—$C_{0-4}$alkyl;

$R_{11}$ is $C_{1-4}$alkyl, halo$C_{1-4}$alkyl, $C_{1-4}$alkoxy$C_{1-4}$alkyl, hydroxy$C_{1-4}$alkyl, cyano$C_{1-4}$alkyl, halogen, —CN, —$CONR_7R_{14}$, —$COR_{14}$, —$CO_2R_{15}$, —$OR_{14}$, —$OCONR_7R_{14}$, —$SO_2R_{15}$, —$SO_2NR_7R_{14}$, —$NR_7R_{14}$, —$NR_7COR_{14}$, —$NR_7CONR_7R_{14}$, —$NR_7CO_2R_{15}$ or —$NR_7SO_2R_{16}$;

$R_{12}$ is hydrogen or $R_{13}$;

$R_{13}$ is $C_{1-4}$alkyl, halo$C_{1-4}$alkyl, $C_{1-4}$alkoxy$C_{1-4}$alkyl, hydroxy$C_{1-4}$alkyl, cyano$C_{1-4}$alkyl, or $Cy_2$-$C_{0-4}$alkyl; wherein $Cy_2$ is optionally substituted with one or more $R_{11}$;

$R_{14}$ is hydrogen or $R_{15}$;

$R_{15}$ is $C_{1-4}$alkyl, halo$C_{1-4}$alkyl, $C_{1-4}$alkoxy$C_{1-4}$alkyl, hydroxy$C_{1-4}$alkyl or cyano$C_{1-4}$alkyl;

$Cy_1$ is a 3- to 7-membered monocyclic or 6- to 11-membered bicyclic ring, which is saturated, partially unsaturated or aromatic, and which is carbocyclic or heterocyclic containing from 1 to 4 heteroatoms independently selected from N, S and O, wherein said ring is bonded to the rest of the molecule through any available C atom, and wherein one or more C or S ring atoms are optionally oxidized forming CO, SO or $SO_2$; and $Cy_2$ is a 3- to 7-membered monocyclic or 6- to 11-membered bicyclic ring, which is saturated, partially unsaturated or aromatic, and which is carbocyclic or heterocyclic containing from 1 to 4 heteroatoms independently selected from N, S and O, wherein said ring is bonded to the rest of the molecule through any available C or N atom, and wherein one or more C or S ring atoms are optionally oxidized forming CO, SO or $SO_2$.

in another embodiment, the invention relates to a compound of formula I or II

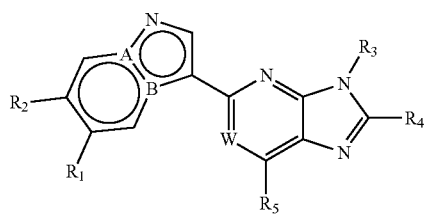

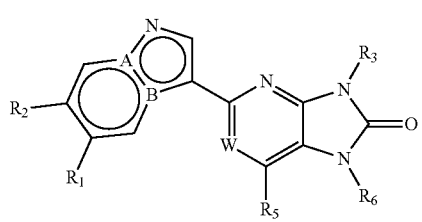

wherein

A is carbon and B is nitrogen, or A is nitrogen and B is carbon;

W CH or N;

$R_1$ and $R_2$ independently are hydrogen, $C_{1-4}$alkyl, halo$C_{1-4}$alkyl, hydroxy$C_{1-4}$alkyl, cyano$C_{1-4}$alkyl, $C_{1-4}$alkoxy$C_{1-4}$alkyl, halogen, —CN, —$OR_8$ or —$SR_8$;

$R_3$ is $C_{1-4}$alkyl, $R_9$—$C_{1-4}$alkyl, $Cy_1$ or $Cy_2$-$C_{1-4}$alkyl, wherein $Cy_1$ and $Cy_2$ are optionally substituted with one or more $R_{10}$;

$R_4$ is hydrogen, $C_{1-4}$alkyl, halo$C_{1-4}$alkyl, $C_{1-4}$alkoxy $C_{1-4}$alkyl, hydroxy$C_{1-4}$alkyl, cyano$C_{1-4}$alkyl, $R_{12}R_7N$—$C_{0-4}$alkyl, $R_{13}CONR_7$—$C_{0-4}$alkyl, $R_{13}R_7NCO$—$C_{0-4}$alkyl, $R_{12}R_7NCONR_7$—$C_{0-4}$alkyl, $R_{13}CO_2NR_7$—$C_{0-4}$alkyl, $R_{13}SO_2NR_7$—$C_{0-4}$alkyl, —$OR_{12}$ or $Cy_2$-$C_{0-4}$alkyl; wherein $Cy_2$ is optionally substituted with one or more $R_{11}$;

$R_5$ is hydrogen, $C_{1-4}$alkyl, halo$C_{1-4}$alkyl, $C_{1-4}$alkoxy $C_{1-4}$alkyl, hydroxy$C_{1-4}$alkyl, cyano$C_{1-4}$alkyl, halogen, —CN, —$OR_{12}$, —$NR_7R_{12}$, or $Cy_2$-$C_{0-4}$alkyl, wherein $Cy_2$ is optionally substituted with one or more $R_{11}$;

$R_6$ is hydrogen, $C_{1-4}$alkyl, $C_{1-4}$alkoxy$C_{1-4}$alkyl, hydroxy$C_{1-4}$alkyl, $R_{12}R_7N$—$C_{1-4}$alkyl, $R_{19}CO$—$C_{0-4}$alkyl, $R_{16}CO_2$—$C_{0-4}$alkyl, $Cy_1$ or $Cy_2$-$C_{1-4}$alkyl, wherein $Cy_1$ and $Cy_2$ are optionally substituted with one or more $R_{11}$;

$R_7$ is hydrogen or $C_{1-4}$alkyl;

$R_8$ is hydrogen, $C_{1-4}$alkyl, halo$C_{1-4}$alkyl, hydroxy $C_{1-4}$alkyl, or $C_{1-4}$alkoxy$C_{1-4}$alkyl;

$R_9$ is halogen, —CN, —$CONR_7R_{12}$, —$COR_{13}$, —$CO_2R_{12}$, —$OR_{12}$, —$OCONR_7R_{12}$, —$SO_2R_{13}$, —$SO_2NR_7R_{12}$, —$NR_7R_{12}$, —$NR_7COR_{12}$, —$NR_7CONR_7R_{12}$, —$NR_7CO_2R_{13}$ or —$NR_7SO_2R_{13}$;

$R_{10}$ is $C_{1-4}$alkyl or $R_9$—$C_{0-4}$alkyl;

$R_{11}$ is $C_{1-4}$alkyl, halo$C_{1-4}$alkyl, $C_{1-4}$alkoxy$C_{1-4}$alkyl, hydroxy$C_{1-4}$alkyl, cyano$C_{1-4}$alkyl, halogen, —CN, —$CONR_7R_{14}$, —$COR_{14}$, —$CO_2R_{15}$, —$OCONR_7R_{14}$, —$SO_2NR_{15}$, —$SO_2NR_7R_{14}$, —$NR_7R_{14}$, —$NR_7COR_{14}$, —$NR_7CONR_7R_{14}$, —$NR_7CO_2R_{15}$ or —$NR_7SO_2R_{15}$;

$R_{12}$ is hydrogen or $R_{13}$;

$R_{13}$ is $C_{1-4}$alkyl, halo$C_{1-4}$alkyl, $C_{1-4}$alkoxy$C_{1-4}$alkyl, hydroxy$C_{1-4}$alkyl, cyano$C_{1-4}$alkyl, or $Cy_2$-$C_{0-4}$alkyl; wherein $Cy_2$ is optionally substituted with one or more $R_{11}$;

$R_{14}$ is hydrogen or $R_{15}$;

$R_{15}$ is $C_{1-4}$alkyl, halo$C_{1-4}$alkyl, $C_{1-4}$alkoxy$C_{1-4}$alkyl, hydroxy$C_{1-4}$alkyl or cyano$C_{1-4}$alkyl;

$R_{16}$ is $C_{1-4}$alkyl, halo$C_{1-4}$alkyl, $C_{1-4}$alkoxy$C_{1-4}$alkyl or cyano$C_{1-4}$alkyl;

$Cy_1$ is a 3- to 7-membered monocyclic or 6- to 11-membered bicyclic ring, which is saturated, partially unsaturated or aromatic, and which is carbocyclic or heterocyclic containing from 1 to 4 heteroatoms independently selected from N, S and O, wherein said ring is bonded to the rest of the molecule through any available C atom, and wherein one or more C or S ring atoms are optionally oxidized forming CO, SO or $SO_2$; and $Cy_2$ is a 3- to 7-membered monocyclic or 6- to 11-membered bicyclic ring, which is saturated, partially unsaturated or aromatic, and which is carbocyclic or heterocyclic containing from 1 to 4 heteroatoms independently selected from N, S and O, wherein said ring is bonded to the rest of the molecule through any available C or N atom, and wherein one or more C or S ring atoms are optionally oxidized forming CO, SO or $SO_2$.

In another embodiment, the invention relates to the compounds of formula I.

In another embodiment, the invention relates to the compounds of formula II.

In another embodiment, the invention relates to the compounds of formula I or II wherein A is carbon and B is nitrogen.

In another embodiment, the invention relates to the compounds of formula I or II wherein A is nitrogen and B is carbon.

In another embodiment, the invention relates to the compounds of formula I or II wherein W is CH.

In another embodiment, the invention relates to the compounds of formula I or II wherein W is N.

In another embodiment, the invention relates to the compounds of formula I or II wherein $R_1$ and $R_2$ independently are hydrogen, halogen, —CN, —$OR_8$ or —$SR_8$, preferably hydrogen or —CN.

In another embodiment, the invention relates to the compounds of formula I or II wherein $R_2$ is hydrogen.

In another embodiment, the invention relates to the compounds of formula I or II wherein $R_2$ is —CN.

In another embodiment, the invention relates to the compounds of formula I or II wherein $R_1$ is hydrogen, halogen, —CN, —$OR_8$ or —$SR_8$, more preferably hydrogen or —CN; and $R_2$ is hydrogen.

In another embodiment, the invention relates to the compounds of formula I or II wherein $R_1$ is hydrogen or —CN.

In another embodiment, the invention relates to the compounds of formula I or II wherein $R_1$ is hydrogen.

In another embodiment, the invention relates to the compounds of formula I or II wherein $R_1$ is hydrogen; and $R_2$ is hydrogen.

In another embodiment, the invention relates to the compounds of formula I or II wherein $R_1$ is —CN; and $R_2$ is hydrogen.

In another embodiment, the invention relates to the compounds of formula I or II wherein $R_3$ is $R_9$—$C_{1-4}$alkyl, $Cy_1$ or $Cy_2$-$C_{1-4}$alkyl, wherein $Cy_1$ and $Cy_2$ are optionally substituted with one or more $R_{10}$.

In another embodiment, the invention relates to the compounds of formula I or II wherein $R_3$ is $R_9$—$C_{1-4}$alkyl.

In another embodiment, the invention relates to the compounds of formula I or II wherein $R_3$ is $Cy_1$, which is optionally substituted with one or more $R_{10}$.

In another embodiment, the invention relates to the compounds of formula I or II wherein $R_3$ is $Cy_1$ and $Cy_1$ is a 3- to 7-membered monocyclic or 6- to 11-membered bicyclic ring, which is saturated, partially unsaturated or aromatic, and which is carbocyclic or heterocyclic containing from 1 to 4 heteroatoms independently selected from N, S and O, wherein said ring is bonded to the rest of the molecule through any available C atom, and wherein one or more C or S ring atoms are optionally oxidized forming CO, SO or $SO_2$; wherein said $Cy_1$ is optionally substituted with one or more $R_{10}$ provided that if the ring contains a nitrogen atom that can be substituted, then said nitrogen atom is substituted with one $R_{10}$.

In another embodiment, the invention relates to the compounds of formula I or II wherein $R_3$ is $Cy_1$; and $Cy_1$ in $R_3$ is a 3- to 7-membered monocyclic ring, which is saturated, partially unsaturated or aromatic, and which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$; and wherein said $Cy_1$ is optionally substituted with one or more $R_{10}$.

In another embodiment, the invention relates to the compounds of formula I or II wherein $R_3$ is $Cy_1$; and $Cy_1$ in $R_3$ is a 3- to 7-membered saturated monocyclic ring, which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$; and wherein said $Cy_1$ is optionally substituted with one or more $R_{10}$.

In another embodiment, the invention relates to the compounds of formula I or II wherein $R_3$ is $Cy_1$; and $Cy_1$ in $R_3$ is a 5- to 6-membered saturated monocyclic ring, which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$; and wherein said $Cy_1$ is optionally substituted with one or more $R_{10}$.

In another embodiment, the invention relates to the compounds of formula I or II wherein $R_3$ is $Cy_1$; and $Cy_1$ in $R_3$ is a 5- to 6-membered saturated monocyclic ring, which is carbocyclic or heterocyclic containing from 1 to 3 heteroatoms independently selected from N, S and O, at least one of which is N; wherein said ring is bonded to the rest of the molecule through any available C atom, and wherein one or more C or S ring atoms are optionally oxidized forming CO, SO or $SO_2$; and wherein said $Cy_1$ is optionally substituted with one or more $R_{10}$.

In another embodiment, the invention relates to the compounds of formula I or II wherein $R_3$ is $Cy_1$; and $Cy_1$ in $R_3$ is a 3- to 7-membered, preferably 5- to 6-membered saturated monocyclic ring, which is heterocyclic containing from 1 to 3 heteroatoms independently selected from N, S and O, at least one of which is N; wherein said ring is bonded to the rest of the molecule through any available C atom, and wherein one or more C or S ring atoms are optionally oxidized forming CO, SO or $SO_2$; and wherein said $Cy_1$ is optionally substituted with one or more $R_{10}$.

In another embodiment, the invention relates to the compounds of formula I or II wherein $R_3$ is piperidinyl or pyrrolidinyl, preferably piperidin-3-yl or pyrrolidin-3-yl, which are optionally substituted with one or more $R_{10}$.

In another embodiment, the invention relates to the compounds of formula I or II wherein $R_3$ is piperidinyl or pyrrolidinyl, preferably piperidin-3-yl or pyrrolidin-3-yl, which are substituted with one $R_{10}$ on the N atom of the piperidinyl or pyrrolidinyl ring and which are optionally further substituted with one or more $R_{10}$ groups.

In another embodiment, the invention relates to the compounds of formula II wherein $R_3$ is piperidinyl or pyrrolidinyl, preferably piperidin-3-yl or pyrrolidin-3-yl, which are optionally substituted with one or more $R_{10}$.

In another embodiment, the invention relates to the compounds of formula II wherein $R_3$ is piperidinyl or pyrrolidinyl, preferably piperidin-3-yl or pyrrolidin-3-yl, which are substituted with one $R_{10}$ on the N atom of the piperidinyl or pyrrolidinyl ring and which are optionally further substituted with one or more $R_{10}$ groups.

In another embodiment, the invention relates to the compounds of formula I or II wherein $R_3$ is piperidinyl, preferably piperidin-3-yl, which are optionally substituted with one or more $R_{10}$.

In another embodiment, the invention relates to the compounds of formula I or II wherein $R_3$ is piperidinyl, preferably piperidin-3-yl, substituted with one $R_{10}$ on the N atom of the piperidinyl ring and optionally further substituted with one or more $R_{10}$ groups.

In another embodiment, the invention relates to the compounds of formula II wherein $R_3$ is piperidinyl, preferably piperidin-3-yl, which are optionally substituted with one or more $R_{10}$.

In another embodiment, the invention relates to the compounds of formula II wherein $R_3$ is piperidinyl, preferably piperidin-3-yl, substituted with one $R_{10}$ on the N atom of the piperidinyl ring and optionally further substituted with one or more $R_{10}$ groups.

In another embodiment, the invention relates to the compounds of formula I or II wherein $R_3$ is a cycle of formula

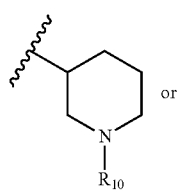

$Cy_{1a}$ or

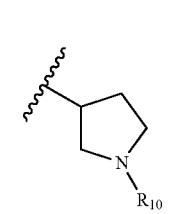

$Cy_{1b}$ wherein $Cy_{1a}$ and $Cy_{1b}$ are optionally substituted with one or more further $R_{10}$.

In another embodiment, the invention relates to the compounds of formula I or II wherein $R_3$ is a cycle of formula

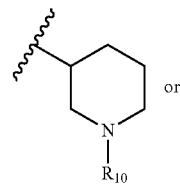

$Cy_{1a}$ or

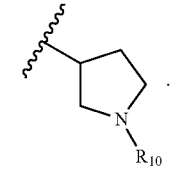

$Cy_{1b}$

In another embodiment, the invention relates to the compounds of formula II wherein $R_3$ is a cycle of formula

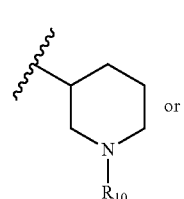

$Cy_{1a}$ or

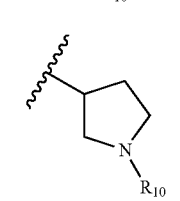

$Cy_{1b}$ wherein $Cy_{1a}$ and $Cy_{1b}$ are optionally substituted with one or more further $R_{10}$.

In another embodiment, the invention relates to the compounds of formula II wherein $R_3$ is a cycle of formula

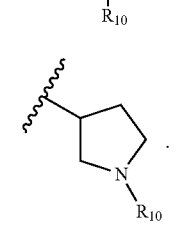

$Cy_{1a}$ or $Cy_{1b}$

In another embodiment, the invention relates to the compounds of formula I or II wherein $R_3$ is a cycle of formula $Cy_{1a}$.

In another embodiment, the invention relates to the compounds of formula II wherein $R_3$ is a cycle of formula $Cy_{1a}$.

In another embodiment, the invention relates to the compounds of formula I or II wherein $R_3$ is a cycle of formula

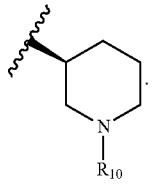

In another embodiment, the invention relates to the compounds of formula II wherein $R_3$ is a cycle of formula

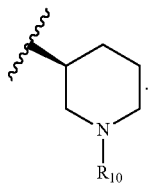

In another embodiment, the invention relates to the compounds of formula I or II wherein $R_3$ is a cycle of formula $Cy_{1a}$ and $Cy_{1a}$ has the (S)-stereochemistry.

In another embodiment, the invention relates to the compounds of formula II wherein $R_3$ is a cycle of formula $Cy_{1a}$ and $Cy_{1a}$ has the (S)-stereochemistry.

In another embodiment, the invention relates to the compounds of formula I or II wherein $R_3$ is a cycle of formula $Cy_{1b}$.

In another embodiment, the invention relates to the compounds of formula I or II wherein $R_3$ is $Cy_2$-$C_{1-4}$alkyl, wherein $Cy_2$ is optionally substituted with one or more $R_{10}$.

In another embodiment, the invention relates to the compounds of formula I or II wherein $R_3$ is $Cy_2$-$C_{1-4}$alkyl; and $Cy_2$ is a 3- to 7-membered monocyclic ring, which is saturated, partially unsaturated or aromatic, and which is carbocyclic or heterocyclic containing from 1 to 3 heteroatoms independently selected from N, S and O, wherein said ring is bonded to the rest of the molecule through any available C o N atom, and wherein one or more C or S ring atoms are optionally oxidized forming CO, SO or $SO_2$; and wherein said $Cy_2$ is optionally substituted with one or more $R_{10}$.

In another embodiment, the invention relates to the compounds of formula I or II wherein $R_4$ is hydrogen, $C_{1-4}$alkyl, $R_{12}R_7N$—$C_{0-4}$alkyl or $Cy_2$-$C_{0-4}$alkyl, preferably hydrogen, $C_{1-4}$alkyl, —$NR_7R_{12}$ or $Cy_2$; wherein $Cy_2$ is optionally substituted with one or more $R_{11}$.

In another embodiment, the invention relates to the compounds of formula I or II wherein $R_5$ is hydrogen or $Cy_2$; wherein $Cy_2$ is optionally substituted with one or more $R_{11}$.

In another embodiment, the invention relates to the compounds of formula I or II wherein $R_5$ is hydrogen or $Cy_2$; and $Cy_2$ is a 3- to 7-membered monocyclic ring, which is saturated, partially unsaturated or aromatic, and which is carbocyclic or heterocyclic containing from 1 to 3 heteroatoms independently selected from N, S and O, wherein said ring is bonded to the rest of the molecule through any available C o N atom, and wherein one or more C or S ring atoms are optionally oxidized forming CO, SO or $SO_2$; and wherein said $Cy_2$ is optionally substituted with one or more $R_{11}$.

In another embodiment, the invention relates to the compounds of formula I or II wherein $R_5$ is hydrogen.

In another embodiment, the invention relates to the compounds of formula I or II wherein $R_6$ is $C_{1-4}$alkyl, $C_{1-4}$alkoxy$C_{1-4}$alkyl, hydroxy$C_{1-4}$alkyl, $R_{12}R_7N$—$C_{1-4}$alkyl, $R_{16}CO$—$C_{0-4}$alkyl, $R_{16}CO_2$—$C_{0-4}$alkyl, $R_{16}CO$—O—$C_{1-4}$alkyl, cyano$C_{1-4}$alkyl, $Cy_1$ or $Cy_2$-$C_{1-4}$alkyl, wherein $Cy_1$ and $Cy_2$ are optionally substituted with one or more $R_{11}$.

In another embodiment, the invention relates to the compounds of formula I or II wherein $R_6$ is hydrogen, $C_{1-4}$alkyl, $C_{1-4}$alkoxy$C_{1-4}$alkyl, hydroxy$C_{1-4}$alkyl, $R_{12}R_7N$—$C_{1-4}$alkyl, $R_{16}CO$—$C_{0-4}$alkyl, $R_{16}CO_2$—$C_{0-4}$alkyl, $Cy_1$ or $Cy_2$-$C_{1-4}$alkyl, wherein $Cy_1$ and $Cy_2$ are optionally substituted with one or more $R_{11}$.

In another embodiment, the invention relates to the compounds of formula I or II wherein $R_6$ is $C_{1-4}$alkyl, $C_{1-4}$alkoxy$C_{1-4}$alkyl, hydroxy$C_{1-4}$alkyl, $R_{12}R_7N$—$C_{1-4}$alkyl, $R_{16}CO$—$C_{0-4}$alkyl, $R_{16}CO_2$—$C_{0-4}$alkyl, $Cy_1$ or $Cy_2$-$C_{1-4}$alkyl, wherein $Cy_1$ and $Cy_2$ are optionally substituted with one or more $R_{11}$.

In another embodiment, the invention relates to the compounds of formula I or II wherein $R_6$ is $C_{1-4}$alkyl, $C_{1-4}$alkoxy$C_{1-4}$alkyl, hydroxy$C_{1-4}$alkyl, $R_{12}R_7N$—$C_{1-4}$alkyl, $R_{16}CO$—$C_{0-4}$alkyl, $R_{16}CO_2$—$C_{0-4}$alkyl or $R_{16}CO$—O—$C_{1-4}$alkyl.

In another embodiment, the invention relates to the compounds of formula I or II wherein $R_6$ is hydrogen, $C_{1-4}$alkyl, $C_{1-4}$alkoxy$C_{1-4}$alkyl, hydroxy$C_{1-4}$alkyl, $R_{12}R_7N$—$C_{1-4}$alkyl, $R_{16}CO$—$C_{0-4}$alkyl or $R_{16}CO_2$—$C_{0-4}$alkyl.

In another embodiment, the invention relates to the compounds of formula I or II wherein $R_6$ is $C_{1-4}$alkyl, $C_{1-4}$alkoxy$C_{1-4}$alkyl, hydroxy$C_{1-4}$alkyl, $R_{12}R_7N$—$C_{1-4}$alkyl, $R_{16}CO$—$C_{0-4}$alkyl or $R_{16}CO_2$—$C_{0-4}$alkyl.

In another embodiment, the invention relates to the compounds of formula I or II wherein $R_6$ is hydrogen, $C_{1-4}$alkyl, $C_{1-4}$alkoxy$C_{1-4}$alkyl, hydroxy$C_{1-4}$alkyl or $R_{12}R_7N$—$C_{1-4}$alkyl.

In another embodiment, the invention relates to the compounds of formula I or II wherein $R_6$ is hydrogen or $C_{1-4}$alkyl, preferably hydrogen, methyl or ethyl.

In another embodiment, the invention relates to the compounds of formula I or II wherein $R_6$ is $C_{1-4}$alkyl, preferably methyl or ethyl.

In another embodiment, the invention relates to the compounds of formula II wherein $R_6$ is $C_{1-4}$alkyl, preferably methyl or ethyl.

In another embodiment, the invention relates to the compounds of formula II wherein $R_6$ is methyl.

In another embodiment, the invention relates to the compounds of formula II wherein $R_6$ is ethyl.

In another embodiment, the invention relates to the compounds of formula I or II wherein $R_9$ is —$CONR_7R_{12}$, —$COR_{13}$, —$CO_2R_{12}$, —$OR_{12}$, —$OCONR_7R_{12}$, —$SO_2R_{13}$, —$SO_2NR_7R_{12}$, —$NR_7R_{12}$, —$NR_7COR_{12}$, —$NR_7CONR_7R_{12}$, —$NR_7CO_2R_{13}$ or —$NR_7SO_2R_{13}$, preferably $R_9$ is —$COR_{13}$.

In another embodiment, the invention relates to the compounds of formula I or II wherein $R_{10}$ is $R_9$—$C_{0-4}$alkyl, preferably $R_9$.

In another embodiment, the invention relates to the compounds of formula I or II wherein $R_{10}$ is $R_9$; and $R_9$ in $R_{10}$ is —$COR_{13}$ or —$SO_2R_{13}$. In another embodiment, the invention relates to the compounds of formula I or II wherein $R_{10}$ is $R_9$; and $R_9$ in $R_{10}$ is —$COR_{13}$.

In another embodiment, the invention relates to the compounds of formula I or II wherein $R_{13}$ is $C_{1-4}$alkyl, haloC$_{1-4}$alkyl, $C_{1-4}$alkoxyC$_{1-4}$alkyl, hydroxyC$_{1-4}$alkyl, cyanoC$_{1-4}$alkyl or Cy$_2$-C$_{0-4}$alkyl; wherein Cy$_2$ is optionally substituted with one or more $R_{11}$.

In another embodiment, the invention relates to the compounds of formula I or II wherein $R_{13}$ is $C_{1-5}$alkyl, haloC$_{1-4}$alkyl, $C_{1-4}$alkoxyC$_{1-4}$alkyl, hydroxyC$_{1-4}$alkyl or cyanoC$_{1-4}$alkyl, preferably $C_{1-4}$alkyl or cyanoC$_{1-4}$alkyl, more preferably methyl, isopropyl or cyanomethyl, and still more preferably methyl or cyanomethyl.

In another embodiment, the invention relates to the compounds of formula I or II wherein $R_{13}$ is $C_{1-4}$alkyl, haloC$_{1-4}$alkyl, $C_{1-4}$alkoxyC$_{1-4}$alkyl, hydroxyC$_{1-4}$alkyl or cyanoC$_{1-4}$alkyl, preferably $C_{1-4}$alkyl or cyanoC$_{1-4}$alkyl, more preferably methyl, isopropyl or cyanomethyl, and still more preferably methyl or cyanomethyl.

In another embodiment, the invention relates to the compounds of formula I or II wherein $R_{13}$ is methyl.

In another embodiment, the invention relates to the compounds of formula I or II wherein $R_{13}$ is isopropyl.

In another embodiment, the invention relates to the compounds of formula I or II wherein $R_{13}$ is cyanomethyl.

In another embodiment, the invention relates to the compounds of formula I or II wherein $R_{13}$ is Cy$_2$-C$_{0-4}$alkyl wherein Cy$_2$ is optionally substituted with one or more $R_{11}$.

In another embodiment, the invention relates to the compounds of formula I or II wherein $R_9$ is —CONR$_7$R$_{12}$, —COR$_{13}$, —CO$_2$R$_{13}$, —OR$_{12}$, —OCONR$_7$R$_{12}$, —SO$_2$R$_{13}$, —SO$_2$NR$_7$R$_{12}$, —NR$_7$R$_{12}$, —NR$_7$COR$_{12}$, —NR$_7$CONR$_7$R$_{12}$, —NR$_7$CO$_2$R$_{13}$ or —NR$_7$SO$_2$R$_{13}$, preferably —CO$_2$R$_{13}$; and $R_{13}$ is $C_{1-4}$alkyl, haloC$_{1-4}$alkyl, $C_{1-4}$alkoxyC$_{1-4}$alkyl, hydroxyC$_{1-4}$alkyl or cyanoC$_{1-4}$alkyl, preferably $C_{1-4}$alkyl or cyanoC$_{1-4}$alkyl, and more preferably methyl or cyanomethyl.

In another embodiment, the invention relates to the compounds of formula I or II wherein $R_{10}$ is $R_9$; $R_9$ in $R_{10}$ is —COR$_{15}$; and $R_{13}$ is $C_{1-4}$alkyl, haloC$_{1-4}$alkyl, $C_{1-4}$alkoxyC$_{1-4}$alkyl, hydroxyC$_{1-4}$alkyl or cyanoC$_{1-4}$alkyl, preferably $C_{1-4}$alkyl or cyanoC$_{1-4}$alkyl, and more preferably methyl or cyanomethyl.

In another embodiment, the invention relates to the compounds of formula I or II wherein $R_3$ is $R_9$—C$_{1-4}$alkyl; and $R_9$ is —CONR$_7$R$_{12}$, —COR$_{13}$, —CO$_2$R$_{12}$, —OR$_{12}$, —OCONR$_7$R$_{12}$, —SO$_2$R$_{13}$, —SO$_2$NR$_7$R$_{12}$, —NR$_7$R$_{12}$, —NR$_7$COR$_{12}$, —NR$_7$CONR$_7$R$_{12}$, —NR$_7$CO$_2$R$_{13}$ or —NR$_7$SO$_2$R$_{13}$.

In another embodiment, the invention relates to the compounds of formula I or II wherein $R_3$ is $R_9$—C$_{1-4}$alkyl;

$R_9$ is —CONR$_7$R$_{12}$, —COR$_{13}$, —CO$_2$R$_{13}$, —OR$_{12}$, —OCONR$_7$R$_{12}$, —SO$_2$R$_{13}$, —SO$_2$NR$_7$R$_{12}$, —NR$_7$R$_{12}$, —NR$_7$COR$_{12}$, —NR$_7$CONR$_7$R$_{12}$, —NR$_7$CO$_2$R$_{13}$ or —NR$_7$SO$_2$R$_{13}$; and $R_{13}$ is $C_{1-4}$alkyl, haloC$_{1-4}$alkyl, $C_{1-4}$alkoxyC$_{1-4}$alkyl, hydroxyC$_{1-4}$alkyl or cyanoC$_{1-4}$alkyl.

In another embodiment, the invention relates to the compounds of formula I or II wherein $R_3$ is Cy$_1$, preferably piperidinyl or pyrrolidinyl, more preferably piperidinyl-3-yl or pyrrolidinyl-3yl; wherein Cy$_1$ in $R_3$ is optionally substituted with one or more $R_{10}$; and $R_{10}$ is $R_9$—C$_{0-4}$alkyl, preferably more preferably —COR$_{13}$ or —SO$_2$R$_{13}$.

In another embodiment, the invention relates to the compounds of formula I or II wherein $R_3$ is a cycle of formula

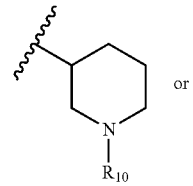

Cy$_{1a}$ or

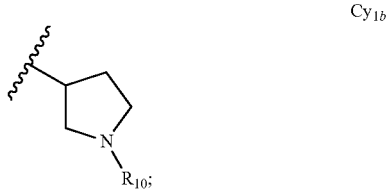

Cy$_{1b}$ and $R_{10}$ is $R_9$—C$_{0-4}$alkyl, preferably $R_9$, more preferably —COR$_{13}$ or —SO$_2$R$_{13}$.

In another embodiment, the invention relates to the compounds of formula II wherein $R_3$ is a cycle of formula

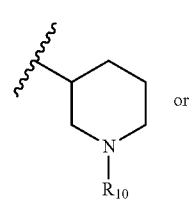

Cy$_{1a}$ or

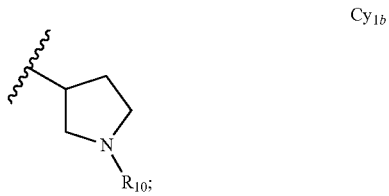

Cy$_{1b}$ and $R_{10}$ is $R_9$—C$_{0-4}$alkyl, preferably $R_9$, more preferably —COR$_{13}$ or —SO$_2$R$_{13}$.

In another embodiment, the invention relates to the compounds of formula I or II wherein $R_3$ is a cycle of formula

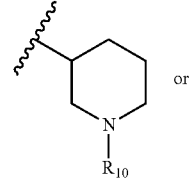

Cy$_{1a}$ or

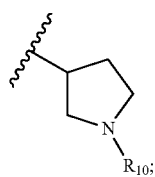

$R_{10}$ is $R_9$—$C_{0-4}$alkyl, preferably $R_9$;
$R_9$ is —$COR_{13}$ or —$SO_2R_{13}$; and
$R_{13}$ is $C_{1-4}$alkyl, halo$C_{1-4}$alkyl, $C_{1-4}$alkoxy$C_{1-4}$alkyl, hydroxy$C_{1-4}$alkyl or cyano$C_{1-4}$alkyl, preferably $C_{1-4}$alkyl or cyano$C_{1-4}$alkyl, and more preferably methyl or cyanomethyl.

In another embodiment, the invention relates to the compounds of formula II wherein $R_3$ is a cycle of formula

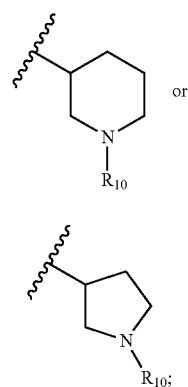

$R_{10}$ is $R_9$—$C_{0-4}$alkyl, preferably $R_9$;
$R_9$ is —$COR_{13}$ or —$SO_2R_{13}$; and
$R_{13}$ is $C_{1-4}$alkyl, halo$C_{1-4}$alkyl, $C_{1-4}$alkoxy$C_{1-4}$alkyl, hydroxy$C_{1-4}$alkyl or cyano$C_{1-4}$alkyl, preferably $C_{1-4}$alkyl or cyano$C_{1-4}$alkyl and more preferably methyl or cyanomethyl.

In another embodiment, the invention relates to the compounds of formula I or II wherein $R_3$ is a cycle of formula $Cy_{1a}$; and
$R_{10}$ is $R_9$—$C_{0-4}$alkyl, preferably $R_9$, more preferably —$COR_{13}$ or —$SO_2R_{13}$ still more preferably —$COR_{13}$.

In another embodiment, the invention relates to the compounds of formula II wherein $R_3$ is a cycle of formula $Cy_{1a}$; and
$R_{10}$ is $R_9$—$C_{0-4}$alkyl, preferably $R_9$, more preferably —$COR_{13}$ or —$SO_2R_{13}$ still more preferably —$COR_{13}$.

In another embodiment, the invention relates to the compounds of formula I or II wherein $R_3$ is a cycle of formula $Cy_{1a}$;
$R_{10}$ is $R_9$—$C_{0-4}$alkyl, preferably $R_9$, more preferably —$COR_{13}$ or —$SO_2R_{13}$, still more preferably —$COR_{13}$; and
$R_{13}$ is $C_{1-4}$alkyl, halo$C_{1-4}$alkyl, $C_{1-4}$alkoxy$C_{1-4}$alkyl, hydroxy$C_{1-4}$alkyl or cyano$C_{1-4}$alkyl, preferably $C_{1-4}$alkyl or cyano$C_{1-4}$alkyl, and more preferably methyl or cyanomethyl.

In another embodiment, the invention relates to the compounds of formula II wherein $R_3$ is a cycle of formula $Cy_{1a}$;
$R_{10}$ is $R_9$—$C_{0-4}$alkyl, preferably $R_9$, more preferably —$COR_{13}$ or —$SO_2R_{13}$, still more preferably —$COR_{13}$; and
$R_{13}$ is $C_{1-4}$alkyl, halo$C_{1-4}$alkyl, $C_{1-4}$alkoxy$C_{1-4}$alkyl, hydroxy$C_{1-4}$alkyl or cyano$C_{1-4}$alkyl, preferably $C_{1-4}$alkyl or cyano$C_{1-4}$alkyl, and more preferably methyl or cyanomethyl.

In another embodiment, the invention relates to the compounds of formula I or II wherein $R_3$ is a cycle of formula $Cy_{1a}$ with (S)-stereochemistry;
$R_{10}$ is $R_9$—$C_{0-4}$alkyl, preferably $R_9$, more preferably —$COR_{13}$ or —$SO_2R_{13}$, still more preferably —$COR_{13}$; and
$R_{13}$ is $C_{1-4}$alkyl, halo$C_{1-4}$alkyl, $C_{1-4}$alkoxy$C_{1-4}$alkyl, hydroxy$C_{1-4}$alkyl or cyano$C_{1-4}$alkyl, preferably $C_{1-4}$alkyl or cyano$C_{1-4}$alkyl, and more preferably methyl or cyanomethyl.

In another embodiment, the invention relates to the compounds of formula II wherein $R_3$ is a cycle of formula $Cy_{1a}$ with (S)-stereochemistry;
$R_{10}$ is $R_9$—$C_{0-4}$alkyl, preferably $R_9$, more preferably —$COR_{13}$ or —$SO_2R_{13}$, still more preferably —$COR_{13}$; and
$R_{13}$ is $C_{1-4}$alkyl, halo$C_{1-4}$alkyl, $C_{1-4}$alkoxy$C_{1-4}$alkyl, hydroxy$C_{1-4}$alkyl or cyano$C_{1-4}$alkyl, preferably $C_{1-4}$alkyl or cyano$C_{1-4}$alkyl, and more preferably methyl or cyanomethyl.

In another embodiment, the invention relates to the compounds of formula I or II wherein $R_3$ is a cycle of formula $Cy_{1b}$; and
$R_{10}$ is $R_9$—$C_{0-4}$alkyl, preferably $R_9$, more preferably —$SO_2R_{13}$, In another embodiment, the invention relates to the compounds of formula II wherein $R_3$ is a cycle of formula $Cy_{1b}$; and
$R_{10}$ is $R_9$—$C_{0-4}$alkyl, preferably $R_9$, more preferably —$SO_2R_{13}$.

In another embodiment, the invention relates to the compounds of formula I or II wherein $Cy_1$ is a 3- to 7-membered monocyclic ring, which is saturated, partially unsaturated or aromatic, and which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$.

In another embodiment, the invention relates to the compounds of formula I or II wherein $Cy_1$ is a 3- to 7-membered saturated monocyclic ring, which is carbocyclic or heterocyclic containing from 1 to 3 heteroatoms independently selected from N, S and O, wherein said ring is bonded to the rest of the molecule through any available C atom, and wherein one or more C ar S ring atoms are optionally oxidized forming CO, SO or $SO_2$.

In another embodiment, the invention relates to the compounds of formula I or II wherein $Cy_1$ is a 5- to 6-membered saturated monocyclic ring, which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$.

In another embodiment, the invention relates to the compounds of formula I or II wherein $Cy_1$ is a 5- to 6-membered saturated monocyclic ring, which is carbocyclic or heterocyclic containing from 1 to 3 heteroatoms independently selected from N, S and O, at least one of which is N; wherein said ring is bonded to the rest of the molecule through any available C atom, and wherein one or more C or S ring atoms are optionally oxidized forming CO, SO or $SO_2$.

In another embodiment, the invention relates to the compounds of formula I or II wherein $Cy_1$ is a 5- to 6-membered saturated monocyclic ring, which is heterocyclic containing from 1 to 3 heteroatoms independently selected from N, S and O, at least one of which is N; wherein said ring is bonded to the rest of the molecule through any available C atom, and wherein one or more C or S ring atoms are optionally oxidized forming CO, SO or $SO_2$ In another embodiment, the invention relates to the compounds of formula I or II wherein $Cy_1$ is piperidinyl or pyrrolidinyl, preferably piperidinyl-3-yl or pyrrolidinyl-3-yl.

In another embodiment, the invention relates to the compounds of formula I or II wherein $Cy_2$ is a 3- to 7-membered monocyclic ring, which is saturated, partially unsaturated or aromatic, and which is carbocyclic or heterocyclic containing from 1 to 3 heteroatoms independently selected from N, S and O, wherein said ring is bonded to the rest of the molecule through any available C o N atom, and wherein one or more C or S ring atoms are optionally oxidized forming CO, SO or $SO_2$.

In another embodiment, the invention relates to the compounds of formula I or II wherein $Cy_2$ is a 3- to 7-membered saturated monocyclic ring, which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$.

In another embodiment, the invention relates to the compounds of formula I or II wherein $Cy_2$ is a 5- to 6-membered saturated monocyclic ring, which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$.

In another embodiment, the invention relates to the compounds of formula I or II wherein $Cy_2$ is a 5- to 6-membered saturated monocyclic ring, which is carbocyclic or heterocyclic containing from 1 to 3 heteroatoms independently selected from N, S and O, at least one of which is N; wherein said ring is bonded to the rest of the molecule through any available C atom, and wherein one or more C or S ring atoms are optionally oxidized forming CO, SO or $SO_2$.

In another embodiment, the invention relates to the compounds of formula I or II wherein $Cy_2$ is piperidinyl or pyrrolidinyl.

In another embodiment, the invention relates to the compounds of formula I or II wherein;
A is nitrogen and B is carbon; and
$R_1$ and $R_2$ independently are hydrogen, halogen, —CN, —$OR_8$ or —$SR_8$, preferably hydrogen or —CN.

In another embodiment, the invention relates to the compounds of formula I or II wherein:
A is nitrogen and B is carbon;
$R_1$ is hydrogen, $C_{1-4}$alkyl, halo$C_{1-4}$alkyl, hydroxy$C_{1-4}$alkyl, cyano$C_{1-4}$alkyl, $C_{1-4}$alkoxy$C_{1-4}$alkyl, halogen, —CN, —$OR_8$ or —$SR_8$, preferably hydrogen, halogen, —CN, —$OR_8$ or —$SR_8$, and more preferably hydrogen or —CN; and
$R_2$ is hydrogen.

In another embodiment, the invention relates to the compounds of formula I or II wherein A is nitrogen and B is carbon; $R_1$ and $R_2$ are hydrogen.

In another embodiment, the invention relates to the compounds of formula I or II wherein:
$R_1$ and $R_2$ independently are hydrogen, halogen, —CN, —$OR_8$ or —$SR_8$, and more preferably hydrogen or —CN; and
$R_3$ is $R_9$—$C_{1-4}$alkyl, $Cy_1$ or $Cy_2$-$C_{1-4}$alkyl, wherein $Cy_1$ and $Cy_2$ are optionally substituted with one or more $R_{10}$.

In another embodiment, the invention relates to the compounds of formula I or II wherein:
$R_1$ is hydrogen, $C_{1-4}$alkyl, halo$C_{1-4}$alkyl, hydroxy$C_{1-4}$alkyl, cyano$C_{1-4}$alkyl, $C_{1-4}$alkoxy$C_{1-4}$alkyl, halogen, —CN, —$OR_8$ or —$SR_8$, preferably hydrogen, halogen, —CN, —$OR_8$ or —$SR_8$, and more preferably hydrogen or —CN;
$R_2$ is hydrogen; and
$R_3$ is $R_9$—$C_{1-4}$alkyl, $Cy_1$ or $Cy_2$-$C_{1-4}$alkyl, wherein $Cy_1$ and $Cy_2$ are optionally substituted with one or more $R_{10}$.

In another embodiment, the invention relates to the compounds of formula I or II wherein $R_1$ and $R_2$ are hydrogen; and $R_3$ is $R_9$—$C_{1-4}$alkyl, $Cy_1$ or $Cy_2$-$C_{1-4}$alkyl, wherein $Cy_1$ and $Cy_2$ are optionally substituted with one or more $R_{10}$.

In another embodiment, the invention relates to the compounds of formula I or II wherein:
$R_1$ is hydrogen, $C_{1-4}$alkyl, halo$C_{1-4}$alkyl, hydroxy$C_{1-4}$alkyl, cyano$C_{1-4}$alkyl, $C_{1-4}$alkoxy$C_{1-4}$alkyl, halogen, —CN, —$OR_8$ or —$SR_8$, preferably hydrogen, halogen, —CN, —$OR_8$ or —$SR_8$, and more preferably hydrogen or —CN;
$R_2$ is hydrogen; and
$R_3$ is $R_9$—$C_{1-4}$alkyl.

In another embodiment, the invention relates to the compounds of formula I or II wherein:
$R_1$ is hydrogen, $C_{1-4}$alkyl, halo$C_{1-4}$alkyl, hydroxy$C_{1-4}$alkyl, cyano$C_{1-4}$alkyl, $C_{1-4}$alkoxy$C_{1-4}$alkyl, halogen, —CN, —$OR_8$ or —$SR_8$, preferably hydrogen, halogen, —CN, —$OR_8$ or —$SR_8$, and more preferably hydrogen or —CN;
$R_2$ is hydrogen; and
$R_3$ is $Cy_1$, which is optionally substituted with one or more $R_{10}$.

In another embodiment, the invention relates to the compounds of formula I or II wherein $R_1$ and $R_2$ are hydrogen; and $R_3$ is $Cy_1$, which is optionally substituted with one or more $R_{10}$.

In another embodiment, the invention relates to the compounds of formula I or II wherein:
$R_1$ is hydrogen, $C_{1-4}$alkyl, halo$C_{1-4}$alkyl, hydroxy$C_{1-4}$alkyl, cyano$C_{1-4}$alkyl, $C_{1-4}$alkoxy$C_{1-4}$alkyl, halogen, —CN, —$OR_8$ or —$SR_8$, preferably hydrogen, halogen, —CN, —$OR_8$ or —$SR_8$, and more preferably hydrogen or —CN;
$R_2$ is hydrogen;
$R_3$ is $Cy_1$, wherein $Cy_1$ in $R_3$ is a 3- to 7-membered monocyclic ring, which is saturated, partially unsaturated or aromatic, and which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$; and wherein said $Cy_1$ is optionally substituted with one or more $R_{10}$.

In another embodiment, the invention relates to the compounds of formula I or II wherein:
$R_1$ is hydrogen, $C_{1-4}$alkyl, halo$C_{1-4}$alkyl, hydroxy$C_{1-4}$alkyl, cyano$C_{1-4}$alkyl, $C_{1-4}$alkoxy$C_{1-4}$alkyl, halogen, —CN, —$OR_8$ or —$SR_8$, preferably hydrogen, halogen, —CN, —$OR_8$ or —$SR_8$, and more preferably hydrogen or —CN;
$R_2$ is hydrogen;
$R_3$ is $Cy_1$, wherein $Cy_1$ in $R_3$ is a 3- to 7-membered, preferably 5- to 6-membered, saturated monocyclic ring, which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$; and more preferably $Cy_1$ in $R_3$ is piperidinyl or pyrrolidinyl, even more preferably piperidin-3-yl or pyrrolidin-3-yl; wherein said $Cy_1$ is optionally substituted with one or more $R_{10}$.

In another embodiment, the invention relates to the compounds of formula I or II wherein A is nitrogen and B is carbon;

$R_1$ is hydrogen, $C_{1-4}$alkyl, halo$C_{1-4}$alkyl, hydroxy$C_{1-4}$alkyl, cyano$C_{1-4}$alkyl, $C_{1-4}$alkoxy$C_{1-4}$alkyl, halogen, —CN, —$OR_8$ or —$SR_8$, preferably hydrogen, halogen, —CN, —$OR_8$ or —$SR_8$, and more preferably hydrogen or —CN;

$R_2$ is hydrogen; and $R_3$ is $R_9$—$C_{1-4}$alkyl, $Cy_1$ or $Cy_2$-$C_{1-4}$alkyl, wherein $Cy_1$ and $Cy_2$ are optionally substituted with one or more $R_{10}$.

In another embodiment, the invention relates to the compounds of formula I or II wherein A is nitrogen and B is carbon; $R_1$ and $R_2$ are hydrogen; and $R_3$ is $R_9$—$C_{1-4}$alkyl, $Cy_1$ or $Cy_2$-$C_{1-4}$alkyl, wherein $Cy_1$ and $Cy_2$ are optionally substituted with one or more $R_{10}$.

In another embodiment, the invention relates to the compounds of formula I or II wherein A is nitrogen and B is carbon;

$R_1$ is hydrogen, $C_{1-4}$alkyl, halo$C_{1-4}$alkyl, hydroxy$C_{1-4}$alkyl, cyano$C_{1-4}$alkyl, $C_{1-4}$alkoxy$C_{1-4}$alkyl, halogen, —CN, —$OR_8$ or —$SR_8$, preferably hydrogen, halogen, —CN, —$OR_8$ or —$SR_8$, and more preferably hydrogen or —CN;

$R_2$ is hydrogen; and $R_3$ is $R_9$—$C_{1-4}$alkyl.

In another embodiment, the invention relates to the compounds of formula I or II wherein A is nitrogen and B is carbon; $R_1$ and $R_2$ are hydrogen; and $R_3$ is $R_9$—$C_{1-4}$alkyl.

In another embodiment, the invention relates to the compounds of formula I or II wherein A is nitrogen and B is carbon;

$R_1$ is hydrogen, $C_{1-4}$alkyl, halo$C_{1-4}$alkyl, hydroxy$C_{1-4}$alkyl, cyano$C_{1-4}$alkyl, $C_{1-4}$alkoxy$C_{1-4}$alkyl, halogen, —CN, —$OR_8$ or —$SR_8$, preferably hydrogen, halogen, —CN, —$OR_8$ or —$SR_8$, and more preferably hydrogen or —CN;

$R_2$ is hydrogen; and $R_3$ is $Cy_1$, which is optionally substituted with one or more $R_{10}$.

In another embodiment, the invention relates to the compounds of formula I or II wherein A is nitrogen and B is carbon; $R_1$ and $R_2$ are hydrogen; and $R_3$ is $Cy_1$, which is optionally substituted with one or more $R_{10}$.

In another embodiment, the invention relates to the compounds of formula I or II wherein A is nitrogen and B is carbon;

$R_1$ is hydrogen, $C_{1-4}$alkyl, halo$C_{1-4}$alkyl, hydroxy $C_{1-4}$alkyl, cyano$C_{1-4}$alkyl, $C_{1-4}$alkoxy$C_{1-4}$alkyl, halogen, —CN, —$OR_8$ or —$SR_8$, preferably hydrogen, halogen, —CN, —$OR_8$ or —$SR_8$, and more preferably hydrogen or —CN;

$R_2$ is hydrogen; and $R_3$ is $Cy_1$, wherein $Cy_1$ in $R_3$ is a 3- to 7-membered monocyclic ring, which is saturated, partially unsaturated or aromatic, and which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$; and wherein said $Cy_1$ is optionally substituted with one or more $R_{10}$.

In another embodiment, the invention relates to the compounds of formula I or II wherein A is nitrogen and B is carbon;

$R_1$ is hydrogen, $C_{1-4}$alkyl, halo$C_{1-4}$alkyl, hydroxy$C_{1-4}$alkyl, cyano$C_{1-4}$alkyl, $C_{1-4}$alkoxy$C_{1-4}$alkyl, halogen, —CN, —$OR_8$ or —$SR_8$, preferably hydrogen, halogen, —CN, —$OR_8$ or —$SR_8$, and more preferably hydrogen or —CN;

$R_2$ is hydrogen; and $R_3$ is $Cy_1$, wherein $Cy_1$ in $R_3$ is a 3- to 7-membered, preferably 5- to 6-membered, saturated monocyclic ring, which is carbocyclic or heterocyclic containing from 1 to 3 heteroatoms independently selected from N, S and O, wherein said ring is bonded to the rest of the molecule through any available O atom, and wherein one or more C or S ring atoms are optionally oxidized forming CO, SO or $SO_2$; and more preferably $Cy_1$ in $R_3$ is piperidinyl or pyrrolidinyl, even more preferably piperidin-3-yl or pyrrolidin-3-yl; wherein said $Cy_1$ is optionally substituted with one or more $R_{10}$.

In another embodiment, the invention relates to the compounds of formula I or II wherein A is nitrogen and B is carbon;

$R_1$ is hydrogen, $C_{1-4}$alkyl, halo$C_{1-4}$alkyl, hydroxy$C_{1-4}$alkyl, cyano$C_{1-4}$alkyl, $C_{1-4}$alkoxy$C_{1-4}$alkyl, halogen, —CN, —$OR_8$ or —$SR_8$, preferably hydrogen, halogen, —CN, —$OR_8$ or —$SR_8$, and more preferably hydrogen or —CN;

$R_2$ is hydrogen; and $R_3$ is a cycle of formula $Cy_{1a}$, preferably with (S)-stereochemistry.

In another embodiment, the invention relates to the compounds of formula II wherein A is nitrogen and B is carbon;

$R_1$ is hydrogen, $C_{1-4}$alkyl, halo$C_{1-4}$alkyl, hydroxy$C_{1-4}$alkyl, cyano$C_{1-4}$alkyl, $C_{1-4}$alkoxy$C_{1-4}$alkyl, halogen, —CN, —$OR_8$ or —$SR_8$, preferably hydrogen, halogen, —CN, —$OR_8$ or —$SR_8$, and more preferably hydrogen or —CN;

$R_2$ is hydrogen; and $R_3$ is a cycle of formula $Cy_{1a}$, preferably with (S)-stereochemistry.

In another embodiment, the invention relates to the compounds of formula I or II wherein A is nitrogen and B is carbon; and $R_5$ is hydrogen.

In another embodiment, the invention relates to the compounds of formula I or II wherein A is nitrogen and B is carbon;

$R_1$ is hydrogen, halogen, —CN, —$OR_8$ or —$SR_8$, preferably hydrogen or —CN; and $R_2$ is hydrogen; and $R_5$ is hydrogen.

In another embodiment, the invention relates to the compounds of formula I or II wherein A is nitrogen and B is carbon; $R_1$ and $R_2$ are hydrogen; and $R_5$ is hydrogen.

In another embodiment, the invention relates to the compounds of formula I or II wherein:

$R_1$ is hydrogen, halogen, —CN, —$OR_8$ or —$SR_8$, preferably hydrogen or —CN; and $R_2$ is hydrogen;

$R_6$ is hydrogen; and $R_6$ is hydrogen or $C_{1-4}$alkyl, preferably hydrogen, methyl or ethyl.

In another embodiment, the invention relates to the compounds of formula I or II wherein $R_1$ and $R_2$ are hydrogen; $R_5$ is hydrogen; and $R_6$ is hydrogen or $C_{1-4}$alkyl, preferably hydrogen, methyl or ethyl.

In another embodiment, the invention relates to the compounds of formula I or II wherein:

$R_1$ is hydrogen, halogen, —CN, —$OR_8$ or —$SR_8$, preferably hydrogen or —CN; and $R_2$ is hydrogen;

$R_5$ is hydrogen; and $R_6$ is $C_{1-4}$alkyl, preferably methyl or ethyl.

In another embodiment, the invention relates to the compounds of formula I or II wherein $R_1$ and $R_2$ are hydrogen; $R_5$ is hydrogen; and $R_6$ is $C_{1-4}$alkyl, preferably methyl or ethyl.

In another embodiment, the invention relates to the compounds of formula I or II wherein:

$R_1$ is hydrogen, halogen, —CN, —$OR_8$ or —$SR_8$, preferably hydrogen or —CN; and $R_2$ is hydrogen;

$R_3$ is $R_9$—$C_{1-4}$alkyl, $Cy_1$ or $Cy_2$-$C_{1-4}$alkyl, wherein $Cy_1$ and $Cy_2$ are optionally substituted with one or more $R_{10}$; and $R_5$ is hydrogen.

In another embodiment, the invention relates to the compounds of formula I or II wherein:

$R_1$ and $R_2$ are hydrogen;

$R_3$ is $R_9$—$C_{1-4}$alkyl, $Cy_1$ or $Cy_2$-$C_{1-4}$alkyl, wherein $Cy_1$ and $Cy_2$ are optionally substituted with one or more $R_{10}$; and $R_5$ is hydrogen.

In another embodiment, the invention relates to the compounds of formula I or II wherein:

$R_1$ is hydrogen, halogen, —CN, —$OR_8$ or —$SR_8$, preferably hydrogen or —CN; and $R_2$ is hydrogen;

$R_3$ is $R_9$—$C_{1-4}$alkyl; and $R_5$ is hydrogen.

In another embodiment, the invention relates to the compounds of formula I or II wherein:

$R_1$ is hydrogen, halogen, —CN, —$OR_8$ or —$SR_8$, preferably hydrogen or —CN; and $R_2$ is hydrogen;

$R_3$ is $Cy_1$, which is optionally substituted with one or more $R_{10}$; and $R_5$ is hydrogen.

In another embodiment, the invention relates to the compounds of formula I or II wherein:

$R_1$ and $R_2$ are hydrogen;

$R_3$ is $Cy_1$, which is optionally substituted with one or more $R_{10}$; and $R_5$ is hydrogen.

In another embodiment, the invention relates to the compounds of formula I or II wherein:

$R_1$ is hydrogen, halogen, —CN, —$OR_8$ or —$SR_8$, preferably hydrogen or —CN; and $R_2$ is hydrogen;

$R_3$ is $Cy_1$, wherein $Cy_1$ in $R_3$ is a 3- to 7-membered monocyclic ring, which is saturated, partially unsaturated or aromatic, and which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$; and wherein said $Cy_1$ is optionally substituted with one or more $R_{10}$; and $R_5$ is hydrogen.

In another embodiment, the invention relates to the compounds of formula I or II wherein:

$R_1$ is hydrogen, halogen, —CN, —$OR_8$ or —$SR_8$, preferably hydrogen or —CN; and $R_2$ is hydrogen;

$R_3$ is $Cy_1$, wherein $Cy_1$ in $R_3$ is a 3- to 7-membered, preferably 5- to 6-membered, saturated monocyclic ring, which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$; and more preferably $Cy_1$ in $R_3$ is piperidinyl or pyrrolidinyl, even more preferably piperidin-3-yl or pyrrolidin-3-yl; wherein said $Cy_1$ is optionally substituted with one or more $R_{10}$; and $R_5$ is hydrogen.

In another embodiment, the invention relates to the compounds of formula I or II wherein:

$R_1$ is hydrogen, halogen, —CN, —$OR_8$ or —$SR_8$, preferably hydrogen or —CN; and $R_2$ is hydrogen;

$R_3$ is a cycle of formula $Cy_{1a}$, preferably with (S)-stereochemistry; and $R_5$ is hydrogen.

In another embodiment, the invention relates to the compounds of formula II wherein:

$R_1$ is hydrogen, halogen, —CN, —$OR_8$ or —$SR_8$, preferably hydrogen or —CN; and $R_2$ is hydrogen;

$R_3$ is a cycle of formula $Cy_{1a}$, preferably with (S)-stereochemistry; and $R_5$ is hydrogen.

In another embodiment, the invention relates to the compounds of formulator II wherein A is nitrogen and B is carbon;

$R_1$ is hydrogen, halogen, —CN, —$OR_8$ or —$SR_8$, preferably hydrogen or —CN; and $R_2$ is hydrogen;

$R_3$ is hydrogen; and $R_6$ is hydrogen or $C_{1-4}$alkyl, preferably hydrogen, methyl or ethyl.

In another embodiment, the invention relates to the compounds of formula I or II wherein A is nitrogen and B is carbon;

$R_1$ and $R_2$ are hydrogen;

$R_5$ is hydrogen; and $R_6$ is hydrogen or $C_{1-4}$alkyl, preferably hydrogen, methyl or ethyl.

In another embodiment, the invention relates to the compounds of formula I or II wherein A is nitrogen and B is carbon;

$R_1$ is hydrogen, halogen, —CN, —$OR_8$ or —$SR_8$, preferably hydrogen or —CN; and $R_2$ is hydrogen;

$R_5$ is hydrogen; and $R_6$ is $C_{1-4}$alkyl, preferably methyl or ethyl.

In another embodiment, the invention relates to the compounds of formula I or II wherein A is nitrogen and B is carbon;

$R_1$ and $R_2$ are hydrogen;

$R_5$ is hydrogen; and $R_6$ is $C_{1-4}$alkyl, preferably methyl or ethyl.

In another embodiment, the invention relates to the compounds of formula I or II wherein:

W is CH;

$R_1$ is hydrogen, halogen, —CN, —$OR_8$ or —$SR_8$, preferably hydrogen or —CN; and $R_2$ is hydrogen;

$R_3$ is $R_9$—$C_{1-4}$alkyl, $Cy_1$ or $Cy_2$-$C_{1-4}$alkyl, wherein $Cy_1$ and $Cy_2$ are optionally substituted with one or more $R_{10}$; and $R_5$ is hydrogen.

In another embodiment, the invention relates to the compounds of formula I or II wherein:

W is CH;

$R_1$ and $R_2$ are hydrogen;

$R_3$ is $R_9$—$C_{1-4}$alkyl, $Cy_1$ or $Cy_2$-$C_{1-4}$alkyl, wherein $Cy_1$ and $Cy_2$ are optionally substituted with one or more $R_{10}$; and $R_5$ is hydrogen.

In another embodiment, the invention relates to the compounds of formula I or II wherein:

W is CH;

$R_1$ is hydrogen, halogen, —CN, —$OR_8$ or —$SR_8$, preferably hydrogen or —CN; and $R_2$ is hydrogen;

$R_3$ is $R_9$—$C_{1-4}$alkyl; and $R_5$ is hydrogen.

In another embodiment, the invention relates to the compounds of formula I or II wherein:

W is CH;

$R_1$ is hydrogen, halogen, —CN, —$OR_8$ or —$SR_8$, preferably hydrogen or —CN, more preferably hydrogen; and $R_2$ is hydrogen;

$R_3$ is $Cy_1$, which is optionally substituted with one or more $R_{10}$; and $R_5$ is hydrogen.

In another embodiment, the invention relates to the compounds of formula I or II wherein:

W is CH;

$R_1$ is hydrogen, halogen, —CN, —$OR_8$ or —$SR_8$, preferably hydrogen or —CN, more preferably hydrogen; and $R_2$ is hydrogen;

$R_3$ is $Cy_1$, wherein $Cy_1$ in $R_3$ is a 3- to 7-membered monocyclic ring, which is saturated, partially unsaturated or aromatic, and which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$; and wherein said $Cy_1$ is optionally substituted with one or more $R_{10}$; and $R_5$ is hydrogen.

In another embodiment, the invention relates to the compounds of formula I or II wherein:

W is CH;

$R_1$ is hydrogen, halogen, —CN, —$OR_8$ or —$SR_8$, preferably hydrogen or —CN, more preferably hydrogen; and $R_2$ is hydrogen;

$R_3$ is $Cy_1$, wherein $Cy_1$ in $R_3$ is a 3- to 7-membered, preferably 5- to 6-membered, saturated monocyclic ring, which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$; and more preferably $Cy_1$ in $R_3$ is piperidinyl or pyrrolidinyl, even more preferably piperidin-3-yl or pyrrolidin-3-yl; wherein said $Cy_2$ is optionally substituted with one or more $R_{10}$; and $R_5$ is hydrogen.

In another embodiment, the invention relates to the compounds of formula I or II wherein:

W is CH;

$R_1$ is hydrogen, halogen, —CN, —$OR_8$ or —$SR_8$, preferably hydrogen or —CN, more preferably hydrogen; and $R_2$ is hydrogen;

$R_3$ is a cycle of formula $Cy_{1a}$, preferably with (S)-stereochemistry; and $R_5$ is hydrogen.

In another embodiment, the invention relates to the compounds of formula II wherein:

W is CH;

$R_1$ is hydrogen, halogen, —CN, —$OR_8$ or —$SR_8$, preferably hydrogen or —CN, more preferably hydrogen; and $R_2$ is hydrogen;

$R_3$ is a cycle of formula $Cy_{1a}$, preferably with (3)-stereochemistry; and $R_5$ is hydrogen.

In another embodiment, the invention relates to the compounds of formula I or II wherein:

W is N;

$R_1$ is hydrogen, halogen, —CN, —$OR_8$ or —$SR_8$, preferably hydrogen or —CN; and $R_2$ is hydrogen;

$R_3$ is $R_9$—$C_{1-4}$alkyl, $Cy_1$ or $Cy_2$-$C_{1-4}$alkyl, wherein $Cy_1$ and $Cy_2$ are optionally substituted with one or more $R_{10}$; and $R_5$ is hydrogen.

In another embodiment, the invention relates to the compounds of formula I or II wherein:

W is N;

$R_1$ and $R_2$ are hydrogen;

$R_3$ is $R_9$—$C_{1-4}$alkyl, $Cy_1$ or $Cy_2$-$C_{1-4}$alkyl, wherein $Cy_1$ and $Cy_2$ are optionally substituted with one or more $R_{10}$; and $R_5$ is hydrogen.

In another embodiment, the invention relates to the compounds of formula I or II wherein:

W is N;

$R_1$ is hydrogen, halogen, —CN, —$OR_8$ or —$SR_8$, preferably hydrogen or —CN; and $R_2$ is hydrogen;

$R_3$ is $R_9$—$C_{1-4}$alkyl; and $R_5$ is hydrogen.

In another embodiment, the invention relates to the compounds of formula I or II wherein:

W is N;

$R_1$ is hydrogen, halogen, —CN, —$OR_8$ or —$SR_8$, preferably hydrogen or —CN, more preferably hydrogen; and $R_2$ is hydrogen;

$R_3$ is $Cy_1$, which is optionally substituted with one or more $R_{10}$; and $R_5$ is hydrogen.

In another embodiment, the invention relates to the compounds of formula I or II wherein;

W is N;

$R_1$ is hydrogen, halogen, —CN, —$OR_8$ or —$SR_8$, preferably hydrogen or —CN, more preferably hydrogen; and $R_2$ is hydrogen;

$R_3$ is $Cy_1$, wherein $Cy_1$ in $R_3$ is a 3- to 7-membered monocyclic ring, which is saturated, partially unsaturated or aromatic, and which is carbocyclic or heterocyclic containing from 1 to 3 heteroatoms independently selected from N, S and O, wherein said ring is bonded to the rest of the molecule through any available O atom, and wherein one or more C or S ring atoms are optionally oxidized forming CO, SO or $SO_2$; and wherein said $Cy_1$ is optionally substituted with one or more $R_{10}$; and $R_5$ is hydrogen.

In another embodiment, the invention relates to the compounds of formula I or II wherein:

W is N;

$R_1$ is hydrogen, halogen, —CN, —$OR_8$ or —$SR_8$, preferably hydrogen or —CN, more preferably hydrogen; and $R_2$ is hydrogen;

$R_3$ is $Cy_1$, wherein $Cy_1$ in $R_3$ is a 3- to 7-membered, preferably 5- to 6-membered, saturated monocyclic ring, which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$; and more preferably $Cy_1$ in $R_3$ is piperidinyl or pyrrolidinyl, even more preferably piperidin-3-yl or pyrrolidin-3-yl; wherein said $Cy_1$ is optionally substituted with one or more $R_{10}$; and $R_5$ is hydrogen.

In another embodiment, the invention relates to the compounds of formula I or II wherein;

A is nitrogen and B is carbon;

$R_1$ is hydrogen, halogen, —CN, —$OR_8$ or —$SR_8$, preferably hydrogen or —CN; and $R_2$ is hydrogen;

$R_3$ is $R_9$—$C_{1-4}$alkyl, $Cy_1$ or $Cy_2$-$C_{1-4}$alkyl, wherein $Cy_1$ and $Cy_2$ are optionally substituted with one or more $R_{10}$; and $R_5$ is hydrogen.

In another embodiment, the invention relates to the compounds of formula I or II wherein:

A is nitrogen and B is carbon;

$R_1$ and $R_2$ are hydrogen;

$R_3$ is $R_9$—$C_{1-4}$alkyl, $Cy_1$ or $Cy_2$-$C_{0-4}$alkyl, wherein $Cy_1$ and $Cy_2$ are optionally substituted with one or more $R_{10}$; and $R_5$ is hydrogen.

In another embodiment, the invention relates to the compounds of formula for II wherein:
A is nitrogen and B is carbon;
$R_1$ is hydrogen, halogen, —CN, —$OR_8$ or —$SR_8$, preferably hydrogen or —CN; and $R_2$ is hydrogen;
$R_3$ is $R_9$—$C_{1-4}$alkyl; and
$R_5$ is hydrogen.

In another embodiment, the invention relates to the compounds of formula I or II wherein:
A is nitrogen and B is carbon;
$R_1$ is hydrogen, halogen, —CN, —$OR_8$ or —$SR_8$, preferably hydrogen or —CN, more preferably hydrogen; and $R_2$ is hydrogen;
$R_3$ is $Cy_1$, which is optionally substituted with one or more $R_{10}$; and
$R_5$ is hydrogen.

In another embodiment, the invention relates to the compounds of formula I or II wherein:
A is nitrogen and B is carbon;
$R_1$ is hydrogen, halogen, —CN, —$OR_8$ or —$SR_8$, preferably hydrogen or —CN, more preferably hydrogen; and $R_2$ is hydrogen;
$R_3$ is $Cy_1$, wherein $Cy_1$ in $R_3$ is a 3- to 7-membered monocyclic ring, which is saturated, partially unsaturated or aromatic, and which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$; and wherein said $Cy_1$ is optionally substituted with one or more $R_{10}$; and
$R_5$ is hydrogen.

In another embodiment, the invention relates to the compounds of formula I or II wherein:
A is nitrogen and B is carbon;
$R_1$ is hydrogen, halogen, —CN, —$OR_8$ or —$SR_8$, preferably hydrogen or —CN, more preferably hydrogen; and $R_2$ is hydrogen;
$R_3$ is $Cy_1$, wherein $Cy_1$ in $R_3$ is a 3- to 7-membered, preferably 5- to 6-membered, saturated monocyclic ring, which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$; and more preferably $Cy_1$ in $R_3$ is piperidinyl or pyrrolidinyl, even more preferably piperidin-3-yl or pyrrolidin-3-yl; wherein said $Cy_1$ is optionally substituted with one or more $R_{10}$; and
$R_5$ is hydrogen.

In another embodiment, the invention relates to the compounds of formula I or II wherein:
A is nitrogen and B is carbon;
$R_1$ is hydrogen, halogen, —CN, —$OR_8$ or —$SR_8$, preferably hydrogen or —CN, more preferably hydrogen; and $R_2$ is hydrogen;
$R_3$ is a cycle of formula $Cy_{1a}$, preferably with (S)-stereochemistry; and
$R_5$ is hydrogen.

In another embodiment, the invention relates to the compounds of formula II wherein:
A is nitrogen and B is carbon;
$R_1$ is hydrogen, halogen, —CN, —$OR_8$ or —$SR_8$, preferably hydrogen or —CN, more preferably hydrogen; and $R_2$ is hydrogen;
$R_3$ is a cycle of formula $Cy_{1a}$, preferably with (8)-stereochemistry; and
$R_5$ is hydrogen.

In another embodiment, the invention relates to the compounds of formula I or II wherein:
$R_1$ is hydrogen, halogen, —CN, —$OR_8$ or —$SR_8$, preferably hydrogen or —CN; and $R_2$ is hydrogen;
$R_3$ is $R_9$—$C_{1-4}$alkyl, $Cy_1$ or $Cy_2$-$C_{1-4}$alkyl, wherein $Cy_1$ and $Cy_2$ are optionally substituted with one or more $R_{10}$;
$R_4$ is hydrogen, $C_{1-4}$alkyl, $R_{12}R_7N$—$C_{0-4}$alkyl or $Cy_2$-$C_{0-4}$alkyl, preferably hydrogen, $C_{1-4}$alkyl, —$NR_7R_{12}$ or $Cy_2$; wherein $Cy_2$ are optionally substituted with one or more $R_{11}$;
$R_5$ is hydrogen; and
$R_6$ is hydrogen, $C_{1-4}$alkyl, $C_{1-4}$alkoxy$C_{1-4}$alkyl, hydroxy$C_{1-4}$alkyl or $R_{12}R_7N$—$C_{1-4}$alkyl, preferably hydrogen or $C_{1-4}$alkyl and more preferably hydrogen, methyl or ethyl.

In another embodiment, the invention relates to the compounds of formula I or II wherein:
$R_1$ and $R_2$ are hydrogen;
$R_3$ is $R_9$—$C_{1-4}$alkyl, $Cy_1$ or $Cy_2$-$C_{1-4}$alkyl, wherein $Cy_1$ and $Cy_2$ are optionally substituted with one or more $R_{10}$;
$R_4$ is hydrogen, $C_{1-4}$alkyl, $R_{12}R_7N$—$C_{0-4}$alkyl or $Cy_2$-$C_{0-4}$alkyl, preferably hydrogen, $C_{1-4}$alkyl, —$NR_7R_{12}$ or $Cy_2$; wherein $Cy_2$ are optionally substituted with one or more $R_{11}$;
$R_5$ is hydrogen; and
$R_6$ is hydrogen, $C_{1-4}$alkyl, $C_{1-4}$alkoxy$C_{1-4}$alkyl, hydroxy$C_{1-4}$alkyl or $R_{12}R_7N$—$C_{1-4}$alkyl, preferably hydrogen or $C_{1-4}$alkyl and more preferably hydrogen, methyl or ethyl.

In another embodiment, the invention relates to the compounds of formula I or II wherein:
$R_1$ is hydrogen, halogen, —CN, —$OR_8$ or —$SR_8$, preferably hydrogen or —CN; and $R_2$ is hydrogen;
$R_3$ is $R_9$—$C_{1-4}$alkyl;
$R_4$ is hydrogen, $C_{1-4}$alkyl, $R_{12}R_7N$—$C_{0-4}$alkyl or $Cy_2$-$C_{0-4}$alkyl, preferably hydrogen, $C_{1-4}$alkyl, —$NR_7R_{12}$ or $Cy_2$; wherein $Cy_2$ are optionally substituted with one or more $R_{11}$;
$R_5$ is hydrogen; and
$R_6$ is hydrogen, $C_{1-4}$alkyl, $C_{1-4}$alkoxy$C_{1-4}$alkyl, hydroxy$C_{1-4}$alkyl or $R_{12}R_7N$—$C_{1-4}$alkyl, preferably hydrogen or $C_{1-4}$alkyl and more preferably hydrogen, methyl or ethyl.

In another embodiment, the invention relates to the compounds of formula I or II wherein:
$R_1$ is hydrogen, halogen, —CN, —$OR_8$ or —$SR_8$, preferably hydrogen or —CN; and $R_2$ is hydrogen;
$R_3$ is $Cy_1$ which is optionally substituted with one or more $R_{10}$;
$R_4$ is hydrogen, $C_{1-4}$alkyl, $R_{12}R_7N$—$C_{0-4}$alkyl or $Cy_2$-$C_{0-4}$alkyl, preferably hydrogen, $C_{1-4}$alkyl, —$NR_7R_{12}$ or $Cy_2$; wherein $Cy_2$ are optionally substituted with one or more $R_{11}$;
$R_5$ is hydrogen; and
$R_6$ is hydrogen, $C_{1-4}$alkyl, $C_{1-4}$alkoxy$C_{1-4}$alkyl, hydroxy$C_{1-4}$alkyl or $R_{12}R_7N$—$C_{1-4}$alkyl, preferably hydrogen or $C_{1-4}$alkyl and more preferably hydrogen, methyl or ethyl.

In another embodiment, the invention relates to the compounds of formula I or II wherein:
$R_1$ is hydrogen, halogen, —CN, —$OR_8$ or —$SR_8$, preferably hydrogen or —CN; and $R_2$ is hydrogen;
$R_3$ is $Cy_1$, wherein $Cy_1$ in $R_3$ is a 3- to 7-membered monocyclic ring, which is saturated, partially unsaturated or aromatic, and which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$; and wherein said $Cy_1$ is optionally substituted with one or more $R_{10}$;

$R_4$ is hydrogen, $C_{1-4}$alkyl, $R_{12}R_7N$—$C_{0-4}$alkyl or $Cy_2$-$C_{0-4}$alkyl, preferably hydrogen, $C_{1-4}$alkyl, —$NR_7R_{12}$ or $Cy_2$; wherein $Cy_2$ are optionally substituted with one or more $R_{11}$;

$R_5$ is hydrogen; and $R_6$ is hydrogen, $C_{1-4}$alkyl, $C_{1-4}$alkoxy$C_{1-4}$alkyl, hydroxy$C_{1-4}$alkyl or $R_{12}R_7N$—$C_{1-4}$alkyl, preferably hydrogen or $C_{1-4}$alkyl and more preferably hydrogen, methyl or ethyl.

In another embodiment, the invention relates to the compounds of formula I or II wherein:

$R_1$ is hydrogen, halogen, —CN, —$OR_8$ or —$SR_8$, preferably hydrogen or —CN; and $R_2$ is hydrogen;

$R_3$ is $Cy_1$, wherein $Cy_1$ in $R_3$ is a 3- to 7-membered, preferably 5- to 6-membered, saturated monocyclic ring, which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$; and more preferably $Cy_1$ in $R_3$ is piperidinyl or pyrrolidinyl, even more preferably piperidin-3-yl or pyrrolidin-3-yl; wherein said $Cy_1$ is optionally substituted with one or more $R_{10}$;

$R_4$ is hydrogen, $C_{1-4}$alkyl, $R_{12}R_7N$—$C_{0-4}$alkyl or $Cy_2$-$C_{0-4}$alkyl, preferably hydrogen, $C_{1-4}$alkyl, —$NR_7R_{12}$ or $Cy_2$; wherein $Cy_2$ are optionally substituted with one or more $R_{11}$;

$R_5$ is hydrogen; and $R_6$ is hydrogen, $C_{1-4}$alkyl, $C_{1-4}$alkoxy-$C_{1-4}$alkyl, hydroxy$C_{1-4}$alkyl or $R_{12}R_7N$—$C_{1-4}$alkyl, preferably hydrogen or $C_{1-4}$alkyl and more preferably hydrogen, methyl or ethyl.

In another embodiment, the invention relates to the compounds of formula I or II wherein;

A is nitrogen and B is carbon;

$R_1$ is hydrogen, halogen; —CN, —$OR_8$ or —$SR_8$, preferably hydrogen or —CN; and $R_2$ is hydrogen;

$R_3$ is $R_9$—$C_{1-4}$alkyl, $Cy_1$ or $Cy_2$-$C_{1-4}$alkyl, wherein $Cy_1$ and $Cy_2$ are optionally substituted with one or more $R_{10}$;

$R_4$ is hydrogen, $C_{1-4}$alkyl, $R_{12}R_7N$—$C_{0-4}$alkyl or $Cy_2$-$C_{0-4}$alkyl, preferably hydrogen, $C_{1-4}$alkyl, —$NR_7R_{12}$ or $Cy_2$; wherein $Cy_2$ are optionally substituted with one or more $R_{11}$;

$R_5$ is hydrogen; and $R_6$ is hydrogen, $C_{1-4}$alkyl, $C_{1-4}$alkoxy$C_{1-4}$alkyl, hydroxy$C_{1-4}$alkyl or $R_{12}R_7N$—$C_{1-4}$alkyl, preferably hydrogen or $C_{1-4}$alkyl and more preferably hydrogen, methyl or ethyl, In another embodiment, the invention relates to the compounds of formula I or II wherein:

A is nitrogen and B is carbon;

$R_1$ and $R_2$ are hydrogen;

$R_3$ is $R_9$—$C_{1-4}$alkyl, $Cy_1$ or $Cy_2$-$C_{1-4}$alkyl, wherein $Cy_1$ and $Cy_2$ are optionally substituted with one or more $R_{10}$;

$R_4$ is hydrogen, $C_{1-4}$alkyl, $R_{12}R_7N$—$C_{0-4}$alkyl or $Cy_2$-$C_{0-4}$alkyl, preferably hydrogen, $C_{1-4}$alkyl, —$NR_7R_{12}$ or $Cy_2$; wherein $Cy_2$ are optionally substituted with one or more $R_{11}$;

$R_5$ is hydrogen; and $R_6$ is hydrogen, $C_{1-4}$alkyl, $C_{1-4}$alkoxy$C_{1-4}$alkyl, hydroxy$C_{1-4}$alkyl or $R_{12}R_7N$—$C_{1-4}$alkyl, preferably hydrogen or $C_{1-4}$alkyl and more preferably hydrogen, methyl or ethyl.

In another embodiment, the invention relates to the compounds of formula I or II wherein;

A is nitrogen and B is carbon;

$R_1$ is hydrogen, halogen, —CN, —$OR_8$ or —$SR_8$, preferably hydrogen or —CN; and $R_2$ is hydrogen;

$R_3$ is $Cy_1$, which is optionally substituted with one or more $R_{10}$;

$R_4$ is hydrogen, $C_{1-4}$alkyl, $R_{12}R_7N$—$C_{0-4}$alkyl or $Cy_2$-$C_{0-4}$alkyl, preferably hydrogen, $C_{1-4}$alkyl, —$NR_7R_{12}$ or $Cy_2$; wherein $Cy_2$ are optionally substituted with one or more $R_{11}$;

$R_5$ is hydrogen; and $R_6$ is hydrogen, $C_{1-4}$alkyl, $C_{1-4}$alkoxy$C_{1-4}$alkyl, hydroxy$C_{1-4}$alkyl or $R_{12}R_7N$—$C_{1-4}$alkyl, preferably hydrogen or $C_{1-4}$alkyl and more preferably hydrogen, methyl or ethyl.

In another embodiment, the invention relates to the compounds of formula I or II wherein:

A is nitrogen and B is carbon;

$R_1$ is hydrogen, halogen, —CN, —$OR_8$ or —$SR_8$, preferably hydrogen or —CN; and $R_2$ is hydrogen;

$R_3$ is $Cy_1$, wherein $Cy_1$ in $R_3$ is a 3- to 7-membered monocyclic ring, which is saturated, partially unsaturated or aromatic, and which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$; and wherein said $Cy_2$ is optionally substituted with one or more $R_{10}$;

$R_4$ is hydrogen, $C_{1-4}$alkyl, $R_{12}R_7N$—$C_{0-4}$alkyl or $Cy_2$-$C_{0-4}$alkyl, preferably hydrogen, $C_{1-4}$alkyl, —$NR_7R_{12}$ or $Cy_2$; wherein $Cy_2$ are optionally substituted with one or more $R_{11}$;

$R_5$ is hydrogen; and $R_6$ is hydrogen, $C_{1-4}$alkyl, $C_{1-4}$alkoxy$C_{1-4}$alkyl, hydroxy$C_{1-4}$alkyl or $R_{12}R_7N$—$C_{1-4}$alkyl, preferably hydrogen or $C_{1-4}$alkyl and more preferably hydrogen, methyl or ethyl.

In another embodiment, the invention relates to the compounds of formula I or II wherein:

A is nitrogen and B is carbon;

$R_1$ is hydrogen, halogen, —CN, —$OR_8$ or —$SR_8$, preferably hydrogen or —CN; and $R_2$ is hydrogen;

$R_3$ is $Cy_1$, wherein $Cy_1$ in $R_3$ is a 3- to 7-membered, preferably 5- to 6-membered, saturated monocyclic ring, which is carbocyclic or heterocyclic containing from 1 to 3 heteroatoms independently selected from N, S and O, wherein said ring is bonded to the rest of the molecule through any available C atom; and wherein one or more C or S ring atoms are optionally oxidized forming CO, SO or $SO_2$; and more preferably $Cy_1$ in $R_3$ is piperidinyl or pyrrolidinyl, even more preferably piperidin-3-yl or pyrrolidin-3-yl; wherein said $Cy_1$ is optionally substituted with one or more $R_{10}$;

$R_4$ is hydrogen, $C_{1-4}$alkyl, $R_{12}R_7N$—$C_{0-4}$alkyl or $Cy_2$-$C_{0-4}$alkyl, preferably hydrogen, $C_{1-4}$alkyl, —$NR_7R_{12}$ or $Cy_2$; wherein $Cy_2$ are optionally substituted with one or more $R_{11}$;

$R_5$ is hydrogen; and $R_6$ is hydrogen, $C_{1-4}$alkyl, $C_{1-4}$alkoxy$C_{1-4}$alkyl, hydroxy$C_{1-4}$alkyl or $R_{12}R_7N$—$C_{1-4}$alkyl, preferably hydrogen or $C_{1-4}$alkyl and more preferably hydrogen, methyl or ethyl.

In another embodiment, the invention relates to the compounds of formula I wherein:

A is nitrogen and B is carbon;

$R_1$ is hydrogen, halogen, —CN, —$OR_8$ or —$SR_8$, preferably hydrogen or —CN; and $R_2$ is hydrogen;

$R_3$ is $R_9$—$C_{1-4}$alkyl, $Cy_1$ or $Cy_2$-$C_{1-4}$alkyl, wherein $Cy_1$ and $Cy_2$ are optionally substituted with one or more $R_{10}$;

$R_4$ is hydrogen, $C_{1-4}$alkyl, $R_{12}R_7N$—$C_{0-4}$alkyl or $Cy_2$-$C_{0-4}$alkyl, preferably hydrogen, $C_{1-4}$alkyl, —$NR_7R_{12}$ or $Cy_2$; wherein $Cy_2$ is optionally substituted with one or more $R_{11}$; and $R_5$ is hydrogen.

In another embodiment, the invention relates to the compounds of formula I wherein:

A is nitrogen and B is carbon;
$R_1$ and $R_2$ are hydrogen;
$R_3$ is $R_9$—$C_{1-4}$alkyl, $Cy_1$ or $Cy_2$-$C_{1-4}$alkyl, wherein $Cy_1$ and $Cy_2$ are optionally substituted with one or more $R_{10}$;
$R_4$ is hydrogen, $C_{1-4}$alkyl, $R_{12}R_7N$—$C_{0-4}$alkyl or $Cy_2$-$C_{0-4}$alkyl, preferably hydrogen, $C_{1-4}$alkyl, —$NR_7R_{12}$ or $Cy_2$; wherein $Cy_2$ is optionally substituted with one or more $R_{11}$; and
$R_5$ is hydrogen.

In another embodiment, the invention relates to the compounds of formula I wherein:

A is nitrogen and B is carbon;
$R_1$ is hydrogen, halogen, —CN, —$OR_8$ or —$SR_8$, preferably hydrogen or —CN; and $R_2$ is hydrogen;
$R_3$ is $Cy_1$, which is optionally substituted with one or more $R_{10}$;
$R_4$ is hydrogen, $C_{1-4}$alkyl, $R_{12}R_7N$—$C_{0-4}$alkyl or $Cy_2$-$C_{0-4}$alkyl, preferably hydrogen, $C_{1-4}$alkyl, —$NR_7R_{12}$ or $Cy_2$; wherein $Cy_2$ is optionally substituted with one or more $R_{11}$; and
$R_5$ is hydrogen.

In another embodiment, the invention relates to the compounds of formula I wherein:

A is nitrogen and B is carbon;
$R_1$ is hydrogen, halogen, —CN, —$OR_8$ or —$SR_8$, preferably hydrogen or —CN; and $R_2$ is hydrogen;
$R_3$ is $Cy_1$, wherein $Cy_1$ in $R_3$ is a 3- to 7-membered monocyclic ring, which is saturated, partially unsaturated or aromatic, and which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$; and wherein said $Cy_1$ is optionally substituted with one or more $R_{10}$;
$R_4$ is hydrogen, $C_{1-4}$alkyl, $R_{12}R_7N$—$C_{0-4}$alkyl or $Cy_2$-$C_{0-4}$alkyl, preferably hydrogen, $C_{1-4}$alkyl, —$NR_7R_{12}$ or $Cy_2$; wherein $Cy_2$ is optionally substituted with one or more $R_{11}$; and
$R_5$ is hydrogen.

In another embodiment, the invention relates to the compounds of formula I wherein:

A is nitrogen and B is carbon;
$R_1$ is hydrogen, halogen, —CN, —$OR_8$ or —$SR_8$, preferably hydrogen or —CN; and $R_2$ is hydrogen;
$R_3$ is $Cy_1$, wherein $Cy_1$ in $R_3$ is a 3- to 7-membered, preferably 5- to 6-membered, saturated monocyclic ring, which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$; and more preferably $Cy_1$ in $R_3$ is piperidinyl or pyrrolidinyl; wherein said $Cy_1$ is optionally substituted with one or more $R_{10}$;
$R_4$ is hydrogen, $C_{1-4}$alkyl, $R_{12}R_7N$—$C_{0-4}$alkyl or $Cy_2$-$C_{0-4}$alkyl, preferably hydrogen, $C_{1-4}$alkyl, —$NR_7R_{12}$ or $Cy_2$; wherein $Cy_2$ is optionally substituted with one or more $R_{11}$; and
$R_5$ is hydrogen.

In another embodiment, the invention relates to the compounds of formula II wherein:

A is nitrogen and B is carbon;
$R_1$ is hydrogen, halogen, —CN, —$OR_8$ or —$SR_8$, preferably hydrogen or —CN; and $R_2$ is hydrogen;
$R_3$ is $R_9$—$C_{1-4}$alkyl, $Cy_1$ or $Cy_2$-$C_{1-4}$alkyl, wherein $Cy_1$ and $Cy_2$ are optionally substituted with one or more $R_{10}$;
$R_5$ is hydrogen; and
$R_6$ is hydrogen, $C_{1-4}$alkyl, $C_{1-4}$alkoxy$C_{1-4}$alkyl, hydroxy$C_{1-4}$alkyl or $NR_7R_{12}$—$C_{1-4}$alkyl, preferably hydrogen or $C_{1-4}$alkyl, more preferably $C_{1-4}$alkyl and even more preferably methyl or ethyl.

In another embodiment, the invention relates to the compounds of formula II wherein:

A is nitrogen and B is carbon;
$R_1$ and $R_2$ are hydrogen;
$R_3$ is $R_9$—$C_{1-4}$alkyl, $Cy_1$ or $Cy_2$-$C_{1-4}$alkyl, wherein $Cy_1$ and $Cy_2$ are optionally substituted with one or more $R_{10}$;
$R_5$ is hydrogen; and
$R_6$ is hydrogen, $C_{1-4}$alkyl, $C_{1-4}$alkoxy$C_{1-4}$alkyl, hydroxy$C_{1-4}$alkyl or $NR_7R_{12}$—$C_{1-4}$alkyl, preferably hydrogen or $C_{1-4}$alkyl, more preferably $C_{1-4}$alkyl and even more preferably methyl or ethyl.

In another embodiment, the invention relates to the compounds of formula wherein:

A is nitrogen and B is carbon;
$R_1$ is hydrogen, halogen, —CN, —$OR_8$ or —$SR_8$, preferably hydrogen or —CN, more preferably hydrogen; and $R_2$ is hydrogen;
$R_3$ is $Cy_1$, which is optionally substituted with one or more $R_{10}$;
$R_5$ is hydrogen; and
$R_6$ is hydrogen, $C_{1-4}$alkyl, $C_{1-4}$alkoxy$C_{1-4}$alkyl, hydroxy$C_{1-4}$alkyl or $NR_7R_{12}$—$C_{1-4}$alkyl, preferably hydrogen or $C_{1-4}$alkyl, more preferably $C_{1-4}$alkyl and even more preferably methyl or ethyl.

In another embodiment, the invention relates to the compounds of formula II wherein:

A is nitrogen and B is carbon;
$R_1$ is hydrogen, halogen, —CN, —$OR_8$ or —$SR_8$, preferably hydrogen or —CN, more preferably hydrogen; and $R_2$ is hydrogen;
$R_3$ is $Cy_1$, wherein $Cy_1$ in $R_3$ is a 3- to 7-membered monocyclic ring, which is saturated, partially unsaturated or aromatic, and which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$; and wherein said $Cy_1$ is optionally substituted with one or more $R_{10}$;
$R_5$ is hydrogen; and
$R_6$ is hydrogen, $C_{1-4}$alkyl, $C_{1-4}$alkoxy$C_{1-4}$alkyl, hydroxy$C_{1-4}$alkyl or $NR_7R_{12}$—$C_{1-4}$alkyl, preferably hydrogen or $C_{1-4}$alkyl, more preferably $C_{1-4}$alkyl and even more preferably methyl or ethyl.

In another embodiment, the invention relates to the compounds of formula II wherein:

A is nitrogen and B is carbon;
$R_1$ is hydrogen, halogen, —CN, —$OR_8$ or —$SR_8$, preferably hydrogen or —CN; and $R_2$ is hydrogen;
$R_3$ is $Cy_1$, wherein $Cy_1$ in $R_3$ is a 3- to 7-membered, preferably 5- to 6-membered, saturated monocyclic ring, which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$; and more preferably $Cy_1$ in $R_3$ is piperidinyl or pyrrolidinyl, even more preferably piperidin-3-yl or pyrrolidin-3-yl; wherein said $Cy_1$ is optionally substituted with one or more $R_{10}$;
$R_5$ is hydrogen; and $R_6$ is hydrogen, $C_{1-4}$alkyl, $C_{1-4}$alkoxy$C_{1-4}$alkyl, hydroxy$C_{1-4}$alkyl or $NR_7R_{12}$—$C_{1-4}$alkyl, preferably hydrogen or $C_{1-4}$alkyl, more preferably $C_{1-4}$alkyl, and even more preferably methyl or ethyl.

In another embodiment, the invention relates to the compounds of formula II wherein:

A is nitrogen and B is carbon;
$R_1$ is hydrogen or —CN, preferably hydrogen; and $R_2$ is hydrogen;
$R_3$ is a cycle of formula $Cy_{1a}$ or $Cy_{1b}$;
$R_5$ is hydrogen; and
$R_6$ is hydrogen, $C_{1-4}$alkyl, $C_{1-4}$alkoxy$C_{1-4}$alkyl, hydroxy$C_{1-4}$alkyl, $R_{12}R_7N$—$C_{1-4}$alkyl, $R_{16}CO$—$C_{0-4}$alkyl or $R_{16}CO_2$—$C_{0-4}$alkyl, preferably $C_{1-4}$alkyl, $C_{1-4}$alkoxy$C_{1-4}$alkyl, hydroxy$C_{1-4}$alkyl, $R_{12}R_7C_{1-4}$alkyl, $R_{16}CO$—$C_{0-4}$alkyl or $R_{16}CO_2$—$C_{0-4}$alkyl, more preferably $C_{1-4}$alkyl, and even more preferably methyl or ethyl.

In another embodiment, the invention relates to the compounds of formula II wherein:

A is nitrogen and B is carbon;
$R_1$ is hydrogen or —CN, preferably hydrogen; and $R_2$ is hydrogen;
$R_3$ is a cycle of formula $Cy_{1a}$, preferably with (S)-stereochemistry;
$R_5$ is hydrogen; and
$R_6$ is hydrogen, $C_{1-4}$alkyl, $C_{1-4}$alkoxy$C_{1-4}$alkyl, hydroxy$C_{1-4}$alkyl, $R_{12}R_7N$—$C_{1-4}$alkyl, $R_{16}CO$—$C_{0-4}$alkyl or $R_{16}CO_2$—$C_{0-4}$alkyl, preferably $C_{1-4}$alkyl, $C_{1-4}$alkoxy$C_{1-4}$alkyl, hydroxy$C_{1-4}$alkyl, $R_{16}CO$—$C_{0-4}$alkyl or $R_{16}CO_2$—$C_{0-4}$alkyl, more preferably $C_{1-4}$alkyl, and even more preferably methyl or ethyl.

In another embodiment, the invention relates to the compounds of formula II wherein:

$R_3$ is a cycle of formula $Cy_{1a}$ or $Cy_{1b}$;
$R_5$ is hydrogen;
$R_{10}$ is —$COR_{13}$ or —$SO_2R_{13}$ and
$R_{13}$ is $C_{1-4}$alkyl, halo$C_{1-4}$alkyl, $C_{1-4}$alkoxy$C_{1-4}$alkyl, hydroxy$C_{1-4}$alkyl or cyano$C_{1-4}$alkyl, preferably $C_{1-4}$alkyl or cyano$C_{1-4}$alkyl, and more preferably methyl or cyanomethyl.

In another embodiment, the invention relates to the compounds of formula II wherein:

$R_3$ is a cycle of formula $Cy_{1a}$, preferably with (S)-stereochemistry;
$R_5$ is hydrogen;
$R_{10}$ is —$COR_{13}$; and
$R_{13}$ is $C_{1-4}$alkyl, halo$C_{1-4}$alkyl, $C_{1-4}$alkoxy$C_{1-4}$alkyl, hydroxy$C_{1-4}$alkyl or cyano$C_{1-4}$alkyl, preferably $C_{1-4}$alkyl or cyano$C_{1-4}$alkyl, and more preferably methyl or cyanomethyl.

In another embodiment, the invention relates to the compounds of formula II wherein:

W is CH;
$R_3$ is a cycle of formula $Cy_{1a}$, preferably with (S)-stereochemistry;
$R_5$ is hydrogen;
$R_{10}$ is —$COR_{13}$; and
$R_{13}$ is $C_{1-4}$alkyl, halo$C_{1-4}$alkyl, $C_{1-4}$alkoxy$C_{1-4}$alkyl, hydroxy$C_{1-4}$alkyl or cyano$C_{1-4}$alkyl, preferably $C_{1-4}$alkyl or cyano$C_{1-4}$alkyl, and more preferably methyl or cyanomethyl.

In another embodiment, the invention relates to the compounds of formula II wherein:

W is N;
$R_3$ is a cycle of formula $Cy_{1a}$, preferably with (S)-stereochemistry;
$R_5$ is hydrogen;
$R_{10}$ is —$COR_{13}$; and $R_{13}$ is $C_{1-4}$alkyl, halo$C_{1-4}$alkyl, $C_{1-4}$alkoxy$C_{1-4}$alkyl, hydroxy$C_{1-4}$alkyl or cyano$C_{1-4}$alkyl, preferably $C_{1-4}$alkyl or cyano$C_{1-4}$alkyl, and more preferably methyl or cyanomethyl.

In another embodiment, the invention relates to the compounds of formula II wherein:

A is nitrogen and B is carbon;
$R_1$ is hydrogen or —CN, preferably hydrogen; and $R_2$ is hydrogen;
$R_3$ is a cycle of formula $Cy_{1a}$, preferably with (S)-stereochemistry;
$R_5$ is hydrogen; and
$R_{10}$ is —$COR_{13}$.

In another embodiment, the invention relates to the compounds of formula II wherein:

A is nitrogen and B is carbon;
$R_1$ is hydrogen or —CN, preferably hydrogen; and $R_2$ is hydrogen;
$R_3$ is a cycle of formula $Cy_{1a}$, preferably with (S)-stereochemistry;
$R_5$ is hydrogen;
$R_{10}$ is —$COR_{13}$; and
$R_{13}$ is $C_{1-4}$alkyl, halo$C_{1-4}$alkyl, $C_{1-4}$alkoxy$C_{1-4}$alkyl, hydroxy$C_{1-4}$alkyl or cyano$C_{1-4}$alkyl, preferably $C_{1-4}$alkyl or cyano$C_{1-4}$alkyl, and more preferably methyl or cyanomethyl.

In another embodiment, the invention relates to the compounds of formula II wherein:

$R_3$ is a cycle of formula $Cy_{1a}$ or $Cy_{1b}$;
$R_5$ is hydrogen;
$R_6$ is hydrogen, $C_{1-4}$alkyl, $C_{1-4}$alkoxy$C_{1-4}$alkyl, hydroxy$C_{1-4}$alkyl, $R_{12}R_7N$—$C_{1-4}$alkyl, $R_{16}CO$—$C_{0-4}$alkyl or $R_{16}CO_2$—$C_{0-4}$alkyl, preferably $C_{1-4}$alkyl, $C_{1-4}$alkoxy$C_{1-4}$alkyl, hydroxy$C_{1-4}$alkyl, $R_{12}R_7N$—$C_{1-4}$alkyl, $R_{16}CO$—$C_{0-4}$alkyl or $R_{16}CO_2$—$C_{0-4}$alkyl, more preferably $C_{1-4}$alkyl, and even more preferably methyl or ethyl;
$R_{10}$ is —$COR_{13}$ or —$SO_2R_{13}$; and
$R_{13}$ is $C_{1-4}$alkyl, halo$C_{1-4}$alkyl, $C_{1-4}$alkoxy$C_{1-4}$alkyl, hydroxy$C_{1-4}$alkyl or cyano$C_{1-4}$alkyl, preferably $C_{1-4}$alkyl or cyano$C_{1-4}$alkyl, and more preferably methyl or cyanomethyl.

In another embodiment, the invention relates to the compounds of formula II wherein:

$R_3$ is a cycle of formula $Cy_{1a}$, preferably with (S-stereochemistry;
$R_5$ is hydrogen;
$R_6$ is hydrogen, $C_{1-4}$alkyl, $C_{1-4}$alkoxy$C_{1-4}$alkyl, hydroxy$C_{1-4}$alkyl, $R_{12}R_7N$—$C_{1-4}$alkyl, $R_{16}CO$—$C_{0-4}$alkyl or $R_{16}CO_2$—$C_{0-4}$alkyl, preferably $C_{1-4}$alkyl, $C_{1-4}$alkoxy-$C_{1-4}$alkyl, hydroxy$C_{1-4}$alkyl, $R_{12}R_7N$—$C_{1-4}$alkyl, $R_{16}CO$—$C_{0-4}$alkyl or $R_{16}CO_2$—$C_{0-4}$alkyl, more preferably $C_{1-4}$alkyl, and even more preferably methyl or ethyl;
$R_{10}$ is —$COR_{13}$; and
$R_{13}$ is $C_{1-4}$alkyl, halo$C_{1-4}$alkyl, $C_{1-4}$alkoxy$C_{1-4}$alkyl, hydroxy$C_{1-4}$alkyl or cyano$C_{1-4}$alkyl, preferably $C_{1-4}$alkyl or cyano$C_{1-4}$alkyl, and more preferably methyl or cyanomethyl.

In another embodiment, the invention relates to the compounds of formula II wherein:

A is nitrogen and B is carbon;
$R_1$ is hydrogen or —CN, preferably hydrogen; and $R_2$ is hydrogen;
$R_3$ is a cycle of formula $Cy_{1a}$ or $Cy_{1b}$;
$R_5$ is hydrogen;
$R_6$ is hydrogen, $C_{1-4}$alkyl, $C_{1-4}$alkoxy$C_{1-4}$alkyl, hydroxy$C_{1-4}$alkyl, $R_{12}R_7N$—$C_{1-4}$alkyl, $R_{16}CO$—$C_{0-4}$alkyl or $R_{16}CO_2$—$C_{0-4}$alkyl, preferably $C_{1-4}$alkyl, $C_{1-4}$alkoxy$C_{1-4}$alkyl, hydroxy$C_{1-4}$alkyl, $R_{12}R_7N$—$C_{1-4}$alkyl, $R_{16}CO$—$C_{0-4}$alkyl or $R_{16}CO_2$—$C_{0-4}$alkyl, more preferably $C_{1-4}$alkyl, and even more preferably methyl or ethyl; and
$R_{10}$ is —$COR_{13}$ or —$SO_2R_{13}$.

In another embodiment, the invention relates to the compounds of formula II wherein:

A is nitrogen and B is carbon;
$R_1$ is hydrogen or —CN, preferably hydrogen; and $R_2$ is hydrogen;
$R_3$ is a cycle of formula $Cy_{1a}$, preferably with (S)-stereochemistry;
$R_5$ is hydrogen;
$R_6$ is hydrogen, $C_{1-4}$alkyl, $C_{1-4}$alkoxy$C_{1-4}$alkyl, hydroxy$C_{1-4}$alkyl, $R_{12}R_7N$—$C_{1-4}$alkyl, $R_{16}CO$—$C_{0-4}$alkyl or $R_{16}CO_2$—$C_{0-4}$alkyl, preferably $C_{1-4}$alkyl, $C_{1-4}$alkoxy$C_{1-4}$alkyl, hydroxy$C_{1-4}$alkyl, $R_{12}R_7N$—$C_{1-4}$alkyl, $R_{16}CO$—$C_{0-4}$alkyl or $R_{16}CO_2$—$C_{0-4}$alkyl, more preferably $C_{1-4}$alkyl, and even more preferably methyl or ethyl;
$R_{10}$ is —$COR_{13}$; and
$R_{13}$ is $C_{1-4}$alkyl, halo$C_{1-4}$alkyl, $C_{1-4}$alkoxy$C_{1-4}$alkyl, hydroxy$C_{1-4}$alkyl or cyano$C_{1-4}$alkyl, preferably $C_{1-4}$alkyl or cyano$C_{1-4}$alkyl, and more preferably methyl or cyanomethyl.

In another embodiment, the invention relates to the compounds of formula II wherein:

A is nitrogen and B is carbon;
W is CH;
$R_1$ is hydrogen or —CN, preferably hydrogen; and $R_2$ is hydrogen;
$R_3$ is a cycle of formula $Cy_{1a}$, preferably with (S)-stereochemistry;
$R_5$ is hydrogen;
$R_6$ is hydrogen, $C_{1-4}$alkyl, $C_{1-4}$alkoxy$C_{1-4}$alkyl, hydroxy$C_{1-4}$alkyl, $R_{12}R_7N$—$C_{1-4}$alkyl, $R_{16}CO$—$C_{0-4}$alkyl or $R_{16}CO_2$—$C_{0-4}$alkyl, preferably $C_{1-4}$alkyl, $C_{1-4}$alkoxy$C_{1-4}$alkyl, hydroxy$C_{1-4}$alkyl, $R_{12}R_7N$—$C_{1-4}$alkyl, $R_{16}CO$—$C_{0-4}$alkyl or $R_{16}CO_2$—$C_{0-4}$alkyl, more preferably $C_{1-4}$alkyl, and even more preferably methyl or ethyl;
$R_{10}$ is —$COR_{13}$; and
$R_{13}$ is $C_{1-4}$alkyl, halo$C_{1-4}$alkyl, $C_{1-4}$alkoxy-$C_{1-4}$alkyl, hydroxy$C_{1-4}$alkyl or cyano$C_{1-4}$alkyl, preferably $C_{1-4}$alkyl or cyano$C_{1-4}$alkyl and more preferably methyl or cyanomethyl.

In another embodiment, the invention relates to the compounds of formula II wherein:

A is nitrogen and B is carbon;
W is N;
$R_1$ is hydrogen or —CN, preferably hydrogen; and $R_2$ is hydrogen;
$R_3$ is a cycle of formula $Cy_{1a}$, preferably with (S)-stereochemistry;
$R_5$ is hydrogen;
$R_6$ is hydrogen, $C_{1-4}$alkyl, $C_{1-4}$alkoxy$C_{1-4}$alkyl, hydroxy$C_{1-4}$alkyl, $R_{12}R_7N$—$C_{1-4}$alkyl, $R_{16}CO$—$C_{0-4}$alkyl or $R_{16}CO_2$—$C_{0-4}$alkyl, preferably $C_{1-4}$alkyl, $C_{1-4}$alkoxy$C_{1-4}$alkyl, hydroxy$C_{1-4}$alkyl, $R_{12}R_7N$—$C_{1-4}$alkyl, $R_{16}CO$—$C_{0-4}$alkyl or $R_{16}CO_2$—$C_{0-4}$alkyl, more preferably $C_{1-4}$alkyl, and even more preferably methyl or ethyl;
$R_{10}$ is —$COR_{13}$; and
$R_{13}$ is $C_{1-4}$alkyl, halo$C_{1-4}$alkyl, $C_{1-4}$alkoxy$C_{1-4}$alkyl, hydroxy$C_{1-4}$alkyl or cyano$C_{1-4}$alkyl, preferably $C_{1-4}$alkyl or cyano$C_{1-4}$alkyl, and more preferably methyl or cyanomethyl.

In another embodiment, the invention relates to the compounds of formula II wherein:

A is nitrogen and B is carbon;
$R_1$ is hydrogen or —CN, preferably hydrogen; and $R_2$ is hydrogen;
$R_3$ is a cycle of formula $Cy_{1a}$, preferably with the (S)-stereochemistry;
$R_5$ is hydrogen;
$R_6$ is $C_{1-4}$alkyl, preferably methyl or ethyl;
$R_{10}$ is —$COR_{13}$; and
$R_{13}$ is $C_{1-4}$alkyl or cyano$C_{1-4}$alkyl, preferably methyl or cyanomethyl.

In another embodiment, the invention relates to the compounds of formula II wherein:

A is nitrogen and B is carbon;
W is CH;
$R_1$ is hydrogen or —CN, preferably hydrogen; and $R_2$ is hydrogen;
$R_3$ is a cycle of formula $Cy_{1a}$, preferably with the (S)-stereochemistry;
$R_5$ is hydrogen;
$R_6$ is $C_{1-4}$alkyl, preferably methyl or ethyl;
$R_{10}$ is —$COR_{13}$; and
$R_{13}$ is $C_{1-4}$alkyl or cyano$C_{1-4}$alkyl, preferably methyl or cyanomethyl.

In another embodiment, the invention relates to the compounds of formula II wherein:

A is nitrogen and B is carbon;
W is N;
$R_1$ is hydrogen or —CN, preferably hydrogen; and $R_2$ is hydrogen;
$R_3$ is a cycle of formula $Cy_{1a}$, preferably with the (S)-stereochemistry;
$R_5$ is hydrogen;
$R_6$ is $C_{1-4}$alkyl, preferably methyl or ethyl;
$R_{10}$ is —$COR_{13}$; and
$R_{13}$ is $C_{1-4}$alkyl or cyano$C_{1-4}$alkyl, preferably methyl or cyanomethyl.

In another embodiment, the invention relates to the compounds of formula II wherein:

A is nitrogen and B is carbon;
$R_1$ is hydrogen and $R_2$ is hydrogen;
$R_3$ is a cycle of formula $Cy_{1a}$ with the (S)-stereochemistry;
$R_5$ is hydrogen;
$R_6$ is $C_{1-4}$alkyl, preferably methyl or ethyl;
$R_{10}$ is —$COR_{13}$; and
$R_{13}$ is $C_{1-4}$alkyl or cyano$C_{1-4}$alkyl, preferably methyl or cyanomethyl.

In another embodiment, the invention relates to the compounds of formula II wherein:

A is nitrogen and B is carbon;
$R_1$ is hydrogen or —CN, preferably hydrogen; and $R_2$ is hydrogen;
$R_3$ is a cycle of formula $Cy_{1b}$;
$R_5$ is hydrogen;
$R_6$ is $C_{1-4}$alkyl, preferably methyl or ethyl; and $R_{10}$ is —$SO_2R_{13}$.

Furthermore, the present invention covers all possible combinations of the particular and preferred embodiments described above.

In another embodiment, the invention relates to a compound of formula I or II selected from the list of compounds described in examples 1 to 37.

In another embodiment, the invention relates to a compound of formula I or II that provides more than 50% inhibition of JAK3 activity at 10 μM, more preferably at 1 μM and still more preferably at 0.1 μM, in a JAK3 assay such as the one described in example 38.

In an additional embodiment, the invention relates to a compound according to formula I or II that provides more than 50% inhibition of JAK2 activity at 10 μM, more preferably at 1 μM and still more preferably at 0.1 μM, in a JAK2 assay such as the one described in example 39.

The compounds of the present invention contain one or more basic nitrogens and may, therefore, form salts with organic or inorganic acids. Examples of these salts include: salts with inorganic acids such as hydrochloric acid, hydrobromic acid, hydroiodic acid, nitric acid, perchloric acid, sulfuric acid or phosphoric acid; and salts with organic acids such as methanesulfonic acid, trifluoromethanesulfonic acid, ethanesulfonic acid, benzenesulfonic acid, p-toluenesulfonic acid, fumaric acid, oxalic acid, acetic acid, maleic acid, ascorbic acid, citric acid, lactic acid, tartaric acid, malonic acid, glycolic acid, succinic acid and propionic acid, among others. Some of the compounds of the present invention may contain one or more acidic protons and, therefore, they may also form salts with bases. Examples of these salts include: salts with inorganic cations such as sodium, potassium, calcium, magnesium, lithium, aluminium, zinc, et; and salts formed with pharmaceutically acceptable amines such as ammonia, alkylamines, hydroxylalkylamines, lysine, arginine, N-methylglucamine, procaine and the like.

There is no limitation on the type of salt that can be used, provided that these are pharmaceutically acceptable when they are used for therapeutic purposes. The term pharmaceutically acceptable salt refers to those salts which are, according to medical judgment, suitable for use in contact with the tissues of humans and other mammals without undue toxicity, irritation, allergic response and the like. Pharmaceutically acceptable salts are well known in the art.

The salts of a compound of formula I or II can be obtained during the final isolation and purification of the compounds of the invention or can be prepared by treating a compound of formula I or II with a sufficient amount of the desired acid or base to give the salt in the conventional manner. The salts of the compounds of formula I or II can be converted into other salts of the compounds of formula I or II by ion exchange using ionic exchange resins.

The compounds of formula I or II and their salts may differ in some physical properties but they are equivalent for the purposes of the present invention. All salts of the compounds of formula I or II are included within the scope of the invention.

The compounds of the present invention may form complexes with solvents in which they are reacted or from which they are precipitated or crystallized. These complexes are known as solvates. As used herein, the term solvate refers to a complex of variable stoichiometry formed by a solute (a compound of formula I or II or a salt thereof) and a solvent. Examples of solvents include pharmaceutically acceptable solvents such as water, ethanol and the like. A complex with water is known as a hydrate. Solvates of compounds of the invention (or salts thereof), including hydrates, are included within the scope of the invention.

The compounds of formula I or II may exist in different physical forms, i.e. amorphous and crystalline forms. Moreover, the compounds of the invention may have the ability to crystallize in more than one form, a characteristic which is known as polymorphism. Polymorphs can be distinguished by various physical properties well known in the art such as X-ray diffraction pattern, melting point or solubility. All physical forms of the compounds of formula I or N, including all polymorphic forms ("polymorphs") thereof, are included within the scope of the invention.

Some of the compounds of the present invention may exist as several diastereoisomers and/or several optical isomers. Diastereoisomers can be separated by conventional techniques such as chromatography or fractional crystallization. Optical isomers can be resolved by conventional techniques of optical resolution to give optically pure isomers. This resolution can be carried out on any chiral synthetic intermediate or on products of formula I or II. Optically pure isomers can also be individually obtained using enantiospecific synthesis. The present invention covers all individual isomers as well as mixtures thereof (for example racemic mixtures or mixtures of diastereomers), whether obtained by synthesis or by physically mixing them.

The present invention further covers all unlabeled and isotopically labeled forms of the compounds of formula I or II.

The present invention further covers all tautomeric forms of the compounds of formula I or II.

The compounds of formula I or II can be obtained by following the processes described below. As it will be obvious to one skilled in the art, the exact method used to prepare a given compound may vary depending on its chemical structure. Moreover, in some of the processes described below it may be necessary or advisable to protect the reactive or labile groups with conventional protecting groups. Both the nature of these protecting groups and the procedures for their introduction and removal are well known in the art (see for example Greene T. W. and Wuts P. G. M, "Protecting Groups in Organic Synthesis", John Wiley & Sons, $3^{rd}$ edition, 1999). As an example, as protecting group of an amino function the tert-butoxycarbonyl (BOO) group can be used. Whenever a protecting group is present, a later deprotection step will be required, which can be performed under standard conditions in organic synthesis, such as those described in the above-mentioned reference.

In general, compounds of formula I or II can be obtained from a compound of formula VI, as shown in the following scheme:

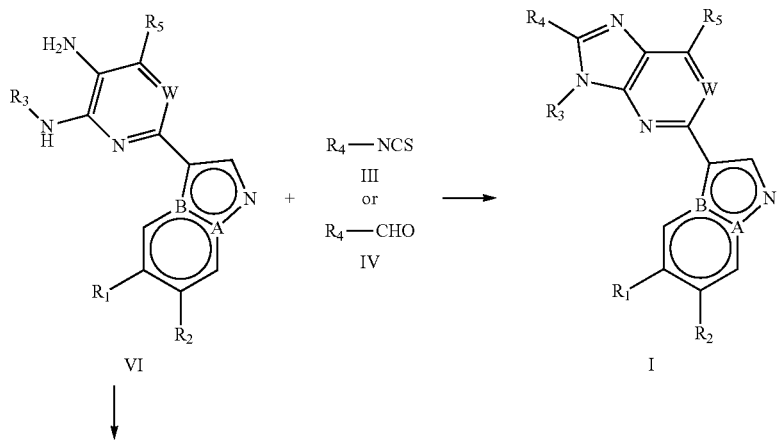

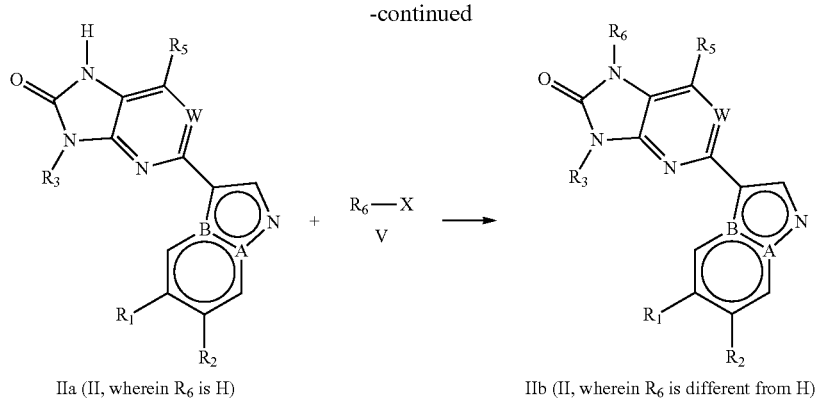

IIa (II, wherein R$_6$ is H)     IIb (II, wherein R$_6$ is different from H)

wherein A, B, W, R$_1$, R$_2$, R$_3$R$_4$ and R$_5$ have the meaning previously described in relation with a compound of formula I or II; R$_6$ in a compound of formula V or IIb has the meaning previously described in relation with a compound of formula I or II, except hydrogen; and X is a leaving group.

The compounds of formula I can be obtained by reacting a compound of formula VI with either the corresponding isothiocyanate III or aldehyde IV.

The reaction with an isothiocyanate III may be performed in the presence of 1-ethyl-3-(3-dimethylaminopropyl)carbodiimide, in a suitable solvent such as dichloromethane, and heating at a suitable temperature usually comprised between 100 and 200° C. The heating may be thermal or by irradiating with microwaves at a wattage that allows reaching the temperature mentioned above.

The reaction between compounds of formula VI and IV can be carried out in a suitable solvent such as ethanol, butanol, N,N-dimethylformamide or dimethylacetamide, in the presence of an acid such as acetic acid, p-toluenesulfonic acid or sodium bisulfite, and heating, preferably at a temperature comprised between 100 and 200° C. The heating may be thermal or by irradiating with microwaves at a wattage that allows reaching the temperature mentioned above. When required, the reaction can be completed by subsequent addition of water.

The compounds of formula II (i.e. compounds of formula IIa and IIb) can be obtained from a compound of formula VI.

The compounds of formula IIa (i.e. a compound of formula II wherein R$_6$ is hydrogen) can be obtained by reaction of a compound of formula VI with a synthetic equivalent for the CO synthon. Any such synthetic equivalent disclosed in the literature can in principle be used, for example 1,1-carbonyldiimidazole (CDI), phosgene, diphosgene or triphosgene. The reaction is conducted in the presence of a base such as N,N-diisopropylethylamine; and in a suitable solvent such as tetrahydrofuran (THF), and preferably at room temperature. The reaction can be completed by subsequent addition of water.

The compounds of formula IIb (i.e. a compound of formula II wherein R$_6$ is different from hydrogen) can be obtained by alkylation of a compound of formula IIa with an alkylating agent R$_6$—X (V), wherein X represents a leaving group and R$_6$ is different from H; suitable examples of X include among others halogen such as Cl, Br or I, mesylate, tosylate or triflate. This reaction may be carried out in the presence of a base such as Cs$_2$CO$_3$, K$_2$CO$_3$, NaOH, tert-BuOK or NaH, in a suitable solvent, such as acetone, toluene, 1,2-dimethoxyethane, and preferably dimethylformamide, at a suitable temperature, comprised between 0° C. and reflux.

The compounds of formula VI can be obtained by reduction of a compound of formula VII as shown in the following scheme:

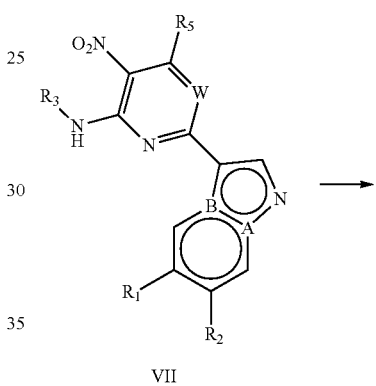

VII

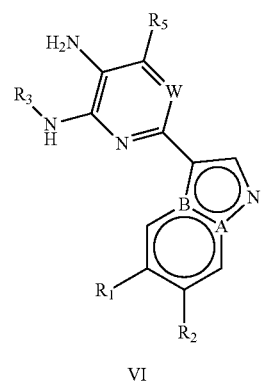

VI wherein A, B, W, R$_1$, R$_2$, R$_3$ and R$_5$ have the meaning previously described in relation with a compound of formula I or II.

The reaction may be carried out with hydrogen gas, using a platinum catalyst, such as PVC in the presence of thiophene in diisopropylethylamine; in a suitable solvent such as EtOH and preferably at room temperature.

The compounds of formula VII can be obtained by reacting a compound of formula VIII with either a compound of formula IX or X, as shown in the following scheme

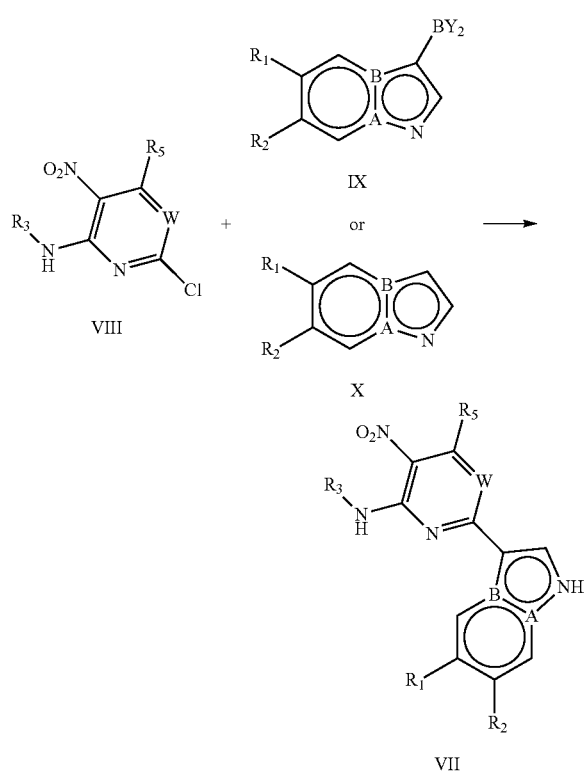

wherein A, B, W, $R_1$, $R_2$, $R_3$ and $R_5$ has the meaning previously described in relation with a compound of formula I or II; and $BY_2$ is a boronic acid or ester.

The reaction between compounds of formula VIII and IX may be carried out using the conditions described in the Literature for Suzuki's coupling reactions. For example, the reaction may be carried out in the presence of a Pd catalyst such as $Pd(PPh_3)_4$; in the presence of a base such as $Na_2CO_3$; in a mixture of solvents such as a dimethoxyethane and water; and heating.

The direct coupling between compounds of formula VIII and X can be performed using a palladium catalyst such as for example tetrakis (triphenylphosphine)palladium(0) (Pd $(PPh_3)_4$) and preferably paladium (II) acetate $Pd(OAc)_2$ in the presence of triphenylphosphine, and a base, such as for example triethylamine and preferably potassium acetate. The reaction is usually carried out under anhydrous and anaerobic conditions. The reaction may be carried out in a solvent such as dioxane, N,N-dimethylformamide, toluene and preferably in dimethylacetamide and heating at a temperature usually comprised between 60° C.-100° C.

Compounds of formula IX and formula X can be easily obtained from commercial compounds by known methods.

Additionally, the compounds of formula VII wherein A is nitrogen and B is carbon (i.e. VIIa) can be obtained by reacting a compound of formula XI with a compound of formula XII, as shown in the following scheme:

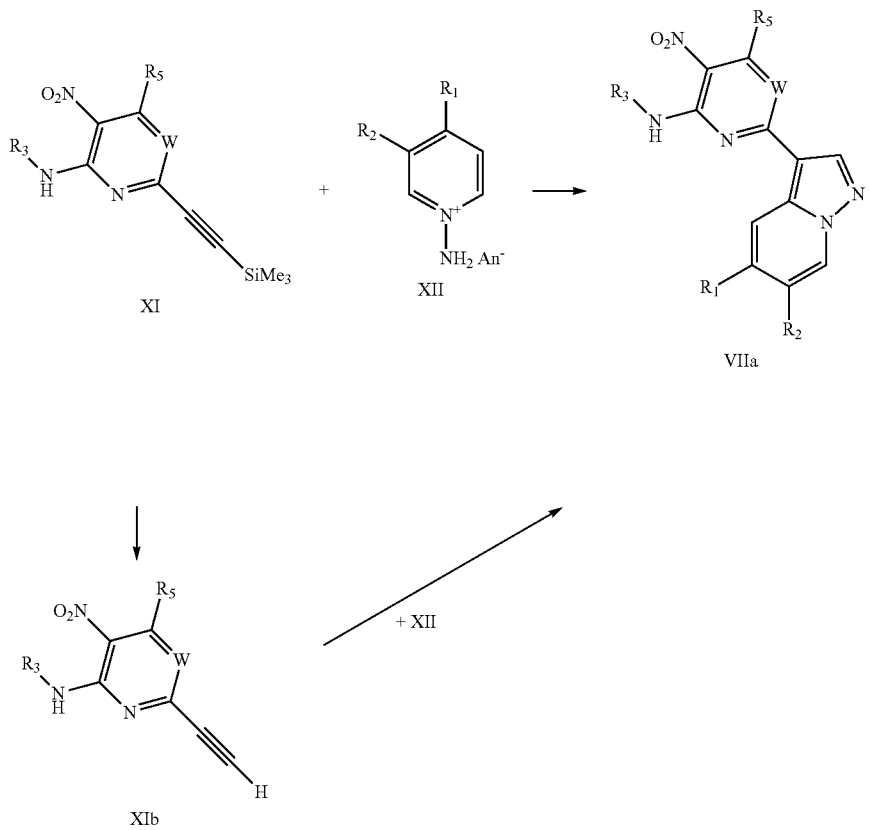

wherein W, $R_1$, $R_2$, $R_3$ and $R_5$ have the meaning previously described in relation with a compound of formula I or II; and An is iodine, 2,4-dinitrophenolate, p-toluensulphonate or 2,4,6-trimethylbencenosulphonate.

The reaction may be carried out in the presence of tetra-n-butylammonium fluoride (TBAF) in THF and of a base such as 1,5-diazabicyclo[4.3.0]non-5-ene (DBN) or 1,4-diazabicyclo[2.2.2]octane (DABCO), preferably 1,8-diazabicyclo[5.4.0]undec-7-ene (DBU), in a solvent such as N,N-dimethylformamide, dimethylsulfoxide, dichloromethane, toluene or acetonitrile, preferably acetonitrile, and at a temperature comprised between −78° C. and room temperature.

Alternatively the compounds of formula VIIa can be obtained by reacting a compound of formula XII with the deprotected derivative of the compound of formula XI (XIb) obtained by using standard conditions.

The compounds of formula XII can be obtained by reaction of a compound of formula XIII with aminosulfonic acid in the presence of a HI aqueous solution; and of a base such as $K_2CO_3$, NaOH or KOH; in a solvent such as dichloromethane, tetrahydrofuran, water, ethanol, methanol, isopropanol or acetonitrile; and heating preferably at reflux, as shown in the following scheme:

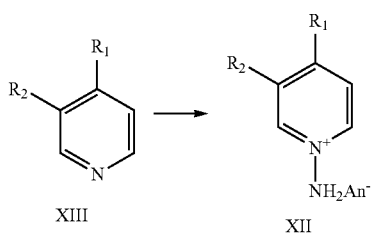

wherein $R_1$ and $R_2$ have the meaning previously described in relation with a compound of formula I or II; and An has the meaning described above.

The compounds of formula XI can be obtained by reaction of a compound of formula VIII with trimethylsilylacetylene, as shown in the following scheme:

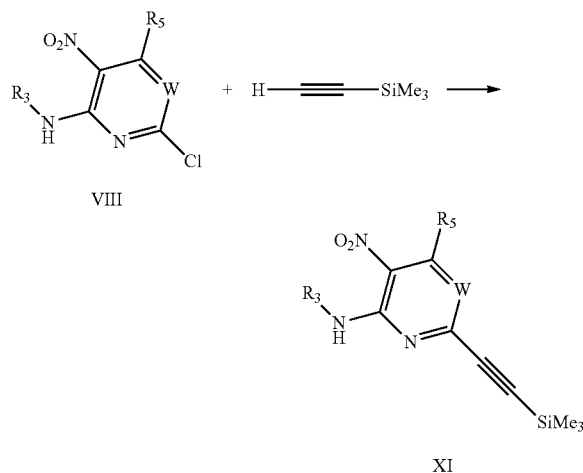

wherein W, $R_3$ and $R_5$ have the meaning previously described in relation with a compound of formula I or II.

The reaction with trimethylsilylacetylene may be carried out under Sonogashira conditions, using a palladium catalyst such as for example tetrakis (triphenylphosphino)palladium (0) (Pd(PPh$_3$)$_4$), preferably bis(triphenylphosphino)dichloropalladium(II) (Pd(Ph$_3$P)$_2$Cl$_2$) in the presence of triphenylphospine, a Cu (I) catalyst as a cocatalyst, such as CuI, and a base, such as diethylamine. N,N-diisopropylethylamine, triethylamine or isopropylethylamine. The reaction is usually carried out under anhydrous and anaerobic conditions. The reaction may be carried out in a solvent such as dioxane, N,N-dimethylformamide, tetrahydrofuran or toluene, at room temperature or by heating.

The compounds of formula VIII can be obtained by reaction of a compound of formula XIV with a compound of formula XV, as shown in the following scheme:

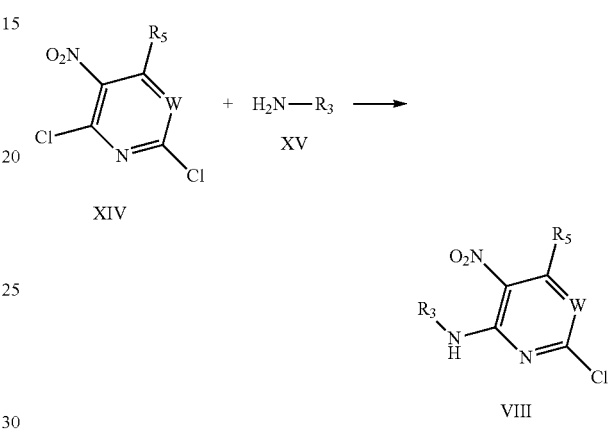

wherein W, $R_3$ and $R_5$ have the meaning previously described in relation with a compound of formula I or II.

The reaction between the compounds of formula XIV and XV may be carried out in the presence of a base such as diisopropylethylamine, diethylamine or triethylamine, in a suitable solvent such as THF or acetonitrile, and at a temperature comprised between −78° C. and room temperature.

The compounds of formula XIV and XV are commercial or may be easily obtained from commercial compounds using standard procedures.

Furthermore, some compounds of the present invention can also be obtained from other compounds of formula I or II by appropriate conversion reactions of functional groups in one or several steps, using well-known reactions in organic chemistry under the standard experimental conditions. Said transformations can be carried out for example upon $R_3$ and include, for example the substitution of a primary or secondary amine by treatment with an alkylating agent, the reaction of an acid or ester with an amine to obtain the corresponding amide, the conversion of an amine into a sulfonamide and the hydrolysis of an ester to obtain a carboxylic acid. In some of these conversions it may be necessary or advisable to protect the reactive or unstable groups by means of conventional protective groups.

As it will be obvious to those skilled in the art, these interconversion reactions can be carried out upon the compounds of formula I or II as well as upon any suitable synthesis intermediate thereof.

As mentioned above, the compounds of the present invention act by inhibiting JAK/STAT signaling pathways, particularly by inhibiting JAK3 activity. Therefore, the compounds of the invention are expected to be useful to treat or prevent diseases in which JAKs, particularly JAK3, play a role in mammals, including human beings. These diseases include, but are not limited to, transplant rejection; immune, autoimmune and inflammatory diseases; neurodegenerative diseases; and proliferative disorders (see e.g. O'Shea J. J. et al, Nat. Rev. Drug. Discov, 2004, 3(7):555-64; Cetkovic-Cvrlje M. et al, Curr. Pharm, Des, 2004, 10(15):1767-84; Cetkovic-Cvrlje M. at al, Arch. Immunol. Ther. Exp. (Warsz), 2004, 52(2):69-82).

Acute or chronic transplant rejection reactions that can be treated or prevented with the compounds of the present invention include any kind of cell, tissue or organ xenotransplants or allografts, such as of heart, lung, liver, kidney, pancreas, uterus, joints, pancreatic islets, bone marrow, limbs, cornea, skin, hepatocytes, pancreatic beta cells, pluripotential cells, neuronal cells and myocardial cells, as well as graft-versus-host reactions (see e.g. Rousvoal G. et al, Transpl. Int. 2006, 19(12):1014-21; Borie D C. et al, Transplantation 2005, 79(7):791-801; Paniagua R. et al, Transplantation 2005, 80(9):1283-92; Higuchi T. et al., J. Heart Lung Transplant. 2005, 24(10):1557-64; Sëmann M D, at al, Transpl Int 2004, 17(9):481-89; Silva Jr H T. et al, Drugs 2006, 66(13):1665-1684).

Immune, autoimmune or inflammatory diseases that can be treated or prevented with the compounds of the present invention include among others, rheumatic diseases (e.g. rheumatoid arthritis and psoriatic arthritis), autoimmune hematological disorders (e.g. hemolytic anemia, aplastic anemia, idiopathic thrombocytopenia, and neutropenia), autoimmune gastritis and inflammatory bowel diseases (e.g. ulcerative colitis and Crohn's disease), scleroderma, type I diabetes and complications from diabetes, type B hepatitis, type C hepatitis, primary biliary cirrhosis, myasthenia gravis, multiple sclerosis, systemic lupus erythematosus, psoriasis, atopic dermatitis, contact dermatitis, eczema, skin sunburns, suppression of HIV replication, infertility of autoimmune origin, autoimmune thyroid disease (Grave's disease), interstitial cystitis, mast cell-mediated allergic reactions such as asthma, angiodema, anaphylaxis, bronchitis, rhinitis and sinusitis, and inflammatory or autoimmune ocular diseases such as dry eye syndrome, glaucoma, Sjögren's syndrome, uveitis and retinopathy of prematurity (see e.g. Sorbera L A. et al, Drugs of the Future 2007, 32(4674-680; O'Shea J. J. et al, Nat. Rev. Drug. Discov. 2004, 3(7):555-64; Cetkovic-Cvrlje M. et al, Curr, Pharm. Des. 2004, 10(15):1767-84; Muller-Ladner U. et al, J. Immunol. 2000, 164(7): 3894-3901; Walker J G. et al, Ann. Rheum. Dis. 2006, 65(2):149-56; Milici A J. et al, Arthritis Rheum 0.2006, 54 (9, Suppl): abstr 789; Kremer J M. et al, Arthritis Rheum. 2006, 54, 4116, presentation no. L40; Cetkovic-Cvrlje M. et al, Arch Immunol. Ther. Exp. (Warsz), 2004, 52(2):69-82; Malaviya R. et al, J. Pharmacol. Exp. Ther. 2000, 295(3):912-26; Malaviya R. et al, J. Biol. Chem. 1999, 274(38):27028-38; Wilkinson B et al, Ann. Rheum. Dis. 2007, 66(Suppl 2): Abst, THU0099; Matsumoto M. et al, J. Immunol. 1999, 162(2):1056-63, West K., Curr Opin Inventig Drugs 2009:10(5):491-504, Huang Y. et al., Exp Eye res 2007:85(5):684-95, Killedar S Y et al, Laboratory investigation 2006:86:1243-1260, Egwuagu C. E., Cytokine 2009:47(3):149-156, Byfield G., Investigative Ophtalmology &Viral Science 2009:503360).

Neurodegenerative diseases that can be treated or prevented with the compounds of the present invention include, among others, amyotrophic lateral sclerosis and Alzheimer's disease (see e.g. Trieu V N. et al, Biochem. Biophys, Res. Commun. 2000, 267(1):22-5).

Proliferative disorders that can be treated or prevented with the compounds of the present invention include, among others, leukemias, lymphomas, glioblastoma multiforme, colon carcinoma, as well as thromboembolic and allergic complications associated with these diseases (see e.g. Sudbeck E A. et al, Clin. Cancer Res. 1999, 5(6):1569-82; Narla R K. et al, Olin. Cancer Res. 1998, 4(10):2463-71; Lin Q. et al, Am J. Pathol. 2005, 167(4):969-80; Tibbles H E. et al, J. Biol. Chem. 2001, 276(21):17815-22).

It has been found that certain compounds of formula I or II, besides inhibiting JAK3 activity, also inhibit JAK2 kinase to varying degrees, and therefore can also be useful for the treatment or prevention of any disease mediated by JAK2 kinase. A group of such JAK2-mediated diseases are myeloproliferative disorders, including polycythemia vera, essential thrombocytosis, idiopathic myelofibrosis, chronic myelogenous leukemia, hypereosinophilic syndrome, chronic neutrophilic leukemia, chronic myelomonocytic leukemia, myelofibrosis with myeloid metaplasia, chronic basophilic leukemia, chronic eosinophilic leukemia, systemic mastocytosis and myelodisplastic syndrome (see e.g. Geron I. et al, Cancer cell 2008, 13:321-330; Pardanani A. et al, Leukemia 2007, 21(8):1658-68; Mathur A. et al, Biochem Pharmacol 2009, 78(4):382-9; Manshouri T. et al, Cancer Sci, 2008, 99(6):1265-73; Wernig G. et al, Cancer cell 2008, 13(4):311-20. Elizabeth O. et al, Blood, 111(12: 5663-5671).

Compounds of formula I or II wherein $R_1$ and $R_2$ are hydrogen have been found to be particularly useful as JAK2 inhibitors, and thus can be particularly useful, in addition to treating or preventing all the diseases mentioned in the preceding paragraphs, also for the treatment or prevention of myeloproliferative disorders (MPD).

Thus, another aspect of the invention relates to a compound of formula I or II, or a pharmaceutically acceptable salt thereof for use in the treatment or prevention of a disease mediated by JAK2. More preferably, the disease mediated by JAK2 is a myeloproliferative disorder. In a preferred embodiment, the compounds of formula I or II are those wherein $R_1$ and $R_2$ are hydrogen.

Another aspect of the present invention relates to the use of a compound of formula I or II or a pharmaceutically acceptable salt thereof for the manufacture of a medicament for the treatment or prevention of a disease mediated by JAK2. More preferably, the disease mediated by JAK2 is a myeloproliferative disorder. In a preferred embodiment, the compounds of formula I or II are those wherein $R_1$ and $R_2$ are hydrogen.

Another aspect of the present invention relates to a method of treating or preventing a disease mediated by JAK2 in a subject in need thereof, especially a human being, which comprises administering to said subject a compound of formula I or II, or a pharmaceutically acceptable salt thereof. More preferably, the disease mediated by JAK2 is a myeloproliferative disease. In a preferred embodiment, the compounds of formula I or II are those wherein $R_1$ and $R_2$ are hydrogen Another aspect of the invention relates to a compound of formula I or II, or a pharmaceutically acceptable salt thereof for use in the treatment or prevention of a myeloproliferative disorder. In a preferred embodiment, the myeloproliferative disorder is selected from polycythemia vera, essential thrombocytosis, idiopathic myelofibrosis, chronic myelogenous leukemia, hypereosinophilic syndrome, chronic neutrophilic leukemia, chronic myelomonocytic leukemia, myelofibrosis with myeloid metaplasia, chronic basophilic leukemia, chronic eosinophilic leukemia, systemic mastocytosis and myelodisplastic syndrome. In a preferred embodiment, the compounds of formula I or II are those wherein $R_1$ and $R_2$ are hydrogen.

Another aspect of the invention relates to the use of a compound of formula I or II or a pharmaceutically acceptable salt thereof for the manufacture of a medicament for the treatment or prevention of a myeloproliferative disorder. In a preferred embodiment, the myeloproliferative disorder is selected from polycythemia vera, essential thrombocytosis, idiopathic myelofibrosis, chronic myelogenous leukemia, hypereosinophilic syndrome, chronic neutrophilic leukemia, chronic myelomonocytic leukemia, myelofibrosis with myeloid metaplasia, chronic basophilic leukemia, chronic eosinophilic leukemia, systemic mastocytosis and myelodisplastic syndrome. In a preferred embodiment, the compounds of formula I or II are those wherein $R_1$ and $R_2$ are hydrogen.

Another aspect of the present invention relates to a method of treating or preventing a myeloproliferative disorder in a subject in need thereof, especially a human being, which comprises administering to said subject a compound of formula I or II or a pharmaceutically acceptable salt thereof. In a preferred embodiment, the myeloproliferative disorder is selected from polycythemia vera, essential thrombocytosis, idiopathic myelofibrosis, chronic myelogenous leukemia, hypereosinophilic syndrome, chronic neutrophilic leukemia, chronic myelomonocytic leukemia, myelofibrosis with myeloid metaplasia, chronic basophilic leukemia, chronic eosinophilic leukemia, systemic mastocytosis and myelodisplastic syndrome. In a preferred embodiment, the compounds of formula I or II are those wherein $R_1$ and $R_2$ are hydrogen.

Biological assays that can be used to determine the ability of a compound to inhibit JAKs, particularly JAK3 and JAK2, are well known in the art. For example, a compound to be tested can be incubated in the presence of the desired JAK, such as JAK3 or JAK2, to determine whether inhibition of JAK enzymatic activity occurs, as described in the assay of examples 38 and 39 for JAK3 and JAK2, respectively. Other in vitro useful assays that can be used to measure JAK3-inhibitory activity include cellular assays, for example IL-2-induced proliferation of human T lymphocytes. The immunosuppressive activity of the compounds of the invention can be tested using standard in vivo animal models for immune and autoimmune diseases, which are well known in the art. For example, the following assays can be used: delayed-type hypersensitivity (DTH) (see e.g. the method disclosed in Kudlacz E. at al, Am J. Transplant, 2004, 4(1):51-7, the contents of which are incorporated herein by reference), rheumatoid arthritis models such as collagen-induced arthritis (see e.g. the method disclosed in Holmdahl R et al, APMIS, 1989, 97(7):575-84, the contents of which are incorporated herein by reference), multiple sclerosis models such as experimental autoimmune encephalomyelitis (EAE) (see e.g. the method disclosed in González-Rey et al, Am, J. Pathol. 2006, 168(4): 1179-88, the contents of which are incorporated herein by reference) and transplant rejection models (see e.g. the various animal models disclosed in the references listed above in relation to the treatment of transplant rejection, incorporated herein by reference). The antiproliferative activity of the compounds of the invention can be tested using standard in vivo animal models well known in the art, such as xenograft studies (see e.g Mohammad R H. et al, Pancreas. 1998; 16(1): 19).

For selecting active compounds for JAK3, testing at 10 µM must result in an activity of more than 50% inhibition of JAK3 activity in the test provided in example 38. More preferably, when tested in this assay compounds should exhibit more than 50% inhibition at 1 µM, and still more preferably, they should exhibit more than 50% inhibition at 0.1 µM.

For selecting active compounds for JAK2, testing at 10 µM must result in an activity of more than 50% inhibition of JAK2 activity in the test provided in example 39 More preferably, when tested in this assay compounds should exhibit more than 50% inhibition at 1 µM, and still more preferably, they should exhibit more than 50% inhibition at 0.1 µM.

Assays that can be used to predict the PK profile of a compound are well known in the art. For example, a Caco-2 assay can be used to determine in vitro the potential for oral absorption of a compound. To show a good PK profile the compound must also exhibit a suitable clearance, as determined in a standard test using for example human liver microsomes in an assay such as the one described in example 40.

Standard assays can be used to assess potential toxic effects of drug candidates, all of which are well known in the art. Such tests include e.g. viability assays in different cell lines such as human hepatocyte carcinoma cells (Hep G2), which can be performed following standard procedures, such as the one described in example 41.

The present invention also relates to a pharmaceutical composition that comprises a compound of the present invention (or a pharmaceutically acceptable salt or solvate thereof) and one or more pharmaceutically acceptable excipients. The excipients must be "acceptable" in the sense of being compatible with the other ingredients of the composition and not deleterious to the recipients thereof.

The compounds of the present invention can be administered in the form of any pharmaceutical formulation, the nature of which, as it is well known, will depend upon the nature of the active compound and its route of administration. Any route of administration may be used, for example oral, parenteral, nasal, ocular, rectal and topical administration.

Solid compositions for oral administration include tablets, granulates and capsules. In any case the manufacturing method is based on a simple mixture, dry granulation or wet granulation of the active compound with excipients. These excipients can be, for example, diluents such as lactose, microcrystalline cellulose, mannitol or calcium hydrogenphosphate; binding agents such as for example starch, gelatin or povidone; disintegrants such as sodium carboxymethyl starch or sodium croscarmeliose; and lubricating agents such as for example magnesium stearate, stearic acid or talc. Tablets can be additionally coated with suitable excipients by using known techniques with the purpose of delaying their disintegration and absorption in the gastrointestinal tract and thereby provide a sustained action over a longer period, or simply to improve their organoleptic properties or their stability. The active compound can also be incorporated by coating onto inert pellets using natural or synthetic film-coating agents. Soft gelatin capsules are also possible, in which the active compound is mixed with water or an oily medium, for example coconut oil, mineral oil or olive oil.

Powders and granulates for the preparation of oral suspensions by the addition of water can be obtained by mixing the active compound with dispersing or wetting agents; suspending agents and preservatives. Other excipients can also be added, for example sweetening, flavoring and colouring agents.

Liquid forms for oral administration include emulsions, solutions, suspensions, syrups and elixirs containing commonly used inert diluent, such as purified water, ethanol, sorbitol, glycerol, polyethylene glycols (macrogols) and propylene glycol. Said compositions can also contain coadjuvants such as wetting, suspending, sweetening, flavoring agents, preservatives and buffers.

Injectable preparations, according to the present invention, for parenteral administration, comprise sterile solutions, suspensions or emulsions, in an aqueous or non-aqueous solvent such as propylene glycol, polyethylene glycol or vegetable oils. These compositions can also contain coadjuvants, such as wetting, emulsifying, dispersing agents and preservatives. They may be sterilized by any known method or prepared as sterile solid compositions, which will be dissolved in water or any other sterile injectable medium immediately before use. It is also possible to start from sterile materials and keep them under these conditions throughout all the manufacturing process.

For the rectal administration, the active compound can be preferably formulated as a suppository on an oily base, such as for example vegetable oils or solid semisynthetic glycerides, or on a hydrophilic base such as polyethylene glycols (macrogol).

The compounds of the invention can also be formulated for their topical application for the treatment or prevention of pathologies occurring in zones or organs accessible through this route, such as eyes, skin and the intestinal tract. Formulations include creams, lotions, gels, powders, solutions and patches wherein the compound is dispersed or dissolved in suitable excipients.

For the nasal administration or for inhalation, the compound can be formulated as an aerosol and it can be conveniently released using suitable propellants.

The dosage and frequency of doses will depend upon the nature and severity of the disease to be treated, the age, the general condition and body weight of the patient, as well as the particular compound administered and the route of administration, among other factors. A representative example of a suitable dosage range is from about 0.01 mg/Kg to about 100 mg/Kg per day, which can be administered as a single or divided doses.

The following examples illustrate the scope of the invention.

EXAMPLES

The following abbreviations have been used in the examples:

| | |
|---|---|
| AcOH: | acetic acid |
| AcN: | acetonitrile |
| DBU: | 1,8-diazabicyclo[5.4.0]undec-7-ene |
| DIPEA: | N,N-diisopropylethylamine |
| DMAC: | N,N-dimethylacetamide |
| DMF: | N,N-dimethylformamide |
| EDC: | N-(3-dimethylaminopropyl)-N'-ethylcarbodiimide |
| EtOAc: | ethyl acetate |
| EtOH: | ethanol |
| HATU: | 2-(1H-7-Azabenzotriazol-1-yl)-1,1,3,3-tetramethyl uronium hexafluorophosphate Methanaminium |
| HOBt: | 1-hydroxybenzotriazole |
| HPLC: | high performance liquid chromatography |
| LC-MS: | liquid chromatography-mass spectroscopy |
| MeI: | iodomethane |
| MeOH: | methanol |
| PTSA: | para-toluene sulfonic acid |
| TBAF: | tetrabutylammonium fluoride |
| TBME: | tert-butyl methyl ether |
| TEA: | triethylamine |
| TFA: | trifluoroacetic acid |
| THF: | tetrahydrofurane |
| TLC: | thin layer cromatography |
| $t_R$: | retention time |

One of the following methods was used to determine the LC-MS spectrums:

Method 1: Column SunFire C18 3.5 μm, (100 mm×2.1), flow rate: 0.3 mL/min, eluent A=CH3CN:MeOH 1:1 B=NH$_4$Ac 5 mM pH 7, gradient: 0 min 10% A; 17 min 95% A; 10 min 95% A.

Method 2: Column XBridge, 3.5 μm (50 mm×4.6), temperature: 30° C., flow rate: 2 mL/min, eluent A=NH$_4$HCO$_3$ 10 mM (pH=9). B=AcN, gradient: 0 min 5% B; 4.8 min 100% B;

Method 3: Column XBridge, 3.5 μm (50 mm×4.6), temperature: 50° C., flow rate: 1.6 mL/min, eluent A=NH$_4$HCO$_3$ 10 mM (pH=9), B=AcN, gradient: 0 min 5% B; 3.5 min 1005% B;

Method 4 (Palau): Column Waters Acquity HPLC BEH C18 (1.7 μm, 2.1 mm×50 mm), temperature: 40° C., flow: 0.5 mL/min, eluent: ACN (A)/ammonium bicarbonate 10 mM (B), gradient: 0 min 10% A-3.75 min 90% A Method 5:: Column YMC, 3.5 μm (50 mm×4.6), temperature; 50° C., flow rate: 1.3 mL/min, eluent A=H$_2$O (0.1% HCOOH), B=AcN (0.1% HCOOH), gradient: 0 min 5% B; 3.5 min 100% B.

Reference Example 1

1-Amino-4-trifluoromethylpyridinium 2,4,6-trimethylbenzenesulfonate

To a solution of 4-trifluoromethylpyridine (2.23 g, 15.2 mmol) in CH$_2$Cl$_2$ (66 ml.) at 0° C., O-(mesitylsulfonyl)hydroxylamine (3.27 g, 15.2 mmol) was added. The reaction mixture was stirred at room temperature for 18 h. The reaction mixture was filtered to afford the desired product with quantitative yield.

LC-MS (method 4): $t_R$=1.07 min; m/z=199 (MH$^-$).

Reference Example 2

(S)-3-(4-(1-Acetylpiperidin-3-ylamino)-5-aminopyrimidin-2-yl)pyrazolo[1,5-a]pyridine-5-carbonitrile Following a similar procedure to that described in example 1 (section a to d), but using (S)-1-acetyl-3-aminopiperidine instead of tetrahydro-2H-pyran-4-amine, the desired compound was obtained.

LC-MS (method 3): $t_R$=1.59 min; m/z=377 (MH$^+$).

Following a similar procedure to that described in reference example 2, but using in each case the corresponding starting materials, the following compounds were obtained:

| Reference example | Name | Starting Materials | HPLC method | $t_R$ (min) | m/z |
|---|---|---|---|---|---|
| 2a | (S)-tert-butyl 3-(5-amino-2-(5-methylpyrazolo[1,5-a]pyridin-3-yl)pyrimidin-4-ylamino)piperidine-1-carboxylate | 1-amino-4-methylpyridinium 2,4,6-trimethylbenzenesulfonate (1),, (S)-3-amino-(1-tert-butoxycarbonyl)piperidine and 2,4-dichloro-5-nitropyrimidine | 3 | 2.32 | 424 |

-continued

| Reference example | Name | Starting Materials | HPLC method | $t_R$ (min) | m/z |
|---|---|---|---|---|---|
| 2b | tert-butyl 4-(5-amino-2-(pyrazolo[1,5-a]pyridin-3-yl)pyrimidin-4-ylamino)piperidine-1-carboxylate | 1-aminopyridinium iodide,, 4-amino-(1-tert-butoxycarbonyl)piperidine and 2,4-dichloro-5-nitropyrimidine | 4 | 2.00 | 410 |
| 2c | 2-(pyrazolo[1,5-a]pyridin-3-yl)-N4-(tetrahydro-2H-pyran-4-yl)pyrimidine-4,5-diamine | 1-aminopyridinium iodide, tetrahydro-2H-pyran-4-amine and 2,4-dichloro-5-nitropyrimidine | 3 | 1.55 | 311 |
| 2d | (S)-tert-butyl 3-(3-amino-6-(pyrazolo[1,5-a]pyridin-3-yl)pyridin-2-ylamino)piperidine-1-carboxylate | 1-aminopyridinium iodide, (S)-3-amino-(1-tert-butoxycarbonyl)piperidine and 2,6-dichloro-3-nitropyridine | 3 | 2.43 | 409 |
| 2e | 3-(5-amino-4-(8-fluorochroman-4-ylamino)pyrimidin-2-yl)pyrazolo[1,5-a]pyridine-5-carbonitrile | 1-amino-4-cyanopyridinium 2,4,6-trimethylbenzenesulfonate, 8-fluorochroman-4-amine and 2,4-dichloro-5-nitropyrimidine | 1 | 9.28 | 402 |
| 2f | (S)-3-(6-(1-acetylpiperidin-3-ylamino)-5-aminopyridin-2-yl)pyrazolo[1,5-a]pyridine-5-carbonitrile | 1-amino-4-cyanopyridinium 2,4,6-trimethylbenzenesulfonate, (S)-1-acetyl-3-aminopiperidin and 2,6-dichloro-3-nitropyridine | 3 | 1.58 | 377 |
| 2g | 6-(pyrazolo[1,5-a]pyridin-3-yl)-N2-(tetrahydro-2H-pyran-4-yl)pyridine-2,3-diamine | 1-aminopyridinium iodide, tetrahydro-2H-pyran-4-amine and 2,6-dichloro-3-nitropyridine | 5 | 1.68 | 310 |
| 2h | (S)-tert-butyl 3-(3-amino-6-(5-cyanopyrazolo[1,5-a]pyridin-3-yl)pyridin-2-ylamino)piperidine-1-carboxylate | 1-amino-4-cyanopyridinium 2,4,6-trimethylbenzenesulfonate, (S)-3-amino-(1-tert-butoxycarbonyl)piperidine and 2,6-dichloro-3-nitropyridine | 3 | 2.50 | 434 |
| 2i | 3-(5-amino-4-(trans-4-hydroxycyclohexylamino)pyrimidin-2-yl)pyrazolo[1,5-a]pyridine-5-carbonitrile | 1-amino-4-cyanopyridinium 2,4,6-trimethylbenzenesulfonate, trans-4-aminocyclohexanol and 2,6-dichloro-3-nitropyridine, | 3 | 1.45 | 350 |

(1) described by Zhang at al Journal of Heterocyclic Chemistry: 44; 4; 2007; 919-922

Example 1

3-(8-Oxo-9-tetrahydro-2H-pyran-4-yl-8,9-dihydro-7H-purin-2-yl)pyrazolo[1,5-a]pyridine-5-carbonitrile a) 2-Chloro-5-nitro-N-tetrahydro-2H-pyran-4-ylpyrimidin-4-amine To a solution of 2,4-dichloro-5-nitropyrimidine (1.03 g, 5.15 mmol) in THF (40 mL) at −78° C., DIPEA (2.0 mL, 11.86 mmol) and tetrahydro-2H-pyran-4-amine (0.54 mL, 5.15 mmol) were added. The reaction mixture was stirred from −78 to −50° C. for 5 h. The crude mixture was quenched with H$_2$O (50 mL), extracted with EtOAc (3×40 mL) and the combined organic phases were dried over anhydrous Na$_2$SO$_4$, filtered and concentrated. The crude product thus obtained was chromatographed over silica gel using EtOAc/hexanes mixtures of increasing polarity as eluent, to afford 1.04 g of the desired compound (78% yield).

b) 5-Nitro-N-(tetrahydro-2H-pyran-4-yl)-2-[(trimethylsilyl)ethynyl]pyrimidin-4-amine To a suspension of the compound obtained in the previous section (1.01 g, 3.90 mmol), Pd(PPh$_3$)$_2$Cl$_2$ (137 mg, 0.19 mmol) and CuI (37 mg, 0.19 mmol) in toluene (40 mL), TEA (1.6 mL, 11.7 mmol) and trimethylsilylacetylene (0.7 mL, 5.07 mmol) were added. The reaction mixture was stirred at room temperature for 18 h, quenched with saturated NH$_4$Cl aqueous solution (70 mL) and extracted with EtOAc (3×40 mL). The combined organic phases were dried over anhydrous Na$_2$SO$_4$, filtered and concentrated. The crude residue was chromatographed on a silica gel flash system (SP1 Biotage) using EtOAc/hexanes mixtures of increasing polarity as eluent to afford 0.96 g of the desired product (77% yield).

c) 3-[5-Nitro-4-(tetrahydro-2H-pyran-4-ylamino) pyrimidin-2-yl]pyrazolo[1,5-a]pyridine-5-carbonitrile To a suspension of the compound obtained in the previous section (500 mg, 1.56 mmol) and 1-amino-4-cyanopyridinium 2,4,6-trimethylbenzenesulfonate (498 mg, 1.56 mmol) in AcN (30 mL), at 0° C., 1 M TBAF solution in THF (1.56 mL, 1.56 mmol) and a solution of DBU (0.47 mL, 3.12 mmol) in AcN (10 mL) were added. The reaction mixture was stirred at 0° C. for 5 min and 3 h at room temperature. The reaction mixture was evaporated to dryness. The crude product thus obtained was chromatographed over silica gel using EtOAc/hexanes mixtures of increasing polarity as eluent, to afford 227 mg of the desired compound (48% yield).

d) 3-[5-Amino-4-(tetrahydro-2H-pyran-4-ylamino) pyrimidin-2-yl]pyrazolo[1,5-a]pyridine-5-carbonitrile A mixture of the compound obtained in the previous section (119 mg, 0.32 mmol) in EtOH (12 mL) was hydrogenated with Pt/C5% (149 mg, 0.02 mmol) as a catalyst in the presence of thiophene in DIRER (4% v/v, 9 drops). The reaction mixture was stirred under $H_2$ (g) atmosphere at room temperature for 1.5 h. The reaction mixture was filtered through a plug of Celite® and the solvent was concentrated off to afford 78 mg of the desired product (71% yield).

e) 3-(8-Oxo-9-tetrahydro-2H-pyran-4-yl-8,9-dihydro-7H-purin-2-yl)pyrazolo[1,5-a]pyridine-5-carbonitrile To a solution of the compound obtained in the previous section (78 mg, 0.23 mmol) in THF (7 mL), 1,1'-carbonyldiimidazole. (188 mg, 1.16 mmol) was added. The reaction mixture was stirred at room temperature thr 4 h, quenched with saturated NaCl aqueous solution (15 mL) and extracted with EtOAc (3×15 mL). The combined organic phases were dried over anhydrous $Na_2SO_4$, filtered and concentrated. The crude product thus obtained was chromatographed over silica gel using $MeOH/CH_2Cl_2$ mixtures of increasing polarity as eluent, to afford 5.1 mg of the desired compound (61% yield).

LC-MS (method 1): $t_R$=14.25 min; m/z=362 (MH$^+$).

Following a similar procedure to that described in example 1, but using in each case the corresponding starting materials, the following compounds were obtained:

| Example | Name | Starting Material | HPLC method | $t_R$ (min) | m/z |
|---|---|---|---|---|---|
| 1a | methyl (2R)-2-[2-(5-cyanopyrazolo[1,5-a]pyridin-3-yl)-8-oxo-7,8-dihydro-9H-purin-9-yl]propanoate | D-alanine methyl ester hydrochloride | 1 | 14.48 | 364 |
| 1b | (S)-tert-butyl 3-(2-(5-cyanopyrazolo[1,5-a]pyridin-3-yl)-8-oxo-7H-purin-9(8H)-yl)piperidine-1-carboxylate | (S)-tert-butyl 3-aminopiperidine-1-carboxylate | 2 | 2.23 | 461 |
| 1c | (R)-tert-butyl 3-(2-(5-cyanopyrazolo[1,5-a]pyridin-3-yl)-8-oxo-7H-purin-9(8H)-yl)piperidine-1-carboxylate | (R)-tert-butyl 3-aminopiperidine-1-carboxylate | 2 | 2.23 | 461 |
| 1d | (S)-3-(9-(1-methoxypropan-2-yl)-8-oxo-8,9-dihydro-7H-purin-2-yl)pyrazolo[1,5-a]pyridine-5-carbonitrile | (S)-1-methoxypropan-2-amine | 2 | 1.82 | 350 |
| 1e | 3-(9-(4,4-difluorocyclohexyl)-8-oxo-8,9-dihydro-7H-purin-2-yl)pyrazolo[1,5-a]pyridine-5-carbonitrile | 4,4-difluorocyclohexanamine | 2 | 2.03 | 396 |
| 1f | 3-(9-(1,1-dioxotetrahydrothien-3-yl)-8-oxo-8,9-dihydro-7H-purin-2-yl)pyrazolo[1,5-a]pyridine-5-carbonitrile | 3-amino-1,1-dioxotetrahydrothiophene | 2 | 1.43 | 396 |
| 1g | 3-(9-(2-fluorobenzyl)-8-oxo-8,9-dihydro-7H-purin-2-yl)pyrazolo[1,5-a]pyridine-5-carbonitrile | 2-fluorobenzylamine | 1 | 16.58 | 386 |
| 1h | 3-(9-(4-methoxybut-1-yl)-8-oxo-8,9-dihydro-7H-purin-2-yl)pyrazolo[1,5-a]pyridine-5-carbonitrile | 4-methoxybutan-1-amine | 1 | 15.15 | 396 |
| 1i | methyl (2S)-2-[2-(5-cyanopyrazolo[1,5-a]pyridin-3-yl)-8-oxo-7,8-dihydro-9H-purin-9-yl]propanoate | L-alanine methyl ester hydrochloride | 3 | 1.83 | 436 |
| 1j | 9-(1-acetylpiperidin-4-yl)-2-(5-(trifluoromethyl)pyrazolo[1,5-a]pyridin-3-yl)-7H-purin-8(9H)-one (1) | 1-acetyl-4-aminopiperidine hydrochloride | 4 | 1.68 | 446 |
| 1k | (S)-tert-butyl 3-(2-(5-cyanopyrazolo[1,5-a]pyridin-3-yl)-8-oxo-7H-purin-9(8H)-yl)pyrrolidine-1-carboxylate | (S)-tert-butyl 3-aminopyrrolidine-1-carboxylate | 5 | 2.72 | 447 |
| 1l | (R)-tert-butyl 3-(2-(5-cyanopyrazolo[1,5-a]pyridin-3-yl)-8-oxo-7H-purin-9(8H)-yl)pyrrolidine-1-carboxylate | (R)-tert-butyl 3-aminopyrrolidine-1-carboxylate | 3 | 2.25 | 447 |

-continued

| Example | Name | Starting Material | HPLC method | $t_R$ (min) | m/z |
|---|---|---|---|---|---|
| 1m | (S)-tert-butyl 3-(2-(5-methylpyrazolo[1,5-a]pyridin-3-yl)-8-oxo-7H-purin-9(8H)-yl)piperidine-1-carboxylate (2) | (S)-tert-butyl 3-aminopiperidine-1-carboxylate | 3 | 2.47 | 450 |
| 1n | ethyl 2-(2-(5-cyanopyrazolo[1,5-a]pyridin-3-yl)-8-oxo-7H-purin-9(8H)-yl)acetate | ethyl 2-aminoacetate | 3 | 1.82 | 364 |
| 1o | 3-(9-(trans-4-hydroxycyclohexyl)-8-oxo-8,9-dihydro-7H-purin-2-yl)pyrazolo[1,5-a]pyridine-5-carbonitrile | trans-4-aminocyclohexanol | 3 | 1.55 | 376 |
| 1p | 3-(9-(8-fluorochroman-4-yl)-8-oxo-8,9-dihydro-7H-purin-2-yl)pyrazolo[1,5-a]pyridine-5-carbonitrile | 8-fluorochroman-4-amine | 1 | 15.43 | 428 |
| 1q | tert-butyl 4-(2-(5-cyanopyrazolo[1,5-a]pyridin-3-yl)-8-oxo-7H-purin-9(8H)-yl)piperidine-1-carboxylate | tert-butyl 4-aminopiperidine-1-carboxylate | 3 | 2.33 | 461 |
| 1r | tert-butyl 3-(2-(5-cyanopyrazolo[1,5-a]pyridin-3-yl)-8-oxo-7H-purin-9(8H)-yl)azetidine-1-carboxylate | tert-butyl 3-aminoazetidine-1-carboxylate | 3 | 2.20 | 433 |
| 1s | 9-(1-acetylpiperidin-4-yl)-2-(5-methylpyrazolo[1,5-a]pyridin-3-yl)-7H-purin-8(9H)-one (2) | 1-acetyl-4-aminopiperidine hydrochloride | 4 | 1.38 | 392 |

(1) step c) was performed using reference example 1 instead of 1-amino-4-cyanopyridinium 2,4,6-trimethylbenzenesulfonate
(2) step c) was performed using 1-amino-4-methylpyridinium 2,4,6-trimethylbenzenesulfonate (described by Zhang et al Journal of Heterocyclic Chemistry; 44; 4; 2007; 919-922) instead of 1-amino-4-cyanopyridinium 2,4,6-trimethylbenzenesulfonate Example 2

3-(2-oxo-3-(tetrahydro-2H-pyran-4-yl)-2,3-dihydro-1H-imidazo[4,5-b]pyridin-5-yl)pyrazolo[1,5-a]pyridine-5-carbonitrile a) 6-Chloro-3-nitro-N-(tetrahydro-2H-pyran-4-yl)pyridin-2-amine To a suspension of 2,6-dichloro-3-nitropyridine (6 g, 31.1 mmol) in AcN (200 mL) at 0° C., TEA (9 mL, 62.2 mmol) and tetrahydro-2H-pyran-4-amine (3.15 g, 31.1 mmol) were added. The reaction mixture was stirred at 0° C. for 1.5 h. The reaction crude was tempered and stirred at room temperature for 18 h.
The reaction mixture was evaporated under reduced pressure, dissolved in EtOAc, and washed thrice with saturated $NaHCO_3$ aqueous solution. The combined organic phases were dried over $MgSO_4$ and concentrated to dryness.
The crude residue was chromatographed on a silica gel flash system (ISCO Cornbiflash) using hexanes/TBME mixtures of increasing polarity as eluent to afford 5.23 g of the desired product (65% yield).

b) 3-Nitro-N-(tetrahydro-2H-pyran-4-yl)-6-((trimethylsilyl)ethynyl)pyridin-2-amine Following a similar procedure to that described in example 1, section b, but using the compound obtained in previous section as starting material, the desired compound was obtained (87% yield).

c) 3-(5-Nitro-6-(tetrahydro-2H-pyran-4-ylamino)pyridin-2-yl)pyrazolo[1,5-a]pyridine-5-carbonitrile Following a similar procedure to that described in example 1, section c, but using the compound obtained in previous section as starting material, the desired compound was obtained (16% yield).

d) 3-(5-Amino-6-(tetrahydro-2H-pyran-4-ylamino)pyridin-2-yl)pyrazolo[1,5-a]pyridine-5-carbonitrile Following a similar procedure to that described in example 1, section d, but using the compound obtained in previous section as starting material, the desired compound was obtained (19% yield).

e) Title Compound

Following a similar procedure to that described in example 1, section e, but using the compound obtained in previous section as starting material, the desired compound was obtained (23% yield).

LC-MS (method 3): $t_R$=1.83 min; m/z=361 (MH$^+$)

Following a similar procedure to that described in example 2, but using in each case the corresponding starting materials, the following compounds were obtained:

| Example | Name | Starting Material | HPLC method | $t_R$ (min) | m/z (MH$^+$) |
|---|---|---|---|---|---|
| 2a | (S)-tert-butyl 3-(2-oxo-5-(pyrazolo[1,5-a]pyridin-3-yl)-1H-imidazo[4,5-b]pyridin-3(2H)-yl)piperidine-1-carboxylate | (S)-3-amino-(1-tert-butoxycarbonyl)piperidine and 1-aminopyridinium iodide | 3 | 2.47 | 435 |

-continued

| Example | Name | Starting Material | HPLC method | t_R (min) | m/z (MH+) |
|---|---|---|---|---|---|
| 2b | (R)-tert-butyl 3-(2-oxo-5-(pyrazolo[1,5-a]pyridin-3-yl)-1H-imidazo[4,5-b]pyridin-3(2H)-yl)pyrrolidine-1-carboxylate | (R)-tert-butyl 3-aminopyrrolidine-1-carboxylate and 1-aminopyridinium iodide | 3 | 2.27 | 421 |
| 2c | (S)-tert-butyl 3-(2-oxo-5-(pyrazolo[1,5-a]pyridin-3-yl)-1H-imidazo[4,5-b]pyridin-3(2H)-yl)pyrrolidine-1-carboxylate | (S)-tert-butyl 3-aminopyrrolidine-1-carboxylate and 1-aminopyridinium iodide | 3 | 2.27 | 421 |
| 2d | (S)-tert-butyl 3-(5-(5-cyanopyrazolo[1,5-a]pyridin-3-yl)-2-oxo-1H-imidazo[4,5-b]pyridin-3(2H)-yl)piperidine-1-carboxylate | (S)-3-amino-(1-tert-butoxycarbonyl)piperidine and 1-amino-4-cyanopyridinium 2,4,6-trimethylbenzenesulfonate | 3 | 2.50 | 434 |
| 2e | 5-(pyrazolo[1,5-a]pyridin-3-yl)-3-(tetrahydro-2H-pyran-4-yl)-1H-imidazo[4,5-b]pyridin-2(3H)-one | tetrahydro-2H-pyran-4-amine and 1-aminopyridinium iodide | 3 | 1.80 | 336 |
| 2f | (R)-tert-butyl 3-(2-oxo-5-(pyrazolo[1,5-a]pyridin-3-yl)-1H-imidazo[4,5-b]pyridin-3(2H)-yl)piperidine-1-carboxylate | (R)-3-amino-(1-tert-butoxycarbonyl)piperidine and 1-aminopyridinium iodide | 4 | 2.15 | 435 |

Example 3

2-(Pyrazolo[1,5-a]pyridin-3-yl)-9-(tetrahydro-2H-pyran-4-yl)-7H-purin-8(9H)-one Following a similar procedure to that described in example 1, but using 1-aminopyridinium iodide instead of 1-amino-4-cyanopyridinium 2,4,6-trimethylbenzenesulfonate, the desired compound was obtained (84% yield).

LC-MS (method 3): $t_R$=1.62 min; m/z=337 (MH+).

Following a similar procedure to that described in example 3, but using in each case the corresponding starting materials, the following compounds were obtained:

| Example | Name | Starting Material | HPLC method | t_R (min) | m/z (MH+) |
|---|---|---|---|---|---|
| 3a | 2-(pyrazolo[1,5-a]pyridin-3-yl)-9-((tetrahydro-2H-pyran-4-yl)methyl)-7H-purin-8(9H)-one | (tetrahydro-2H-pyran-4-yl)methanamine | 2 | 1.63 | 351 |
| 3b | (S)-tert-butyl 3-(8-oxo-2-(pyrazolo[1,5-a]pyridin3-yl)-7H-purin-9(8H)-yl)piperidine-1-carboxylate | (S)-tert-butyl-3-aminopiperidine-1-carboxylate | 2 | 2.33 | 436 |
| 3c | 9-(2-methoxyethyl)-2-(pyrazolo[1,5-a]pyridin-3-yl)-7H-purin-8(9H)-one | 2-methoxyethylamine | 2 | 1.55 | 311 |
| 3d | 9-(8-fluorochroman-4-yl)-2-(pyrazolo[1,5-a]pyridin-3-yl)-7H-purin-8(9H)-one | 8-fluorochroman-4-amine | 1 | 16.07 | 403 |
| 3e | methyl (2S)-2-(8-oxo-2-(pyrazolo[1,5-a]pyridin-3-yl)-7,8-dihydro-9H-purin-9-yl)propanoate | L-alanine methyl ester hydrochloride | 3 | 1.73 | 339 |
| 3f | (S)-tert-butyl 3-(8-oxo-2-(pyrazolo[1,5-a]pyridin-3-yl)-7H-purin-9(8H)-yl)pyrrolidine-1-carboxylate | (S)-tert-butyl 3-aminopyrrolidine-1-carboxylate | 3 | 2.13 | 422 |
| 3g | tert-butyl 4-(8-oxo-2-(pyrazolo[1,5-a]pyridin-3-yl)-7H-purin-9(8H)-yl)piperidine-1-carboxylate | tert-butyl 4-aminopiperidine-1-carboxylate | 3 | 2.35 | 461 |
| 3h | 9-(1-methylpiperidin-4-yl)-2-(pyrazolo[1,5-a]pyridin-3-yl)-7H-purin-8(9H)-one | 1-methylpiperidin-4-amine | 4 | 1.38 | 350 |
| 3i | 5-(pyrazolo[1,5-a]pyridin-3-yl)-3-(2,2,6,6-tetramethylpiperidin-4-yl)-1H-imidazo[4,5-b]pyridin-2(3H)-one | 2,2,6,6-tetramethylpiperidin-4-amine | 4 | 1.48 | 391 |

Example 4

3-(7-Methyl-8-oxo-9-tetrahydro-2H-pyran-4-yl-8,9-dihydro-7H-purin-2-yl)pyrazolo[1,5-a]pyridine-5-carbonitrile To a solution of example 1 (48 mg. 0.13 mmol) in DMF (6 mL), 55-65% NaH dispersion in mineral oil (7.3 mg, 0.18 mmol) was added and the resulting solution was stirred at room temperature for 10 min. Then MeI (0.015 mL, 0.25 mmol) was added and the reaction mixture was stirred for 15 h at room temperature. The reaction mixture was quenched with saturated NaCl aqueous solution (10 mL) and extracted with EtOAc (3×10 mL) and $CH_2Cl_2$ (2×10 mL), The combined organic phases were dried over anhydrous $Na_2SO_4$, filtered and concentrated. The crude product thus obtained was chromatographed over silica gel using MeOH/$CH_2Cl_2$ mixtures of increasing polarity as eluent, to afford 50 mg of the desired compound (quantitative yield).

LC-MS (method 1): $t_R$=15.48 min: m/z=376 (MH$^+$).

Following a similar procedure to that described in example 4, but using in each case the corresponding starting materials, the following compounds were obtained:

| Example | Name | Starting Material | HPLC method | $t_R$ (min) | m/z |
|---|---|---|---|---|---|
| 4a | (S)-tert-butyl 3-(2-(5-cyanopyrazolo[1,5-a]pyridin-3-yl)-7-methyl-8-oxo-7H-purin-9(8H)-yl)piperidine-1-carboxylate | Example 1b | 2 | 3.22 | 475 |
| 4b | (R)-tert-butyl 3-(2-(5-cyanopyrazolo[1,5-a]pyridin-3-yl)-7-methyl-8-oxo-7H-purin-9(8H)-yl)piperidine-1-carboxylate | Example 1c | 2 | 3.22 | 475 |
| 4c | 9-(8-fluorochroman-4-yl)-7-methyl-2-(pyrazolo[1,5-a]pyridin-3-yl)-7H-purin-8(9H)-one | Example 3d | 1 | 16.83 | 417 |

Example 5

(S)-tert-Butyl 3-(7-methyl-8-oxo-2-(pyrazolo[1,5-a]pyridine-3-yl)-7H-purin-9(8H)-yl)piperidine-1-carboxylate To a solution of example 3b (70 mg, 0.160 mmol) in DMF (3.5 mL), at 0° C., $^t$BuOK (27 mg, 0.24 mmol) and MeI (0.019 mL, 0.32 mmol) were added. The reaction mixture was stirred at room temperature for 20 min and evaporated to dryness. The crude residue was chromatographed on a silica gel flash system (ISCO Rf) using $CH_2Cl_2$/MeOH mixtures of increasing polarity as eluent to afford 64 mg of the desired product (89% yield).

LC-MS (method 3): $t_R$=2.58 min; m/z=450 (MH$^+$).

Following a similar procedure to that described in example 5, but using in each case the corresponding starting materials, the following compounds were obtained:

| Example | Name | Starting Material | HPLC method | $t_R$ (min) | m/z (MH$^+$) |
|---|---|---|---|---|---|
| 5a | 7-methyl-2-(pyrazolo[1,5-a]pyridin-3-yl)-9-(tetrahydro-2H-pyran-4-yl)-7H-purin-8(9H)-one | example 3 | 2 | 1.83 | 351 |
| 5b | 3-(1-methyl-2-oxo-3-(tetrahydro-2H-pyran-4-yl)-2,3-dihydro-1H-imidazo[4,5-b]pyridin-5-yl)pyrazolo[1,5-a]pyridine-5-carbonitrile | example 2 | 2 | 2.62 | 375 |
| 5c | 9-(2-methoxyethyl)-7-methyl-2-(pyrazolo[1,5-a]pyridin-3-yl)-7H-purin-8(9H)-one | Example 3c | 2 | 1.77 | 325 |
| 5d | 7-methyl-2-(pyrazolo[1,5-a]pyridin-3-yl)-9-[(tetrahydro-2H-pyran-4-yl)methyl]-7H-purin-8(9H)-one | Example 3a | 2 | 1.87 | 365 |
| 5e | 3-(9-(4,4-difluorocyclohexyl)-7-methyl-8-oxo-8,9-dihydro-7H-purin-2-yl)pyrazolo[1,5-a]pyridine-5-carbonitrile | Example 1e | 2 | 2.32 | 410 |
| 5f | 3-(9-(1,1-dioxotetrahydrothien-3-yl)-8,9-dihydro-7-methyl-8-oxopurin-2-yl)pyrazolo[1,5-a]pyridine-5-carbonitrile. | Example 1f | 2 | 1.75 | 410 |
| 5g | (S)-tert-butyl 3-(5-(5-cyanopyrazolo[1,5-a]pyridin-3-yl)-1-methyl-2-oxo-1H-imidazo[4,5-b]pyridin-3(2H)-yl)piperidine-1-carboxylate | Example 2d | 2 | 2.54 | 474 |
| 5h | 3-(9-(2-fluorobenzyl)-7-methyl-8-oxo-8,9-dihydro-7H-purin-2-yl)pyrazolo[1,5-a]pyridine-5-carbonitrile | Example 1g | 1 | 17.66 | 400 |
| 5i | 9-(1-acetylpiperidin-4-yl)-7-methyl-2-(5-(trifluoromethyl)pyrazolo[1,5-a]pyridin-3-yl)-7H-purin-8(9H)-one | Example 1j | 4 | 1.85 | 460 |

-continued

| Example | Name | Starting Material | HPLC method | $t_R$ (min) | m/z (MH+) |
|---|---|---|---|---|---|
| 5j | (S)-tert-butyl 3-(1-methyl-2-oxo-5-(pyrazolo[1,5-a]pyridin-3-yl)-1H-imidazo[4,5-b]pyridin-3(2H)-yl)piperidine-1-carboxylate | Example 2a | 3 | 2.73 | 449 |
| 5k | (S)-tert-butyl 3-(2-(5-cyanopyrazolo[1,5-a]pyridin-3-yl)-7-methyl-8-oxo-7H-purin-9(8H)-yl)pyrrolidine-1-carboxylate | Example 1k | 3 | 2.52 | 461 |
| 5l | (R)-tert-butyl 3-(2-(5-cyanopyrazolo[1,5-a]pyridin-3-yl)-7-methyl-8-oxo-7H-purin-9(8H)-yl)pyrrolidine-1-carboxylate | Example 1l | 3 | 2.50 | 461 |
| 5m | (S)-tert-butyl 3-(7-methyl-8-oxo-2-(pyrazolo[1,5-a]pyridin-3-yl)-7H-purin-9(8H)-yl)pyrrolidine-1-carboxylate | Example 3f | 3 | 2.40 | 436 |
| 5n | (R)-tert-butyl 3-(1-methyl-2-oxo-5-(pyrazolo[1,5-a]pyridin-3-yl)-1H-imidazo[4,5-b]pyridin-3(2H)-yl)pyrrolidine-1-carboxylate | Example 2b | 3 | 2.50 | 435 |
| 5o | (S)-tert-butyl 3-(1-methyl-2-oxo-5-(pyrazolo[1,5-a]pyridin-3-yl)-1H-imidazo[4,5-b]pyridin-3(2H)-yl)pyrrolidine-1-carboxylate | Example 2c | 5 | 2.98 | 436 |
| 5p | (S)-tert-Butyl 3-(1-ethyl-2-oxo-5-(pyrazolo[1,5-a]pyridin-3-yl)-1H-imidazo[4,5-b]pyridin-3(2H)-yl)piperidine-1-carboxylate (1) | Example 2a | 4 | 2.57 | 463 |
| 5q | tert-butyl 4-(7-methyl-8-oxo-2-(pyrazolo[1,5-a]pyridin-3-yl)-7H-purin-9(8H)-yl)piperidine-1-carboxylate | Example 3g | 3 | 2.68 | 475 |
| 5r | (S)-tert-butyl 3-(7-methyl-8-oxo-2-(pyrazolo[1,5-a]pyridin-3-yl)-7H-purin-9(8H)-yl)piperidine-1-carboxylate | Example 3b | 3 | 2.62 | 450 |
| 5s | 1-methyl-5-(pyrazolo[1,5-a]pyridin-3-yl)-3-(tetrahydro-2H-pyran-4-yl)-1H-imidazo[4,5-b]pyridin-2(3H)-one | Example 2e | 3 | 2.02 | 350 |
| 5t | (R)-tert-butyl 3-(1-methyl-2-oxo-5-(pyrazolo[1,5-a]pyridin-3-yl)-1H-imidazo[4,5-b]pyridin-3(2H)-yl)piperidine-1-carboxylate | Example 2f | 3 | 2.73 | 449 |
| 5u | tert-butyl 4-(2-(5-cyanopyrazolo[1,5-a]pyridin-3-yl)-7-methyl-8-oxo-7H-purin-9(8H)-yl)piperidine-1-carboxylate | Example 1q | 3 | 2.68 | 475 |
| 5v | tert-butyl 3-(2-(5-cyanopyrazolo[1,5-a]pyridin-3-yl)-7-methyl-8-oxo-7H-purin-9(8H)-yl)azetidine-1-carboxylate | Example 1r | 3 | 2.47 | 447 |

(1) ethyl iodide instead of methyl iodide as starting material.

Example 6

(S)-3-(8-oxo-9-(piperidin-3-yl)-8,9-dihydro-7H-purin-2-yl)pyrazolo[1,5-a]pyridine-5-carbonitrile hydrochloride To a solution of example 1b (45 mg, 0.10 mmol) in dioxane (3 mL), 4 M HCl solution in dioxane (2 mL, 8.0 mmol) was added. The reaction mixture was stirred at room temperature for 1 h. The reaction mixture was evaporated to dryness to give 48 mg of the desired compound (100% yield).

LC-MS (method 2): $t_R$=1.73 min; m/z=361 (MH+).

Following a similar procedure to that described in example 6, but using in each case the corresponding starting materials, the following compounds were obtained:

| Example | Compound name | Starting material | HPLC method | $t_R$ (min) | m/z (MH+) |
|---|---|---|---|---|---|
| 6a | (R)-3-(8-oxo-9-(piperidin-3-yl)-8,9-dihydro-7H-purin-2-yl)pyrazolo[1,5-a]pyridine-5-carbonitrile hydrochloride | Example 1c | 2 | 1.73 | 361 |

-continued

| Example | Compound name | Starting material | HPLC method | $t_R$ (min) | m/z (MH$^+$) |
|---|---|---|---|---|---|
| 6b | (R)-3-(7-methyl-8-oxo-9-(piperidin-3-yl)-8,9-dihydro-7H-purin-2-yl)pyrazolo[1,5-a]pyridine-5-carbonitrile hydrochloride | Example 4b | 2 | 2.05 | 375 |
| 6c | (S)-3-(7-methyl-8-oxo-9-(piperidin-3-yl)-8,9-dihydro-7H-purin-2-yl)pyrazolo[1,5-a]pyridine-5-carbonitrile hydrochloride | Example 4a | 2 | 2.05 | 375 |
| 6d | 9-(piperidin-4-yl)-2-(pyrazolo[1,5-a]pyridin-3-yl)-7H-purin-8(9H)-one | Example 3g | 2 | 1.28 | 336 |
| 6e | (S)-3-(2-oxo-3-(piperidin-3-yl)-2,3-dihydro-1H-imidazo[4,5-b]pyridin-5-yl)pyrazolo[1,5-a]pyridine-5-carbonitrile hydrochloride | Example 2d | 2 | 1.54 | 360 |
| 6f | (S)-3-(1-methyl-2-oxo-3-(piperidin-3-yl)-2,3-dihydro-1H-imidazo[4,5-b]pyridin-5-yl)pyrazolo[1,5-a]pyridine-5-carbonitrile hydrochloride | Example 5g | 2 | 1.68 | 374 |
| 6g | (S)-1-methyl-3-(piperidin-3-yl)-5-(pyrazolo[1,5-a]pyridin-3-yl)-1H-imidazo[4,5-b]pyridin-2(3H)-one hydrochloride | Example 5j | 1 | 12.46 | 349 |
| 6h | (S)-3-(7-methyl-8-oxo-9-(pyrrolidin-3-yl)-8,9-dihydro-7H-purin-2-yl)pyrazolo[1,5-a]pyridine-5-carbonitrile hydrochloride | Example 5k | 3 | 1.62 | 361 |
| 6i | (R)-3-(7-methyl-8-oxo-9-(pyrrolidin-3-yl)-8,9-dihydro-7H-purin-2-yl)pyrazolo[1,5-a]pyridine-5-carbonitrile hydrochloride | Example 5l | 3 | 1.62 | 361 |
| 6j | (S)-2-(pyrazolo[1,5-a]pyridin-3-yl)-9-(pyrrolidin-3-yl)-7H-purin-8(9H)-one hydrochloride | Example 3f | 3 | 1.23 | 322 |
| 6k | (S)-7-methyl-2-(pyrazolo[1,5-a]pyridin-3-yl)-9-(pyrrolidin-3-yl)-7H-purin-8(9H)-one hydrochloride | Example 5m | 3 | 1.48 | 336 |
| 6l | (S)-3-(8-oxo-9-(pyrrolidin-3-yl)-8,9-dihydro-7H-purin-2-yl)pyrazolo[1,5-a]pyridine-5-carbonitrile hydrochloride (1) | Example 1k | 3 | 1.35 | 347 |
| 6m | (R)-1-methyl-5-(pyrazolo[1,5-a]pyridin-3-yl)-3-(pyrrolidin-3-yl)-1H-imidazo[4,5-b]pyridin-2(3H)-one hydrochloride | Example 5n | 3 | 1.57 | 335 |
| 6n | (R)-5-(pyrazolo[1,5-a]pyridin-3-yl)-3-(pyrrolidin-3-yl)-1H-imidazo[4,5-b]pyridin-2(3H)-one hydrochloride (1) | Example 2b | 3 | 1.40 | 321 |
| 6o | (R)-3-(8-oxo-9-(pyrrolidin-3-yl)-8,9-dihydro-7H-purin-2-yl)pyrazolo[1,5-a]pyridine-5-carbonitrile hydrochloride (1) | Example 1l | 3 | 1.33 | 347 |
| 6p | (S)-2-(pyrazolo[1,5-a]pyridin-3-yl)-9-(pyrrolidin-3-yl)-7H-purin-8(9H)-one hydrochloride | Example 2c | 3 | 1.40 | 321 |
| 6q | (S)-1-methyl-5-(pyrazolo[1,5-a]pyridin-3-yl)-3-(pyrrolidin-3-yl)-1H-imidazo[4,5-b]pyridin-2(3H)-one hydrochloride | Example 5o | 3 | 1.57 | 335 |
| 6r | (S)-2-(5-methylpyrazolo[1,5-a]pyridin-3-yl)-9-(piperidin-3-yl)-7H-purin-8(9H)-one hydrochloride | Example 1m | 3 | 1.57 | 350 |
| 6s | (S)-1-ethyl-3-(piperidin-3-yl)-5-(pyrazolo[1,5-a]pyridin-3-yl)-1H-imidazo[4,5-b]pyridin-2(3H)-one hydrochloride | Example 5p | 4 | 1.56 | 363 |
| 6t | 7-methyl-9-(piperidin-4-yl)-2-(pyrazolo[1,5-a]pyridin-3-yl)-7H-purin-8(9H)-one hydrochloride | Example 5q | 4 | 1.23 | 350 |
| 6u | (S)-7-methyl-9-(piperidin-3-yl)-2-(pyrazolo[1,5-a]pyridin-3-yl)-7H-purin-8(9H)-one hydrochloride | Example 5r | 3 | 1.67 | 350 |
| 6v | (S)-9-(piperidin-3-yl)-2-(pyrazolo[1,5-a]pyridin-3-yl)-7H-purin-8(9H)-one hydrochloride | Example 3b | 3 | 1.43 | 336 |

| Example | Compound name | Starting material | HPLC method | $t_R$ (min) | m/z (MH$^+$) |
|---|---|---|---|---|---|
| 6w | (R)-1-methyl-3-(piperidin-3-yl)-5-(pyrazolo[1,5-a]pyridin-3-yl)-1H-imidazo[4,5-b]pyridin-2(3H)-one | Example 5t | 3 | 1.77 | 349 |
| 6x | (S)-3-(piperidin-3-yl)-5-(pyrazolo[1,5-a]pyridin-3-yl)-1H-imidazo[4,5-b]pyridin-2(3H)-one hydrochloride | Example 2a | 3 | 1.60 | 335 |
| 6y | 3-(7-methyl-8-oxo-9-(piperidin-4-yl)-8,9-dihydro-7H-purin-2-yl)pyrazolo[1,5-a]pyridine-5-carbonitrile hydrochloride | Example 5u | 3 | 1.67 | 375 |
| 6z | (S)-3-(3-(piperidin-3-yl)-3H-imidazo[4,5-b]pyridin-5-yl)pyrazolo[1,5-a]pyridine-5-carbonitrile hydrochloride | Example 18e | 3 | 1.68 | 3.44 |
| 6aa | (S)-3-(2-methyl-3-(piperidin-3-yl)-3H-imidazo[4,5-b]pyridin-5-yl)pyrazolo[1,5-a]pyridine-5-carbonitrile hydrochloride | Example 18f | 3 | 1.72 | 358 |
| 6ab | 3-(8-oxo-9-(piperidin-4-yl)-8,9-dihydro-7H-purin-2-yl)pyrazolo[1,5-a]pyridine-5-carbonitrile (1) | Example 1q | 1 | 11.13 | 361 |
| 6ac | 3-(9-(azetidin-3-yl)-7-methyl-8-oxo-8,9-dihydro-7H-purin-2-yl)pyrazolo[1,5-a]pyridine-5-carbonitrile hydrochloride | Example 5v | 3 | 1.50 | 347 |
| 6ad | (S)-3-(piperidin-3-yl)-5-(pyrazolo[1,5-a]pyridin-3-yl)-3H-imidazo[4,5-b]pyridine hydrochloride | Example 18i | 3 | 1.65 | 319 |
| 6ae | (S)-2-methyl-3-(piperidin-3-yl)-5-(pyrazolo[1,5-a]pyridin-3-yl)-3H-imidazo[4,5-b]pyridine hydrochloride | Example 21m | 3 | 1.48 | 333 |

(1) reaction performed with TFA/CH$_2$Cl$_2$ instead of 4M HCl solution in dioxane, and washed with with saturated NaHCO$_3$ aqueous solution.

Example 7

(S)-3-(9-(1-(2-Cyanoacetyl)piperidin-3-yl)-8-oxo-8,9-dihydro-7H-purin-2-yl)pyrazolo[1,5-a]pyridine-5-carbonitrile To a solution of the compound obtained in example 6 (45 mg, 0.095 mmol) in anhydrous DMF (3 mL), 2,5-dioxopyrrolidin-1-yl 2-cyanoacetate (69 mg, 0.38 mmol) and anhydrous TEA (0.09 mL, 0.665 mmol) were added. The reaction mixture was stirred at room temperature for 18 h, and the solvent was concentrated off. It was quenched with saturated NaHCO$_3$ aqueous solution (15 mL) and extracted with EtOAc (3×15 mL). The combined organic phases were dried over anhydrous Mg$_2$SO$_4$, filtered and concentrated. The crude residue was flash chromatographed on a silica gel flash system (ISCO Rf) using hexanes/acetone mixtures of increasing polarity as eluent to afford 11.7 mg of the desired compound (29% yield).

LC-MS (method 2): $t_R$=1.93 min; m/z=428 (MH$^+$).

Following a similar procedure to that described in example 7, but using in each case the corresponding starting materials, the following compounds were obtained:

| Example | Compound name | Starting material | HPLC method | $t_R$ (min) | m/z (MH$^+$) |
|---|---|---|---|---|---|
| 7a | (R)-3-(9-(1-(2-cyanoacetyl)piperidin-3-yl)-8-oxo-8,9-dihydro-7H-purin-2-yl)pyrazolo[1,5-a]pyridine-5-carbonitrile | Example 6a | 2 | 1.93 | 428 |
| 7b | (R)-3-(9-(1-(2-cyanoacetyl)piperidin-3-yl)-7-methyl-8-oxo-8,9-dihydro-7H-purin-2-yl)pyrazolo[1,5-a]pyridine-5-carbonitrile | Example 6b | 2 | 2.30 | 442 |
| 7c | (S)-3-(9-(1-(2-cyanoacetyl)piperidin-3-yl)-7-methyl-8-oxo-8,9-dihydro-7H-purin-2-yl)pyrazolo[1,5-a]pyridine-5-carbonitrile | Example 6c | 2 | 2.30 | 442 |
| 7d | 3-(9-(1-(2-cyanoacetyl)pyrrolidin-3-yl)-7-methyl-8-oxo-8,9-dihydro-7H-purin-2-yl)pyrazolo[1,5-a]pyridine-5-carbonitrile | 3-(7-methyl-8-oxo-9-(pyrrolidin-3-yl)-8,9-dihydro-7H-purin-2-yl)pyrazolo[1,5-a]pyridine-5-carbonitrile hydrochloride (1) | 2 | 1.68 | 428 |

-continued

| Example | Compound name | Starting material | HPLC method | $t_R$ (min) | m/z (MH⁺) |
|---|---|---|---|---|---|
| 7e | 3-(9-((1-(2-cyanoacetyl)piperidin-4-yl)methyl)-7-methyl-8-oxo-8,9-dihydro-7H-purin-2-yl)pyrazolo[1,5-a]pyridine-5-carbonitrile | 3-(7-methyl-8-oxo-9-(piperidin-4-ylmethyl)-8,9-dihydro-7H-purin-2-yl)pyrazolo[1,5-a]pyridine-5-carbonitrile hydrochloride (2) | 2 | 1.80 | 456 |
| 7f | (S)-3-oxo-3-(3-(8-oxo-2-(pyrazolo[1,5-a]pyridin-3-yl)-7H-purin-9(8H)-yl)piperidin-1-yl)propanenitrile | Example 6v | 2 | 2.05 | 403 |
| 7g | (S)-3-(3-(7-methyl-8-oxo-2-(pyrazolo[1,5-a]pyridin-3-yl)-7H-purin-9(8H)-yl)piperidin-1-yl)-3-oxopropanenitrile | Eample 6u | 2 | 2.58 | 417 |
| 7h | (S)-3-(3-(1-(2-cyanoacetyl)piperidin-3-yl)-2-oxo-2,3-dihydro-1H-imidazo[4,5-b]pyridin-5-yl)pyrazolo[1,5-a]pyridine-5-carbonitrile | Example 6e | 2 | 1.64 | 427 |
| 7i | (S)-3-(3-(1-methyl-2-oxo-5-(pyrazolo[1,5-a]pyridin-3-yl)-1H-imidazo[4,5-b]pyridin-3(2H)-yl)piperidin-1-yl)-3-oxopropanenitrile | Example 6g | 5 | 1.95 | 416 |
| 7j | 3-(9-(1-(2-cyanoacetyl)azetidin-3-yl)-7-methyl-8-oxo-8,9-dihydro-7H-purin-2-yl)pyrazolo[1,5-a]pyridine-5-carbonitrile | Example 6ac | 2 | 2.10 | 414 |
| 7k | (S)-3-(3-(2-(5-methylpyrazolo[1,5-a]pyridin-3-yl)-8-oxo-7H-purin-9(8H)-yl)piperidin-1-yl)-3-oxopropanenitrile | Example 6r | 3 | 1.73 | 417 |
| 7l | (S)-3-(3-(1-ethyl-2-oxo-5-(pyrazolo[1,5-a]pyridin-3-yl)-1H-imidazo[4,5-b]pyridin-3(2H)-yl)piperidin-1-yl)-3-oxopropanenitrile | Example 6s | 4 | 1.87 | 430 |
| 7m | 3-oxo-3-(4-(8-oxo-2-(pyrazolo[1,5-a]pyridin-3-yl)-7H-purin-9(8H)-yl)piperidin-1-yl)propanenitrile | Example 6d | 4 | 1.32 | 403 |
| 7n | (S)-3-(3-(1-(2-cyanoacetyl)piperidin-3-yl)-1-methyl-2-oxo-2,3-dihydro-1H-imidazo[4,5-b]pyridin-5-yl)pyrazolo[1,5-a]pyridine-5-carbonitrile | Example 6f | 3 | 2.02 | 441 |
| 7o | (R)-3-(3-(1-methyl-2-oxo-5-(pyrazolo[1,5-a]pyridin-3-yl)-1H-imidazo[4,5-b]pyridin-3(2H)-yl)piperidin-1-yl)-3-oxopropanenitrile | Example 6w | 4 | 1.71 | 416 |
| 7p | (S)-3-oxo-3-(3-(2-oxo-5-(pyrazolo[1,5-a]pyridin-3-yl)-1H-imidazo[4,5-b]pyridin-3(2H)-yl)piperidin-1-yl)propanenitrile | Example 6x | 3 | 1.75 | 402 |
| 7q | 3-(9-(1-(2-cyanoacetyl)piperidin-4-yl)-7-methyl-8-oxo-8,9-dihydro-7H-purin-2-yl)pyrazolo[1,5-a]pyridine-5-carbonitrile | Example 6y | 3 | 1.82 | 442 |
| 7r | (S)-3-(3-(1-(2-cyanoacetyl)piperidin-3-yl)-3H-imidazo[4,5-b]pyridin-5-yl)pyrazolo[1,5-a]pyridine-5-carbonitrile | Example 6z | 5 | 2.20 | 411 |
| 7s | (S)-3-(3-(1-(2-cyanoacetyl)piperidin-3-yl)-2-methyl-3H-imidazo[4,5-b]pyridin-5-yl)pyrazolo[1,5-a]pyridine-5-carbonitrile | Example 6aa | 5 | 2.09 | 425 |
| 7t | (S)-3-(3-(2-methyl-5-(pyrazolo[1,5-a]pyridin-3-yl)-3H-imidazo[4,5-b]pyridin-3-yl)piperidin-1-yl)-3-oxopropanenitrile | Example 6ae | 3 | 1.85 | 400 |
| 7u | (S)-3-oxo-3-(3-(5-(pyrazolo[1,5-a]pyridin-3-yl)-3H-imidazo[4,5-b]pyridin-3-yl)piperidin-1-yl)propanenitrile | Example 6ad | 3 | 1.77 | 386 |

(1) obtained as example 6, but using tert-butyl 3-aminopyrrolidine-1-carboxylate as starting material.
(2) obtained as example 6, but using tert-butyl 4-(aminomethyl)piperidine-1-carboxylate as starting material.

Example 8

(S)-3-(9-(1-Acetylpiperidin-3-yl)-8-oxo-8,9-dihydro-7H-purin-2-yl)pyrazolo[1,5-a]pyridine-5-carbonitrile To a solution of the compound obtained in example 6 (31 mg, 0.063 mmol) in anhydrous DMF (3 mL), acetic anhydride (0.007 mL, 0.08 mmol) and anhydrous TEA (0.02 mL, 0,127 mmol) were added. The reaction mixture was stirred at room temperature for 18 h, and the solvent was concentrated off. It was quenched with saturated NaHCO$_3$ aqueous solution (15 mL) and extracted with EtOAc (3×15 mL). The combined organic phases were dried over anhydrous Mg$_2$SO$_4$, filtered and concentrated. The crude residue was flash chromatographed on a silica gel flash system (ISCO Rf) using hexanes/acetone mixtures of increasing polarity as eluent to afford 14.5 mg of the desired compound (57% yield).

LC-MS (method 2): $t_R$=1.87 min; m/z=403 (MH$^+$).

Following a similar procedure to that described in example 8, but using in each case the corresponding starting materials, the following compounds were obtained:

| Example | Compound name | Starting material | HPLC method | $t_R$ (min) | m/z (MH$^+$) |
|---|---|---|---|---|---|
| 8a | (S)-9-(1-acetylpiperidin-3-yl)-2-(pyrazolo[1,5-a]pyridin-3-yl)-7H-purin-8(9H)-one | Example 6v | 2 | 1.55 | 378 |
| 8b | 3-(9-(1-acetylpiperidin-4-yl)-8-oxo-8,9-dihydro-7H-purin-2-yl)pyrazolo[1,5-a]pyridine-5-carbonitrile | Example 6ab | 1 | 13.31 | 403 |
| 8c | 9-(1-acetylpiperidin-4-yl)-2-(pyrazolo[1,5-a]pyridin-3-yl)-7H-purin-8(9H)-one | Example 6d | 4 | 1.30 | 378 |
| 8d | (S)-3-(1-isobutyrylpiperidin-3-yl)-5-(pyrazolo[1,5-a]pyridin-3-yl)-1H-imidazo[4,5-b]pyridin-2(3H)-one (1) | Example 6x | 3 | 2.00 | 405 |
| 8e | (S)-3-(9-(1-acetylpiperidin-3-yl)-7-methyl-8-oxo-8,9-dihydro-7H-purin-2-yl)pyrazolo[1,5-a]pyridine-5-carbonitrile | Example 6c | 3 | 1.88 | 417 |
| 8f | (S)-3-(1-acetylpiperidin-3-yl)-5-(pyrazolo[1,5-a]pyridin-3-yl)-1H-imidazo[4,5-b]pyridin-2(3H)-one | Example 6x | 3 | 1.72 | 377 |
| 8g | 3-(9-(1-acetylpiperidin-4-yl)-7-methyl-8-oxo-8,9-dihydro-7H-purin-2-yl)pyrazolo[1,5-a]pyridine-5-carbonitrile | Example 6y | 3 | 1.78 | 417 |
| 8h | 3-(9-(1-acetylazetidin-3-yl)-7-methyl-8-oxo-8,9-dihydro-7H-purin-2-yl)pyrazolo[1,5-a]pyridine-5-carbonitrile | Example 6ac | 3 | 1.62 | 389 |

(1) using isobutyryl chloride instead of acetic anhydride as starting material.

Example 9

(S)-3-(9-(1-(Methylsulfonyl)piperidin-3-yl)-8-oxo-8,9-dihydro-7H-purin-2-yl)pyrazolo[1,5-a]pyridine-5-carbonitrile To a solution of the compound obtained in example 6 (31 mg, 0.063 mmol) in anhydrous DMF (3 mL), methanesulphonic anhydride (13 mg, 0.08 mmol) and anhydrous TEA (0.02 mL, 0.127 mmol) were added. The reaction mixture was stirred at room temperature for 18 h, and the solvent was concentrated off. It was quenched with saturated NaHCO$_3$ aqueous solution (15 mL) and extracted with EtOAc (3×15 mL). The combined organic phases were dried over anhydrous Mg$_2$SO$_4$, filtered and concentrated. The crude residue was chromatographed on a silica gel flash system (ISCO Rf) using hexanes/acetone mixtures of increasing polarity as eluent to afford 14.3 mg of the titled compound (52% yield).

LC-MS (method 1 PCB): $t_R$=2.08 min; m/z=439 (MH$^+$).

Following a similar procedure to that described in example 9, but using the corresponding starting materials, the following compounds were obtained:

| Example | Compound name | Starting material | HPLC method | $t_R$ (min) | m/z (MH$^+$) |
|---|---|---|---|---|---|
| 9a | (S)-9-(1-(methylsulfonyl)piperidin-3-yl)-2-(pyrazolo[1,5-a]pyridin-3-yl)-7H-purin-8(9H)-one | Example 6v and methanesulphonyl chloride | 2 | 1.70 | 414 |
| 9b | (S)-3-(8-oxo-9-(1-(propylsulfonyl)piperidin-3-yl)-8,9-dihydro-7H-purin-2-yl)pyrazolo[1,5-a]pyridine-5-carbonitrile | Example 6 and propane-1-sulfonyl chloride | 5 | 2.48 | 467 |
| 9c | (S)-3-(8-oxo-9-(1-(2,2,2-trifluoroethylsulfonyl)piperidin-3-yl)-8,9-dihydro-7H-purin-2-yl)pyrazolo[1,5-a]pyridine-5-carbonitrile | Example 6 and 2,2,2-trifluoroethanesulfonyl chloride | 5 | 2.55 | 507 |
| 9d | (S)-3-(9-(1-(isobutylsulfonyl)piperidin-3-yl)-8-oxo-8,9-dihydro-7H-purin-2-yl)pyrazolo[1,5-a]pyridine-5-carbonitrile | Example 6 and 2-methylpropane-1-sulfonyl chloride | 3 | 2.70 | 481 |
| 9e | (S)-3-(8-oxo-9-(1-(3,3,3-trifluoropropylsulfonyl)piperidin-3-yl)-8,9-dihydro-7H-purin-2-yl)pyrazolo[1,5-a]pyridine-5-carbonitrile | Example 6 and 3,3,3-trifluoropropane-1-sulfonyl chloride | 3 | 2.70 | 521 |
| 9f | (S)-1-methyl-3-(1-(methylsulfonyl)piperidin-3-yl)-5-(pyrazolo[1,5-a]pyridin-3-yl)-1H-imidazo[4,5-b]pyridin-2(3H)-one | Example 6g and methanesulphonyl chloride | 4 | 1.81 | 427 |
| 9g | (S)-2-(5-methylpyrazolo[1,5-a]pyridin-3-yl)-9-(1-(methylsulfonyl)piperidin-3-yl)-7H-purin-8(9H)-one | Example 6r and methanesulphonyl chloride | 3 | 1.87 | 428 |
| 9h | 7-(2-oxopropyl)-9-(1-(2-oxopropyl)piperidin-4-yl)-2-(pyrazolo[1,5-a]pyridin-3-yl)-7H-purin-8(9H)-one | Example 6d and 1-chloropropan-2-one | 4 | 1.66 | 448 |
| 9i | 9-(1-acetylpiperidin-4-yl)-7-methyl-2-(pyrazolo[1,5-a]pyridin-3-yl)-7H-purin-8(9H)-one | Example 6t and acetyl choride | 4 | 1.42 | 392 |
| 9j | (S)-3-(3-(1-isobutyrylpiperidin-3-yl)-2-oxo-2,3-dihydro-1H-imidazo[4,5-b]pyridin-5-yl)pyrazolo[1,5-a]pyridine-5-carbonitrile | Example 6e and isobutyryl chloride | 5 | 2.52 | 430 |
| 9k | (S)-3-(3-(1-(methylsulfonyl)piperidin-3-yl)-2-oxo-2,3-dihydro-1H-imidazo[4,5-b]pyridin-5-yl)pyrazolo[1,5-a]pyridine-5-carbonitrile | Example 6e and methanesulphonyl chloride | 3 | 1.92 | 438 |
| 9l | (S)-3-(7-methyl-9-(1-(methylsulfonyl)piperidin-3-yl)-8-oxo-8,9-dihydro-7H-purin-2-yl)pyrazolo[1,5-a]pyridine-5-carbonitrile | Example 6c and methanesulphonyl chloride | 3 | 2.05 | 453 |
| 9m | (S)-3-(9-(1-(ethylsulfonyl)piperidin-3-yl)-8-oxo-8,9-dihydro-7H-purin-2-yl)pyrazolo[1,5-a]pyridine-5-carbonitrile | Example 6 and ethylsulphonyl chloride | 3 | 1.90 | 453 |
| 9n | (S)-3-(9-(1-isobutyrylpiperidin-3-yl)-8-oxo-8,9-dihydro-7H-purin-2-yl)pyrazolo[1,5-a]pyridine-5-carbonitrile | Example 6 and isobutyryl chloride | 3 | 1.95 | 431 |
| 9o | 3-(7-methyl-9-(1-(methylsulfonyl)piperidin-4-yl)-8-oxo-8,9-dihydro-7H-purin-2-yl)pyrazolo[1,5-a]pyridine-5-carbonitrile | Example 6y and methanesulphonyl chloride | 3 | 1.95 | 453 |
| 9p | 3-(9-(1-(methylsulfonyl)piperidin-4-yl)-8-oxo-8,9-dihydro-7H-purin-2-yl)pyrazolo[1,5-a]pyridine-5-carbonitrile | Example 6ab and methanesulphonyl chloride | 1 | 14.06 | 439 |
| 9q | (S)-3-(1-(methylsulfonyl)piperidin-3-yl)-5-(pyrazolo[1,5-a]pyridin-3-yl)-1H-imidazo[4,5-b]pyridin-2(3H)-one | Example 6x and methanesulphonyl chloride | 3 | 1.85 | 413 |
| 9r | 3-(7-methyl-9-(1-(methylsulfonyl)azetidin-3-yl)-8-oxo-8,9-dihydro-7H-purin-2-yl)pyrazolo[1,5-a]pyridine-5-carbonitrile | Example 6ac and methanesulphonyl chloride | 3 | 2.30 | 425 |

-continued

| Example | Compound name | Starting material | HPLC method | $t_R$ (min) | m/z (MH+) |
|---|---|---|---|---|---|
| 9s | (S)-3-(3-(1-acetylpiperidin-3-yl)-2-oxo-2,3-dihydro-1H-imidazo[4,5-b]pyridin-5-yl)pyrazolo[1,5-a]pyridine-5-carbonitrile | Example 6e and acetyl chloride | 5 | 2.25 | 402 |
| 9t | (S)-3-(1-(2-methoxyacetyl)piperidin-3-yl)-1-methyl-5-(pyrazolo[1,5-a]pyridin-3-yl)-1H-imidazo[4,5-b]pyridin-2(3H)-one | Example 6g and 2-methoxyacetyl chloride | 4 | 1.68 | 421 |
| 9u | (S)-1-methyl-5-(pyrazolo[1,5-a]pyridin-3-yl)-3-(1-(2,2,2-trifluoroethylsulfonyl)piperidin-3-yl)-1H-imidazo[4,5-b]pyridin-2(3H)-one | Example 6g and 2,2,2-trifluoroethanesulfonyl chloride | 4 | 2.17 | 495 |

Example 10

(S)-3-(9-(1-(2-(Dimethylamino)acetyl)piperidin-3-yl)-8-oxo-8,9-dihydro-7H-purin-2-yl)pyrazolo[1,5-a]pyridine-5-carbonitrile To a solution of N,N-dimethylglycine (10 mg, 0.095 mmol) in anhydrous DMF (2 mL). HOBt.H$_2$O was added. After 15 min, EDC.HCl (24 mg, 0.126 mmol) and the compound obtained in example 6 (31 mg, 0.063 mmol) were added. The reaction mixture was stirred at room temperature for 2.5 h and the solvent was concentrated off. It was quenched with saturated NaHCO$_3$ aqueous solution (15 mL) and extracted with EtOAc (3×15 mL). The combined organic phases were dried over anhydrous Mg$_2$SO$_4$, filtered and concentrated. The crude residue was chromatographed on a silica gel flash system (ISCO Rf) using hexanes/acetone mixtures of increasing polarity as eluent to afford 8.2 mg of the titled compound (29% yield).

LC-MS (method 3): $t_R$=1.67 min: m/z=446 (MH+).

Following a similar procedure to that described in example 10, but using the corresponding starting material, the following compound was obtained:

| Example | Name | Starting Material | HPLC method | $t_R$ (min) | m/z (MH+) |
|---|---|---|---|---|---|
| 10a | (S)-3-(9-(1-(2-hydroxyacetyl)piperidin-3-yl)-8-oxo-8,9-dihydro-7H-purin-2-yl)pyrazolo[1,5-a]pyridine-5-carbonitrile | Example 6 and glicolic acid | 3 | 1.52 | 419 |
| 10b | (S)-3-(9-(1-(2-hydroxy-2-methylpropanoyl)piperidin-3-yl)-8-oxo-8,9-dihydro-7H-purin-2-yl)pyrazolo[1,5-a]pyridine-5-carbonitrile | Example 6 and 2-hydroxy-2-methylpropanoic acid | 3 | 1.75 | 447 |
| 10c | 3-(8-oxo-9-((S)-1-((S)-tetrahydrofuran-2-carbonyl)piperidin-3-yl)-8,9-dihydro-7H-purin-2-yl)pyrazolo[1,5-a]pyridine-5-carbonitrile | Example 6 and (S)-tetrahydrofuran-2-carboxylic acid | 3 | 1.75 | 459 |
| 10d | (S)-3-(9-(1-(2-methoxyacetyl)piperidin-3-yl)-8-oxo-8,9-dihydro-7H-purin-2-yl)pyrazolo[1,5-a]pyridine-5-carbonitrile | Example 6 and 2-methoxyacetic acid | 3 | 1.65 | 433 |
| 10e | (S)-3-(9-(1-(2-ethylbutanoyl)piperidin-3-yl)-8-oxo-8,9-dihydro-7H-purin-2-yl)pyrazolo[1,5-a]pyridine-5-carbonitrile | Example 6 and 2-ethylbutanoic acid | 3 | 2.20 | 459 |
| 10f | (S)-3-(9-(1-(2-(3-methylisoxazol-5-yl)acetyl)piperidin-3-yl)-8-oxo-8,9-dihydro-7H-purin-2-yl)pyrazolo[1,5-a]pyridine-5-carbonitrile | Example 6 and 2-(3-methylisoxazol-5-yl)acetic acid | 3 | 1.82 | 484 |
| 10g | 3-(9-((S)-1-((S)-2-methoxypropanoyl)piperidin-3-yl)-8-oxo-8,9-dihydro-7H-purin-2-yl)pyrazolo[1,5-a]pyridine-5-carbonitrile | Example 6 and (S)-2-methoxypropanoic acid | 5 | 2.23 | 447 |

-continued

| Example | Name | Starting Material | HPLC method | $t_R$ (min) | m/z (MH+) |
|---|---|---|---|---|---|
| 10h | (S)-3-(8-oxo-9-(1-(3,3,3-trifluoropropanoyl)piperidin-3-yl)-8,9-dihydro-7H-purin-2-yl)pyrazolo[1,5-a]pyridine-5-carbonitrile | Example 6 and 3,3,3-trifluoropropanoic acid | 3 | 1.97 | 471 |
| 10i | (S)-2-(5-methylpyrazolo[1,5-a]pyridin-3-yl)-9-(1-propionylpiperidin-3-yl)-7H-purin-8(9H)-one | Example 6r and propionic acid | 3 | 1.85 | 406 |
| 10j | (S)-9-(1-(2-methoxyacetyl)piperidin-3-yl)-2-(5-methylpyrazolo[1,5-a]pyridin-3-yl)-7H-purin-8(9H)-one | Example 6r and 2-methoxyacetic acid | 3 | 1.72 | 422 |
| 10k | (S)-7-(2-methoxyacetyl)-9-(1-(2-methoxyacetyl)piperidin-3-yl)-2-(5-methylpyrazolo[1,5-a]pyridin-3-yl)-7H-purin-8(9H)-one | Example 6r and 2-methoxyacetic acid | 3 | 2.13 | 494 |
| 10l | (S)-9-(1-acetylpiperidin-3-yl)-2-(5-methylpyrazolo[1,5-a]pyridin-3-yl)-7H-purin-8(9H)-one | Example 6r and acetic acid | 3 | 1.70 | 392 |
| 10m | (S)-9-(1-(2-hydroxyacetyl)piperidin-3-yl)-2-(5-methylpyrazolo[1,5-a]pyridin-3-yl)-7H-purin-8(9H)-one | Example 6r and 2-hydroxyacetic acid | 3 | 1.60 | 408 |
| 10n | (S)-3-(9-(1-(cyclopropanecarbonyl)piperidin-3-yl)-8-oxo-8,9-dihydro-7H-purin-2-yl)pyrazolo[1,5-a]pyridine-5-carbonitrile | Example 6 and cyclopropanecarboxylic acid | 3 | 1.88 | 429 |
| 10o | (S)-3-(1-(2-hydroxy-2-methylpropanoyl)piperidin-3-yl)-1-methyl-5-(pyrazolo[1,5-a]pyridin-3-yl)-1H-imidazo[4,5-b]pyridin-2(3H)-one | Example 6g and 2-hydroxy-2-methylpropanoic acid | 4 | 1.76 | 435 |
| 10p | (S)-3-(1-(2-hydroxyacetyl)piperidin-3-yl)-1-methyl-5-(pyrazolo[1,5-a]pyridin-3-yl)-1H-imidazo[4,5-b]pyridin-2(3H)-one | Example 6g and 2-hydroxyacetic acid | 4 | 1.59 | 407 |
| 10q | (S)-3-(1-(2-(dimethylamino)acetyl)piperidin-3-yl)-1-methyl-5-(pyrazolo[1,5-a]pyridin-3-yl)-1H-imidazo[4,5-b]pyridin-2(3H)-one | Example 6g and N,N-dimethylglicine | 4 | 1.65 | 434 |
| 10r | 1-methyl-5-(pyrazolo[1,5-a]pyridin-3-yl)-3-((S)-1-((S)-tetrahydrofuran-2-carbonyl)piperidin-3-yl)-1H-imidazo[4,5-b]pyridin-2(3H)-one | Example 6g and (S)-tetrahydrofuran-2-carboxylic acid | 4 | 1.76 | 447 |
| 10s | (S)-1-methyl-5-(pyrazolo[1,5-a]pyridin-3-yl)-3-(1-(3,3,3-trifluoropropanoyl)piperidin-3-yl)-1H-imidazo[4,5-b]pyridin-2(3H)-one | Example 6g and 3,3,3-trifluoropropanoic acid | 4 | 1.99 | 459 |

Example 11

(S)-3-(2-(5-Cyanopyrazolo[1,5-a]pyridin-3-yl)-8-oxo-7H-purin-9(8H)-yl)-N,N-dimethyl piperidine-1-sulfonamide To a solution of the compound obtained in example 6 (110 mg, 0.22 mmol) in anhydrous DMF (3 mL), N,N-dimethylsulfamoyl chloride (0.03 mL, 0.27 mmol) and anhydrous TEA (0.13 mL, 0.90 mmol) were added. The reaction mixture was stirred at room temperature for 18 h, and the solvent was concentrated off. It was quenched with saturated NaHCO₃ aqueous solution (15 mL) and extracted with EtOAc (3×15 mL). The combined organic phases were dried over anhydrous Mg₂SO₄, filtered and concentrated. The crude residue was chromatographed on a silica gel flash system (ISCO Rf) using hexanes/acetone mixtures of increasing polarity as eluent to afford 39.2 mg of the titled compound (38% yield).

LC-MS (method 1): $t_R$=1.95 min; m/z=468 (MH+).

Following a similar procedure to that described in example 11, but using the corresponding starting materials, the following compound was obtained:

| Example | Name | Starting Materials | HPLC method | tR (min) | m/z (MH+) |
|---|---|---|---|---|---|
| 11a | (S)-N,N-dimethyl-3-(1-methyl-2-oxo-5-(pyrazolo[1,5-a]pyridin-3-yl)-1H-imidazo[4,5-b]pyridin-3(2H)-yl)piperidine-1-sulfonamide | Example 6g | 4 | 2.05 | 456 |

Example 12

3-(9-(1-Acetylpyrrolidin-3-yl)-7-methyl-8-oxo-8,9-dihydro-7H-purin-2-yl)pyrazolo[1,5-a]pyridine-5-carbonitrile a) tert-Butyl 3-(2-(5-cyanopyrazolo[1,5-a]pyridin-3-yl)-8-oxo-TH-purin-9(8H)-yl)pyrrolidine-1-carboxylate Following a similar procedure to that described in example 1, but using tert-butyl 3-aminopyrrolidine-1-carboxylate instead of tetrahydro-2H-pyran-4-amine, the desired compound was obtained.

b) tert-Butyl 3-(2-(5-cyanopyrazolo[1,5-a]pyridin-3-yl)-7-methyl-8-oxo-7H-purin-9(8H)-yl)pyrrolidine-1-carboxylate Following a similar procedure to that described in example 5, but using the compound obtained in previous section as starting material, the desired compound was obtained (25% yield).

c) 3-(7-Methyl-8-oxo-9-(pyrrolidin-3-yl)-8,9-dihydro-7H-purin-yl)pyrazolo[1,5-a]pyridine-5-carbonitrile hydrochloride Following a similar procedure to that described in example 6, but using the compound obtained in previous section as starting material, the desired compound was obtained (100% yield).

d) Title Compound

Following a similar procedure to that described in example 8, but using the compound obtained in previous section as starting material, the desired compound was obtained (22% yield).

LC-MS (method 2): $t_R$=1.67 min; m/z=403 (MH$^+$).

Example 13

3-(7-Methyl-9-(1-(methylsulfonyl)pyrrolidin-3-yl)-8-oxo-8,9-dihydro-7H-purin-yl)pyrazolo[1,5-a]pyridine-5-carbonitrile Following a similar procedure to that described in example 9, but using the compound obtained in example 12 section c as starting material, the desired compound was obtained (15% yield).

LC-MS (method 2): $t_R$=1.83 min; m/z=439 (MH$^+$).

Following a similar procedure to that described in example 13, but using the corresponding starting materials, the following compounds were obtained;

| Example | Name | Starting Material | HPLC method | $t_R$ (min) | m/z (MH$^+$) |
|---|---|---|---|---|---|
| 13a | (S)-3-(7-methyl-9-(1-(methylsulfonyl)pyrrolidin-3-yl)-8-oxo-8,9-dihydro-7H-purin-2-yl)pyrazolo[1,5-a]pyridine-5-carbonitrile | Example 6h | 3 | 2.35 | 439 |
| 13b | (R)-3-(7-methyl-9-(1-(methylsulfonyl)pyrrolidin-3-yl)-8-oxo-8,9-dihydro-7H-purin-2-yl)pyrazolo[1,5-a]pyridine-5-carbonitrile | Example 6i | 3 | 2.35 | 439 |
| 13c | (S)-9-(1-(methylsulfonyl)pyrrolidin-3-yl)-2-(pyrazolo[1,5-a]pyridin-3-yl)-7H-purin-8(9H)-one | Example 6j | 3 | 1.53 | 400 |
| 13d | (S)-7-methyl-9-(1-(methylsulfonyl)pyrrolidin-3-yl)-2-(pyrazolo[1,5-a]pyridin-3-yl)-7H-purin-8(9H)-one | Example 6k | 3 | 1.77 | 414 |
| 13e | (S)-3-(9-(1-(methylsulfonyl)pyrrolidin-3-yl)-8-oxo-8,9-dihydro-7H-purin-2-yl)pyrazolo[1,5-a]pyridine-5-carbonitrile | Example 6l | 3 | 1.63 | 425 |
| 13f | (R)-1-methyl-3-(1-(methylsulfonyl)pyrrolidin-3-yl)-5-(pyrazolo[1,5-a]pyridin-3-yl)-1H-imidazo[4,5-b]pyridin-2(3H)-one | Example 6m | 3 | 1.90 | 413 |
| 13g | (R)-3-(1-(methylsulfonyl)pyrrolidin-3-yl)-5-(pyrazolo[1,5-a]pyridin-3-yl)-1H-imidazo[4,5-b]pyridin-2(3H)-one | Example 6n | 3 | 1.72 | 399 |
| 13h | (R)-3-(9-(1-(methylsulfonyl)pyrrolidin-3-yl)-8-oxo-8,9-dihydro-7H-purin-2-yl)pyrazolo[1,5-a]pyridine-5-carbonitrile | Example 6o | 3 | 1.62 | 425 |
| 13i | (S)-3-(1-(methylsulfonyl)pyrrolidin-3-yl)-5-(pyrazolo[1,5-a]pyridin-3-yl)-1H-imidazo[4,5-b]pyridin-2(3H)-one | Example 6p | 3 | 1.72 | 399 |

| Example | Name | Starting Material | HPLC method | $t_R$ (min) | m/z (MH$^+$) |
|---|---|---|---|---|---|
| 13j | (S)-1-methyl-3-(1-(methylsulfonyl)pyrrolidin-3-yl)-5-(pyrazolo[1,5-a]pyridin-3-yl)-1H-imidazo[4,5-b]pyridin-2(3H)-one | Example 6q | 3 | 1.92 | 413 |
| 13k | (S)-7-methyl-9-(1-(methylsulfonyl)piperidin-3-yl)-2-(pyrazolo[1,5-a]pyridin-3-yl)-7H-purin-8(9H)-one | Example 6u | 3 | 1.93 | 428 |

Example 14

(2R)-2-[2-(5-Cyanopyrazolo[1,5-a]pyridin-3-yl)-8-oxo-7,8-dihydro-9H-purin-9-yl]propanoic acid To a suspension of example 1a (65 mg, 018 mmol) in dioxane (1.6 mL) and H$_2$O (0.8 mL) at 0° C., LiOH.H$_2$O (15 mg, 0.36 mmol) was added. The reaction mixture was stirred at 0° C. for 1 h and room temperature for 26 h. The pH of the solution was adjusted to 5 by adding 10% HCl aqueous solution. The solvent was removed under vacuum and the resulting solid was suspended in Et$_2$O (10 mL) and concentrated. The resulting solid was washed with water (2×5 mL), hexanes (3 mL) and Et$_2$O (2×5 mL) to afford 57 mg of the desired product (91%).

LC-MS (method 1): $t_R$=13.59 min; m/z=350 (MH$^+$).

Following a similar procedure to that described in example 14, but using the corresponding starting materials, the following compounds were obtained:

| Example | Name | Starting Material | HPLC method | $t_R$ (min) | m/z (MH$^+$) |
|---|---|---|---|---|---|
| 14a | (2S)-2-[2-(5-Cyanopyrazolo[1,5-a]pyridin-3-yl)-8-oxo-7,8-dihydro-9H-purin-9-yl]propanoic acid | Example 1i | 1 | 13.59 | 350 |
| 14b | (S)-2-(8-oxo-2-(pyrazolo[1,5-a]pyridin-3-yl)-7H-purin-9(8H)-yl)propanoic acid | Example 3e | 3 | 1.10 | 325 |

Example 15

(2R)-2-[2-(5-Cyanopyrazolo[1,5-a]pyridin-3-yl)-8-oxo-7,8-dihydro-9H-purin-9-yl]-N-(2,2,2-trifluoroethyl)propanamide To a solution of HOBt.H$_2$O (31 mg, 0.20 mmol) and TEA (0.068 mL, 0.49 mmol) in THF (1 mL), example 14 (70 mg, 0.20 mmol) was added. After 15 min, EDC.HCl (40 mg, 0.21 mmol) and 2,2,2-trifluoroethylamine hydrochloride (14.6 mg, 0.11 mmol) were added and the resulting mixture was stirred at room temperature for 3.5 days. Then, it was quenched with H$_2$O (5 mL) and extracted with EtOAc (3×15 mL). The combined organic phases were dried over anhydrous Na$_2$SO$_4$, filtered and concentrated. The crude product thus obtained was chromatographed over silica gel using MeOH/CH$_2$Cl$_2$ mixtures of increasing polarity as eluent, to afford 18 mg of the desired compound (50% yield).

LC-MS (method 1): $t_R$=15.34 min; m/z=431 (MH$^+$).

Following a similar procedure to that described in example 15, but using the corresponding starting material, the following compound was obtained:

| Example | Name | Starting Material | HPLC method | $t_R$ (min) | m/z (MH$^+$) |
|---|---|---|---|---|---|
| 15a | (2R)-(2-(5-cyanopyrazolo[1,5-a]pyridin-3-yl)-8-oxo-7H-purin-9(8H)-yl)-N-methylpropanamide | Example 14 and N-methylamine | 1 | 13.62 | 363 |
| 15b | (2S)-2-[2-(5-cyanopyrazolo[1,5-a]pyridin-3-yl)-8-oxo-7,8-dihydro-9H-purin-9-yl]-3-methyl-N-(2,2,2-trifluoroethyl)butanamide | (2S)-2-[2-(5-cyanopyrazolo[1,5-a]pyridin-3-yl)-8-oxo-7,8-dihydro-9H-purin-9-yl)-3-methylbutanoic acid (1) and 2,2,2-trifluoroethylamine | 3 | 2.08 | 459 |
| 15c | (R)-2-(2-(5-cyanopyrazolo[1,5-a]pyridin-3-yl)-8-oxo-7H-purin-9(8H)-yl)-N-(2-hydroxyethyl)propanamide | Example 14 and 2-aminoethanol | 3 | 1.35 | 393 |
| 15d | (R)-2-(2-(5-cyanopyrazolo[1,5-a]pyridin-3-yl)-8-oxo-7H-purin-9(8H)-yl)-N-(cyclopropylmethyl)propanamide | Example 14 and cyclopropylmethanamine | 3 | 1.75 | 403 |

| Example | Name | Starting Material | HPLC method | $t_R$ (min) | m/z (MH$^+$) |
|---|---|---|---|---|---|
| 15e | (R)-2-(2-(5-cyanopyrazolo[1,5-a]pyridin-3-yl)-8-oxo-7H-purin-9(8H)-yl)-N-(2-(dimethylamino)ethyl)propanamide | Example 14 and N1,N1-dimethylethane-1,2-diamine | 3 | 1.48 | 420 |
| 15f | (R)-2-(2-(5-cyanopyrazolo[1,5-a]pyridin-3-yl)-8-oxo-7H-purin-9(8H)-yl)-N-ethylpropanamide | Example 14 and N-ethylamine | 3 | 1.57 | 377 |
| 15g | (R)-2-(2-(5-cyanopyrazolo[1,5-a]pyridin-3-yl)-8-oxo-7H-purin-9(8H)-yl)-N-isopropylpropanamide | Example 14 and N-isopropylamine | 3 | 1.70 | 391 |
| 15h | (R)-2-(2-(5-cyanopyrazolo[1,5-a]pyridin-3-yl)-8-oxo-7H-purin-9(8H)-yl)-N,N-dimethylpropanamide | Example 14 and N,N-dimethylamine | 3 | 1.53 | 377 |
| 15i | (S)-2-(2-(5-cyanopyrazolo[1,5-a]pyridin-3-yl)-8-oxo-7H-purin-9(8H)-yl)-N-(2,2,2-trifluoroethyl)propanamide | Example 14a and 2,2,2-trifluoroethylamine | 3 | 1.72 | 431 |
| 15j | (S)-N-methyl-2-(8-oxo-2-(pyrazolo[1,5-a]pyridin-3-yl)-7H-purin-9(8H)-yl)propanamide | Example 14b and N-methylamine | 3 | 1.35 | 338 |
| 15k | (S)-N,N-dimethyl-2-(8-oxo-2-(pyrazolo[1,5-a]pyridin-3-yl)-7H-purin-9(8H)-yl)propanamide | Example 14b and N,N-dimethylamine | 5 | 1.90 | 352 |

(1) Obtained as example 14 but using HCl/Dioxane 4M/H$_2$O (1:1) instead of LiOH•H2O, and L-Valine methyl ester hydrochloride as starting material.

Example 16

3-(7-(2-Methoxyethyl)-8-oxo-9-(tetrahydro-2H-pyran-4-yl)-8,9-dihydro-7H-purin-2-yl)pyrazolo[1,5-a]pyridine-5-carbonitrile To a solution of example 1 (50 mg, 0.14 mmol) in DMF (8 mL), 55-65% NaH dispersion in mineral oil (6 mg, 0.15 mmol) was added and the resulting solution was stirred at room temperature for 10 min. Then 2-bromoethyl methyl ether (0.032 mL, 0.34 mmol) was added and the reaction mixture was stirred at 50° C. for 14.5 h. The reaction mixture was quenched with H$_2$O (10 mL) and extracted with EtOAc (3×10 mL). The combined organic phases were dried over anhydrous Na$_2$SO$_4$, filtered and concentrated. The crude product thus obtained was chromatographed over silica gel using EtOAc/hexanes mixtures of increasing polarity as eluent, to afford 36 mg of the desired compound (62% yield).

LC-MS (method 1): $t_R$=16.17 min; m/z=420 (MH$^+$).

Following a similar procedure to that described in example 16, but using in each case the corresponding starting materials, the following compounds were obtained:

| Example | Name | Starting Material | HPLC method | $t_R$ (min) | m/z (MH$^+$) |
|---|---|---|---|---|---|
| 16a | (S)-3-(9-(1-(2-cyanoacetyl)piperidin-3-yl)-7-(2-(dimethylamino)ethyl)-8-oxo-8,9-dihydro-7H-purin-2-yl)pyrazolo[1,5-a]pyridine-5-carbonitrile | 2-bromo-N,N-dimethylethanamine and example 1b (1) | 2 | 1.95 | 499 |
| 16b | (S)-3-(7-(2-(dimethylamino)ethyl)-8-oxo-9-(piperidin-3-yl)-8,9-dihydro-7H-purin-2-yl)pyrazolo[1,5-a]pyridine-5-carbonitrile | 2-bromo-N,N-dimethylethanamine and example 1b (2) | 2 | 1.83 | 432 |
| 16c | 7-(2-(dimethylamino)ethyl)-2-(pyrazolo[1,5-a]pyridin-3-yl)-9-(tetrahydro-2H-pyran-4-yl)-7H-purin-8(9H)-one) | 2-bromo-N,N-dimethylethanamine and example 3 | 2 | 1.921 | 408 |
| 16d | 3-(7-(2-(dimethylamino)ethyl)-8-oxo-9-(tetrahydro-2H-pyran-4-yl)-8,9-dihydro-7H-purin-2-yl)pyrazolo[1,5-a]pyridine-5-carbonitrile | 2-bromo-N,N-dimethylethanamine and example 1 | 1 | 14.79 | 433 |
| 16e | 3-(7-(2-(dimethylamino)ethyl)-9-(8-fluorochroman-4-yl)-8-oxo-8,9-dihydro-7H-purin-2-yl)pyrazolo[1,5-a]pyridine-5-carbonitrile | 2-bromo-N,N-dimethylethanamine and example 1p | 4 | 2.12 | 499 |
| 16f | 3-(9-(8-fluorochroman-4-yl)-7-(2-methoxyethyl)-8-oxo-8,9-dihydro-7H-purin-2-yl)pyrazolo[1,5-a]pyridine-5-carbonitrile | 2-bromoethyl methyl ether and example 1p | 4 | 2.20 | 486 |
| 16g | 3-(9-(8-fluorochroman-4-yl)-7-(3-hydroxypropyl)-8-oxo-8,9-dihydro-7H-purin-2-yl)pyrazolo[1,5-a]pyridine-5-carbonitrile | 3-bromopropan-1-ol and example 1p | 4 | 1.96 | 486 |

| Example | Name | Starting Material | HPLC method | $t_R$ (min) | m/z (MH$^+$) |
|---|---|---|---|---|---|
| 16h | (S)-3-(3-(1-(2-(dimethylamino)ethyl)-2-oxo-5-(pyrazolo[1,5-a]pyridin-3-yl)-1H-imidazo[4,5-b]pyridin-3(2H)-yl)piperidin-1-yl)-3-oxopropanenitrile | 2-bromo-N,N-dimethylethanamine and example 2a (1) | 4 | 1.73 | 473 |
| 16i | (S)-3-(3-(1-(2-methoxyethyl)-2-oxo-5-(pyrazolo[1,5-a]pyridin-3-yl)-1H-imidazo[4,5-b]pyridin-3(2H)-yl)piperidin-1-yl)-3-oxopropanenitrile | 2-bromoethyl methyl ether and example 2a (1) | 4 | 1.82 | 460 |
| 16j | (S)-3-(3-(1-(cyclopropylmethyl)-2-oxo-5-(pyrazolo[1,5-a]pyridin-3-yl)-1H-imidazo[4,5-b]pyridin-3(2H)-yl)piperidin-1-yl)-3-oxopropanenitrile | (bromomethyl)cyclopropane and example 2a (1) | 4 | 2.08 | 456 |

(1) followed by a similar procedure to that described in example 6 (tert-butoxtcarbonyl cleavage) and 7 (amide formation).
(2) followed by tert-butoxycarbonyl cleavage as example 6

Example 17

3-(7-(2-Hydroxyethyl)-8-oxo-9-(tetrahydro-2H-pyran-4-yl)-8,9-dihydro-7H-purin-2-yl)pyrazolo[1,5-a]pyridine-5-carbonitrile a) 3-(7-(2-(tert-Butyldimethylsilyloxy)ethyl)-8-oxo-9-(tetrahydro-2H-pyran-4-yl)-8,9-dihydro-7H-purin-2-yl)pyrazolo[1,5-a]pyridine-5-carbonitrile To a solution of example 1 (50 mg, 0.14 mmol) in DMF (8 mL), 55-65% NaH dispersion in mineral oil (6 mg, 0.15 mmol) was added. The resulting solution was stirred at room temperature for 10 min. Then (2-bromoethoxy)-tert-butyldimethylsilane (0.074 mL, 0.34 mmol) was added and the reaction was stirred at 50° C. for 14.5 h. The reaction mixture was quenched with H$_2$O (10 mL) and extracted with EtOAc (3×10 mL). The combined organic phases were dried over anhydrous Na$_2$SO$_4$, filtered and concentrated. The crude product thus obtained was chromatographed over silica gel using hexanes/EtOAc mixtures of increasing polarity as eluent, to afford 55 mg of the desired compound (76% yield).

b) Title Compound

To a solution of the compound obtained in the previous section (55 mg, 0.10 mmol) in THF (5 mL) 1 M TBAF solution in THF (0.14 mL, 0.14 mmol) was added and the resulting solution was stirred at room temperature for 1 h. The reaction mixture was quenched with H$_2$O (10 mL) and extracted with EtOAc (3×10 mL) and CH$_2$Cl$_2$ (2×10 mL). The combined organic phases were dried over anhydrous Na$_2$SO$_4$, filtered and concentrated. The crude product thus obtained was chromatographed over silica gel using MeOH/EtOAc mixtures of increasing polarity as eluent, to afford 39 mg of the desired compound (91% yield).

LC-MS (method 1): $t_R$=14.13 min: m/z=406 (MH$^+$).

Following a similar procedure to that described in example 17, but using in each case the corresponding starting materials, the following compounds were obtained:

| Example | Name | Starting Material | HPLC method | $t_R$ (min) | m/z (MH$^+$) |
|---|---|---|---|---|---|
| 17a | (S)-3-(9-(1-(2-cyanoacetyl)piperidin-3-yl)-7-(2-hydroxyethyl)-8-oxo-8,9-dihydro-7H-purin-2-yl)pyrazolo[1,5-a]pyridine-5-carbonitrile | Example 1b (1) | 1 | 1.68 | 472 |
| 17b | (S)-3-(7-(2-hydroxyethyl)-8-oxo-9-(piperidin-3-yl)-8,9-dihydro-7H-purin-2-yl)pyrazolo[1,5-a]pyridine-5-carbonitrile hydrochloride | Example 1b (2) | 1 | 1.55 | 405 |
| 17c | 3-(9-(8-fluorochroman-4-yl)-7-(2-hydroxyethyl)-8-oxo-8,9-dihydro-7H-purin-2-yl)pyrazolo[1,5-a]pyridine-5-carbonitrile | Example 1p | 1 | 15.99 | 472 |

(1) Followed by a similar procedure to that described in example 6 (tert-butoxtcarbonyl cleavage) and 7 (amide formation).
(2) Followed by tert-butoxycarbonyl cleavage as example 6

Example 18

3-(9-Tetrahydro-2H-pyran-4-yl-9H-purin-2-yl)pyrazolo[1,5-a]pyridine-5-carbonitrile To a suspension of the compound obtained in example 1 section d (100 mg, 0.30 mmol) in EtOH (1 mL), PTSA monohydrate (5.7 mg, 0.03 mmol) and triethylorthoformate (1 mL) were added. The reaction mixture was heated in a OEM Explorer microwave oven at 123° C. and 270 W for 30 min. Then, it was evaporated to dryness. The crude product thus obtained was chromatographed over silica gel using MeOH/EtOAc mixtures of increasing polarity as eluent, to afford 81 mg of the desired compound (79% yield).

LC-MS (method 1): $t_R$=14.56 min; m/z=346 (MH$^+$).

Following a similar procedure to that described in example 18, but using in each case the corresponding starting materials, the following compounds were obtained:

| Example | Name | Starting Material | HPLC method | $t_R$ (min) | m/z (MH$^+$) |
|---|---|---|---|---|---|
| 18a | 3-(8-methyl-9-tetrahydro-2H-pyran-4-yl-9H-purin-2-yl)pyrazolo[1,5-a]pyridine-5-carbonitrile | Example 1 section d and triethylorthoacetate | 1 | 14.77 | 360 |
| 18b | 3-(9-(4,4-difluorocyclohexyl)-8-methyl-9H-purin-2-yl)pyrazolo[1,5-a]pyridine-5-carbonitrile | triethylorthoacetate and 3-(5-amino-4-(4,4-difluorocyclohexylamino)pyrimidin-2-yl)pyrazolo[1,5-a]pyridine-5-carbonitrile (1) | 2 | 2.17 | 394 |
| 18c | 3-(9-(1,1-dioxotetrahydrothien-3-yl)-8-methyl-9H-purin-2-yl)pyrazolo[1,5-a]pyridine-5-carbonitrile | triethylorthoacetate and 3-(5-amino-4-(1,1-dioxotetrahydrothien-3-yl)aminopyrimidin-2-yl)pyrazolo[1,5-a]pyridine-5-carbonitrile (2) | 2 | 1.65 | 394 |
| 18d | 5-(pyrazolo[1,5-a]pyridin-3-yl)-3-(tetrahydro-2H-pyran-4-yl)-3H-imidazo[4,5-b]pyridine | Reference example 2g and triethylorthoformate | 3 | 1.85 | 320 |
| 18e | (S)-tert-butyl 3-(5-(5-cyanopyrazolo[1,5-a]pyridin-3-yl)-3H-imidazo[4,5-b]pyridin-3-yl)piperidine-1-carboxylate | Reference example 2h and triethylorthoformate | 3 | 2.33 | 444 |
| 18f | (S)-tert-butyl 3-(5-(5-cyanopyrazolo[1,5-a]pyridin-3-yl)-2-methyl-3H-imidazo[4,5-b]pyridin-3-yl)piperidine-1-carboxylate | Reference example 2h and triethylorthoacetate | 3 | 2.57 | 458 |
| 18g | 2-methyl-5-(pyrazolo[1,5-a]pyridin-3-yl)-3-(tetrahydro-2H-pyran-4-yl)-3H-imidazo[4,5-b]pyridine | Reference example 2g and triethylorthoacetate | 3 | 1.92 | 334 |
| 18h | 3-(9-(trans-4-hydroxycyclohexyl)-8-methyl-9H-purin-2-yl)pyrazolo[1,5-a]pyridine-5-carbonitrile | Reference example 2j and triethylorthoacetate | 3 | 1.70 | 374 |
| 18i | (S)-tert-butyl 3-(5-(pyrazolo[1,5-a]pyridin-3-yl)-3H-imidazo[4,5-b]pyridin-3-yl)piperidine-1-carboxylate | Reference example 2d and triethylorthoformate | 3 | 1.77 | 386 |

(1) obtained in example 1e section d
(2) obtained in example 1f section d

Example 19

3-(3-(Tetrahydro-2H-pyran-4-yl)-3H-imidazo[4,5-b]pyridin-5-yl)pyrazolo[1,5-a]pyridine-5-carbonitrile To a suspension of the compound obtained in example 2 section d (33.6 mg, 0.1 mmol) in EtOH (1.5 mL), citric acid (2 mg, 0.1 mmol) and triethyl orthoformate (340 µL, 2 mmol) were added. The reaction mixture was heated in a CEM Explorer microwave oven at 145° C. and 270 W for 2.5 hours. The crude residue was chromatographed on a silica gel flash system (ISCO Rf) using hexanes/acetone mixtures of increasing polarity as eluent to afford 14.2 mg of the desired product (41% yield).

LC-MS (method 3): $t_R$=1.76 min; m/z=345 (MH$^+$).

Following a similar procedure to that described in example 19, but using the corresponding starting material, the following compound was obtained:

| Example | Name | Starting Material | HPLC method | $t_R$ (min) | m/z (MH$^+$) |
|---|---|---|---|---|---|
| 19a | (S)-3-(3-(1-acetylpiperidin-3-yl)-3H-imidazo[4,5-b]pyridin-5-yl)pyrazolo[1,5-a]pyridine-5-carbonitrile | Reference example 2f | 5 | 2.22 | 386 |

Example 20

3-(2-Methyl-3-(tetrahydro-2H-pyran-4-yl)-3H-imidazo[4,5-b]pyridin-5-yl)pyrazolo[1,5-a]pyridine-5-carbonitrile To a solution of the compound obtained in example 2 section d (56.4 mg, 0,169 mmol) in EtOH (1.5 mL), PTSA monohydrate (3.21 mg, 0.017 mmol) and triethyl orthoacetate (547 mg, 3.37 mmol) were added. The reaction mixture was heated in a OEM Explorer microwave oven at 145° C. and 270 W for 2.5 hours. The crude residue was chromatographed on a silica gel flash system (ISCO Rf) using $CH_2Cl_2$/MeOH mixtures of increasing polarity a eluent to afford the desired product (15% yield).

LC-MS (method 3): $t_R$=1.79 min; m/z=359.5 ($MH^+$).

Example 21

3-(8-(1-Methyl-1H-imidazol-2-yl)-9-(tetrahydro-2H-pyran-4-yl)-9H-purin-2-yl)pyrazolo[1,5-a]pyridine-5-carbonitrile To a solution of the compound obtained in example 1 section d (100 mg, 0.30 mmol) in AcOH (0.025 mL) and DMA (2.5 mL), 1-methyl-1H-imidazole-2-carbaldehyde (46 mg, 0.42 mmol) was added. The reaction mixture was stirred in a sealed tube at 140° C. for 19 h. The crude mixture was quenched with $H_2O$ (10 mL), extracted with EtOAc (3×10 mL) and the combined organic phases were dried over anhydrous $Na_2SO_4$, filtered and concentrated. The crude product thus obtained was chromatographed over silica gel using hexanes/EtOAc mixtures of increasing polarity as eluent, to afford 40 mg of the desired compound (31% yield).

LC-MS (method 1): $t_R$=16.436 min; m/z=426 ($MH^+$).

Following a similar procedure to that described in example 21, but using the corresponding starting material, the following compound was obtained:

| Example | Name | Starting Material | HPLC method | $t_R$ (min) | m/z ($MH^+$) |
|---|---|---|---|---|---|
| 21a | 3-(8-(pyrimidin-5-yl)-9-(tetrahydro-2H-pyran-4-yl)-9H-purin-2-yl)pyrazolo[1,5-a]pyridine-5-carbonitrile | Example 1 section d and pyrimidine-5-carbaldehyde | 4 | 1.67 | 424 |
| 21b | 3-(9-(8-fluorochroman-4-yl)-8-(pyrimidin-5-yl)-9H-purin-2-yl)pyrazolo[1,5-a]pyridine-5-carbonitrile | Reference example 2e and pyrimidine-5-carbaldehyde | 1 | 16.34 | 490 |
| 21c | 3-(9-(8-fluorochroman-4-yl)-8-(1-methyl-1H-imidazol-2-yl)-9H-purin-2-yl)pyrazolo[1,5-a]pyridine-5-carbonitrile | Reference example 2e and 1-methyl-1H-imidazole-2-carbaldehyde | 1 | 18.4 | 492 |
| 21d | 2-(pyrazolo[1,5-a]pyridin-3-yl)-8-(1H-pyrrol-2-yl)-9-(tetrahydro-2H-pyran-4-yl)-9H-purine | Reference example 2c and 1H-pyrrole-2-carbaldehyde | 3 | 2.15 | 386 |
| 21e | 8-(5-methylthiophen-2-yl)-2-(pyrazolo[1,5-a]pyridin-3-yl)-9-(tetrahydro-2H-pyran-4-yl)-9H-purine | Reference example 2c and 5-methylthiophene-2-carbaldehyde | 3 | 2.52 | 417 |
| 21f | 8-(1-methyl-1H-imidazol-2-yl)-2-(pyrazolo[1,5-a]pyridin-3-yl)-9-(tetrahydro-2H-pyran-4-yl)-9H-purine | Reference example 2c and 1-methyl-1H-imidazole-2-carbaldehyde | 3 | 2.05 | 401 |
| 21g | 2-(pyrazolo[1,5-a]pyridin-3-yl)-9-(tetrahydro-2H-pyran-4-yl)-8-(2,2,2-trifluoroethyl)-9H-purine | Reference example 2c and 3,3,3-trifluoropropanal | 3 | 2.22 | 403 |
| 21h | 8-(1H-pyrazol-3-yl)-2-(pyrazolo[1,5-a]pyridin-3-yl)-9-(tetrahydro-2H-pyran-4-yl)-9H-purine | Reference example 2c and 1H-pyrazole-3-carbaldehyde | 3 | 1.83 | 387 |
| 21i | 8-(1-methyl-1H-pyrrol-2-yl)-2-(pyrazolo[1,5-a]pyridin-3-yl)-9-(tetrahydro-2H-pyran-4-yl)-9H-purine | Reference example 2c and 1-methyl-1H-pyrrole-2-carbaldehyde | 3 | 2.33 | 400 |
| 21j | 2-(2-(pyrazolo[1,5-a]pyridin-3-yl)-9-(tetrahydro-2H-pyran-4-yl)-9H-purin-8-yl)thiazole | Reference example 2c and thiazole-2-carbaldehyde | 3 | 2.43 | 404 |
| 21k | 2-(pyrazolo[1,5-a]pyridin-3-yl)-9-(tetrahydro-2H-pyran-4-yl)-8-(thiophen-2-yl)-9H-purine | Reference example 2c and thiophene-2-carbaldehyde | 3 | 2.32 | 403 |
| 21l | (S)-3-(9-(1-acetylpiperidin-3-yl)-8-(pyrimidin-5-yl)-9H-purin-2-yl)pyrazolo[1,5-a]pyridine-5-carbonitrile | Reference example 2 and pyrimidine-5-carbaldehyde | 3 | 1.8 | 465 |
| 21m | (S)-tert-butyl 3-(2-methyl-5-(pyrazolo[1,5-a]pyridin-3-yl)-3H-imidazo[4,5-b]pyridin-3-yl)piperidine-1-carboxylate | Reference example 2d and acetaldehydee | 3 | 2.60 | 433 |

Example 22

3-[8-(Ethylamino)-9-tetrahydro-2H-pyran-4-yl-9H-purin-2-yl]pyrazolo[1,5-a]pyridine-5-carbonitrile To a suspension of the compound obtained in example 1 section d (100 mg, 0.30 mmol) in $CH_2Cl_2$ (2 mL), ethyl isothiocyanate (0.042 ml, 0.48 mmol), EDC.HCl (171 mg, 0.89 mmol) and DIPEA (0.25 ml, 1.49 mmol) were added. The reaction mixture was heated in a CEM Explorer microwave oven at 80° C. and 150 W for 30 min. Then, it was evaporated to dryness. The crude product thus obtained was chromatographed over silica gel using MeOH/EtOAc mixtures of increasing polarity as eluent, to afford 42 mg of the desired compound (36% yield).

LC-MS (method 1): $t_R$=15.64 min; m/z=389 (MH$^+$).

Following a similar procedure to that described in example 22, but using the corresponding starting material, the following compound was obtained:

| Example | Name | Starting Material | HPLC method | $t_R$ (min) | m/z (MH$^+$) |
|---|---|---|---|---|---|
| 22a | 3-(8-(pyridin-3-ylamino)-9-(tetrahydro-2H-pyran-4-yl)-9H-purin-2-yl)pyrazolo[1,5-a]pyridine-5-carbonitrile | Example 1 section d, pyridine-3-isothiocyanate | 1 | 16.20 | 438 |
| 22b | 3-(8-(ethylamino)-9-(8-fluorochroman-4-yl)-9H-purin-2-yl)pyrazolo[1,5-a]pyridine-5-carbonitrile | Reference example 2e and ethyl isothiocyanate | 1 | 17.07 | 455 |
| 22c | 3-(9-(8-fluorochroman-4-yl)-8-(pyridin-3-ylamino)-9H-purin-2-yl)pyrazolo[1,5-a]pyridine-5-carbonitrile | Reference example 2e and pyridine-3-isothiocyanate | 1 | 17.22 | 504 |

Example 23

8-Cyclopentyl-2-(pyrazolo[1,5-a]pyridin-3-yl)-9-(tetrahydro-2H-pyran-4-yl)-9H-purine To a solution of reference example 2c (0.05 g, 0.16 mmol) in DMF (1 mL), cyclopentanecarbaldehyde (0.018 mL, 0.17 mmol) and sodium bisulfite (0.030 g, 0.29 mmol) were added. The reaction mixture was stirred at 130° C. for 6 h. The solvent was concentrated off and the crude residue was chromatographed on a silica gel flash system (ISCO Companion) using $CH_2Cl_2$/MeOH mixtures of increasing polarity as eluent to afford 37 mg of the desired product (60% yield).

LC-MS (method 3): =2.40 min; m/z=389 (MH$^+$).

Following a similar procedure to that described in example 23, but using in each case the corresponding starting materials, the following compounds were obtained:

| Example | Name | Starting Material | HPLC method | $t_R$ (min) | m/z (MH$^+$) |
|---|---|---|---|---|---|
| 23a | (S)-3-(9-(1-acetylpiperidin-3-yl)-8-ethyl-9H-purin-2-yl)pyrazolo[1,5-a]pyridine-5-carbonitrile | Reference example 2 and propionaldehyde | 5 | 2.42 | 415 |
| 23b | (S)-3-(9-(1-acetylpiperidin-3-yl)-8-isopropyl-9H-purin-2-yl)pyrazolo[1,5-a]pyridine-5-carbonitrile | Reference example 2 and isobutyraldehyde | 5 | 2.57 | 429 |
| 23c | (S)-3-(9-(1-acetylpiperidin-3-yl)-8-methyl-9H-purin-2-yl)pyrazolo[1,5-a]pyridine-5-carbonitrile | Reference example 2 and acetaldehyde | 3 | 1.78 | 401 |
| 23d | 8-cyclopropyl-2-(pyrazolo[1,5-a]pyridin-3-yl)-9-(tetrahydro-2H-pyran-4-yl)-9H-purine | Reference example 2c and cyclopropanecarbaldehyde | 3 | 2.05 | 361 |

Example 24

(S)-3-(1-Acetylpiperidin-3-yl)-1-methyl-5-(pyrazolo[1,5-a]pyridin-3-yl)-1H-imidazo[4,5-b]pyridin-2(3H)-one To a solution of example 6g (250 mg, 0.65 mmol) in pyridine (10 mL), acetyl chloride (0.92 mL, 1.3 mmol) was added. The reaction mixture was stirred at room temperature for 5 h. The solvent was concentrated off and the crude residue was chromatographed on a silica gel flash system (SP1 Biotage) using EtOAc/MeOH mixtures of increasing polarity as eluent to afford 196 mg of the desired product (78% yield).

LC-MS (method 4): $t_R$=1.66 min; m/z=391 (MH$^+$).

Following a similar procedure to that described in example 24, but using in each case the corresponding starting materials, the following compounds were obtained:

| Example | Name | Starting Material | HPLC method | $t_R$ (min) | m/z (MH$^+$) |
|---|---|---|---|---|---|
| 24a | (S)-1-methyl-3-(1-pivaloylpiperidin-3-yl)-5-(pyrazolo[1,5-a]pyridin-3-yl)-1H-imidazo[4,5-b]pyridin-2(3H)-one | Example 6g and pivaloyl chloride | 4 | 2.10 | 433 |
| 24b | (S)-3-(1-(4-fluorobenzoyl)piperidin-3-yl)-1-methyl-5-(pyrazolo[1,5-a]pyridin-3-yl)-1H-imidazo[4,5-b]pyridin-2(3H)-one | Example 6g and 4-fluorobenzoyl chloride | 4 | 2.11 | 472 |
| 24c | (S)-1-methyl-3-(1-propionylpiperidin-3-yl)-5-(pyrazolo[1,5-a]pyridin-3-yl)-1H-imidazo[4,5-b]pyridin-2(3H)-one | Example 6g and propionyl chloride | 4 | 1.79 | 405 |

Example 25

(S)-1-(3-(1-Methyl-2-oxo-5-(pyrazolo[1,5-a]pyridin-3-yl)-1H-imidazo[4,5-b]pyridin-3(2H-1)-yl)piperidine-1-carbonyl)cyclopropanecarbonitrile To a solution of 1-cyano-1-cyclopropanecarboxylic acid (65 mg, 0.58 mmol), in DMF (7 mL), DIEA (0.31 mL, 1.7 mmol), example 6g (248 mg, 0.64 mmol) and HBTU (266 mg, 0.70 mmol) were added. The reaction mixture was stirred at room temperature overnight. The solvent was concentrated off and the crude residue was chromatographed on a silica gel flash system (SP1 Biotage) using EtOAc/MeOH mixtures of increasing polarity as eluent to afford the desired with quantitative yield.

LC-MS (method 4): $t_R$=1.92 min; m/z=442 (MH$^+$).

Following a similar procedure to that described in example 25, but using in each case the corresponding staffing materials, the following compounds were obtained:

| Example | Name | Starting Materials | HPLC method | $t_R$ (min) | m/z (MH$^+$) |
|---|---|---|---|---|---|
| 25a | 9-(1-isobutyrylpiperidin-4-yl)-2-(pyrazolo[1,5-a]pyridin-3-yl)-7H-purin-8(9H)-one | Example 6d and isobutyric acid | 4 | 1.59 | 406 |
| 25b | 9-(1-(2-(dimethylamino)acetyl)piperidin-4-yl)-2-(pyrazolo[1,5-a]pyridin-3-yl)-7H-purin-8(9H)-one | Example 6d and 2-(dimethylamino)acetic acid | 4 | 1.34 | 421 |

Example 26

(S)-Methyl 3-(2-(5-cyanopyrazolo[1,5-a]pyridin-3-yl)-8-oxo-7H-purin-9(8H)-yl)piperidine-1-carboxylate To a solution of example 6 (200 mg, 0.26 mmol) in DMF (2.6 mL), methyl chloroformate (27 mg, 0.28 mmol) and DIPEA (0.068 mL, 0.39 mmol) were added. The reaction mixture was stirred at room temperature overnight. The reaction mixture was evaporated under reduced pressure, dissolved in $CH_2Cl_2$, and washed thrice with saturated $NaHCO_3$ aqueous solution. The combined organic phases were dried over $MgSO_4$ and concentrated to dryness. The crude residue was chromatographed on a silica gel flash system (ISCO Combiflash) using $CH_2Cl_2$/MeOH mixtures of increasing polarity as eluent to afford 36 mg of the desired product (32% yield).

LC-MS (method 5): $t_R$=2.37 min; m/z=419 (MH$^+$).

Following a similar procedure to that described in example 26, but using in each case the corresponding starting materials, the following compounds were obtained:

Example 27

(S)-3-(9-(1-(1-Cyanocyclopropanecarbonyl)piperidin-3-yl)-8-oxo-8,9-dihydro-7H-purin-2-yl)pyrazolo[1,5-a]pyridine-5-carbonitrile Following a similar procedure to that described in example 25, but using HATU instead of HBTU, and example 6 instead of example 6g, the desired compound was obtained (30% yield).

LC-MS (method 3): $t_R$=1.87 min; m/z=454 (MH$^+$).

Following a similar procedure to that described in example 27, but using the corresponding starting materials, the following compound was obtained:

| Example | Name | Starting Materials | HPLC method | tR (min) | m/z (MH+) |
|---|---|---|---|---|---|
| 27a | (S)-3-(9-(1-(1-hydroxycyclopropane- | Example 6 and 1-hydroxy cyclopropane- | 3 | 1.7 | 455 |

| Example | Name | Starting Materials | HPLC method | $t_R$ (min) | m/z (MH$^+$) |
|---|---|---|---|---|---|
| 26a | (S)-ethyl 3-(2-(5-cyanopyrazolo[1,5-a]pyridin-3-yl)-8-oxo-7H-purin-9(8H)-yl)piperidine-1-carboxylate | Example 6 and ethyl chloroformate | 5 | 2.53 | 433 |
| 26b | (S)-isobutyl 3-(2-(5-cyanopyrazolo[1,5-a]pyridin-3-yl)-8-oxo-7H-purin-9(8H)-yl)piperidine-1-carboxylate | Example 6 and isobutyl chloroformate | 5 | 2.82 | 461 |
| 26c | (S)-3-(2-(5-cyanopyrazolo[1,5-a]pyridin-3-yl)-8-oxo-7H-purin-9(8H)-yl)-N-isopropylpiperidine-1-carboxamide | Example 6 and isopropyl isocyanate | 5 | 2.33 | 446 |
| 26d | (S)-N-tert-butyl-3-(2-(5-cyanopyrazolo[1,5-a]pyridin-3-yl)-8-oxo-7H-purin-9(8H)-yl)piperidine-1-carboxamide | Example 6 and tert-butyl isocyanate | 5 | 2.52 | 460° |
| 26e | (S)-ethyl 9-(1-(2-cyanoacetyl)piperidin-3-yl)-8-oxo-2-(pyrazolo[1,5-a]pyridin-3-yl)-8,9-dihydro-7H-purine-7-carboxylate | Example 7f and ethyl chloroformate | 5 | 2.62 | 475 |
| 26f | (S)-3-(3-(7-acetyl-8-oxo-2-(pyrazolo[1,5-a]pyridin-3-yl)-7H-purin-9(8H)-yl)piperidin-1-yl)-3-oxopropanenitrile | Example 7f and acetyl chloride | 5 | 2.60 | 445 |
| 26g | (S)-9-(1-acetylpiperidin-3-yl)-7-methyl-2-(pyrazolo[1,5-a]pyridin-3-yl)-7H-purin-8(9H)-one | Example 6u and acetyl chloride | 3 | 1.80 | 392 |
| 26h | (S)-N-isopropyl-3-(1-methyl-2-oxo-5-(pyrazolo[1,5-a]pyridin-3-yl)-1H-imidazo[4,5-b]pyridin-3(2H)-yl)piperidine-1-carboxamide | Example 7p and isopropyl isocyanate | 4 | 1.85 | 434 |
| 26i | (S)-3-(3-(1-acetyl-2-oxo-5-(pyrazolo[1,5-a]pyridin-3-yl)-1H-imidazo[4,5-b]pyridin-3(2H)-yl)piperidin-1-yl)-3-oxopropanenitrile | Example 7p and acetyl chloride | 4 | 2.01 | 444 |
| 26j | (S)-ethyl 3-(1-(2-cyanoacetyl)piperidin-3-yl)-2-oxo-5-(pyrazolo[1,5-a]pyridin-3-yl)-2,3-dihydro-1H-imidazo[4,5-b]pyridine-1-carboxylate | Example 7p and ethyl chloroformate | 4 | 1.97 | 474 |

| Example Name | Starting Materials | HPLC method | tR (min) | m/z (MH+) |
|---|---|---|---|---|
| carbonyl)piperidin-3-yl)-8-oxo-8,9-dihydro-7H-purin-2-yl)pyrazolo[1,5-a]pyridine-5-carbonitrile | carboxylic acid | | | |

Example 28

(R)-3-(9-(1-Hydroxypropan-2-yl)-8-oxo-8,9-dihydro-7H-purin-2H)pyrazolo[1,5-a]pyridine-5-carbonitrile To a solution of example 14 (60 mg, 0.17 mmol) in THF (10 mL) at 0° C., 1 M THF borane complex solution in THF (0.69 mL, 0.69 mmol) was added. The reaction mixture was stirred at room temperature overnight, quenched with MeOH (10 mL) and the reaction mixture was evaporated under reduced pressure. The crude residue was chromatographed on a silica gel flash system (ISCO Combiflash) using $CH_2Cl_2$/MeOH mixtures of increasing polarity as eluent to afford 4 mg of the desired product (7% yield).
LC-MS (method 3): $t_R$=2.02 min; m/z=336 (MH+).

Example 29

(S)-3-(3-(2-(5-Methylpyrazolo[1,5-a]pyridin-3-yl)-9H-purin-9-yl)piperidin-1-yl)-3-oxopropanenitrile a) (S)-tert-Butyl 3-(2-(5-methylpyrazolo[1,5-a]pyridin-3-yl)-9H-purin-9-yl)piperidine-1-carboxylate Following a similar procedure to that described in example 18, but using reference example 2a instead of the compound obtained in example 1 section d, the desired compound was obtained (10% yield).
LC-MS (method 3): $t_R$=2.53 min; m/z=434 (MH+).

b) (S)-2-(5-Methylpyrazolo[1,5-a]pyridin-3-yl)-9-(piperidin-3-yl)-9H-purine hydrochloride Following a similar procedure to that described in example 6, but using the compound obtained in the previous section, the desired compound was obtained (quantitative yield).
LC-MS (method 3): $t_R$=1.7 min; m/z=334 (MH+).

c) Title Compound

Following a similar procedure to that described in example 7, but using the compound obtained in the previous section, the desired compound was obtained (57% yield).
LC-MS (method 3); $t_R$=1.78 min; m/z=401 (MH+).

Example 30

1-(4-(2-(Pyrazolo[1,5-a]pyridin-3-yl)-9H-purin-9-yl)piperidin-1-yl)ethanone a) 9-(Piperidin-4-yl)-2-(pyrazolo[1,5-a]pyridin-3-yl)-9H-purine hydrochloride Following a similar procedure to that described in example 29 section a and b, but using the compound obtained in reference example 2b instead of reference example 2a, the desired compound was obtained (10% yield).

b) Title Compound

Following a similar procedure to that described in example 24, but using the compound obtained in the previous section, the desired compound was obtained (quantitative yield).
LC-MS (method 4): $t_R$=1.35 min; m/z=362 (MH+),

Example 31

(S)-(9-(1-(2-Cyanoacetyl)piperidin-3-yl)-8-oxo-2-(pyrazolo[1,5-a]pyridin-3-yl)-8,9-dihydro-7H-purin-7-yl)methyl acetate a) (S)-tert-Butyl 3-(7-(acetoxymethyl)-8-oxo-2-(pyrazolo[1,5-a]pyridin-3-yl)-7H-purin-9(81-1)-yl)piperidine-1-carboxylate Following a similar procedure to that described in example 4, but using the compound obtained in example 3b instead of example 1 and bromomethyl acetate instead of methyl iodide, the desired compound was obtained (83% yield).
LC-MS (method 3): $t_R$=2.72 min; m/z=508 (MH+).

b) (S)-(8-Oxo-9-(piperidin-3-yl)-2-(pyrazolo[1,5-a]pyridin-3-yl)-8,9-dihydro-7H-purin-7-yl)methyl acetate hydrochloride Following a similar procedure to that described in example 6, but using the compound obtained in the previous section, the desired compound was obtained (quantitative yield).
LC-MS (method 3): $t_R$=1.80 min; m/z=408 (MH+).

c) Title Compound

Following a similar procedure to that described in example 7, but using the compound obtained in the previous section, the desired compound was obtained (36% yield).
LC-MS (method 3): $t_R$=1.82 min; m/z=475 (MH+).

Following a similar procedure to that described in example 31, but using the corresponding starting materials, the following compound was obtained:

| Example | Name | Starting Materials | HPLC method | tR (min) | m/z (MH+) |
|---|---|---|---|---|---|
| 31a | (S)-(3-(1-(2-cyanoacetyl)piperidin-3-yl)-2-oxo-5-(pyrazolo[1,5-a]pyridin-3-yl)-2,3-dihydro-1H-imidazo[4,5-b]pyridin-1-yl)methyl acetate | Example 7p | 4 | 1.84 | 474 |

Example 32

(R)-3-(9-(1-Hydroxypropan-2-yl)-7-methyl-8-oxo-8,9-dihydro-7H-purin-2-yl)pyrazolo[1,5-a]pyridine-5-carbonitrile To a solution of example 28 (20 mg, 0.06 mmol) in AcN (2 mL) and DMF (0.5 mL) silver (I) oxide (28 mg, 0.12 mmol) and methyl iodide (0.006 mL, 0.09 mmol) were added. The reaction mixture was stirred at room temperature overnight. The reaction mixture was filtered through a plug of Celite® and the solvent was evaporated under reduced pressure. The crude residue was chromatographed on a silica gel flash system (ISCO Combiflash) using CH$_2$Cl$_2$/MeOH mixtures of increasing polarity as eluent to afford 6 mg of the desired product (29% yield).

LC-MS (method 3): $t_R$=1.75 min; m/z=350 (MH$^+$).

Example 33

2-(Pyrazolo[1,5-a]pyridin-3-yl)-9-(tetrahydro-2H-pyran-4-yl)-9H-purin-8-amine

To a solution of reference example 2c (144 mg, 0.46 mmol) in EtOH (4 mL), cyanogen bromide (147 mg, 1.39 mmol) was added. The reaction mixture was stirred at 70° C. overnight. The reaction mixture was evaporated under reduced pressure, dissolved in EtOAc, and washed thrice with saturated NaHCO$_3$ aqueous solution. The combined organic phases were dried over MgSO$_4$ and concentrated to dryness. The reaction crude was used in next step without further purification.

LC-MS (Method 3): $t_R$=1.53 min; m/z=336 (MH$^+$)

Example 34

1-(2-(Pyrazolo[1,5-a]pyridin-3-yl)-9-(tetrahydro-2H-pyran-4-yl)-9H-purin-8-yl)pyrrolidin-2-one To a suspension of example 33 (25 mg, 0.075 mmol) in DMF (1.5 mL), DIPEA (0.04 mL, 0.22 mmol) and 4-bromobutyryl chloride (0.01 mL, 0.082 mmol) were added. The reaction mixture was stirred at room temperature overnight. The solvent was evaporated to dryness and 1.7 mg of the title compound were obtained (yield 6%) after HPLC preparative purification.

LC-MS (method 3): $t_R$=1.82 min; m/z=404 (MH$^+$)

Following a similar procedure to that described in example 34, but using in each case the corresponding starting materials, the following compounds were obtained:

butylchlorodimethylsilane (281 mg, 1.86 mmol) were added. The reaction mixture was stirred at room temperature overnight. The solvent was evaporated to dryness, dissolved in CH$_2$Cl$_2$ and washed thrice with water. The combined organic phases were dried over MgSO$_4$ and concentrated to dryness. The reaction crude was used in next step without further purification LC-MS (method 3): $t_R$=3.38 min; m/z=490 (MH$^+$)

b) 3-(9-(trans-4-(tert-butyldimethylsilyloxy)cyclohexyl)-7-methyl-8-oxo-8,9-dihydro-7H-purin-2-yl) pyrazolo[1,5-a]pyridine-5-carbonitrile Following a similar procedure to that described in example 5, but using the compound obtained in the previous section, the desired compound was obtained (72% yield).

LC-MS (method 2): $t_R$=3.67 min; m/z=504 (MH$^+$).

c) Title Compound

To a suspension of the compound obtained in the previous section (246 mg, 0.488 mmol) in AcN (10 mL), at 0° C., 1 M TBAF solution in THF (0.73 mL, 0.73 mmol) was added. The reaction mixture was stirred at room temperature overnight. The solvent was evaporated to dryness, dissolved in EtOAc and washed thrice with water. The combined organic phases were dried over MgSO4 and concentrated to dryness. The crude residue was chromatographed on a silica gel flash system (ISCO Combiflash) using CH$_2$Cl$_2$/MeOH mixtures of increasing polarity as eluent to afford 77 mg of the desired product (40% yield).

LC-MS (method 3): $t_R$=1.82 min; m/z=390 (MH$^+$).

| Example | Name | Starting Materials | HPLC method | $t_R$ (min) | m/z (MH$^+$) |
|---|---|---|---|---|---|
| 34a | N-(2-(pyrazolo[1,5-a]pyridin-3-yl)-9-(tetrahydro-2H-pyran-4-yl)-9H-purin-8-yl)isobutyramide | Example 33 and isobutyryl chloride | 3 | 1.97 | 406 |
| 34b | N-(2-(pyrazolo[1,5-a]pyridin-3-yl)-9-(tetrahydro-2H-pyran-4-yl)-9H-purin-8-yl)propionamide | Example 33 and propionyl chloride | 3 | 1.77 | 392 |
| 34c | N-(2-(pyrazolo[1,5-a]pyridin-3-yl)-9-(tetrahydro-2H-pyran-4-yl)-9H-purin-8-yl)acetamide | Example 33 and acetyl chloride | 3 | 1.60 | 378 |

Example 35

3-(9-(trans-4-Hydroxycyclohexyl)-7-methyl-5-oxo-8,9-dihydro-7H-purin-2-yl)pyrazolo[1,5-a]carbonitrile a) 3-(9-trans-4-(tert-butyldimethylsilyloxy)cyclohexyl)-8-oxo-8,9-dihydro-7H-purin-2-yl)pyrazolo[1,5-a]pyridine-5-carbonitrile To a suspension of example 1o (584 mg, 1.55 mmol) in DMF (15 mL), imidazole (265 mg, 3.89 mmol) and tert- Example 36

2-(2-(5-Cyanopyrazolo[1,5-a]pyridin-3-yl)-8-oxo-7H-purin-9(8H)-yl)-N-(2,2,2-trifluoroethyl)acetamide a) 2-(2-(5-cyanopyrazolo[1,5-a]pyridin-3-yl)-8-oxo-7H-purin-9(8H)-yl)acetic acid Following a similar procedure to that described in example 14, but using the compound obtained in example in instead of example 1a, the desired compound was obtained LC-MS (method 3): $t_R$=1.05 min; m/z=336 (MH$^+$).

b) Title Compound

Following a similar procedure to that described in example 15, but using the compound obtained in the previous section and 2,2,2-trifluoroethylamine, the desired compound was obtained.

LC-MS (method 3): $t_R$=1.065 min; m/z=417 (MH$^+$).

Following a similar procedure to that described in example 36, but using the corresponding starting materials, the following compound was obtained:

| Example | Name | Starting Materials | HPLC method | tR (min) | m/z (MH+) |
|---|---|---|---|---|---|
| 36a | 2-(2-(5-cyanopyrazolo[1,5-a]pyridin-3-yl)-8-oxo-7H-purin-9(8H)-yl)-N-ethylacetamide | N-ethylamine | 3 | 1.40 | 363 |

Example 37

2-(imidazo[1,2-a]pyridin-3-yl)-7-methyl-9-(tetrahydro-2H-pyran-4-yl)-7H-purin-8(9H)-one a) 2-Chloro-N4-(tetrahydro-2H-pyran-4-yl)pyrimidine-4,5-diamine Following a similar procedure to that described in example 1 section d, but using the compound obtained in example 1 section a instead of the compound obtained in example 1 section c, the desired compound was obtained (quantitative yield).

LC-MS (method 1): $t_R$=6.73 min; m/z=229 (MH$^+$).

b) 2-Chloro-9-(tetrahydro-2H-pyran-4-yl)-7H-purin-8(9H)-one

Following a similar procedure to that described in example 1 section e, but using the compound obtained in the previous section instead of the compound obtained in example 1 section d, the desired compound was obtained (83% yield).

LC-MS (method 1): $t_R$=7.16 min; m/z=254 (MH$^+$).

c) 2-chloro-7-methyl-9-(tetrahydro-2H-pyran-4-yl)-7H-purin-8(9H)-one

Following a similar procedure to that described in example 5, but using the compound obtained in the previous section instead of the compound obtained in example 3b, the desired compound was obtained (58% yield).

LC-MS (method 1): $t_R$=7.51 min; m/z=268 (MH$^+$).

d) Title Compound

To a suspension of the compound obtained the previous section (30 mg, 0.11 mmol) in EtOH (0.5 mL) and dioxane (1 mL), imidazo[1,2-a]pyridine (16 mg, 0.13 mmol), triphenylphosphine (5.8 mg, 0.02 mmol), potassium carbonate (3.1 mg, 0.22 mmol) and palladium (II) acetate (2.5 mg, 0.01 mmol) were added. The reaction mixture was heated in a CEM Explorer microwave oven at 110° C. for 10 min and at 90° C. for 3 h. The reaction mixture was filtered through a plug of Celite® and the solvent was concentrated off. A sample was purified by preparative HPLC.

LC-MS (method 4): $t_R$=1.55 min; m/z=351 (MH$^+$).

Example 38

Inhibition of JAK3 Activity

The inhibition of JAK3 kinase activity was determined in 384-well assay microplates using the Z'-Lyte® Kinase Assay kit-Tyr 6 Peptide kit, supplied by invitrogen (Ref: PV4122), following the manufacturer's instructions, in a final volume of 10 µL per well, 2.5 µL of the product to be tested dissolved in 4% DMSO (final concentration of the product to be tested, 0.1-10000 nM) was incubated with 0.3 µg/mL of the catalytic domain of human JAK3 (amino acid sequence 281-1124), 2 µM of the substrate peptide Z'-Lyte® Tyr 6 and 4 µM of ATP; all components were dissolved in 50 mM pH 7.5 Hepes buffer, 10 mM Magnesium chloride (II), 1 mM EGTA and 0.01% Brij® 35. The reaction was started by the addition of said 4 µM ATP; after incubation for 1 hour at 25° C., 5 µL of A Z'-Lyte® Tyr 6 development reagent was added and the mixture was incubated for 1 hour at 25° C. Phosphorylation was then quantified in each well using a Safire2® fluorescence microplate reader from Tecan.

The compounds 1 to 1b, 1d to 1j, 1n to 1p, 1s, 2, 2e, 3 to 3e, 3h to 3i, 4, 4b to 5i, 5s, 6 to 6b, 6d to 6f, 6x, 7 to 7d, 7f to 16a, and 16c to 17a, 17c to 19, 20 to 29, 31 to 37 showed more than 50% inhibition of JAK3 activity at 1 µM in this assay.

Example 39

Inhibition of JAK2 Activity

The inhibition of JAK2 kinase activity was determined in 384-well assay microplates using the Z'-Lyte® Kinase Assay kit-Tyr 6 Peptide kit, supplied by Invitrogen (Ref: PV4122), following the manufacturer's instructions. In a final volume of 10 µL per well, 2.5 µL of the product to be tested dissolved in 4% DMSO (final concentration of the product to be tested, 0.1-10000 nM) was incubated with 0.5 µg/well of the catalytic domain of human JAK2, 2 µM of the substrate peptide Z'-Lyte® Tyr 6 and 16 µM of ATP; all components were dissolved in 50 mM pH 7.5 Hepes buffer, 10 mM Magnesium chloride (II), 1 mM EGTA and 0.01% Brij® 35. The reaction was started by the addition of said 16 µM ATP; after incubation for 1 hour at 25° C., 5 µL of A Z'-Lyte® Tyr 6 development reagent was added and the mixture was incubated for 1 hour at 25° C. Phosphorylation was then quantified in each well using a Safire2® fluorescence microplate reader from Tecan.

The compounds 1 to 1b, 1e to 1g, 1n to 1p, 1s, 2, 2e, 3, 3b, 3d, 3e, 4, 4c, 5, 5a, 5b, 5e, 5f, 5h, 5i, 5s, 7 to 7c, 7f to 7n, 7p, 7r to 7u, 8 to 8c, 8d, 8f to 8h, 9a, 9b, 9c, 9f, 9g, 9i to 9k, 9m to 9s, 10a, 10b, 10e, 10h, 10i, 10k, 10l, 10m, 10n, 13b to 13k, 15 to 15b, 15 f, 15 h, 15i, 15k, 16, 16a, 16d to 16f, 17 to 17c, 18a, 18b, 18d to 18i, 19, 20, 21a to 21d, 21g to 21i, 21k, 22 to 23, 23d, 24, 24a, 24b, 24c, 25, 26, 26a, 26c, 26d, 26e, 26f, 26g, 27, 27a, 29, 31, 33, 34, 34b, and 35 to 36a showed more than 50% inhibition of JAK2 activity at 1 µM in this assay.

Example 40

Determination of Clearance in Human Liver Microsomes

A single concentration (1 µM in pH7.4 buffer) of a compound to be tested was incubated with human liver microsomes for 0, 10, 30 and 60 minutes at 37° C. (0.4 mg protein/mL). The degree of hepatic metabolism was measured by LC-MS/MS as the decrease in the peak area of the parent compound and expressed as the intrinsic clearance.

Several compounds of the invention were tested in this assay.

Example 41

Cytotoxicity in Hep G2 Cells Assay

Alamar blue (AB) was used to evaluate the possible toxicity of a compound to be tested on Human hepatocyte carcinoma cells (HepG2). The cells (20000 cells/well) were cultured in 96-well plates in the presence of the compound at different concentrations (1 to 20 μM) containing 0.2% DMSO for 72 h at 37° C. After addition of AB, fluorescence was measured. $EC_{50}$ value, defined as the concentration of the compound that results in a decrease in AB fluorescence equivalent to 50% of the control, was calculated.

Several compounds of the invention were tested in this assay.

The invention claimed is:
1. A compound of formula I or II:

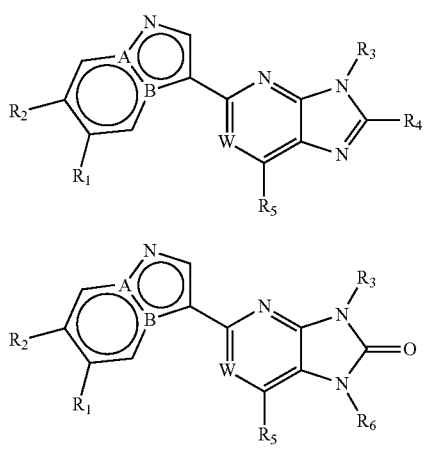

wherein
A is carbon and B is nitrogen, or A is nitrogen and B is carbon;
W is CH or N;
$R_1$ and $R_2$ independently are hydrogen, $C_{1-4}$alkyl, halo$C_{1-4}$alkyl, hydroxy$C_{1-4}$alkyl, cyano$C_{1-4}$alkyl, $C_{1-4}$alkoxy$C_{1-4}$alkyl, halogen, —CN, —$OR_8$ or —$SR_8$;
$R_3$ is $C_{1-4}$alkyl, $R_9$—$C_{1-4}$alkyl, $Cy_1$ or $Cy_2$-$C_{1-4}$alkyl, wherein $Cy_1$ and $Cy_2$ are optionally substituted with one or more $R_{10}$;
$R_4$ is hydrogen, $C_{1-4}$alkyl, halo$C_{1-4}$alkyl, $C_{1-4}$alkoxy$C_{1-4}$alkyl, hydroxy$C_{1-4}$alkyl, cyano$C_{1-4}$alkyl, $R_{12}R_7N$—$C_{0-4}$alkyl, $R_{13}CONR_7$—$C_{0-4}$alkyl, $R_{13}R_7NCO$—$C_{0-4}$alkyl, $R_{12}R_7NCONR_7$—$C_{0-4}$-alkyl, $R_{13}CO_2NR_7$—$C_{0-4}$alkyl, $R_{13}SO_2NR_7$—$C_{0-4}$alkyl, —$OR_{12}$ or $Cy_2$-$C_{0-4}$alkyl; wherein $Cy_2$ is optionally substituted with one or more $R_{11}$;
$R_5$ is hydrogen, $C_{1-4}$alkyl, halo$C_{1-4}$alkyl, $C_{1-4}$alkoxy$C_{1-4}$alkyl, hydroxy$C_{1-4}$alkyl, cyano$C_{1-4}$-alkyl, halogen, —CN, —$OR_{12}$, —$NR_7R_{12}$, or $Cy_2$-$C_{0-4}$alkyl, wherein $Cy_2$ is optionally substituted with one or more $R_{11}$;

$R_6$ is hydrogen, $C_{1-4}$alkyl, $C_{1-4}$alkoxy$C_{1-4}$alkyl, hydroxy$C_{1-4}$alkyl, $R_{12}R_7N$—$C_{1-4}$alkyl, $R_{16}CO$—$C_{0-4}$alkyl, $R_{16}CO_2$—$C_{0-4}$alkyl, $R_{16}CO$—O—$C_{1-4}$alkyl, cyano$C_{1-4}$alkyl, $Cy_1$ or $Cy_2$-$C_{1-4}$alkyl, wherein $Cy_1$ and $Cy_2$ are optionally substituted with one or more $R_{11}$;
$R_7$ is hydrogen or $C_{1-4}$alkyl;
$R_8$ is hydrogen, $C_{1-4}$alkyl, halo$C_{1-4}$alkyl, hydroxy $C_{1-4}$alkyl, or $C_{1-4}$alkoxy$C_{1-4}$alkyl;
$R_9$ is halogen, —CN, —$CONR_7R_{12}$, —$COR_{13}$, —$CO_2R_{12}$, —$OR_{12}$, —$OCONR_7R_{12}$, —$SO_2R_{13}$, —$SO_2NR_7R_{12}$, —$NR_7R_{12}$, —$NR_7COR_{12}$, —$NR_7CONR_7R_{12}$, —$NR_7CO_2R_{13}$ or —$NR_7SO_2R_{13}$;
$R_{10}$ is $C_{1-4}$alkyl or $R_9$—$C_{0-4}$alkyl;
$R_{11}$ is $C_{1-4}$alkyl, $C_{1-4}$alkoxy$C_{1-4}$alkyl, hydroxy$C_{1-4}$alkyl, cyano$C_{1-4}$alkyl, halogen, —CN, —$CONR_7R_{14}$, —$COR_{14}$, —$CO_2R_{15}$, —$OR_{14}$, —$OCONR_7R_{14}$, —$SO_2R_{15}$, —$SO_2NR_7R_{14}$, —$NR_7R_{14}$—$NR_7COR_{14}$, —$NR_7CONR_7R_{14}$, —$NR_7CO_2R_{15}$ or —$NR_7SO_2R_{15}$;
$R_{12}$ is hydrogen or $R_{13}$;
$R_{13}$ is $C_{1-5}$alkyl, halo$C_{1-4}$alkyl, $C_{1-4}$alkoxy$C_{1-4}$alkyl, hydroxy$C_{1-4}$alkyl, cyano$C_{1-4}$alkyl, $Cy_2$-$C_{0-4}$alkyl, or $R_{14}R_7N$—$C_{1-4}$alkyl; wherein $Cy_2$ is optionally substituted with one or more $R_{11}$;
$R_{14}$ is hydrogen or $R_{15}$;
$R_{15}$ is $C_{1-4}$alkyl, halo$C_{1-4}$alkyl, $C_{1-4}$alkoxy$C_{1-4}$alkyl, hydroxy$C_{1-4}$alkyl or cyano$C_{1-4}$alkyl;
$R_{16}$ is $C_{1-4}$alkyl, halo$C_{1-4}$-alkyl, $C_{1-4}$alkoxy$C_{1-4}$alkyl or cyano$C_{1-4}$alkyl;
$Cy_1$ is a 3- to 7-membered monocyclic or 6- to 11-membered bicyclic ring, which is saturated, partially unsaturated or aromatic, and which is carbocyclic or heterocyclic containing from 1 to 4 heteroatoms independently selected from N, S and O, wherein said ring is bonded to the rest of the molecule through any available C atom, and wherein one or more C or S ring atoms are optionally oxidized forming CO, SO or $SO_2$; and
$Cy_2$ is a 3- to 7-membered monocyclic or 6- to 11-membered bicyclic ring, which is saturated, partially unsaturated or aromatic, and which is carbocyclic or heterocyclic containing from 1 to 4 heteroatoms independently selected from N, S and O, wherein said ring is bonded to the rest of the molecule through any available C or N atom, and wherein one or more C or S ring atoms are optionally oxidized forming CO, SO or $SO_2$;
or a pharmaceutically acceptable salt thereof.

2. A compound according to claim 1 having formula I.
3. A compound according to claim 1 having formula II.
4. A compound according to claim 1, wherein A is nitrogen and B is carbon.
5. A compound according to claim 1, wherein W is N.
6. A compound according to claim 1, wherein W is CH.
7. A compound according to claim 1, wherein $R_1$ is hydrogen or —CN.
8. A compound according to claim 7, wherein $R_1$ is H.
9. A compound according to claim 7, wherein $R_1$ is —CN.
10. A compound according to claim 1, wherein $R_2$ is hydrogen.
11. A compound according to claim 1, wherein $R_3$ is $R_9$—$C_{1-4}$alkyl, $Cy_1$ or $Cy_2$-$C_{1-4}$alkyl, wherein $Cy_1$ and $Cy_2$ are optionally substituted with one or more $R_{10}$.
12. A compound according to claim 11, wherein $R_3$ is $R_9$—$C_{1-4}$alkyl.
13. A compound according to claim 11, wherein $R_3$ is $Cy_1$, which is optionally substituted with one or more $R_{10}$.
14. A compound according to claim 1, wherein $Cy_1$ in $R_3$ is a 3- to 7-membered, preferably 5- to 6-membered, saturated monocyclic ring, which is carbocyclic or heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$; and wherein said $Cy_1$ is optionally substituted with one or more $R_{10}$.

15. A compound according to claim 14, wherein $Cy_1$ in $R_3$ is a 3- to 7-membered, preferably 5- to 6-membered, saturated monocyclic ring, which is heterocyclic containing from 1 to 3 heteroatoms independently selected from N, S and O, wherein said ring is bonded to the rest of the molecule through any available C atom, and wherein one or more C or S ring atoms are optionally oxidized forming CO, SO or $SO_2$; and wherein said $Cy_1$ is optionally substituted with one or more $R_{10}$.

16. A compound according to claim 13, wherein $R_3$ is piperidinyl or pyrrolidinyl, which are optionally substituted with one or more $R_{10}$.

17. A compound according to claim 16, wherein $R_3$ is piperidin-3-yl or pyrrolidin-3-yl, which are optionally substituted with one or more $R_{10}$.

18. A compound according to claim 17, wherein $R_3$ is a cycle of formula

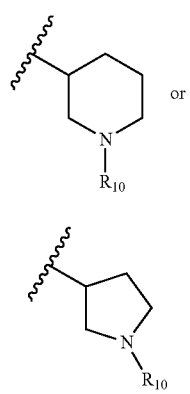

wherein $Cy_{1a}$ and $Cy_{1b}$ are optionally substituted with one or more $R_{10}$.

19. A compound according to claim 18, wherein $R_3$ is a cycle of formula $Cy_{1a}$.

20. A compound according to claim 19, wherein $Cy_{1a}$ has the (S)-stereochemistry.

21. A compound according to claim 18, wherein $R_3$ is a cycle of formula $Cy_{1b}$.

22. A compound according to claim 1, wherein $R_{10}$ is $R_9$—$C_{0-4}$alkyl.

23. A compound according to claim 22, wherein $R_{10}$ is $R_9$.

24. A compound according to claim 23, wherein $R_9$ is —$COR_{13}$ or —$SO_2R_{13}$.

25. A compound according to claim 1, wherein $R_{13}$ is $C_{1-4}$-alkyl or cyano$C_{1-4}$alkyl.

26. A compound according to claim 25, wherein $R_{13}$ is methyl, isopropyl or cyanomethyl.

27. A compound according to claim 1, wherein $R_4$ is hydrogen, $C_{1-4}$alkyl, —$NR_7R_{12}$ or $Cy_2$; wherein $Cy_2$ is optionally substituted with one or more $R_{11}$.

28. A compound according to claim 1, wherein $R_5$ is hydrogen.

29. A compound according to claim 1, wherein $R_6$ is hydrogen, $C_{1-4}$alkyl, $C_{1-4}$alkoxy$C_{1-4}$alkyl, hydroxy$C_{1-4}$alkyl, $R_{12}R_7N$—$C_{1-4}$alkyl, $R_{16}CO$—$C_{0-4}$ alkyl, $R_{16}CO_2$— $C_{0-4}$alkyl, $Cy_1$ or $Cy_2$-$C_{1-4}$alkyl, wherein $Cy_1$ and $Cy_2$ are optionally substituted with one or more $R_{11}$.

30. A compound according to claim 1, wherein $R_6$ is $C_{1-4}$alkyl.

31. A compound according to claim 30, wherein $R_6$ is methyl or ethyl.

32. A compound according to claim 29, wherein $R_6$ is hydrogen or $C_{1-4}$alkyl.

33. A pharmaceutical composition comprising a compound according to claim 1 or a pharmaceutically acceptable salt thereof and one or more pharmaceutically acceptable excipients.

34. A method of treating a disease mediated by a JAK in a subject in need thereof which comprises administering to said subject an effective amount of a compound according to claim 1 or a pharmaceutically acceptable salt thereof, wherein said disease is selected from transplant rejection or rheumatoid arthritis.

35. A process for the preparation of a compound of formula I or II according to claim 1, which comprises:

(a) for a compound of formula I, reacting a compound of formula VI with a compound of formula III

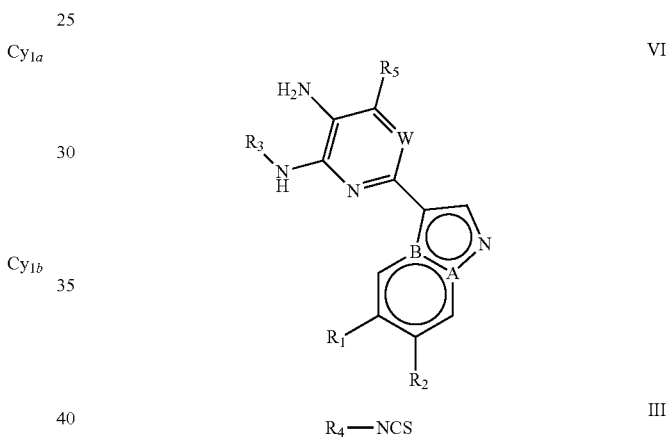

(b) for a compound of formula I, reacting a compound of formula VI with a compound of formula IV

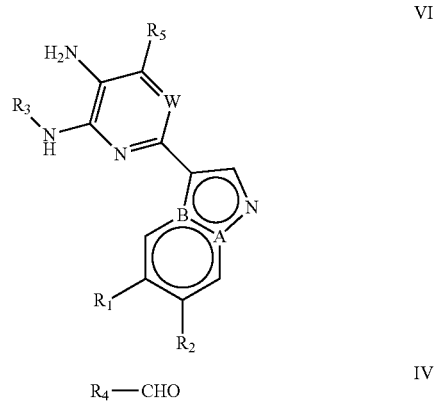

(c) when in a compound of formula II $R_6$ is hydrogen (a compound of formula IIa), reacting a compound of formula VI, as defined above, with a synthetic equivalent for the CO synthon

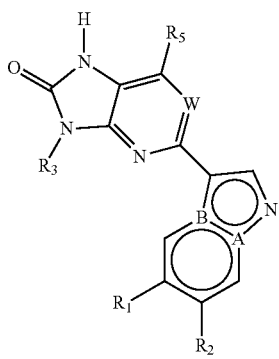

(d) when in a compound of formula II $R_6$ is other than hydrogen, reacting a compound of formula IIa with a compound of formula V ($R_6$—X) in the presence of a base, wherein X is a leaving group.

36. A compound according to claim 1, selected from the group consisting of;

Methyl (2R)-2-[2-(5-cyanopyrazolo[1,5-a]pyridin-3-yl)-8-oxo-7,8-dihydro-9H-purin-9-yl]propanoate,
(S)-tert-butyl 3-(2-(5-cyanopyrazolo[1,5-a]pyridin-3-yl)-8-oxo-7H-purin-9(8H)-yl)piperidine-1-carboxylate,
(R)-tert-butyl 3-(2-(5-cyanopyrazolo[1,5-a]pyridin-3-yl)-8-oxo-7H-purin-9(8H)-yl)piperidine-1-carboxylate,
(S)-3-(9-(1-methoxypropan-2-yl)-8-oxo-8,9-dihydro-7H-purin-2-yl)pyrazolo[1,5-a]pyridine-5-carbonitrile,
3-(9-(4,4-difluorocyclohexyl)-8-oxo-8,9-dihydro-7H-purin-2-yl)pyrazolo[1,5-a]pyridine-5-carbonitrile,
3-(9-(1,1-dioxotetrahydrothien-3-yl)-8-oxo-8,9-dihydro-7H-purin-2-yl)pyrazolo[1,5-a]pyridine-5-carbonitrile,
3-(9-(2-fluorobenzyl)-8-oxo-8,9-dihydro-7H-purin-2-yl) pyrazolo[1,5-a]pyridine-5-carbonitrile,
3-(9-(2-fluorobenzyl)-8-oxo-8,9-dihydro-7H-purin-2-yl) pyrazolo[1,5-a]pyridine-5-carbonitrile,
3-(9-(4-methoxybut-1-yl)-8-oxo-8,9-dihydro-7H-purin-2-yl)pyrazolo[1,5-a]pyridine-5-carbonitrile,
Methyl (2S)-2-[2-(5-cyanopyrazolo[1,5-a]pyridin-3-yl)-8-oxo-7,8-dihydro-9H-purin-9-yl]propanoate,
9-(1-acetylpiperidin-4-yl)-2-(5-(trifluoromethyl)pyrazolo[1,5-a]pyridin-3-yl)-7H-purin-8(9H)-one (1),
(S)-tert-butyl 3-(2-(5-cyanopyrazolo[1,5-a]pyridin-3-yl)-8-oxo-7H-purin-9(8H)-yl)pyrrolidine-1-carboxylate,
(R)-tert-butyl 3-(2-(5-cyanopyrazolo[1,5-a]pyridin-3-yl)-8-oxo-7H-purin-9(8H)-yl)pyrrolidine-1-carboxylate,
(S)-tert-butyl 3-(2-(5-methylpyrazolo[1,5-a]pyridin-3-yl)-8-oxo-7H-purin-9(8H)-yl)piperidine-1-carboxylate (2),
Ethyl 2-(2-(5-cyanopyrazolo[1,5-a]pyridin-3-yl)-8-oxo-7H-purin-9(8H)-yl)acetate,
3-(9-(trans-4-hydroxycyclohexyl)-8-oxo-8,9-dihydro-7H-purin-2-yl)pyrazolo[1,5-a]pyridine-5-carbonitrile,
3-(9-(8-fluorochroman-4-yl)-8-oxo-8,9-dihydro-7H-purin-2-yl)pyrazolo[1,5-e]pyridine-5-carbonitrile,
tert-Butyl 4-(2-(5-cyanopyrazolo[1,5-a]pyridin-3-yl)-8-oxo-7H-purin-9(8H)-yl)piperidine-1-carboxylate,
tert-Butyl 3-(2-(5-cyanopyrazolo[1,5-a]pyridin-3-yl)-8-oxo-7H-purin-9(8H)-yl)azetidine-1-carboxylate,
9-(1-acetylpiperidin-4-yl)-2-(5-methylpyrazolo[1,5-a]pyridin-3-yl)-7H-purin-8(9H)-one (2),
3-(8-Oxo-9-tetrahydro-2H-pyran-4-yl-8,9-dihydro-7H-purin-2-yl)pyrazolo[1,5-a]pyridine-5-carbonitrile,
(S)-tert-Butyl 3-(2-oxo-5-(pyrazolo[1,5-a]pyridin-3-yl)-1H-imidazo[4,5-b]pyridin-3(2H)-yl)piperidine-1-carboxylate,
(R)-tert-Butyl 3-(2-oxo-5-(pyrazolo[1,5-a]pyridin-3-yl)-1H-imidazo[4,5-b]pyridin-3(2H)-yl)pyrrolidine-1-carboxylate,
(S)-tert-Butyl 3-(2-oxo-5-(pyrazolo[1,5-a]pyridin-3-yl)-1H-imidazo[4,5-b]pyridin-3(2H)-yl)pyrrolidine-1-carboxylate,
(S)-tert-Butyl 3-(5-(5-cyanopyrazolo[1,5-a]pyridin-3-yl)-2-oxo-1H-imidazo[4,5-b]pyridin-3(2H)-yl)piperidine-1-carboxylate,
5-(pyrazolo[1,5-a]pyridin-3-yl)-3-(tetrahydro-2H-pyran-4-yl)-1H-imidazo[4,5-b]pyridin-2(3H)-one,
(R)-tert-Butyl 3-(2-oxo-5-(pyrazolo[1,5-a]pyridin-3-yl)-1H-imidazo[4,5-b]pyridin-3(2H)-yl) piperidine-1-carboxylate,
3-(2-Oxo-3-(tetrahydro-2H-pyran-4-yl)-2,3-dihydro-1H-imidazo[4,5-b]pyridin-5-yl)pyrazolo[1,5-a]pyridine-5-carbonitrile,
2-(pyrazolo[1,5-a]pyridin-3-yl)-9-((tetrahydro-2H-pyran-4-yl)methyl)-7H-purin-8(9H)-one,
(S)-tert-Butyl 3-(8-oxo-2-(pyrazolo[1,5-a]pyridin-3-yl)-7H-purin-9(8H)-yl)piperidine-1-carboxylate,
9-(2-methoxyethyl)-2-(pyrazolo[1,5-a]pyridin-3-yl)-7H-purin-8(9H)-one,
9-(8-fluorochroman-4-yl)-2-(pyrazolo[1,5-a]pyridin-3-yl)-7H-purin-8(9H)-one,
Methyl (2S)-2-(8-oxo-2-(pyrazolo[1,5-a]pyridin-3-yl)-7,8-dihydro-9H-purin-9-yl)propanoate,
(S)-tert-butyl 3-(8-oxo-2-(pyrazolo[1,5-a]pyridin-3-yl)-7H-purin-9(8H)-yl)pyrrolidine-1-carboxylate,
tert-Butyl 4-(8-oxo-2-(pyrazolo[1,5-a]pyridin-3-yl)-7H-purin-9(8H)-yl)piperidine-1-carboxylate,
9-(1-methylpiperidin-4-yl)-2-(pyrazolo[1,5-a]pyridin-3-yl)-7H-purin-8(9H)-one,
5-(pyrazolo[1,5-a]pyridin-3-yl)-3-(2,2,6,6-tetramethylpiperidin-4-yl)-1H-imidazo[4,5-b]pyridin-2(3H)-one,
2-(Pyrazolo[1,5-a]pyridin-3-yl)-9-(tetrahydro-2H-pyran-4-yl)-7H-purin-8(9H)-one,
(S)-tert-Butyl 3-(2-(5-cyanopyrazolo[1,5-a]pyridin-3-yl)-7-methyl-8-oxo-7H-purin-9(8H)-yl)piperidine-1-carboxylate,
(R)-tert-Butyl 3-(2-(5-cyanopyrazolo[1,5-a]pyridin-3-yl)-7-methyl-8-oxo-7H-purin-9(8H)-yl)piperidine-1-carboxylate,
9-(8-fluorochroman-4-yl)-7-methyl-2-(pyrazolo[1,5-a]pyridin-3-yl)-7H-purin-8(9H)-one,
3-(7-Methyl-8-oxo-9-tetrahydro-2H-pyran-4-yl-8,9-dihydro-7H-purin-2-yl)pyrazolo[1,5-a]pyridine-5-carbonitrile,
7-methyl-2-(pyrazolo[1,5-a]pyridin-3-yl)-9-(tetrahydro-2H-pyran-4-yl)-7H-purin-8(9H)-one,
3-(1-methyl-2-oxo-3-(tetrahydro-2H-pyran-4-yl)-2,3-dihydro-1H-imidazo[4,5-b]pyridin-5-yl)pyrazolo[1,5-a]pyridine-5-carbonitrile,
9-(2-methoxyethyl)-7-methyl-2-(pyrazolo[1,5-a]pyridin-3-yl)-7H-purin-8(9H)-one,
7-methyl-2-(pyrazolo[1,5-a]pyridin-3-yl)-9-(tetrahydro-2H-pyran-4-yl)methyl)-7H-purin-8(9H)-one,
3-(9-(4,4-difluorocyclohexyl)-7-methyl-8-oxo-8,9-dihydro-7H-purin-2-yl)pyrazolo[1,5-a]pyridine-5-carbonitrile,
3-(9-(1,1-dioxotetrahydrothien-3-yl)-8,9-dihydro-7-methyl-8-oxopurin-2-yl)pyrazolo[1,5-a]pyridine-5-carbonitrile, (S)-tert-Butyl 3-(5-(5-cyanopyrazolo[1,5-a]pyridin-3-yl)-1-methyl-2-oxo-1H-imidazo[4,5-b]pyridin-3(2H)-yl)piperidine-1-carboxylate,
3-(9-(2-fluorobenzyl)-7-methyl-8-oxo-8,9-dihydro-7H-purin-2-yl)pyrazolo[1,5-a]pyridine-5-carbonitrile,
9-(1-acetylpiperidin-4-yl)-7-methyl-2-(5-(trifluoromethyl)pyrazolo[1,5-a]pyridin-3-yl)-7H-purin-8(9H)-one,
(S)-tert-Butyl 3-(1-methyl-2-oxo-5-(pyrazolo[1,5-a]pyridin-3-yl)-1H-imidazo[4,5-b]pyridin-3(2H)-yl)piperidine-1-carboxylate,
(S)-tert-Butyl 3-(2-(5-cyanopyrazolo[1,5-a]pyridin-3-yl)-7-methyl-8-oxo-7H-purin-9(8H)-yl)pyrrolidine-1-carboxylate,
(R)-tert-Butyl 3-(2-(5-cyanopyrazolo[1,5-a]pyridin-3-yl)-7-methyl-8-oxo-7H-purin-9(8H)-yl)pyrrolidine-1-carboxylate,
(S)-tert-Butyl 3-(7-methyl-8-oxo-2-(pyrazolo[1,5-a]pyridin-3-yl)-7H-purin-9(8H)-yl)pyrrolidine-1-carboxylate,
(R)-tert-Butyl 3-(1-methyl-2-oxo-5-(pyrazolo[1,5-a]pyridin-3-yl)-1H-imidazo[4,5-b]pyridin-3(2H)-yl)pyrrolidine-1-carboxylate,
(S)-tert-Butyl 3-(1-methyl-2-oxo-5-(pyrazolo[1,5-a]pyridin-3-yl)-1H-imidazo[4,5-b]pyridin-3(2H)-yl)pyrrolidine-1-carboxylate,
(S)-tert-Butyl 3-(1-ethyl-2-oxo-5-(pyrazolo[1,5-a]pyridin-3-yl)-1H-imidazo[4,5-b]pyridin-3(2H)-yl)piperidine-1-carboxylate,
tert-Butyl 4-(7-methyl-8-oxo-2-(pyrazolo[1,5-a]pyridin-3-yl)-7H-purin-9(8H)-yl)piperidine-1-carboxylate,
(S)-tert-Butyl 3-(7-methyl-8-oxo-2-(pyrazolo[1,5-a]pyridin-3-yl)-7H-purin-9(8H)-yl)piperidine-1-carboxylate,
1-methyl-5-(pyrazolo[1,5-a]pyridin-3-yl)-3-(tetrahydro-2H-pyran-4-yl)-1H-imidazo[4,5-b]pyridin-2(3H)-one,
(R)-tert-Butyl 3-(1-methyl-2-oxo-5-(pyrazolo[1,5-a]pyridin-3-yl)-1H-imidazo[4,5-b]pyridin-3(2H)-yl)piperidine-1-carboxylate,
tert-Butyl 4-(2-(5-cyanopyrazolo[1,5-a]pyridin-3-yl)-7-methyl-8-oxo-7H-purin-9(8H)-yl)piperidine-1-carboxylate,
tert-Butyl 3-(2-(5-cyanopyrazolo[1,5-a]pyridin-3-yl)-7-methyl-8-oxo-7H-purin-9(8H)-yl)azetidine-1-carboxylate,
(S)-tert-Butyl 3-(7-methyl-8-oxo-2-(pyrazolo[1,5-a]pyridine-3-yl)-7H-purin-9(8H)-yl)piperidine-1-carboxylate,
(R)-3-(8-oxo-9-(piperidin-3-yl)-8,9-dihydro-7H-purin-2-yl)pyrazolo[1,5-a]pyridine-5-carbonitrile hydrochloride,
(R)-3-(7-methyl-8-oxo-9-(piperidin-3-yl)-8,9-dihydro-7H-purin-2-yl)pyrazolo[1,5-a]pyridine-5-carbonitrile hydrochloride,
(S)-3-(7-methyl-8-oxo-9-(piperidin-3-yl)-8,9-dihydro-7H-purin-2-yl)pyrazolo[1,5-a]pyridine-5-carbonitrile hydrochloride,
9-(piperidin-4-yl)-2-(pyrazolo[1,5-a]pyridin-3-yl)-7H-purin-8(9H)-one,
(S)-3-(2-oxo-3-(piperidin-3-yl)-2,3-dihydro-1H-imidazo[4,5-b]pyridin-5-yl)pyrazolo[1,5-a]pyridine-5-carbonitrile hydrochloride,
(S)-3-(1-methyl-2-oxo-3-(piperidin-3-yl)-2,3-dihydro-1H-imidazo[4,5-b]pyridin-5-yl)pyrazolo[1,5-a]pyridine-5-carbonitrile hydrochloride,
(S)-1-methyl-3-(piperidin-3-yl)-5-(pyrazolo[1,5-a]pyridin-3-yl)-1H-imidazo[4,5-b]pyridin-2(3H)-one hydrochloride, (S)-3-(7-methyl-8-oxo-9-(pyrrolidin-3-yl)-8,9-dihydro-7H-purin-2-yl)pyrazolo[1,5-a]pyridine-5-carbonitrile hydrochloride,
(R)-3-(7-methyl-8-oxo-9-(pyrrolidin-3-yl)-8,9-dihydro-7H-purin-2-yl)pyrazolo[1,5-a]pyridine-5-carbonitrile hydrochloride,
(S)-2-(pyrazolo[1,5-a]pyridin-3-yl)-9-(pyrrolidin-3-yl)-7H-purin-8(9H)-one hydrochloride,
(S)-7-methyl-2-(pyrazolo[1,5-a]pyridin-3-yl)-9-(pyrrolidin-3-yl)-7H-purin-8(9H)-one hydrochloride,
(S)-3-(8-oxo-9-(pyrrolidin-3-yl)-8,9-dihydro-7H-purin-2-yl)pyrazolo[1,5-a]pyridine-5-carbonitrile hydrochloride,
(R)-1-methyl-5-(pyrazolo[1,5-a]pyridin-3-yl)-3-(pyrrolidin-3-yl)-1H-imidazo[4,5-b]pyridin-2(3H)-one hydrochloride,
(R)-5-(pyrazolo[1,5-a]pyridin-3-yl)-3-(pyrrolidin-3-yl)-1H-imidazo[4,5-b]pyridin-2(3H)-one hydrochloride,
(R)-3-(8-oxo-9-(pyrrolidin-3-yl)-8,9-dihydro-7H-purin-2-yl)pyrazolo[1,5-a]pyridine-5-carbonitrile hydrochloride,
(S)-2-(pyrazolo[1,5-a]pyridin-3-yl)-9-(pyrrolidin-3-yl)-7H-purin-8(9H)-one hydrochloride,
(S)-1-methyl-5-(pyrazolo[1,5-a]pyridin-3-yl)-3-(pyrrolidin-3-yl)-1H-imidazo[4,5-b]pyridin-2(3H)-one hydrochloride,
(S)-2-(5-methylpyrazolo[1,5-a]pyridin-3-yl)-9-(piperidin-3-yl)-7H-purin-8(9H)-one hydrochloride,
(S)-1-ethyl-3-(piperidin-3-yl)-5-(pyrazolo[1,5-a]pyridin-3-yl)-1H-imidazo[4,5-b]pyridin-2(3H)-one hydrochloride,
7-methyl-9-(piperidin-4-yl)-2-(pyrazolo[1,5-a]pyridin-3-yl)-7H-purin-8(9H)-one hydrochloride,
(S)-7-methyl-9-(piperidin-3-yl)-2-(pyrazolo[1,5-a]pyridin-3-yl)-7H-purin-8(9H)-one hydrochloride,
(S)-9-(piperidin-3-yl)-2-(pyrazolo[1,5-a]pyridin-3-yl)-7H-purin-8(9H)-one hydrochloride,
(R)-1-methyl-3-(piperidin-3-yl)-5-(pyrazolo[1,5-a]pyridin-3-yl)-1H-imidazo[4,5-b]pyridin-2(3H)-one,
(S)-3-(piperidin-3-yl)-5-(pyrazolo[1,5-a]pyridin-3-yl)-1H-imidazo[4,5-b]pyridin-2(3H)-one hydrochloride,
3-(7-methyl-8-oxo-9-(piperidin-4-yl)-8,9-dihydro-7H-purin-2-yl)pyrazolo[1,5-a]pyridine-5-carbonitrile hydrochloride,
(S)-3-(3-(piperidin-3-yl)-3H-imidazo[4,5-b]pyridin-5-yl)pyrazolo[1,5-a]pyridine-5-carbonitrile hydrochloride,
(S)-3-(2-methyl-3-(piperidin-3-yl)-3H-imidazo[4,5-b]pyridin-5-yl)pyrazolo[1,5-a]pyridine-5-carbonitrile hydrochloride,
3-(8-oxo-9-(piperidin-4-yl)-8,9-dihydro-7H-purin-2-yl)pyrazolo[1,5-a]pyridine-5-carbonitrile,
3-(9-(azetidin-3-yl)-7-methyl-8-oxo-8,9-dihydro-7H-purin-2-yl)pyrazolo[1,5-a]pyridine-5-carbonitrile hydrochloride,
(S)-3-(piperidin-3-yl)-5-(pyrazolo[1,5-a]pyridin-3-yl)-3H-imidazo[4,5-b]pyridine hydrochloride,
(S)-2-methyl-3-(piperidin-3-yl)-5-(pyrazolo[1,5-a]pyridin-3-yl-3H-imidazo[4,5-b]pyridine hydrochloride,
(S)-3-(8-Oxo-9-(piperidin-3-yl)-8,9-dihydro-7H-purin-2-yl pyrazolo[1,5-a]pyridine-5-carbonitrile hydrochloride,
(R)-3-(9-(1-(2-cyanoacetyl)piperidin-3-yl)-8-oxo-8,9-dihydro-7H-purin-2-yl)pyrazolo[1,5-a]pyridine-5-carbonitrile,
(R)-3-(9-(1-(2-cyanoacetyl)piperidin-3-yl)-7-methyl-8-oxo-8,9-dihydro-7H-purin-2-yl)pyrazolo[1,5-a]pyridine-5-carbonitrile, (S)-3-(9-(1-(2-cyanoacetyl)piperidin-3-yl)-7-methyl-8-oxo-8,9-dihydro-7H-purin-2-yl)pyrazolo[1,5-a]pyridine-5-carbonitrile,
3-(9-(1-(2-cyanoacetyl)pyrrolidin-3-yl)-7-methyl-8-oxo-8,9-dihydro-7H-purin-2-yl pyrazolo[1,5-a]pyridine-5-carbonitrile,
3-(9-((1-(2-cyanoacetyl)piperidin-4-yl)methyl)-7-methyl-8-oxo-8,9-dihydro-7H-purin-2-yl)pyrazolo[1,5-a]pyridine-5-carbonitrile,
(S)-3-oxo-3-(3-(8-oxo-2-(pyrazolo[1,5-a]pyridin-3-yl)-7H-purin-9(8H)-yl)piperidin-1-yl)propanenitrile,
(S)-3-(3-(7-methyl-8-oxo-2-(pyrazolo[1,5-a]pyridin-3-yl)-7H-purin-9(8H)-yl)piperidin-1-yl)-3-oxopropanenitrile,
(S)-3-(3-(1-(2-cyanoacetyl)piperidin-3-yl)-2-oxo-2,3-dihydro-1H-imidazo[4,5-b]pyridin-5-yl)pyrazolo[1,5-a]pyridine-5-carbonitrile,
(S)-3-(3-(1-methyl-2-oxo-5-(pyrazolo[1,5-a]pyridin-3-yl)-1H-imidazo[4,5-b]pyridin-3(2H)-yl)piperidin-1-yl)-3-oxopropanenitrile,
3-(9-(1-(2-cyanoacetyl)azetidin-3-yl)-7-methyl-8-oxo-8,9-dihydro-7H-purin-2-yl pyrazolo[1,5-a]pyridine-5-carbonitrile,
(S)-3-(3-(2-(5-methylpyrazolo[1,5-a]pyridin-3-yl)-8-oxo-7H-purin-9(8H)-yl)piperidin-1-yl)-3-oxopropanenitrile,
(S)-3-(3-(1-ethyl-2-oxo-5-(pyrazolo[1,5-a]pyridin-3-yl)-1H-imidazo[4,5-b]pyridin-3(2H)-yl)piperidin-1-yl)-3-oxopropanenitrile,
3-oxo-3-(4-(8-oxo-2-(pyrazolo[1,5-a]pyridin-3-yl)-7H-purin-9(8H)-yl)piperidin-1-yl)propanenitrile,
(S)-3-(3-(1-(2-cyanoacetyl)piperidin-3-yl)-1-methyl-2-oxo-2,3-dihydro-1H-imidazo[4,5-b]pyridin-5-yl)pyrazolo[1,5-a]pyridine-5-carbonitrile,
(R)-3-(3-(1-methyl-2-oxo-5-(pyrazolo[1,5-a]pyridin-3-yl)-1H-imidazo[4,5-b]pyridin-3(2H)-yl)piperidin-1-yl)-3-oxopropanenitrile,
(S)-3-oxo-3-(3-(2-oxo-5-(pyrazolo[1,5-a]pyridin-3-yl)-1H-imidazo[4,5-b]pyridin-3(2H)-yl)piperidin-1-yl)propanenitrile,
3-(9-(1-(2-cyanoacetyl)piperidin-4-yl)-7-methyl-8-oxo-8,9-dihydro-7H-purin-2-yl)pyrazolo[1,5-a]pyridine-5-carbonitrile,
(S)-3-(3-(1-(2-cyanoacetyl)piperidin-3-yl)-3H-imidazo[4,5-b]pyridin-5-yl)pyrazolo[1,5-a]pyridine-5-carbonitrile,
(S)-3-(3-(1-(2-cyanoacetyl)piperidin-3-yl)-2-methyl-3H-imidazo[4,5-b]pyridin-5-yl)pyrazolo[1,5-a]pyridine-5-carbonitrile,
S)-3-(3-(2-methyl-5-(pyrazolo[1,5-a]pyridin-3-yl)-3H-imidazo[4,5-b]pyridin-3-yl)piperidin-1-yl)-3-oxopropanenitrile,
(S)-3-oxo-3-(3-(5-(pyrazolo[1,5-a]pyridin-3-yl)-3H-imidazo[4,5-b]pyridin-3-yl)piperidin-1-yl)propanenitrile,
(S)-3-(9-(1-(2-Cyanoacetyl)piperidin-3-yl)-8-oxo-8,9-dihydro-7H-purin-2-yl)pyrazolo[1,5-a]pyridine-5-carbonitrile,
(S)-9-(1-acetylpiperidin-3-yl)-2-(pyrazolo[1,5-a]pyridin-3-yl)-7H-purin-8(9H)-one,
3-(9-(1-acetylpiperidin-4-yl)-8-oxo-8,9-dihydro-7H-purin-2-yl)pyrazolo[1,5-a]pyridine-5-carbonitrile,
9-(1-acetylpiperidin-4-yl)-2-(pyrazolo[1,5-a]pyridin-3-yl)-7H-purin-8(9H)-one,
(S)-3-(1-isobutyrylpiperidin-3-yl)-5-(pyrazolo[1,5-a]pyridin-3-yl)-1H-imidazo[4,5-b]pyridin-2(3H)-one,
(S)-3-(9-(1-acetylpiperidin-3-yl)-7-methyl-8-oxo-8,9-dihydro-7H-purin-2-yl)pyrazolo[1,5-a]pyridine-5-carbonitrile,
(S)-3-(1-acetylpiperidin-3-yl)-5-(pyrazolo[1,5-a]pyridin-3-yl)-1H-imidazo[4,5-b]pyridin-2(3H)-one,
3-(9-(1-acetylpiperidin-4-yl)-7-methyl-8-oxo-8,9-dihydro-7H-purin-2-yl)pyrazolo[1,5-a]pyridine-5-carbonitrile,
3-(9-(1-acetylazetidin-3-yl)-7-methyl-8-oxo-8,9-dihydro-7H-purin-2-yl)pyrazolo[1,5-a]pyridine-5-carbonitrile,
(S)-3-(9-(1-Acetylpiperidin-3-yl)-8-oxo-8,9-dihydro-7H-purin-2-yl)pyrazolo[1,5-a]pyridine-5-carbonitrile,
(S)-9-(1-(methylsulfonyl)piperidin-3-yl)-2-(pyrazolo[1,5-a]pyridin-3-yl)-7H-purin-8(9H)-one,
(S)-3-(8-oxo-9-(1-(propylsulfonyl)piperidin-3-yl)-8,9-dihydro-7H-purin-2-yl)pyrazolo[1,5-a]pyridine-5-carbonitrile,
(S)-3-(8-oxo-9-(1-(2,2,2-trifluoroethylsulfonyl)piperidin-3-yl)-8,9-dihydro-7H-purin-2-yl)pyrazolo[1,5-a]pyridine-5-carbonitrile,
(S)-3-(9-(1-(isobutylsulfonyl)piperidin-3-yl)-8-oxo-8,9-dihydro-7H-purin-2-yl pyrazolo[1,5-a]pyridine-5-carbonitrile,
(S)-3-(8-oxo-9-(1-(3,3,3-trifluoropropylsulfonyl)piperidin-3-yl)-8,9-dihydro-7H-purin-2-yl)pyrazolo[1,5-a]pyridine-5-carbonitrile,
S)-1-methyl-3-(1-(methylsulfonyl)piperidin-3-yl)-5-(pyrazolo[1,5-a]pyridin-3-yl)-1H-imidazo[4,5-b]pyridin-2(3H)-one,
(S)-2-(5-methylpyrazolo[1,5-a]pyridin-3-yl)-9-(1-(methylsulfonyl)piperidin-3-yl)-7H-purin-8(9H)-one,
7-(2-oxopropyl)-9-(1-(2-oxopropyl)piperidin-4-yl)-2-(pyrazolo[1,5-a]pyridin-3-yl)-7H-purin-8(9H)-one,
9-(1-acetylpiperidin-4-yl)-7-methyl-2-(pyrazolo[1,5-a]pyridin-3-yl)-7H-purin-8(9H)-one,
(S)-3-(3-(1-isobutyrylpiperidin-3-yl)-2-oxo-2,3-dihydro-1H-imidazo[4,5-b]pyridin-5-yl)pyrazolo[1,5-a]pyridine-5-carbonitrile,
(S)-3-(3-(1-(methylsulfonyl)piperidin-3-yl)-2-oxo-2,3-dihydro-1H-imidazo[4,5-b]pyridin-5-yl)pyrazolo[1,5-a]pyridine-5-carbonitrile,
(S)-3-(7-methyl-9-(1-(methylsulfonyl)piperidin-3-yl)-8-oxo-8,9-dihydro-7H-purin-2-yl)pyrazolo[1,5-a]pyridine-5-carbonitrile,
(S)-3-(9-(1-(ethylsulfonyl)piperidin-3-yl)-8-oxo-8,9-dihydro-7H-purin-2-yl)pyrazolo[1,5-a]pyridine-5-carbonitrile,
(S)-3-(9-(1-isobutyrylpiperidin-3-yl)-8-oxo-8,9-dihydro-7H-purin-2-yl)pyrazolo[1,5-a]pyridine-5-carbonitrile,
3-(7-methyl-9-(1-(methylsulfonyl)piperidin-4-yl)-8-oxo-8,9-dihydro-7H-purin-2-yl)pyrazolo[1,5-a]pyridine-5-carbonitrile,
3-(9-(1-(methylsulfonyl)piperidin-4-yl)-8-oxo-8,9-dihydro-7H-purin-2-yl)pyrazolo[1,5-a]pyridine-5-carbonitrile,
(S)-3-(1-(methylsulfonyl)piperidin-3-yl)-5-(pyrazolo[1,5-a]pyridin-3-yl)-1H-imidazo[4,5-b]pyridin-2(3H)-one,
3-(7-methyl-9-(1-(methylsulfonyl)azetidin-3-yl)-8-oxo-8,9-dihydro-7H-purin-2-yl)pyrazolo[1,5-a]pyridine-5-carbonitrile,
(S)-3-(3-(1-acetylpiperidin-3-yl)-2-oxo-2,3-dihydro-1H-imidazo[4,5-b]pyridin-5-yl)pyrazolo[1,5-a]pyridine-5-carbonitrile,
(S)-3-(1-(2-methoxyacetyl)piperidin-3-yl)-1-methyl-5-(pyrazolo[1,5-a]pyridin-3-yl)-1H-imidazo[4,5-b]pyridin-2(3H)-one, (S)-1-methyl-5-(pyrazolo[1,5-a]pyridin-3-yl)-3-(1-(2,2,2-trifluoroethylsulfonyl)piperidin-3-yl)-1H-imidazo[4,5-b]pyridin-2(3H)-one,
(S)-3-(9-(1-(Methylsulfonyl)piperidin-3-yl)-8-oxo-8,9-dihydro-7H-purin-2-yl)pyrazolo[1,5-a]pyridine-5-carbonitrile,
(S)-3-(9-(1-(2-hydroxyacetyl)piperidin-3-yl)-8-oxo-8,9-dihydro-7H-purin-2-yl)pyrazolo[1,5-a]pyridine-5-carbonitrile,
(S)-3-(9-(1-(2-hydroxy-2-methylpropanoyl)piperidin-3-yl)-8-oxo-8,9-dihydro-7H-purin-2-yl)pyrazolo[1,5-a]pyridine-5-carbonitrile,
3-(8-oxo-9((S)-1((S)-tetrahydrofuran-2-carbonyl)piperidin-3-yl)-8,9-dihydro-7H-purin-2-yl)pyrazolo[1,5-a]pyridine-5-carbonitrile,
(S)-3-(9-(1-(2-methoxyacetyl)piperidin-3-yl)-8-oxo-8,9-dihydro-7H-purin-2-yl)pyrazolo[1,5-a]pyridine-5-carbonitrile,
(S)-3-(9-(1-(2-ethylbutanoyl)piperidin-3-yl)-8-oxo-8,9-dihydro-7H-purin-2-yl)pyrazolo[1,5-a]pyridine-5-carbonitrile,
(S)-3-(9-(1-(2-(3-methylisoxazol-5-yl)acetyl)piperidin-3-yl)-8-oxo-8,9-dihydro-7H-purin-2-yl)pyrazolo[1,5-a]pyridine-5-carbonitrile,
3-(9((S)-1((S)-2-methoxypropanoyl)piperidin-3-yl)-8-oxo-8,9-dihydro-7H-purin-2-yl)pyrazolo[1,5-a]pyridine-5-carbonitrile,
(S)-3-(8-oxo-9-(1-(3,3,3-trifluoropropanoyl)piperidin-3-yl)-8,9-dihydro-7H-purin-2-yl)pyrazolo[1,5-a]pyridine-5-carbonitrile,
(S)-2-(5-methylpyrazolo[1,5-a]pyridin-3-yl)-9-(1-propionylpiperidin-3-yl)-7H-purin-8(9H)-one,
(S)-9-(1-(2-methoxyacetyl)piperidin-3-yl-2-(5-methylpyrazolo[1,5-a]pyridin-3-yl)-7H-purin-8(9H)-one,
(S)-7-(2-methoxyacetyl)-9(1-(2-methoxyacetyl)piperidin-3-yl)-2-(5-methy pyrazolo[1,5-a]pyridin-3-yl)-7H-purin-8(9H)-one,
(S)-9-(1-acetylpiperidin-3-yl)-2-(5-methylpyrazolo[1,5-a]pyridin-3-yl-7H-purin-8(9H)-one,
(S)-9-(1-(2-hydroxyacetyl)piperidin-3-yl-2-methylpyrazolo[1,5-a]pyridin-3-yl)-7H-purin-8(9H)-one,
(S)-3-(9-(1-(cyclopropanecarbonyl piperidin-3-yl)-8-oxo-8,9-dihydro-7H-purin-2-yl)pyrazolo[1,5-a]pyridine-5-carbonitrile,
(S)-3-(1-(2-hydroxy-2-methylpropanoyl)piperidin-3-yl)-1-methyl-5-(pyrazolo[1,5-a]pyridin-3-yl)-1H-imidazo[4,5-b]pyridin-2(3H)-one,
(S)-3-(1-(2-hydroxyacetyl)piperidin-3-yl)-1-methyl-5-(pyrazolo[1,5-a]pyridin-3-yl)-1H-imidazo[4,5-b]pyridin-2(3H)-one,
(S)-3-(1-(2-(dimethylamino)acetyl)piperidin-3-yl)-1-methyl-5-(pyrazolo[1,5-a]pyridin-3-yl)-1H-imidazo[4,5-b]pyridin-2(3H)-one,
1-methyl-5-(pyrazolo[1,5-a]pyridin-3-yl)-3((S)-1((S)-tetrahydrofuran-2-carbonyl)piperidin-3-yl)-1H-imidazo[4,5-b]pyridin-2(3H)-one,
(S)-1-methyl-5-(pyrazolo[1,5-a]pyridin-3-yl)-3-(1-(3,3,3-trifluoropropanoyl)piperidin-3-yl)-1H-imidazo[4,5-b]pyridin-2(3H)-one,
(S)-3-(9-(1-(2-(Dimethylamino)acetyl)piperidin-3-yl)-8-oxo-8,9-dihydro-7H-purin-2-yl)pyrazolo[1,5-a]pyridine-5-carbonitrile,
(S)—N,N-dimethyl-3-(1-methyl-2-oxo-5-(pyrazolo[1,5-a]pyridin-3-yl)-1H-imidazo[4,5-b]pyridin-3(2H)-yl)piperidine-1-sulfonamide,
(S)-3-(2-(5-Cyanopyrazolo[1,5-a]pyridin-3-yl)-8-oxo-7H-purin-9(8H)-yl)-N,N-dimethylpiperidine-1-sulfonamide,
3-(9-(1-Acetylpyrrolidin-3-yl)-7-methyl-8-oxo-8,9-dihydro-7H-purin-2-yl)pyrazolo[1,5-a]pyridine-5-carbonitrile,
(S)-3-(7-methyl-9-(1-(methylsulfonyl)pyrrolidin-3-yl)-8-oxo-8,9-dihydro-7H-purin-2-yl)pyrazolo[1,5-a]pyridine-5-carbonitrile,
(R)-3-(7-methyl-9-(1-(methylsulfonyl)pyrrolidin-3-yl)-8-oxo-8,9-dihydro-7H-purin-2-yl)pyrazolo[1,5-a]pyridine-5-carbonitrile,
(S)-9-(1-(methylsulfonyl)pyrrolidin-3-yl)-2-(pyrazolo[1,5-a]pyridin-3-yl)-7H-purin-8(9H)-one,
(S)-7-methyl-9-(1-(methylsulfonyl)pyrrolidin-3-yl)-2-(pyrazolo[1,5-a]pyridin-3-yl)-7H-purin-8(9H)-one,
(S)-3-(9-(1-(methylsulfonyl)pyrrolidin-3-yl)-8-oxo-8,9-dihydro-7H-purin-2-yl)pyrazolo[1,5-a]pyridine-5-carbonitrile,
(R)-1-methyl-3-(1-(methylsulfonyl)pyrrolidin-3-yl)-5-(pyrazolo[1,5-a]pyridin-3-yl)-H-imidazo[4,5-b]pyridin-2(3H)-one,
(R)-3-(1-(methylsulfonyl)pyrrolidin-3-yl)-5-(pyrazolo[1,5-a]pyridin-3-yl)-1H-imidazo[4,5-b]pyridin-2(3H)-one,
(R)-3-(9-(1-(methylsulfonyl)pyrrolidin-3-yl)-8-oxo-8,9-dihydro-7H-purin-2-yl)pyrazolo[1,5-a]pyridine-5-carbonitrile,
(S)-3-(1-(methylsulfonyl)pyrrolidin-3-yl-5-pyrazolo[1,5-a]pyridin-3-yl)-1H-imidazo[4,5-b]pyridin-2(3H)-one,
(S)-1-methyl-3-(1-(methylsulfonyl)pyrrolidin-3-yl)-5-(pyrazolo[1,5-a]pyridin-3-yl)-1H-imidazo[4,5-b]pyridin-2(3H)-one,
(S)-7-methyl-9-(1-(methylsulfonyl)piperidin-3-yl)-2-(pyrazolo[1,5-a]pyridin-3-yl)-7H-purin-8(9H)-one,
3-(7-Methyl-9-(1-(methylsulfonyl)pyrrolidin-3-yl)-8-oxo-8,9-dihydro-7H-purin-2-yl)pyrazolo[1,5-a]pyridine-5-carbonitrile,
(2S)-2-[2-(5-Cyanopyrazolo[1,5-a]pyridin-3-yl)-8-oxo-7,8-dihydro-9H-purin-9-yl]propanoic acid,
(S)-2-(8-oxo-2-(pyrazolo[1,5-a]pyridin-3-yl)-7H-purin-9(8H)-yl)propanoic acid,
(2R)-2-[2-(5-Cyanopyrazolo[1,5-a]pyridin-3-yl)-8-oxo-7,8-dihydro-9H-purin-9-yl]propanoic acid,
(2R)-2-(2-(5-cyanopyrazolo[1,5-a]pyridin-3-yl)-8-oxo-7H-purin-9(8H)-yl)-N-methylpropanamide,
(2S)-2-2-(5-cyanopyrazolo[1,5-a]pyridin-3-yl)-8-oxo-7,8-dihydro-9H-purin-9-yl)-3-methyl-N-(2,2,2-trifluoroethyl)butanamide,
(R)-2-(2-(5-cyanopyrazolo[1,5-a]pyridin-3-yl)-8-oxo-7H-purin-9(8H)-yl)-N-(2-hydroxyethyl)propanamide,
(R)-2-(2-(5-cyanopyrazolo[1,5-a]pyridin-3-yl)-8-oxo-7H-purin-9(8H)-yl)-N-(cyclopropylmethyl)propanamide,
(R)-2-(2-(5-cyanopyrazolo[1,5-a]pyridin-3-yl)-8-oxo-7H-purin-9(8H)-yl)-N-(2-(dimethylamino)ethyl)propanamide,
(R)-2-(2-(5-cyanopyrazolo[1,5-a]pyridin-3-yl)-8-oxo-7H-purin-9(8H)-yl)-N-ethylpropanamide,
(R)-2-(2-(5-cyanopyrazolo[1,5-a]pyridin-3-yl)-8-oxo-7H-purin-9(8H)-yl)-N-isopropylpropanamide,
(R)-2-(2-(5-cyanopyrazolo[1,5-a]pyridin-3-yl)-8-oxo-7H-purin-9(8H)-yl)-N,N-dimethylpropanamide,
(S)-2-(2-(5-cyanopyrazolo[1,5-a]pyridin-3-yl)-8-oxo-7H-purin-9(8H)-yl)-N-(2,2,2-trifluoroethyl)propanamide,
(S)—N-methyl-2-(8-oxo-2-(pyrazolo[1,5-a]pyridin-3-yl)-7H-purin-9(8H) yl)propanamide, (S)—N,N-dimethyl-2-(8-oxo-2-(pyrazolo[1,5-a]pyridin-3-yl)-7H-purin-9(8H)-yl)propanamide,
(2R)-2-[2-(5-Cyanopyrazolo[1,5-a]pyridin-3-yl)-8-oxo-7,8-dihydro-9H-purin-9-yl]-N-(2,2,2-trifluoroethyl)propanamide,
(S)-3-(9-(1-(2-cyanoacetyl)piperidin-3-yl)-7-(2-(dimethylamino)ethyl)-8-oxo-8,9-dihydro-7H-purin-2-yl)pyrazolo[1,5-a]pyridine-5-carbonitrile,
(S)-3-(7-(2-(dimethylamino)ethyl)-8-oxo-9-(piperidin-3-yl)-8,9-dihydro-7H-purin-2-yl)pyrazolo[1,5-a]pyridine-5-carbonitrile,
7-(2-(dimethylamino)ethyl)-2-(pyrazolo[1,5-a]pyridin-3-yl)-9-(tetrahydro-2H-pyran-4-yl)-7H-purin-8(9H)-one),
3-(7-(2-(dimethylamino)ethyl)-8-oxo-9-(tetrahydro-2H-pyran-4-yl)-8,9-dihydro-7H-purin-2-yl)pyrazolo[1,5-a]pyridine-5-carbonitrile,
3-(7-(2-(dimethylamino)ethyl)-9-(8-fluorochroman-4-yl)-8-oxo-8,9-dihydro-7H-purin-2-yl)pyrazolo[1,5-a]pyridine-5-carbonitrile,
3-(9-(8-fluorochroman-4-yl)-7-(2-methoxyethyl)-8-oxo-8,9-dihydro-7H-purin-2-yl)pyrazolo[1,5-a]pyridine-5-carbonitrile,
3-(9-(8-fluorochroman-4-yl)-7-(3-hydroxypropyl)-8-oxo-8,9-dihydro-7H-purin-2-yl)pyrazolo[1,5-a]pyridine-5-carbonitrile,
(S)-3-(3-(1-(2-(dimethylamino)ethyl)-2-oxo-5-(pyrazolo[1,5-a]pyridin-3-yl)-1H-imidazo[4,5-b]pyridin-3(2H)-yl)piperidin-1-yl)-3-oxopropanenitrile,
(S)-3-(3-(1-(2-methoxyethyl)-2-oxo-5-(pyrazolo[1,5-a]pyridin-3-yl)-1H-imidazo[4,5-b]pyridin-3(2H)-yl)piperidin-1-yl)-3-oxopropanenitrile,
(S)-3-(3-(1-(cyclopropylmethyl)-2-oxo-5-(pyrazolo[1,5-a]pyridin-3-yl)-1H-imidazo[4,5-b]pyridin-3(2H)-yl)piperidin-1-yl)-3-oxopropanenitrile,
3-(7-(2-Methoxyethyl)-8-oxo-9-(tetrahydro-2H-pyran-4-yl)-8,9-dihydro-7H-purin-2-yl)pyrazolo[1,5-a]pyridine-5-carbonitrile,
(S)-3-(9-(1-(2-cyanoacetyl)piperidin-3-yl)-7-(2-hydroxyethyl)-8-oxo-8,9-dihydro-7H-purin-2-yl)pyrazolo[1,5-a]pyridine-5-carbonitrile,
(S)-3-(7-(2-hydroxyethyl)-8-oxo-9-(piperidin-3-yl)-8,9-dihydro-7H-purin-2-yl)pyrazolo[1,5-a]pyridine-5-carbonitrile hydrochloride,
3-(9-(8-fluorochroman-4-yl)-7-(2-hydroxyethyl)-8-oxo-8,9-dihydro-7H-purin-2-yl)pyrazolo[1,5-a]pyridine-5-carbonitrile,
3-(7-(2-Hydroxyethyl)-8-oxo-9-(tetrahydro-2H-pyran-4-yl)-8,9-dihydro-7H-purin-2-yl)pyrazolo[1,5-a]pyridine-5-carbonitrile,
3-(8-methyl-9-tetrahydro-2H-pyran-4-yl-9H-purin-2-yl)pyrazolo[1,5-a]pyridine-5-carbonitrile,
3-(9-(4,4-difluorocyclohexyl)-8-methyl-9H-purin-2-yl)pyrazolo[1,5-a]pyridine-5-carbonitrile,
3-(9-(1,1-dioxotetrahydrothien-3-yl)-8-methyl-9H-purin-2-yl)pyrazolo[1,5-a]pyridine-5-carbonitrile,
5-(pyrazolo[1,5-a]pyridin-3-yl)-3-(tetrahydro-2H-pyran-4-yl)-3H-imidazo[4,5-b]pyridine,
(S)-tert-Butyl 3-(5-(5-cyanopyrazolo[1,5-a]pyridin-3-yl)-3H-imidazo[4,5-b]pyridin-3-yl)piperidine-1-carboxylate,
(S)-tert-Butyl 3-(5-(5-cyanopyrazolo[1,5-a]pyridin-3-yl)-2-methyl-3H-imidazo[4,5-b]pyridin-3-yl)piperidine-1-carboxylate,
2-methyl-5-(pyrazolo[1,5-a]pyridin-3-yl)-3-(tetrahydro-2H-pyran-4-yl)-3H-imidazo[4,5-b]pyridine,
3-(9-(trans-4-hydroxycyclohexyl)-8-methyl-9H-purin-2-yl)pyrazolo[1,5-a]pyridine-5-carbonitrile,
(S)-tert-Butyl 3-(5-(pyrazolo[1,5-a]pyridin-3-yl)-3H-imidazo[4,5-b]pyridin-3-yl)piperidine-1-carboxylate,
3-(9-Tetrahydro-2H-pyran-4-yl-9H-purin-2-yl)pyrazolo[1,5-a]pyridine-5-carbonitrile,
(S)-3-(3-(1-acetylpiperidin-3-yl)-3H-imidazo[4,5-b]pyridin-5-yl)pyrazolo[1,5-a]pyridine-5-carbonitrile,
3-(3-(Tetrahydro-2H-pyran-4-yl)-3H-imidazo[4,5-b]pyridin-5-yl)pyrazolo[1,5-a]pyridine-5-carbonitrile,
3-(2-Methyl-3-(tetrahydro-2H-pyran-4-yl)-3H-imidazo[4,5-b]pyridin-5-yl)pyrazolo[1,5-a]pyridine-5-carbonitrile,
3-(8-(pyrimidin-5-yl)-9-(tetrahydro-2H-pyran-4-yl)-9H-purin-2-yl)pyrazolo[1,5-a]pyridine-5-carbonitrile,
3-(9-(8-fluorochroman-4-yl)-8-(pyrimidin-5-yl)-9H-purin-2-yl)pyrazolo[1,5-a]pyridine-5-carbonitrile,
3-(9-(8-fluorochroman-4-yl)-8-(1-methyl-1H-imidazol-2-yl)-9H-purin-2-yl)pyrazolo[1,5-a]pyridine-5-carbonitrile,
2-(pyrazolo[1,5-a]pyridin-3-yl)-8-(1H-pyrrol-2-yl)-9-(tetrahydro-2H-pyran-4-yl)-9H-purine,
8-(5-methylthiophen-2-yl)-2-(pyrazolo[1,5-a]pyridin-3-yl)-9-(tetrahydro-2H-pyran-4-yl)-9H-purine,
8-(1-methyl-1H-imidazol-2-yl)-2-(pyrazolo[1,5-a]pyridin-3-yl)-9-(tetrahydro-2H-pyran-4-yl)-9H-purine,
2-(pyrazolo[1,5-a]pyridin-3-yl)-9-(tetrahydro-2H-pyran-4-yl)-8-(2,2,2-trifluoroethyl)-9H-purine,
8-(1H-pyrazol-3-yl)-2-(pyrazolo[1,5-a]pyridin-3-yl)-9-(tetrahydro-2H-pyran-4-yl)-9H-purine,
8-(1-methyl-1H-pyrrol-2-yl)-2-(pyrazolo[1,5-a]pyridin-3-yl)-9-(tetrahydro-2H-pyran-4-yl)-9H-purine,
2-(2-(pyrazolo[1,5-a]pyridin-3-yl)-9-(tetrahydro-2H-pyran-4-yl)-9H-purin-8-yl)thiazole,
2-(pyrazolo[1,5-a]pyridin-3-yl)-9-(tetrahydro-2H-pyran-4-yl)-8-thiophen-2-yl)-H-purine,
(S)-3-(9-(1-acetylpiperidin-3-yl)-8-(pyrimidin-5-yl)-9H-purin-2-yl)pyrazolo[1,5-a]pyridine-5-carbonitrile,
(S)-tert-Butyl 3-(2-methyl-5-(pyrazolo[1,5-a]pyridin-3-yl)-3H-imidazo[4,5-b]pyridin-3-yl)piperidine-1-carboxylate,
3-(8-1-Methyl-1H-imidazol-2-yl)-9-(tetrahydro-2H-pyran-4-yl)-9H-purin-2-yl)pyrazolo[1,5-a]pyridine-5-carbonitrile,
3-(8-(pyridin-3-ylamino)-9-(tetrahydro-2H-pyran-4-yl)-9H-purin-2-yl)pyrazolo[1,5-a]pyridine-5-carbonitrile,
3-(8-(ethylamino)-9-(8-fluorochroman-4-yl)-9H-purin-2-yl)pyrazolo[1,5-a]pyridine-5-carbonitrile,
3-(9-(8-fluorochroman-4-yl)-8-(pyridin-3-ylamino)-9H-purin-2-yl)pyrazolo[1,5-a]pyridine-5-carbonitrile,
3-[8-(Ethylamino)-9-tetrahydro-2H-pyran-4-yl-9H-purin-2-yl)pyrazolo[1,5-a]pyridine-5-carbonitrile,
(S)-3-(9-(1-acetylpiperidin-3-yl)-8-ethyl-9H-purin-2-yl)pyrazolo[1,5-a]pyridine-5-carbonitrile,
S)-3-(9-(1-acetylpiperidin-3-yl)-8-isopropyl-9H-purin-2-yl)pyrazolo[1,5-a]pyridine-5-carbonitrile,
(S)-3-(9-(1-acetylpiperidin-3-yl)-8-methyl-9H-purin-2-yl)pyrazolo[1,5-a]pyridine-5-carbonitrile,
8-cyclopropyl-2-(pyrazolo[1,5-a]pyridin-3-yl)-9-(tetrahydro-2H-pyran-4-yl)-9H-purine,
8-Cyclopentyl-2-(pyrazolo[1,5-a]pyridin-3-yl)-9-(tetrahydro-2H-pyran-4-yl)-9H-purine,
(S)-1-methyl-3-(1-pivaloylpiperidin-3-yl)-5-(pyrazolo[1,5-a]pyridin-3-yl)-1H-imidazo[4,5-b]pyridin-2(3H)-one, (S)-3-(1-(4-fluorobenzoyl)piperidin-3-yl)-1-methyl-5-(pyrazolo[1,5-a]pyridin-3-yl)-1H-imidazo[4,5-b]pyridin-2(3H)-one, (S)-1-methyl-3-(1-propionylpiperidin-3-yl)-5-(pyrazolo[1,5-a]pyridin-3-yl)-1H-imidazo[4,5-b]pyridin-2(3H)-one, (S)-3-(1-Acetylpiperidin-3-yl)-1-methyl-5-(pyrazolo[1,5-a]pyridin-3-yl)-1H-imidazo[4,5-b]pyridin-2(3H)-one, 9-(1-isobutyrylpiperidin-4-yl)-2-(pyrazolo[1,5-a]pyridin-3-yl)-7H-purin-8(9H)-one, 9-(1-(2-(dimethylamino)acetyl)piperidin-4-yl)-2-(pyrazolo[1,5-a]pyridin-3-yl)-7H-purin-8(9H)-one, (S)-1-(3-(1-Methyl-2-oxo-5-(pyrazolo[1,5-a]pyridin-3-yl)-1H-imidazo[4,5-b]pyridin-3(2H)-yl)piperidine-1-carbonyl)cyclopropanecarbonitrile, (S)-ethyl 3-(2-(5-cyanopyrazolo[1,5-a]pyridin-3-yl)-8-oxo-7H-purin-9(8H)-yl)piperidine-1-carboxylate, (S)-isobutyl 3-(2-(5-cyanopyrazolo[1,5-a]pyridin-3-yl)-8-oxo-7H-purin-9(8H)-yl)piperidine-1-carboxylate, (S)-3-(2-(5-cyanopyrazolo[1,5-a]pyridin-3-yl)-8-oxo-7H-purin-9(8H)-yl)-N-isopropylpiperidine-1-carboxamide, (S)—N-tert-butyl-3-(2-(5-cyanopyrazolo[1,5-a]pyridin-3-yl)-8-oxo-7H-purin-9(8H)-yl)piperidine-1-carboxamide, (S)-ethyl 9-(1-(2-cyanoacetyl)piperidin-3-yl)-8-oxo-2-(pyrazolo[1,5-a]pyridin-3-yl)-8,9-dihydro-7H-purine-7-carboxylate, (S)-3-(3-(7-acetyl-8-oxo-2-(pyrazolo[1,5-a]pyridin-3-yl)-7H-purin-9(8H)-yl)piperidin-1-yl)-3-oxopropanenitrile, (S)-9-(1-acetylpiperidin-3-yl)-7-methyl-2-(pyrazolo[1,5-a]pyridin-3-yl)-7H-purin-8(9H)-one, (S)—N-isopropyl-3-(1-methyl-2-oxo-5-(pyrazolo[1,5-a]pyridin-3-yl)-H-imidazo[4,5-b]pyridin-3(2H)-yl)piperidine-1-carboxamide, (S)-3-(3-(1-acetyl-2-oxo-5-(pyrazolo[1,5-a]pyridin-3-yl)-1H-imidazo[4,5-b]pyridin-3(2H)-yl)piperidin-1-yl)-3-oxopropanenitrile, (S)-ethyl 3-(1-(2-cyanoacetyl)piperidin-3-yl)-2-oxo-5-(pyrazolo[1,5-a]pyridin-3-yl)-2,3-dihydro-1H-imidazo[4,5-b]pyridine-1-carboxylate, (S)-Methyl 3-(2-(5-cyanopyrazolo[1,5-a]pyridin-3-yl)-8-oxo-7H-purin-9(8H)-yl)piperidine-1-carboxylate, (S)-3-(9-(1-(1-hydroxycyclopropanecarbonyl)piperidin-3-yl)-8-oxo-8,9-dihydro-7H-purin-2-yl)pyrazolo[1,5-a]pyridine-5-carbonitrile, (S)-3-(9-(1-(1-Cyanocyclopropanecarbonyl)piperidin-3-yl)-8-oxo-8,9-dihydro-7H-purin-2-yl)pyrazolo[1,5-a]pyridine-5-carbonitrile, (R)-3-(9-(1-Hydroxypropan-2-yl)-8-oxo-8,9-dihydro-7H-purin-2-yl)pyrazolo[1,5-a]pyridine-5-carbonitrile, (S)-3-(3-(2-(5-Methylpyrazolo[1,5-a]pyridin-3-yl)-9H-purin-9-yl)piperidin-1-yl)-3-oxopropanenitrile, 1-(4-(2-(Pyrazolo[1,5-a]pyridin-3-yl)-9H-purin-9-yl)piperidin-1-yl)ethanone, (S)-(3-(1-(2-cyanoacetyl)piperidin-3-yl)-2-oxo-5-(pyrazolo[1,5-a]pyridin-3-yl)-2,3-dihydro-1H-imidazo[4,5-b]pyridin-1-yl)methyl acetate, (S)-(9-(1-(2-Cyanoacetyl)piperidin-3-yl)-8-oxo-2-(pyrazolo[1,5-a]pyridin-3-yl)-8,9-dihydro-7H-purin-7-yl)methyl acetate, (R)-3-(9-O-Hydroxypropan-2-yl)-7-methyl-8-oxo-8,9-dihydro-7H-purin-2-yl)pyrazolo[1,5-a]pyridine-5-carbonitrile, 2-(Pyrazolo[1,5-a]pyridin-3-yl)-9-(tetrahydro-2H-pyran-4-yl)-9H-purin-8-amine, N-(2-(pyrazolo[1,5-a]pyridin-3-yl)-9-(tetrahydro-2H-pyran-4-yl)-9H-purin-8-yl)isobutyramide, N-(2-(pyrazolo[1,5-a]pyridin-3-yl)-9-(tetrahydro-2H-pyran-4-yl)-9H-purin-8-yl)propionamide, N-(2-(pyrazolo[1,5-a]pyridin-3-yl)-9-(tetrahydro-2H-pyran-4-yl)-9H-purin-8-yl)acetamide, 1-(2-(Pyrazolo[1,5-a]pyridin-3-yl)-9-(tetrahydro-2H-pyran-4-O-9H-purin-8-yl)pyrrolidin-2-one, 3-(9-(trans-4-Hydroxycyclohexyl)-7-methyl-8-oxo-8,9-dihydro-7H-purin-2-yl)pyrazolo[1,5-a]pyridine-5-carbonitrile, 2-(2-(5-cyanopyrazolo[1,5-a]pyridin-3-yl)-8-oxo-7H-purin-9(8H)-yl)-N-ethylacetamide, 2-(2-(5-Cyanopyrazolo[1,5-a]pyridin-3-yl)-8-oxo-7H-purin-9(8H)-yl)-N-(2,2,2-trifluoroethyl)acetamide, and 2-(Imidazo[1,2-a]pyridin-3-yl)-7-methyl-9-(tetrahydro-2H-pyran-4-yl)-7H-purin-8(9H)-one, and a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 8,501,735 B2 | Page 1 of 16 |
| APPLICATION NO. | : 13/504157 | |
| DATED | : August 6, 2013 | |
| INVENTOR(S) | : Carmen Almansa Rosales et al. | |

It is certified that error appears in the above-identified patent and that said Letters Patent is hereby corrected as shown below:

In the Claims
Claim 36, Col. 111, Lines 24-25
"Methyl (2R)-2-[2-(5-cyanopyrazolo[1,5-a]pyridin-3-yl)-8-oxo-7,8-dihydro-9H-purin-9-yl]propanoate,"
should read as
--methyl (R)-2-(2-(5-cyanopyrazolo[1,5-a]pyridin-3-yl)-8-oxo-7,8-dihydro-9H-purin-9-yl)propanoate,--.

Claim 36, Col. 111, Lines 26-27
"(S)-tert-butyl 3-(2-(5-cyanopyrazolo[1,5-a]pyridin-3-yl)-8-oxo-7H-purin-9(8H)-yl)piperidine-1-carboxylate,"
should read as
--(S)-tert-butyl-3-(2-(5-cyanopyrazolo[1,5-a]pyridin-3-yl)-8-oxo-7H-purin-9(8H)-yl)piperidine-1-carboxylate,--.

Claim 36, Col. 111, Lines 27-28
"(R)-tert-butyl 3-(2-(5-cyanopyrazolo[1,5-a]pyridin-3-yl)-8-oxo-7H-purin-9(8H)-yl)piperidine-1-carboxylate,"
should read as
--(R)-tert-butyl-3-(2-(5-cyanopyrazolo[1,5-a]pyridin-3-yl)-8-oxo-7H-purin-9(8H)-yl)piperidine-1-carboxylate,--.

Claim 36, Col. 111, Lines 43-44
"Methyl (2S)-2-[2-(5-cyanopyrazolo[1,5-a]pyridin-3-yl)-8-oxo-7,8-dihydro-9H-purin-9-yl]propanoate,"
should read as
--methyl (2S)-2-(2-(5-cyanopyrazolo[1,5-a]pyridin-3-yl)-8-oxo-7,8-dihydro-9H-purin-9-yl)propanoate,--.

Signed and Sealed this
Sixth Day of May, 2014

Michelle K. Lee
*Deputy Director of the United States Patent and Trademark Office*

Claim 36, Col. 111, Lines 45-46
"9-(1-acetylpiperidin-4-yl)-2-(5-(trifluoromethyl)pyrazolo[1,5-a]pyridin-3-yl)-7H-purin-8(9H)-one (1),"
should read as
--9-(1-acetylpiperidin-4-yl)-2-(5-(trifluoromethyl)pyrazolo[1,5-a]pyridin-3-yl)-7H-purin-8(9H)-one,--.

Claim 36, Col. 111, Lines 47-48
"(S)-tert-butyl 3-(2-(5-cyanopyrazolo[1,5-a]pyridin-3-yl)-8-oxo-7H-purin-9(8H)-yl)pyrrolidine-1-carboxylate,"
should read as
--(S)-tert-butyl-3-(2-(5-cyanopyrazolo[1,5-a]pyridin-3-yl)-8-oxo-7H-purin-9(8H)-yl)pyrrolidine-1-carboxylate,--.

Claim 36, Col. 111, Lines 49-50
"(R)-tert-butyl 3-(2-(5-cyanopyrazolo[1,5-a]pyridin-3-yl)-8-oxo-7H-purin-9(8H)-yl)pyrrolidine-1-carboxylate,"
should read as
--(R)-tert-butyl-3-(2-(5-cyanopyrazolo[1,5-a]pyridin-3-yl)-8-oxo-7H-purin-9(8H)-yl)pyrrolidine-1-carboxylate,--.

Claim 36, Col. 111, Lines 51-52
"(S)-tert-butyl 3-(2-(5-methylpyrazolo[1,5-a]pyridin-3-yl)-8-oxo-7H-purin-9(8H)-yl)piperidine-1-carboxylate (2),"
should read as
--(S)-tert-butyl-3-(2-(5-methylpyrazolo[1,5-a]pyridin-3-yl)-8-oxo-7H-purin-9(8H)-yl)piperidine-1-carboxylate,--.

Claim 36, Col. 111, Lines 54-55
"Ethyl 2-(2-(5-cyanopyrazolo[1,5-a]pyridin-3-yl)-8-oxo-7H-purin-9(8H)-yl)acetate,"
should read as
--ethyl-2-(2-(5-cyanopyrazolo[1,5-a]pyridin-3-yl)-8-oxo-7H-purin-9(8H)-yl)acetate,--.

Claim 36, Col. 111, Lines 58-59
"3-(9-(8-fluorochroman-4-yl)-8-oxo-8,9-dihydro-7H-purin-2-yl)pyrazolo[1,5-e]pyridine-5-carbonitrile,"
should read as
--3-(9-(8-fluorochroman-4-yl)-8-oxo-8,9-dihydro-7H-purin-2-yl)pyrazolo[1,5-a]pyridine-5-carbonitrile,--.

Claim 36, Col. 111, Lines 60-61
"tert-Butyl 4-(2-(5-cyanopyrazolo[1,5-a]pyridin-3-yl)-8-oxo-7H-purin-9(8H)-yl)piperidine-1-carboxylate,"
should read as
--tert-butyl-4-(2-(5-cyanopyrazolo[1,5-a]pyridin-3-yl)-8-oxo-7H-purin-9(8H)-yl)piperidine-1-carboxylate,--.

Claim 36, Col. 111, Lines 62-63
"tert-Butyl 3-(2-(5-cyanopyrazolo[1,5-a]pyridin-3-yl)-8-oxo-7H-purin-9(8H)-yl)azetidine-1-carboxylate,"
should read as
--tert-butyl-3-(2-(5-cyanopyrazolo[1,5-a]pyridin-3-yl)-8-oxo-7H-purin-9(8H)-yl)azetidine-1-carboxylate,--.

Claim 36, Col. 111, Lines 64-65
"9-(1-acetylpiperidin-4-yl)-2-(5-methylpyrazolo[1,5-a]pyridin-3-yl)-7H-purin-8(9H)-one (2),"
should read as
--9-(1-acetylpiperidin-4-yl)-2-(5-methylpyrazolo[1,5-a]pyridin-3-yl)-7H-purin-8(9H)-one,--.

Claim 36, Col. 111, Lines 66-67
"3-(8-Oxo-9-tetrahydro-2H-pyran-4-yl-8,9-dihydro-7H-purin-2-yl)pyrazolo[1,5-a]pyridine-5-carbonitrile,"
should read as
--3-(8-oxo-9-(tetrahydro-2H-pyran-4-yl)-8,9-dihydro-7H-purin-2-yl)pyrazolo[1,5-a]pyridine-5-carbonitrile,--.

Claim 36, Col. 112, Lines 1-3
"(S)-tert-Butyl 3-(2-oxo-5-(pyrazolo[1,5-a]pyridin-3-yl)-1H-imidazo[4,5-b]pyridin-3(2H)-yl)piperidine-1-carboxylate,"
should read as
--(S)-tert-butyl-3-(2-oxo-5-(pyrazolo[1,5-a]pyridin-3-yl)-1H-imidazo[4,5-b]pyridin-3(2H)-yl)piperidine-1-carboxylate,--.

Claim 36, Col. 112, Lines 4-6
"(R)-tert-Butyl 3-(2-oxo-5-(pyrazolo[1,5-a]pyridin-3-yl)-1H-imidazo[4,5-b]pyridin-3(2H)-yl)pyrrolidine-1-carboxylate,"
should read as
--(R)-tert-butyl-3-(2-oxo-5-(pyrazolo[1,5-a]pyridin-3-yl)-1H-imidazo[4,5-b]pyridin-3(2H)-yl)pyrrolidine-1-carboxylate,--.

Claim 36, Col. 112, Lines 7-9
"(S)-tert-Butyl 3-(2-oxo-5-(pyrazolo[1,5-a]pyridin-3-yl)-1H-imidazo[4,5-b]pyridin-3(2H)-yl)pyrrolidine-1-carboxylate,"
should read as
--(S)-tert-butyl-3-(2-oxo-5-(pyrazolo[1,5-a]pyridin-3-yl)-1H-imidazo[4,5-b]pyridin-3(2H)-yl)pyrrolidine-1-carboxylate,--.

Claim 36, Col. 112, Lines 10-12
"(S)-tert-Butyl 3-(5-(5-cyanopyrazolo[1,5-a]pyridin-3-yl)-2-oxo-1H-imidazo[4,5-b]pyridin-3(2H)-yl)piperidine-1-carboxylate,"
should read as --(S)-tert-butyl-3-(5-(5-cyanopyrazolo[1,5-a]pyridin-3-yl)-2-oxo-1H-imidazo[4,5-b]pyridin-3(2H)-yl)piperidine-1-carboxylate,--.

Claim 36, Col. 112, Lines 15-17
"(R)-tert-Butyl 3-(2-oxo-5-(pyrazolo[1,5-a]pyridin-3-yl)-1H-imidazo[4,5-b]pyridin-3(2H)-yl)piperidine-1-carboxylate,"
should read as
--(R)-tert-butyl-3-(2-oxo-5-(pyrazolo[1,5-a]pyridin-3-yl)-1H-imidazo[4,5-b]pyridin-3(2H)-yl)piperidine-1-carboxylate,--.

Claim 36, Col. 112, Lines 23-24
"(S)-tert-Butyl 3-(8-oxo-2-(pyrazolo[1,5-a]pyridin-3-yl)-7H-purin-9(8H)-yl)piperidine-1-carboxylate,"
should read as
--(S)-tert-butyl-3-(8-oxo-2-(pyrazolo[1,5-a]pyridin-3-yl)-7H-purin-9(8H)-yl)piperidine-1-carboxylate,--.

Claim 36, Col. 112, Lines 29-30
"Methyl (2S)-2-(8-oxo-2-(pyrazolo[1,5-a]pyridin-3-yl)-7,8-dihydro-9H-purin-9-yl)propanoate,"
should read as
--methyl (2S)-2-(8-oxo-2-(pyrazolo[1,5-a]pyridin-3-yl)-7,8-dihydro-9H-purin-9-yl)propanoate,--.

Claim 36, Col. 112, Lines 31-32
"(S)-tert-butyl 3-(8-oxo-2-(pyrazolo[1,5-a]pyridin-3-yl)-7H-purin-9(8H)-yl)pyrrolidine-1-carboxylate,"
should read as
--(S)-tert-butyl-3-(8-oxo-2-(pyrazolo[1,5-a]pyridin-3-yl)-7H-purin-9(8H)-yl)pyrrolidine-1-carboxylate,--.

Claim 36, Col. 112, Lines 33-34
"tert-Butyl 4-(8-oxo-2-(pyrazolo[1,5-a]pyridin-3-yl)-7H-purin-9(8H)-yl)piperidine-1-carboxylate,"
should read as
--tert-butyl-4-(8-oxo-2-(pyrazolo[1,5-a]pyridin-3-yl)-7H-purin-9(8H)-yl)piperidine-1-carboxylate,--.

Claim 36, Col. 112, Lines 39-40
"2-(Pyrazolo[1,5-a]pyridin-3-yl)-9-(tetrahydro-2H-pyran-4-yl)-7H-purin-8(9H)-one,"
should read as
--2-(pyrazolo[1,5-a]pyridin-3-yl)-9-(tetrahydro-2H-pyran-4-yl)-7H-purin-8(9H)-one,--.

Claim 36, Col. 112, Lines 41-43
"(S)-tert-Butyl 3-(2-(5-cyanopyrazolo[1,5-a]pyridin-3-yl)-7-methyl-8-oxo-7H-purin-9(8H)-yl)piperidine-1-carboxylate,"
should read as
--(S)-tert-butyl-3-(2-(5-cyanopyrazolo[1,5-a]pyridin-3-yl)-7-methyl-8-oxo-7H-purin-9(8H)-yl)piperidine-1-carboxylate,--.

Claim 36, Col. 112, Lines 44-46
"(R)-tert-Butyl 3-(2-(5-cyanopyrazolo[1,5-a]pyridin-3-yl)-7-methyl-8-oxo-7H-purin-9(8H)-yl)piperidine-1-carboxylate,"
should read as
--(R)-tert-butyl-3-(2-(5-cyanopyrazolo[1,5-a]pyridin-3-yl)-7-methyl-8-oxo-7H-purin-9(8H)-yl)piperidine-1-carboxylate,--.

Claim 36, Col. 112, Lines 49-51
"3-(7-Methyl-8-oxo-9-tetrahydro-2H-pyran-4-yl-8,9-dihydro-7H-purin-2-yl)pyrazolo[1,5-a]pyridine-5-carbonitrile,"
should read as
--3-(7-methyl-8-oxo-9-(tetrahydro-2H-pyran-4-yl)-8,9-dihydro-7H-purin-2-yl)pyrazolo[1,5-a]pyridine-5-carbonitrile,--.

Claim 36, Col. 112, Lines 49-51
"7-methyl-2-(pyrazolo[1,5-a]pyridin-3-yl)-9-(tetrahydro-2H-pyran-4-yl)methyl)-7H-purin-8(9H)-one,"
should read as
--7-methyl-2-(pyrazolo[1,5-a]pyridin-3-yl)-9-((tetrahydro-2H-pyran-4-yl)methyl)-7H-purin-8(9H)-one,--.

Claim 36, Col. 113, Lines 1-3
"(S)-tert-Butyl 3-(5-(5-cyanopyrazolo[1,5-a]pyridin-3-yl)-1-methyl-2-oxo-1H-imidazo[4,5-b]pyridin-3(2H)-yl)piperidine-1-carboxylate,"
should read as
--(S)-tert-butyl-3-(5-(5-cyanopyrazolo[1,5-a]pyridin-3-yl)-1-methyl-2-oxo-1H-imidazo[4,5-b]pyridin-3(2H)-yl)piperidine-1-carboxylate,--.

Claim 36, Col. 113, Lines 9-11
"(S)-tert-Butyl 3-(1-methyl-2-oxo-5-(pyrazolo[1,5-a]pyridin-3-yl)-1H-imidazo[4,5-b]pyridin-3(2H)-yl)piperidine-1-carboxylate,"
should read as
--(S)-tert-butyl-3-(1-methyl-2-oxo-5-(pyrazolo[1,5-a]pyridin-3-yl)-1H-imidazo[4,5-b]pyridin-3(2H)-yl)piperidine-1-carboxylate,--.

Claim 36, Col. 113, Lines 12-14
"(S)-tert-Butyl 3-(2-(5-cyanopyrazolo[1,5-a]pyridin-3-yl)-7-methyl-8-oxo-7H-purin-9(8H)-yl)pyrrolidine-1-carboxylate,"
should read as
--(S)-tert-butyl-3-(2-(5-cyanopyrazolo[1,5-a]pyridin-3-yl)-7-methyl-8-oxo-7H-purin-9(8H)-yl)pyrrolidine-1-carboxylate,--.

Claim 36, Col. 113, Lines 15-17
"(R)-tert-Butyl 3-(2-(5-cyanopyrazolo[1,5-a]pyridin-3-yl)-7-methyl-8-oxo-7H-purin-9(8H)-yl)pyrrolidine-1-carboxylate,"

should read as
--(R)-tert-butyl-3-(2-(5-cyanopyrazolo[1,5-a]pyridin-3-yl)-7-methyl-8-oxo-7H-purin-9(8H)-yl)pyrrolidine-1-carboxylate,--.

Claim 36, Col. 113, Lines 18-20
"(S)-tert-Butyl 3-(7-methyl-8-oxo-2-(pyrazolo[1,5-a]pyridin-3-yl)-7H-purin-9(8H)-yl)pyrrolidine-1-carboxylate,"
should read as
--(S)-tert-butyl-3-(7-methyl-8-oxo-2-(pyrazolo[1,5-a]pyridin-3-yl)-7H-purin-9(8H)-yl)pyrrolidine-1-carboxylate,--.

Claim 36, Col. 113, Lines 21-23
"(R)-tert-Butyl 3-(1-methyl-2-oxo-5-(pyrazolo[1,5-a]pyridin-3-yl)-1H-imidazo[4,5-b]pyridin-3(2H)-yl)pyrrolidine-1-carboxylate,"
should read as
--(R)-tert-butyl-3-(1-methyl-2-oxo-5-(pyrazolo[1,5-a]pyridin-3-yl)-1H-imidazo[4,5-b]pyridin-3(2H)-yl)pyrrolidine-1-carboxylate,--.

Claim 36, Col. 113, Lines 24-26
"(S)-tert-Butyl 3-(1-methyl-2-oxo-5-(pyrazolo[1,5-a]pyridin-3-yl)-1H-imidazo[4,5-b]pyridin-3(2H)-yl)pyrrolidine-1-carboxylate,"
should read as
--(S)-tert-butyl-3-(1-methyl-2-oxo-5-(pyrazolo[1,5-a]pyridin-3-yl)-1H-imidazo[4,5-b]pyridin-3(2H)-yl)pyrrolidine-1-carboxylate,--.

Claim 36, Col. 113, Lines 27-29
"(S)-tert-Butyl 3-(1-ethyl-2-oxo-5-(pyrazolo[1,5-a]pyridin-3-yl)-1H-imidazo[4,5-b]pyridin-3(2H)-yl)piperidine-1-carboxylate,"
should read as
--(S)-tert-butyl-3-(1-ethyl-2-oxo-5-(pyrazolo[1,5-a]pyridin-3-yl)-1H-imidazo[4,5-b]pyridin-3(2H)-yl)piperidine-1-carboxylate,--.

Claim 36, Col. 113, Lines 30-31
"tert-Butyl 4-(7-methyl-8-oxo-2-(pyrazolo[1,5-a]pyridin-3-yl)-7H-purin-9(8H)-yl)piperidine-1-carboxylate,"
should read as
--tert-butyl-4-(7-methyl-8-oxo-2-(pyrazolo[1,5-a]pyridin-3-yl)-7H-purin-9(8H)-yl)piperidine-1-carboxylate,--.

Claim 36, Col. 113, Lines 32-33
"(S)-tert-Butyl 3-(7-methyl-8-oxo-2-(pyrazolo[1,5-a]pyridin-3-yl)-7H-purin-9(8H)-yl)piperidine-1-carboxylate,"
should read as
--(S)-tert-butyl-3-(7-methyl-8-oxo-2-(pyrazolo[1,5-a]pyridin-3-yl)-7H-purin-9(8H)-yl)piperidine-1-carboxylate,--.

Claim 36, Col. 113, Lines 36-38
"(R)-tert-Butyl 3-(1-methyl-2-oxo-5-(pyrazolo[1,5-a]pyridin-3-yl)-1H-imidazo[4,5-b]pyridin-3(2H)-yl)piperidine-1-carboxylate,"
should read as
--(R)-tert-butyl-3-(1-methyl-2-oxo-5-(pyrazolo[1,5-a]pyridin-3-yl)-1H-imidazo[4,5-b]pyridin-3(2H)-yl)piperidine-1-carboxylate,--.

Claim 36, Col. 113, Lines 39-41
"tert-Butyl 4-(2-(5-cyanopyrazolo[1,5-a]pyridin-3-yl)-7-methyl-8-oxo-7H-purin-9(8H)-yl)piperidine-1-carboxylate,"
should read as
--tert-butyl-4-(2-(5-cyanopyrazolo[1,5-a]pyridin-3-yl)-7-methyl-8-oxo-7H-purin-9(8H)-yl)piperidine-1-carboxylate,--.

Claim 36, Col. 113, Lines 42-44
"tert-Butyl 3-(2-(5-cyanopyrazolo[1,5-a]pyridin-3-yl)-7-methyl-8-oxo-7H-purin-9(8H)-yl)azetidine-1-carboxylate,"
should read as
--tert-butyl-3-(2-(5-cyanopyrazolo[1,5-a]pyridin-3-yl)-7-methyl-8-oxo-7H-purin-9(8H)-yl)azetidine-1-carboxylate,--.

Claim 36, Col. 113, Lines 45-47
"(S)-tert-Butyl 3-(7-methyl-8-oxo-2-(pyrazolo[1,5-a]pyridine-3-yl)-7H-purin-9(8H)-yl)piperidine-1-carboxylate,"
should read as
--(S)-tert-butyl-3-(7-methyl-8-oxo-2-(pyrazolo[1,5-a]pyridine-3-yl)-7H-purin-9(8H)-yl)piperidine-1-carboxylate,--.

Claim 36, Col. 113, Lines 48-50
"(R)-3-(8-oxo-9-(piperidin-3-yl)-8,9-dihydro-7H-purin-2-yl)pyrazolo[1,5-a]pyridine-5-carbonitrile hydrochloride,"
should read as
--(R)-3-(8-oxo-9-(piperidin-3-yl)-8,9-dihydro-7H-purin-2-yl)pyrazolo[1,5-a]pyridine-5-carbonitrile hydrochloride,--.

Claim 36, Col. 113, Lines 65-67
"(S)-1-methyl-3-(piperidin-3-yl)-5-(pyrazolo[1,5-a]pyridin-3-yl)-1H-imidazo[4,5-b]pyridin-2(3H)-one hydrochloride,"
should read as
--(S)-1-methyl-3-(piperidin-3-yl)-5-(pyrazolo[1,5-a]pyridin-3-yl)-1H-imidazo[4,5-b]pyridin-2(3H)-one hydrochloride,--.

Claim 36, Col. 114, Lines 11-13
"(S)-3-(8-oxo-9-(pyrrolidin-3-yl)-8,9-dihydro-7H-purin-2-yl)pyrazolo[1,5-a]pyridine-5-carbonitrile hydrochloride,"

should read as
--(S)-3-(8-oxo-9-(pyrrolidin-3-yl)-8,9-dihydro-7H-purin-2-yl)pyrazolo[1,5-a]pyridine-5-carbonitrile hydrochloride,--.

Claim 36, Col. 114, Lines 14-16
"(R)-1-methyl-5-(pyrazolo[1,5-a]pyridin-3-yl)-3-(pyrrolidin-3-yl)-1H-imidazo[4,5-b]pyridin-2(3H)-one hydrochloride,"
should read as
--(R)-1-methyl-5-(pyrazolo[1,5-a]pyridin-3-yl)-3-(pyrrolidin-3-yl)-1H-imidazo[4,5-b]pyridin-2(3H)-one hydrochloride,--.

Claim 36, Col. 114, Lines 19-21
"(R)-3-(8-oxo-9-(pyrrolidin-3-yl)-8,9-dihydro-7H-purin-2-yl)pyrazolo[1,5-a]pyridine-5-carbonitrile hydrochloride,"
should read as
--(R)-3-(8-oxo-9-(pyrrolidin-3-yl)-8,9-dihydro-7H-purin-2-yl)pyrazolo[1,5-a]pyridine-5-carbonitrile hydrochloride,--.

Claim 36, Col. 114, Lines 24-26
"(S)-1-methyl-5-(pyrazolo[1,5-a]pyridin-3-yl)-3-(pyrrolidin-3-yl)-1H-imidazo[4,5-b]pyridin-2(3H)-one hydrochloride,"
should read as
--(S)-1-methyl-5-(pyrazolo[1,5-a]pyridin-3-yl)-3-(pyrrolidin-3-yl)-1H-imidazo[4,5-b]pyridin-2(3H)-one hydrochloride,--.

Claim 36, Col. 114, Lines 29-31
"(S)-1-ethyl-3-(piperidin-3-yl)-5-(pyrazolo[1,5-a]pyridin-3-yl)-1H-imidazo[4,5-b]pyridin-2(3H)-one hydrochloride,"
should read as
--(S)-1-ethyl-3-(piperidin-3-yl)-5-(pyrazolo[1,5-a]pyridin-3-yl)-1H-imidazo[4,5-b]pyridin-2(3H)-one hydrochloride,--.

Claim 36, Col. 114, Lines 59-61
"(S)-3-(8-Oxo-9-(piperidin-3-yl)-8,9-dihydro-7H-purin-2-yl)pyrazolo[1,5-a]pyridine-5-carbonitrile hydrochloride,"
should read as
--(S)-3-(8-oxo-9-(piperidin-3-yl)-8,9-dihydro-7H-purin-2-yl)pyrazolo[1,5-a]pyridine-5-carbonitrile hydrochloride,--.

Claim 36, Col. 115, Lines 4-6
"3-(9-(1-(2-cyanoacetyl)-pyrrolidin-3-yl)-7-methyl-8-oxo-8,9-dihydro-7H-purin-2-yl pyrazolo[1,5-a]pyridine-5-carbonitrile,"
should read as
--3-(9-(1-(2-cyanoacetyl)-pyrrolidin-3-yl)-7-methyl-8-oxo-8,9-dihydro-7H-purin-2-yl)pyrazolo[1,5-a]pyridine-5-carbonitrile,--.

Claim 36, Col. 115, Lines 22-23
"3-(9-(1-(2-cyanoacetyl)azetidin-3-yl)-7-methyl-8-oxo-8,9-dihydro-7H-purin-2-yl pyrazolo[1,5-a]pyridine-5-carbonitrile,"
should read as
--3-(9-(1-(2-cyanoacetyl)azetidin-3-yl)-7-methyl-8-oxo-8,9-dihydro-7H-purin-2-yl)pyrazolo[1,5-a]pyridine-5-carbonitrile,--.

Claim 36, Col. 115, Lines 55-57
"(S)-3-(9-(1-(2-Cyanoacetyl)piperidin-3-yl)-8-oxo-8,9-dihydro-7H-purin-2-yl)pyrazolo[1,5-a]pyridine-5-carbonitrile,"
should read as
--(S)-3-(9-(1-(2-cyanoacetyl)piperidin-3-yl)-8-oxo-8,9-dihydro-7H-purin-2-yl)pyrazolo[1,5-a]pyridine-5-carbonitrile,--.

Claim 36, Col. 116, Lines 11-12
"(S)-3-(9-(1-Acetylpiperidin-3-yl)-8-oxo-8,9-dihydro-7H-purin-2-yl)pyrazolo[1,5-a]pyridine-5-carbonitrile,"
should read as
--(S)-3-(9-(1-acetylpiperidin-3-yl)-8-oxo-8,9-dihydro-7H-purin-2-yl)pyrazolo[1,5-a]pyridine-5-carbonitrile,--.

Claim 36, Col. 116, Lines 21-23
"(S)-3-(9-(1-(isobutylsulfonyl)piperidin-3-yl)-8-oxo-8,9-dihydro-7H-purin-2-yl pyrazolo[1,5-a]pyridine-5-carbonitrile,"
should read as
--(S)-3-(9-(1-(isobutylsulfonyl)piperidin-3-yl)-8-oxo-8,9-dihydro-7H-purin-2-yl)pyrazolo[1,5-a]pyridine-5-carbonitrile,--.

Claim 36, Col. 116, Lines 27-29
"S)-1-methyl-3-(1-(methylsulfonyl)piperidin-3-yl)-5-(pyrazolo[1,5-a]pyridin-3-yl)-1H-imidazo[4,5-b]pyridin-2(3H)-one,"
should read as
--(S)-1-methyl-3-(1-(methylsulfonyl)piperidin-3-yl)-5-(pyrazolo[1,5-a]pyridin-3-yl)-1H-imidazo[4,5-b]pyridin-2(3H)-one,--.

Claim 36, Col. 117, Lines 4-6
"(S)-3-(9-(1-(Methylsulfonyl)piperidin-3-yl)-8-oxo-8,9-dihydro-7H-purin-2-yl)pyrazolo[1,5-a]pyridine-5-carbonitrile,"
should read as
--(S)-3-(9-(1-(methylsulfonyl)piperidin-3-yl)-8-oxo-8,9-dihydro-7H-purin-2-yl)pyrazolo[1,5-a]pyridine-5-carbonitrile,--.

Claim 36, Col. 117, Lines 35-37
"(S)-7-(2-methoxyacetyl)-9(1-(2-methocyacetyl)piperidin-3-yl)-2-(5-methy pyrazolo[1,5-a]pyridin-3-yl)-7H-purin-8(9H)-one,"

should read as
--(S)-7-(2-methoxyacetyl)-9(1-(2-methocyacetyl)piperidin-3-yl)-2-(5-methylpyrazolo[1,5-a]pyridin-3-yl)-7H-purin-8(9H)-one,--.

Claim 36, Col. 117, Lines 42-44
"(S)-3-(9-(1-(cyclopropanecarbonyl piperidin-3-yl)-8-oxo-8,9-dihydro-7H-purin-2-yl)pyrazolo[1,5-a]pyridine-5-carbonitrile,"
should read as
--(S)-3-(9-(1-(cyclopropanecarbonyl)piperidin-3-yl)-8-oxo-8,9-dihydro-7H-purin-2-yl)pyrazolo[1,5-a]pyridine-5-carbonitrile,--.

Claim 36, Col. 117, Lines 60-62
"(S)-3-(9-(1-(2-(Dimethylamino)acetyl)piperidin-3-yl)-8-oxo-8,9-dihydro-7H-purin-2-yl)pyrazolo[1,5-a]pyridine-5-carbonitrile,"
should read as
--(S)-3-(9-(1-(2-(dimethylamino)acetyl)piperidin-3-yl)-8-oxo-8,9-dihydro-7H-purin-2-yl)pyrazolo[1,5-a]pyridine-5-carbonitrile,--.

Claim 36, Col. 117, Lines 63-65
"—(S)-N,N-dimethyl-3-(1-methyl-2-oxo-5-(pyrazolo[1,5-a]pyridin-3-yl)-1H-imidazo[4,5-b]pyridin-3(2H)-yl)piperidine-1-sulfonamide,"
should read as
--(S)-N,N-dimethyl-3-(1-methyl-2-oxo-5-(pyrazolo[1,5-a]pyridin-3-yl)-1H-imidazo[4,5-b]pyridin-3(2H)-yl)piperidine-1-sulfonamide,--.

Claim 36, Col. 118, Lines 1-3
"(S)-3-(2-(5-Cyanopyrazolo[1,5-a]pyridin-3-yl)-8-oxo-7H-purin-9(8H)-yl)-N,N-dimethylpiperidine-1-sulfonamide,"
should read as
--(S)-3-(2-(5-cyanopyrazolo[1,5-a]pyridin-3-yl)-8-oxo-7H-purin-9(8H)-yl)-N,N-dimethylpiperidine-1-sulfonamide,--.

Claim 36, Col. 118, Lines 4-6
"3-(9-(1-Acetylpyrrolidin-3-yl)-7-methyl-8-oxo-8,9-dihydro-7H-purin-2-yl)pyrazolo[1,5-a]pyridine-5-carbonitrile,"
should read as
--3-(9-(1-acetylpyrrolidin-3-yl)-7-methyl-8-oxo-8,9-dihydro-7H-purin-2-yl)pyrazolo[1,5-a]pyridine-5-carbonitrile,--.

Claim 36, Col. 118, Lines 20-22
"(R)-1-methyl-3-(1-(methylsufonyl)pyrrolidin-3-yl)-5-(pyrazolo[1,5-a]pyridin-3-yl)-H-imidazo[4,5-b]pyridine-2(3H)-one,"
should read as
--(R)-1-methyl-3-(1-(methylsufonyl)pyrrolidin-3-yl)-5-(pyrazolo[1,5-a]pyridin-3-yl)-1H-imidazo[4,5-b]pyridine-2(3H)-one,--.

Claim 36, Col. 118, Lines 36-38
"3-(7-Methyl-9-(1-(methylsulfonyl)pyrrolidin-3-yl)-8-oxo-8,9-dihydro-7H-purin-2-yl)pyrazolo[1,5-a]pyridine-5-carbonitrile,"
should read as
--3-(7-methyl-9-(1-(methylsulfonyl)pyrrolidin-3-yl)-8-oxo-8,9-dihydro-7H-purin-2-yl)pyrazolo[1,5-a]pyridine-5-carbonitrile,--.

Claim 36, Col. 118, Lines 39-40
"(2S)-2-[2-(5-Cyanopyrazolo[1,5-a]pyridin-3-yl)-8-oxo-7,8-dihydro-9H-purin-9-yl]propanoic acid,"
should read as
--(2S)-2-(2-(5-cyanopyrazolo[1,5-a]pyridin-3-yl)-8-oxo-7,8-dihydro-9H-purin-9-yl)propanoic acid--.

Claim 36, Col. 118, Lines 43-44
"(2R)-2-[2-(5-Cyanopyrazolo[1,5-a]pyridin-3-yl)-8-oxo-7,8-dihydro-9H-purin-9-yl]propanoic acid,"
should read as
--(2R)-2-(2-(5-cyanopyrazolo[1,5-a]pyridin-3-yl)-8-oxo-7,8-dihydro-9H-purin-9-yl)propanoic acid,--.

Claim 36, Col. 118, Line 66-67,
"(S)—N-methyl-2-(8-oxo-2-pyrazolo[1,5-a]pyridin-3-yl)-7H-purin-9(8H) yl)propanamide,"
should read as
--(S)-N-methyl-2-(8-oxo-2-pyrazolo[1,5-a]pyridin-3-yl)-7H-purin-9(8H)-yl)propanamide,--.

Claim 36, Col. 119, Lines 1-2
"—(S)-N,N-dimethyl-2-(8-oxo-2-(pyrazolo[1,5-a]pyridin-3-yl)-7H-purin-9(8H)-yl)propanamide,"
should read as
--(S)-N,N-dimethyl-2-(8-oxo-2-(pyrazolo[1,5-a]pyridin-3-yl)-7H-purin-9(8H)-yl)propanamide,--.

Claim 36, Col. 119, Lines 3-5
"(2R)-2-[2-(5-Cyanopyrazolo[1,5-a]pyridin-3-yl)-8-oxo-7,8-dihydro-9H-purin-9-yl]-N-(2,2,2-trifluoroethyl)propanamide,"
should read as
--(2R)-2-(2-(5-cyanopyrazolo[1,5-a]pyridin-3-yl)-8-oxo-7,8-dihydro-9H-purin-9-yl)-N-(2,2,2-trifluoroethyl)propanamide,--.

Claim 36, Col. 119, Lines 36-38
"3-(7-(2-Methoxyethyl)-8-oxo-9-(tetrahydro-2H-pyran-4-yl)-8,9-dihydro-7H-purin-2-yl)pyrazolo[1,5-a]pyridine-5-carbonitrile,"
should read as
--3-(7-(2-methoxyethyl)-8-oxo-9-(tetrahydro-2H-pyran-4-yl)-8,9-dihydro-7H-purin-2-yl)pyrazolo[1,5-a]pyridine-5-carbonitrile,--.

Claim 36, Col. 119, Lines 48-50
"3-(7-(2-Hydroxyethyl)-8-oxo-9-(tetrahydro-2H-pyran-4-yl)-8,9-dihydro-7H-purin-2-yl)pyrazolo[1,5-a]pyridine-5-carbonitrile,"
should read as ---3-(7-(2-hydroxyethyl)-8-oxo-9-(tetrahydro-2H-pyran-4-yl)-8,9-dihydro-7H-purin-2-yl)pyrazolo[1,5-a]pyridine-5-carbonitrile,--.

Claim 36, Col. 119, Lines 59-61
"(S)-tert-Butyl 3-(5-(5-cyanopyrazolo[1,5-a]pyridin-3-yl)-3H-imidazo[4,5-b]pyridin-3-yl)piperidine-1-carboxylate,"
should read as
--(S)-tert-butyl-3-(5-(5-cyanopyrazolo[1,5-a]pyridin-3-yl)-3H-imidazo[4,5-b]pyridin-3-yl)piperidine-1-carboxylate,--.

Claim 36, Col. 119, Lines 62-64
"(S)-tert-Butyl 3-(5-(5-cyanopyrazolo[1,5-a]pyridin-3-yl)-2-methyl-3H-imidazo[4,5-b]pyridin-3-yl)piperidine-1-carboxylate,"
should read as
--(S)-tert-butyl-3-(5-(5-cyanopyrazolo[1,5-a]pyridin-3-yl)-2-methyl-3H-imidazo[4,5-b]pyridin-3-yl)piperidine-1-carboxylate,--.

Claim 36, Col. 120, Lines 3-4
"(S)-tert-Butyl 3-(5-(pyrazolo[1,5-a]pyridin-3-yl)-3H-imidazo[4,5-b]pyridin-3-yl)piperidine-1-carboxylate,"
should read as
--(S)-tert-butyl-3-(5-(pyrazolo[1,5-a]pyridin-3-yl)-3H-imidazo[4,5-b]pyridin-3-yl) piperidine-1-carboxylate,--.

Claim 36, Col. 120, Lines 5-6
"3-(9-Tetrahydro-2H-pyran-4-yl-9H-purin-2-yl)pyrazolo[1,5-a]pyridine-5-carbonitrile,"
should read as
--3-(9-tetrahydro-2H-pyran-4-yl-9H-purin-2-yl)pyrazolo[1,5-a]pyridine-5-carbonitrile,--.

Claim 36, Col. 120, Lines 9-10
"3-(3-(Tetrahydro-2H-pyran-4-yl)-3H-imidazo[4,5-b]pyridin-5-yl)pyrazolo[1,5-a]pyridine-5-carbonitrile,"
should read as
--3-(3-(tetrahydro-2H-pyran-4-yl)-3H-imidazo[4,5-b]pyridin-5-yl)pyrazolo[1,5-a]pyridine-5-carbonitrile,--.

Claim 36, Col. 120, Lines 11-13
"3-(2-Methyl-3-(tetrahydro-2H-pyran-4-yl)-3H-imidazo[4,5-b]pyridin-5-yl)pyrazolo[1,5-a]pyridine-5-carbonitrile,"
should read as
--3-(2-methyl-3-(tetrahydro-2H-pyran-4-yl)-3H-imidazo[4,5-b]pyridin-5-yl)pyrazolo[1,5-a]pyridine-5-carbonitrile,--.

Claim 36, Col. 120, Lines 35-36
"2-(pyrazolo[1,5-a]pyridine-3-yl)-9-(tetrahydro-2H-pyran-4-yl)-8-thiophen-2-yl)-H-purine,"

should read as
--2-(pyrazolo[1,5-a]pyridine-3-yl)-9-(tetrahydro-2H-pyran-4-yl)-8-thiophen-2-yl)-9H-purine,--.

Claim 36, Col. 120, Lines 39-41
"(S)-tert-Butyl 3-(2-methyl-5-(pyrazolo[1,5-a]pyridin-3-yl)-3H-imidazo[4,5-b]pyridin-3-yl)piperidine-1-carboxylate,"
should read as
--(S)-tert-butyl-3-(2-methyl-5-(pyrazolo[1,5-a]pyridin-3-yl)-3H-imidazo[4,5-b]pyridin-3-yl)piperidine-1-carboxylate,--.

Claim 36, Col. 120, Lines 42-44
"3-(8-1-Methyl-1H-imidazol-2-yl)-9-(tetrahydro-2H-pyran-4-yl)-9H-purin-2-yl)pyrazolo[1,5-a]pyridine-5-carbonitrile,"
should read as
--3-(8-(1-methyl-1H-imidazol-2-yl)-9-(tetrahydro-2H-pyran-4-yl)-9H-purin-2-yl)pyrazolo[1,5-a]pyridine-5-carbonitrile,--.

Claim 36, Col. 120, Lines 51-52
"3-[8-(Ethylamino)-9-tetrahydro-2H-pyran-4-yl-9H-purin-2-yl]pyrazolo[1,5-a]pyridine-5-carbonitrile,"
should read as
--3-(8-(ethylamino)-9-tetrahydro-2H-pyran-4-yl-9H-purin-2-yl)pyrazolo[1,5-a]pyridine-5-carbonitrile,--.

Claim 36, Col. 120, Lines 55-56
"S)-3-(9-(1-acetylpiperidin-3-yl)-8-isopropyl-9H-purin-2-yl)pyrazolo[1,5-a]pyridine-5-carbonitrile,"
should read as
--(S)-3-(9-(1-acetylpiperidin-3-yl)-8-isopropyl-9H-purin-2-yl)pyrazolo[1,5-a]pyridine-5-carbonitrile,--.

Claim 36, Col. 120, Lines 61-62
"8-Cyclopentyl-2-(pyrazolo[1,5-a]pyridin-3-yl)-9-(tetrahydro-2H-pyran-4-yl)-9H-purine,"
should read as
--8-cyclopentyl-2-(pyrazolo[1,5-a]pyridin-3-yl)-9-(tetrahydro-2H-pyran-4-yl)-9H-purine,--.

Claim 36, Col. 121, Lines 7-8
"(S)-3-(1-Acetylpiperidin-3-yl)-1-methyl-5-(pyrazolo[1,5-a]pyridin-3-yl)-1H-imidazo[4,5-b]pyridin-2(3H)-one,"
should read as
--(S)-3-(1-acetylpiperidin-3-yl)-1-methyl-5-(pyrazolo[1,5-a]pyridin-3-yl)-1H-imidazo[4,5-b]pyridin-2(3H)-one,--.

Claim 36, Col. 121, Lines 13-15
"(S)-1-(3-(1-Methyl-2-oxo-5-(pyrazolo[1,5-a]pyridin-3-yl)-1H-imidazo[4,5-b]pyridin-3(2H)-yl)piperidine-1-carbonyl)cyclopropanecarbonitrile,"

should read as
--(S)-1-(3-(1-methyl-2-oxo-5-(pyrazolo[1,5-a]pyridin-3-yl)-1H-imidazo[4,5-b]pyridin-3(2H)-yl)piperidine-1-carbonyl)cyclopropanecarbonitrile,--.

Claim 36, Col. 121, Lines 16-17
"(S)-ethyl 3-(2-(5-cyanopyrazolo[1,5-a]pyridin-3-yl)-8-oxo-7H-purin-9(8H)-yl)piperidine-1-carboxylate,"
should read as
--(S)-ethyl-3-(2-(5-cyanopyrazolo[1,5-a]pyridin-3-yl)-8-oxo-7H-purin-9(8H)-yl)piperidine-1-carboxylate,--.

Claim 36, Col. 121, Lines 18-19
"(S)-isobutyl 3-(2-(5-cyanopyrazolo[1,5-a]pyridin-3-yl)-8-oxo-7H-purin-9(8H)-yl)piperidine-1-carboxylate,"
should read as
--(S)-isobutyl-3-(2-(5-cyanopyrazolo[1,5-a]pyridin-3-yl)-8-oxo-7H-purin-9(8H)-yl)piperidine-1-carboxylate,--.

Claim 36, Col. 121, Lines 23-24
"(S)—N-tert-butyl-3-(2-(5-cyanopyrazolo[1,5-a]pyridin-3-yl)-8-oxo-7H-purin-9(8H)-yl)piperidine-1-carboxamide,"
should read as
--(S)-N-tert-butyl-3-(2-(5-cyanopyrazolo[1,5-a]pyridin-3-yl)-8-oxo-7H-purin-9(8H)-yl)piperidine-1-carboxamide,--.

Claim 36, Col. 121, Lines 25-27
"-(S)-ethyl 9-(1-(2-cyanoacetyl)piperidin-3-yl)-8-oxo-2-(pyrazolo[1,5-a]pyridin-3-yl)-8,9-dihydro-7H-purine-7-carboxylate,"
should read as
--(S)-ethyl-9-(1-(2-cyanoacetyl)piperidin-3-yl)-8-oxo-2-(pyrazolo[1,5-a]pyridin-3-yl)-8,9-dihydro-7H-purine-7-carboxylate,--.

Claim 36, Col. 121, Lines 33-35,
"(S)—N-isopropyl-3-(1-methyl-2-oxo-5-(pyrazolo[1,5-a]pyridin-3-yl)-H-imidazo[4,5-b]pyridine-3(2H)-yl)piperidine-1-carboxamide,"
should read as
--(S)-N-isopropyl-3-(1-methyl-2-oxo-5-(pyrazolo[1,5-a]pyridin-3-yl)-1H-imidazo[4,5-b]pyridine-3(2H)-yl)piperidine-1-carboxamide,--.

Claim 36, Col. 121, Lines 39-41
"(S)-ethyl 3-(1-(2-cyanoacetyl)piperidin-3-yl)-2-oxo-5-(pyrazolo[1,5-a]pyridin-3-yl)-2,3-dihydro-1H-imidazo[4,5-b]pyridine-1-carboxylate,"
should read as
--(S)-ethyl 3-(1-(2-cyanoacetyl)piperidin-3-yl)-2-oxo-5-(pyrazolo[1,5-a]pyridin-3-yl)-2,3-dihydro-1H-imidazo[4,5-b]pyridine-1-carboxylate,--.

Claim 36, Col. 121, Lines 42-43
"(S)-Methyl 3-(2-(5-cyanopyrazolo[1,5-a]pyridin-3-yl)-8-oxo-7H-purin-9(8H)-yl)piperidine-1-carboxylate,"
should read as
--(S)-methyl-3-(2-(5-cyanopyrazolo[1,5-a]pyridin-3-yl)-8-oxo-7H-purin-9(8H)-yl)piperidine-1-carboxylate,--.

Claim 36, Col. 122, Lines 4-6
"(S)-3-(9-(1-(1-Cyanocyclopropanecarbonyl)piperidin-3-yl)-8-oxo-8,9-dihydro-7H-purin-2-yl)pyrazolo[1,5-a]pyridine-5-carbonitrile,"
should read as
--(S)-3-(9-(1-(1-cyanocyclopropanecarbonyl)piperidin-3-yl)-8-oxo-8,9-dihydro-7H-purin-2-yl)pyrazolo[1,5-a]pyridine-5-carbonitrile,--.

Claim 36, Col. 122, Lines 7-8
"(R)-3-(9-(1-Hydroxypropan-2-yl)-8-oxo-8,9-dihydro-7H-purin-2-yl)pyrazolo[1,5-a]pyridine-5-carbonitrile,"
should read as
--(R)-3-(9-(1-hydroxypropan-2-yl)-8-oxo-8,9-dihydro-7H-purin-2-yl)pyrazolo[1,5-a]pyridine-5-carbonitrile,--.

Claim 36, Col. 122, Lines 9-10
"(S)-3-(3-(2-(5-Methylpyrazolo[1,5-a]pyridin-3-yl)-9H-purin-9-yl)piperidin-1-yl)-3-oxopropanenitrile,"
should read as
--(S)-3-(3-(2-(5-methylpyrazolo[1,5-a]pyridin-3-yl)-9H-purin-9-yl)piperidin-1-yl)-3-oxopropanenitrile,--.

Claim 36, Col. 122, Lines 11-12
"1-(4-(2-(Pyrazolo[1,5-a]pyridin-3-yl)-9H-purin-9-yl)piperidin-1-yl)ethanone,"
should read as
--1-(4-(2-(pyrazolo[1,5-a]pyridin-3-yl)-9H-purin-9-yl)piperidin-1-yl)ethanone,--.

Claim 36, Col. 122, Lines 16-18
"(S)-(9-(1-(2-Cyanoacetyl)piperidin-3-yl)-8-oxo-2-(pyrazolo[1,5-a]pyridin-3-yl)-8,9-dihydro-7H-purin-7-yl)methyl acetate,"
should read as
--(S)-(9-(1-(2-cyanoacetyl)piperidin-3-yl)-8-oxo-2-(pyrazolo[1,5-a]pyridin-3-yl)-8,9-dihydro-7H-purin-7-yl)methyl acetate,--.

Claim 36, Col. 122, Lines 19-21
"(R)-3-(9-O-Hydroxypropan-2-yl)-7-methyl-8-oxo-8,9-dihydro-7H-purin-2-yl)pyrazolo[1,5-a]pyridine-5-carbonitrile,"
should read as --(R)-3-(9-1-hydroxypropan-2-yl)-7-methyl-8-oxo-8,9-dihydro-7H-purin-2-yl)pyrazolo[1,5-a]pyridine-5-carbonitrile,--.

Claim 36, Col. 122, Lines 22-23
"2-(Pyrazolo[1,5-a]pyridin-3-yl)-9-(tetrahydro-2H-pyran-4-yl)-9H-purin-8-amine,"
should read as
--2-(pyrazolo[1,5-a]pyridin-3-yl)-9-(tetrahydro-2H-pyran-4-yl)-9H-purin-8-amine,--.

Claim 36, Col. 122, Lines 30-31
"1-(2-(Pyrazolo[1,5-a]pyridine-3-yl)-9-(tetrahydro-2H-pyran-4-O-9H-purin-8-yl)pyrrolidin-2-one,"
should read as
--1-(2-(pyrazolo[1,5-a]pyridine-3-yl)-9-(tetrahydro-2H-pyran-4-yl)-9H-purin-8-yl)pyrrolidin-2-one,--.

Claim 36, Col. 122, Lines 22-23
"3-(9-(trans-4-Hydroxycyclohexyl)-7-methyl-8-oxo-8,9-dihydro-7H-purin-2-yl)pyrazolo[1,5-a]pyridine-5-carbonitrile,"
should read as
--3-(9-(trans-4-hydroxycyclohexyl)-7-methyl-8-oxo-8,9-dihydro-7H-purin-2-yl)pyrazolo[1,5-a]pyridine-5-carbonitrile,--.

Claim 36, Col. 122, Lines 36-37
"2-(2-(5-Cyanopyrazolo[1,5-a]pyridin-3-yl)-8-oxo-7H-purin-9(8H)-yl)-N-(2,2,2-trifluoroethyl)acetamide,"
should read as
--2-(2-(5-cyanopyrazolo[1,5-a]pyridin-3-yl)-8-oxo-7H-purin-9(8H)-yl)-N-(2,2,2-trifluoroethyl)acetamide,--.

Claim 36, Col. 122, Lines 38-39
"2-(Imidazo[1,2-a]pyridin-3-yl)-7-methyl-9-(tetrahydro-2H-pyran-4-yl)-7H-purin-8(9H)-one,"
should read as
--2-(imidazo[1,2-a]pyridin-3-yl)-7-methyl-9-(tetrahydro-2H-pyran-4-yl)-7H-purin-8(9H)-one,--.